(12) United States Patent
Wissner et al.

(10) Patent No.: US 6,288,082 B1
(45) Date of Patent: Sep. 11, 2001

(54) SUBSTITUTED 3-CYANOQUINOLINES

(75) Inventors: Allan Wissner, Ardsley; Hwei-Ru Tsou; Dan M. Berger, both of New City; Middleton B. Floyd, Jr., Suffern; Philip R. Hamann, Gernerville; Nan Zhang, Eastchester, all of NY (US); Mark E. Salvati, Lawrenceville; Philip Frost, Morris Township, both of NJ (US)

(73) Assignee: American Cyanamid Company, Madison, NJ (US)

( * ) Notice: Subject to any disclaimer, the term of this patent is extended or adjusted under 35 U.S.C. 154(b) by 0 days.

(21) Appl. No.: 09/406,573

(22) Filed: Sep. 24, 1999

Related U.S. Application Data

(60) Provisional application No. 60/150,693, filed on Sep. 29, 1998.

(51) Int. Cl.[7] .................... A61K 31/47; C07D 213/68; C07D 213/74

(52) U.S. Cl. ................ 514/313; 514/300; 514/312; 514/234.8; 514/235.2; 514/253; 540/506; 544/112; 544/128; 544/237; 544/300; 544/316; 544/350; 544/354; 544/356; 544/363; 546/19; 546/90; 546/122; 546/143; 546/153; 546/159; 546/160; 546/162

(58) Field of Search .................. 546/160, 159, 546/153, 162; 514/312, 313

(56) References Cited

U.S. PATENT DOCUMENTS

| 5,480,883 | 1/1996 | Spada et al. | 514/249 |
|---|---|---|---|
| 5,686,457 | 11/1997 | Traxler et al. | 514/258 |
| 6,002,008 | * 12/1999 | Wissner et al. | 546/160 |

FOREIGN PATENT DOCUMENTS

| 0520722 | 12/1992 | (EP) . |
| 0566226 | 10/1993 | (EP) . |
| 0602851 | 6/1994 | (EP) . |
| 0635498 | 1/1995 | (EP) . |
| 0635507 | 1/1995 | (EP) . |
| 9515758 | 6/1995 | (WO) . |
| 9519774 | 7/1995 | (WO) . |
| 9519970 | 7/1995 | (WO) . |
| 9521613 | 8/1995 | (WO) . |
| 9523141 | 8/1995 | (WO) . |
| 9524190 | 9/1995 | (WO) . |
| 9609294 | 3/1996 | (WO) . |
| 9633977 | 10/1996 | (WO) . |
| 9633978 | 10/1996 | (WO) . |
| 9633979 | 10/1996 | (WO) . |
| 9633980 | 10/1996 | (WO) . |
| 9633981 | 10/1996 | (WO) . |
| 9802434 | 1/1998 | (WO) . |
| 9802438 | 1/1998 | (WO) . |
| 9813350 | 4/1998 | (WO) . |
| 9843960 | 10/1998 | (WO) . |

OTHER PUBLICATIONS

Burke, T.R., *Drugs Future*, 17, 119 (1992).
Chang, C.J. et al., *J. Nat. Prod.*, 55, 1529 (1992).
Du J. et al., *Am. J. Physiol.*, 269 (2 Pt 1), 487 (1995).
Nauta J. et al., *Pediatric Research*, 37(6), 755 (1995).
Gattone, V.H. et al., *Developmental Biology*, 169(2), 504 (1995).
Wilson, P.D. et al., *Eur. J. Cell Biol.*, 61(1), 131 (1993).
Ife, R.J. et al., *J. Med. Chem.*, 35(18), 3413 (1992).
Gazit, A. et al., *J. Med. Chem.*, 35(11), 2170 (1996).
Dolle, R.E. et al., *J. Med. Chem.*, 372, 2627, (1994).
Maguire, M.P. et al., *J. Med. Chem.*, 37, 2129 (1994).
Fry, D.W. et al., *Science*, 265, 1093 (1994).
Rewcastle, A.J. et al., *J. Med. Chem.*, 39, 267, (1996).
Bridges, A.J. et al., *J. Med. Chem.*, 39, 267 (1996).

* cited by examiner

*Primary Examiner*—Bernard Dentz
(74) *Attorney, Agent, or Firm*—John W. Hogan, Jr.

(57) ABSTRACT

This invention provides compounds of formula I having the structure

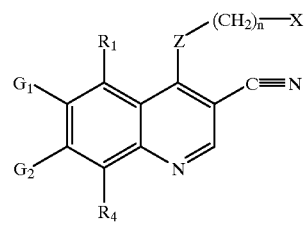

wherein $G_1$, $G_2$, $R_1$, $R_4$, Z, n, and X are defined in the specification or a pharmaceutically acceptable salt thereof which are useful as antineoplastic agents and in the treatment of polycystic kidney disease.

15 Claims, No Drawings

SUBSTITUTED 3-CYANOQUINOLINES

This application claims the benefit of U.S. Provisional Application No. 60/150,693 filed Sep. 29, 1998; the entire disclosure of which incorporated herein by reference.

BACKGROUND OF THE INVENTION

This invention relates to certain substituted 3-cyano quinoline compounds as well as the pharmaceutically acceptable salts thereof. The compounds of the present invention inhibit the action of certain growth factor receptor protein tyrosine kinases (PTK) and other protein kinases thereby inhibiting the abnormal growth of certain cell types. The compounds of this invention are therefore useful for the treatment of certain diseases that are the result of deregulation of these PTKs. The compounds of this invention are anti-cancer agents and are useful for the treatment of cancer in mammals. In addition, the compounds of this invention are useful for the treatment of polycystic kidney disease in mammals. This invention also relates to the manufacture of said 3-cyano quinolines, their use for the treatment of cancer and polycystic kidney disease, and the pharmaceutical preparations containing them.

Protein tyrosine kinases are a class of enzymes that catalyze the transfer of a phosphate group from ATP to a tyrosine residue located on a protein substrate. Protein tyrosine kinases clearly play a role in normal cell growth. Many of the growth factor receptor proteins function as tyrosine kinases and it is by this process that they effect signaling. The interaction of growth factors with these receptors is a necessary event in normal regulation of cell growth. However, under certain conditions, as a result of either mutation or overexpression, these receptors can become deregulated; the result of which is uncontrolled cell proliferation which can lead to tumor growth and ultimately to the disease known as cancer [Wilks A. F., *Adv. Cancer Res.*, 60, 43 (1993) and Parsons, J. T.; Parsons, S. J., *Important Advances in Oncology*, DeVita V. T. Ed., J. B. Lippincott Co., Phila., 3 (1993)]. Among the growth factor receptor kinases and their proto-oncogenes that have been identified and which are targets of the compounds of this invention are the epidermal growth factor receptor kinase (EGF-R kinase, the protein product of the erbB oncogene), and the product produced by the erbB-2 (also referred to as the neu or HER2) oncogene. Since the phosphorylation event is a necessary signal for cell division to occur and since overexpressed or mutated kinases have been associated with cancer, an inhibitor of this event, a protein tyrosine kinase inhibitor, will have therapeutic value for the treatment of cancer and other diseases characterized by uncontrolled or abnormal cell growth. For example, overexpression of the receptor kinase product of the erbB-2 oncogene has been associated with human breast and ovarian cancers [Slamon, D. J., et. al., *Science*, 244, 707 (1989) and *Science*, 235, 1146 (1987)]. Deregulation of EGF-R kinase has been associated with epidermoid tumors [Reiss, M., et. al., *Cancer Res.*, 51, 6254 (1991)], breast tumors [Macias, A., et. al., *Anticancer Res.*, 7, 459 (1987)], and tumors involving other major organs [Gullick, W. J., *Brit Med. Bull.*, 47, 87 (1991)]. Because of the importance of the role played by deregulated receptor kinases in the pathogenesis of cancer, many recent studies have dealt with the development of specific PTK inhibitors as potential anti-cancer therapeutic agents [some recent reviews: Burke. T. R., *Drugs Future*, 17, 119 (1992) and Chang, C. J.; Geahlen, R. L., *J. Nat. Prod.*, 55, 1529 (1992)]. The compounds of this invention inhibit the kinase activity of EGF-R and are therefore useful for treating certain disease states, such as cancer, that result, at least in part, from deregulation of this receptor. The compounds of this invention are also useful for the treatment and prevention of certain pre-cancerous conditions, such as the growth of colon polyps, that result, at least in part, from deregulation of this receptor.

It is also known that deregulation of EGF receptors is a factor in the growth of epithelial cysts in the disease described as polycystic kidney disease [Du J., Wilson P. D., *Amer. J. Physiol.*, 269(2 Pt 1), 487 (1995); Nauta J., et al., *Pediatric Research*, 37(6), 755 (1995); Gattone V. H., et al., *Developmental. Biology*, 169(2), 504 (1995); Wilson P. D., et al., *Eur. J. Cell Biol.*, 61(1), 131, (1993)]. The compounds of this invention, which inhibit the catalytic function of the EGF receptors, are consequently useful for the treatment of this disease.

The mitogen-activated protein kinase (MAPK) pathway is a major pathway in the cellular signal transduction cascade from growth factors to the cell nucleus. The pathway involves kinases at two levels: MAP kinase kinases (MAPKK), and their substrates MAP kinases (MAPK). There are different isoforms in the MAP kinase family. (For review, see Rony Seger and Edwin G. Krebs, FASEB, Vol. 9, 726, June 1995). The compounds of this invention can inhibit the action of two of these kinases: MEK, a MAP kinase kinase, and its substrate ERK, a MAP kinase. MEK is activated by phosphorylation on two serine residues by upstream kinases such as members of the raf family. When activated, MEK catalyzes phosphorylation on a threonine and a tyrosine residue of ERK. The activated ERK then phosphorylates and activates transcription factors in the nucleus, such as fos and jun, or other cellular targets with PXT/SP sequences. ERK, a p42 MAPK is found to be essential for cell proliferation and differentiation. Over-expression and/or over-activation of Mek or ERK has been found to be associated with various human cancers (For example, Vimala S. Sivaraman, Hsien-yu Wang, Gerard J. Nuovo, and Craig C. Malbon, J. Clin. Invest. Vol. 99, No. 7April 1997). It has been demonstrated that inhibition of MEK prevents activation of ERK and subsequent activation of ERK substrates in cells, resulting in inhibition of cell growth stimulation and reversal of the phenotype of ras-transformed cells (David T. Dudley, Long Pang, Stuart J. Decker, Alexander J. Bridges, and Alan R. Saltiel, PNAS, Vol. 92, 7686, August 1995). Since, as demonstrated below, the compounds of this invention can inhibit the coupled action of MEK and ERK, they are useful for the treatment of diseases such as cancer which are characterized by uncontrolled cell proliferation and which, at least in part, depend on the MAPK pathway.

Epithelial Cell Kinase (ECK) is a receptor protein tyrosine kinase (RPTK) belonging to the EPH (Erythropoietin Producing Hepatoma) family. Although originally identified as an epithelial lineage-specific tyrosine kinase, ECK has subsequently been shown to be expressed on vascular endothelial cells, smooth muscle cells, and fibroblasts. ECK is a type I transmembrane glycoprotein with the extracellular ligand-binding domain consisting of a cysteine-rich region followed by three fibronectin type III repeats. The intracellular domain of ECK possesses a tyrosine kinase catalytic domain that initiates a signal transduction cascade reflecting the ECK function. ECK binds and is subsequently activated by its counter-receptor, Ligand for Eph-Related Kinase (LERK)-1, which is an immediate early response gene product readily inducible in a lineage-unrestricted manner with proinflammatory cytokines such as IL-1 or TNF. Soluble LERK-1 has been shown to stimulate angiogenesis in part by stimulating ECK in a murine model of corneal angiogenesis. Unlike their normal counterparts, tumor cells of various lineages constitutively express LERK-1 and this expression can further be upregulated by hypoxia and proinflammatory cytokines. Many of these tumor cells also express ECK at higher levels than their normal counterparts, thereby creating an opportunity for autocrine stimulation via ECK : LERK-1 interaction. The increased expression of both ECK and LERK-1 has been correlated with the transformation of melanomas from the noninvasive horizontal phase of growth into very invasive vertically growing metastatic melanomas. Together, the ECK:LERK-1 interaction is believed to promote tumor growth via its tumor growth promoting and angiogenic effects. Thus, the inhibition of the ECK tyrosine kinase activity mediating signaling cascade induced by its binding and cross-linking to LERK-l may be therapeutically beneficial in cancer, inflammatory diseases, and hyperproliferative disorders. As is shown below, the compounds of this invention inhibit the tyrosine kinase activity of ECK and are therefore useful for the treatment of the aforementioned disorders.

Growth of most solid tumors is dependent on the angiogenesis involving activation, proliferation and migration of vascular endothelial cells and their subsequent differentiation into capillary tubes. Angiogenization of tumors allows them access to blood-derived oxygen and nutrients, and also provides them adequate perfusion. Hence inhibiting angiogenesis is an important therapeutic strategy in not only cancer but also in a number of chronic diseases such as rheumatoid arthritis, psoriasis, diabetic retinopathy, age-related macular degeneration, and so on. Tumor cells produce a number of angiogenic molecules. Vascular Endothelial Growth Factor (VEGF) is one such angiogenic factor. VEGF, a homodimeric disulfide-linked member of the PDGF family, is an endothelial cell-specific mitogen and is known to cause profound increase in the vascular endothelial permeability in the affected tissues. VEGF is also a senescence-preventing survival factor for endothelial cells. Almost all nucleated tissues in the body possess the capability to express VEGF in response to various stimuli including hypoxia, glucose deprivation, advanced glycation products, inflammatory cytokines, etc. Growth-promoting angiogenic effects of VEGF are mediated predominantly via its signaling receptor Kinase insert Domain containing Receptor (KDR). The expression of KDR is low on most endothelial cells; however, activation with angiogenic agents results in a significant upregulation of KDR on endothelial cells. Most angiogenized blood vessels express high levels of KDR. KDR is a receptor protein tyrosine kinase with an extracellular VEGF-binding domain consisting of 7 immunoglobulin-like domains and a cytoplasmic domain containing the catalytic tyrosine kinase domain split by a kinase-insert region. Binding to VEGF causes dimerization of KDR resulting in its autophosphorylation and initiation of signaling cascade. Tyrosine kinase activity of KDR is essential for mediation of its functional effects as a receptor for VEGF. Inhibition of KDR-mediated functional effects by inhibiting KDR's catalytic activity is considered to be an important therapeutic strategy in the treatment of angiogenized disease states including cancer. As is shown below, the compounds of this invention inhibit the tyrosine kinase activity of KDR and are therefore useful for the treatment of the aforementioned disease states.

In addition to the above utilities some of the compounds of this invention are useful for the preparation of other compounds of this invention.

The compounds of this invention are certain substituted 3-cyano quinolines. Throughout this patent application, the quinoline ring system will be numbered as indicated in the formula below; the numbering for the quinazoline ring system is also shown:

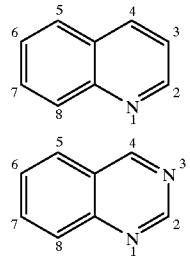

No 3-cyano quinolines have been reported that have biological activity as inhibitors of protein tyrosine kinases. A 3-cyano quinoline with a 4-(2-methyl anilino) substituent having gastric ($H^+/K^+$)-ATPase inhibitory activity at high concentrations has been described [Ife R. J., et al., *J. Med. Chem.*, 35(18), 3413 (1992)].

There are quinolines that do not have the 3-cyano substituent and, unlike the compounds of this invention, are unsubstituted at the 4-position but are reported to be inhibitors of protein tyrosine kinases [Gazit A., et al., *J. Med. Chem.*, 39(11), 2170 (1996)]. A series of quinolines that have a 3-pyridyl substituent and no substituent at the 4-position have been described as inhibitors of platelet derived growth factor receptor kinase [Dolle R. E., et al., *J. Med. Chem.*, 372, 2627 (1994) and Maguire M. P., et al., *J. Med. Chem.*, 372, 129 (1994)]. The patent applications WO 96/09294 and WO-9813350 describe inhibitors of protein tyrosine kinases that include 4-anilino quinolines with a large variety of substituents on positions 5–8 but which must also have a hydrogen or fluorine atom at position 3. The U.S. Pat. No. 5,480,883 describes quinoline derivatives that are inhibitors of protein tyrosine kinases but these derivatives do not have the unique combination of substituents, including the 3-cyano group, contained in the compounds of the present invention. The applications WO-9802434 and WO-9802438 describe quinoline derivatives that are tyrosine kinase inhibitors but these quinolines do not have the important 3-cyano substituent .

In addition to quinolines, certain quinazoline derivatives that are similar, in some respects, to the compounds of this invention are known to be inhibitors of protein tyrosine kinases. The application EP-520722 describes 4-anilinoquinazolines that contain simple substituents such as chloro, trifluoromethyl, or nitro groups at positions 5 to 8. The application EP-566226 is similar but with a much larger variety of substituents now allowed at positions 5 to 8. The application WO-9609294 describes compounds with similar substituents at positions 5 to 8 and with the substituent at to 4-position consisting of some polycyclic ring systems. Some simple substituted quinazolines are also described in the applications WO-9524190, WO-9521613, and WO-9515758. The applications EP-602851 and WO-9523141 cover similar quinazoline derivatives where the aryl group attached at position 4 can be a variety of heterocyclic ring structures. The application EP-635498 describes certain quinazoline derivatives that have alkenoylamino and alkynoylamino groups among the substituents at position 6 and a halogen atom at position 7. The application WO-9519774 describes compounds where one or more of the carbon atoms at positions 5–8 can be replaced with heteroatoms resulting in a large variety of bicyclic systems where the left-hand ring is a 5 and 6-membered heterocyclic ring; in addition, a variety of substituents are allowed on the left-hand ring. The application EP-682027-A1 describes certain pyrrolopyrimidine inhibitors of PTKs. The application WO-9519970 describes compounds in which the left-hand aromatic ring of the basic quinazoline structure has been replaced with a wide variety of different heterocyclic rings so that the resulting inhibitors are tricyclic. The application EP-635507 describes quinazolines where an additional 5 or 6-membered heterocyclic ring with optional substitution is fused at positions 5 and 6.

In addition to the aforementioned patent applications, a number of publications describe 4-anilinoquinazolines: Fry, D. W., et. al., Science, 265, 1093 (1994), Rewcastle G. W., et. al., J. Med. Chem., 38, 3482 (1995), and Bridges, A. J., et. al., J. Med. Chem., 39, 267, (1996). There are no publications that describe 3-cyano quinolines as PTK inhibitors.

DESCRIPTION OF THE INVENTION

This invention provides a compound of formula 1:

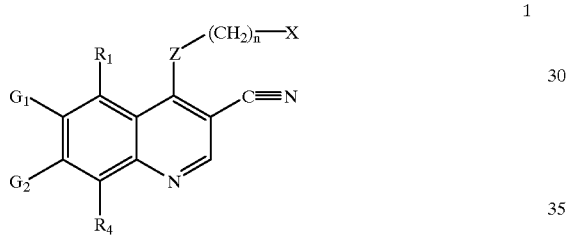

wherein:

X is a bicyclic aryl or bicyclic heteroaryl ring system of 8 to 12 atoms where the bicyclic heteroaryl ring contains 1 to 4 heteroatoms selected from N, O, and S with the proviso that the bicyclic heteroaryl ring does not contain O—O, S—S, or S—O bonds and where the bicyclic aryl or bicyclic heteroaryl ring may be optionally mono- di-, tri, or tetra-substituted with a substituent selected from the group consisting of halogen, oxo, thio, alkyl of 1–6 carbon atoms, alkenyl of 2–6 carbon atoms, alkynyl of 2–6 carbon atoms, azido, hydroxyalkyl of 1–6 carbon atoms, halomethyl, alkoxymethyl of 2–7 carbon atoms, alkanoyloxymethyl of 2–7 carbon atoms, alkoxy of 1–6 carbon atoms, alkylthio of 1–6 carbon atoms, hydroxy, trifluoromethyl, cyano, nitro, carboxy, carboalkoxy of 2–7 carbon atoms, carboalkyl of 2–7 carbon atoms, phenoxy, phenyl, thiophenoxy, benzoyl, benzyl, amino, alkylamino of 1–6 carbon atoms, dialkylamino of 2 to 12 carbon atoms, phenylamino, benzylamino, alkanoylamino of 1–6 carbon atoms, alkenoylamino of 3–8 carbon atoms, alkynoylamino of 3–8 carbon atoms, carboxyalkyl of 2–7 carbon atoms, carboalkoxyalky of 3–8 carbon atoms, aminoalkyl of 1–5 carbon atoms, N-alkylaminoalkyl of 2–9 carbon atoms, N,N-dialkylaminoalkyl of 3–10 carbon atoms, N-alkylaminoalkoxy of 2–9 carbon atoms, N,N-dialkylaminoalkoxy of 3–10 carbon atoms, mercapto, and benzoylamino; or X is a radical having the formula:

$$\diagup\!^{A}\!\diagdown_{T}\!\diagup\!^{L}$$

wherein

A is a pyridinyl, pyrimidinyl, or phenyl ring; wherein the pyridinyl, pyrimidinyl, or phenyl ring may be optionally mono- or di-substituted with a substituent selected from the group consisting of halogen, alkyl of 1–6 carbon atoms, alkenyl of 2–6 carbon atoms, alkynyl of 2–6 carbon atoms, azido, hydroxyalkyl of 1–6 carbon atoms, halomethyl, alkoxymethyl of 2–7 carbon atoms, alkanoyloxymethyl of 2–7 carbon atoms, alkoxy of 1–6 carbon atoms, alkylthio of 1–6 carbon atoms, hydroxy, trifluoromethyl, cyano, nitro, carboxy, carboalkoxy of 2–7 carbon atoms, carboalkyl of 2–7 carbon atoms, phenoxy, phenyl, thiophenoxy, benzoyl, benzyl, amino, alkylamino of 1–6 carbon atoms, dialkylamino of 2 to 12 carbon atoms, phenylamino, benzylamino, alkanoylamino of 1–6 carbon atoms, alkenoylamino of 3–8 carbon atoms, alkynoylamino of 3–8 carbon atoms, carboxyalkyl of 2–7 carbon atoms, carboalkoxyalky of 3–8 carbon atoms, aminoalkyl of 1–5 carbon atoms, N-alkylaminoalkyl of 2–9 carbon atoms, N,N-dialkylaminoalkyl of 3–10 carbon atoms, N-alkylaminoalkoxy of 2–9 carbon atoms, N,N-dialkylaminoalkoxy of 3–10 carbon atoms, mercapto, and benzoylamino;

T is bonded to a carbon of A and is:
—NH(CH$_2$)$_m$—, —O(CH$_2$)$_m$—, —S(CH$_2$)$_m$—, —NR(CH$_2$)$_m$—, —(CH$_2$)$_m$— —(CH$_2$)$_m$NH—, —(CH$_2$)$_m$O—, —(CH$_2$)$_m$S—, or —(CH$_2$)$_m$NR—;

L is an unsubsitituted phenyl ring or a phenyl ring mono-, di-, or tri-substituted with a substituent selected from the group consisting of halogen, alkyl of 1–6 carbon atoms, alkenyl of 2–6 carbon atoms, alkynyl of 2–6 carbon atoms, azido, hydroxyalkyl of 1–6 carbon atoms, halomethyl, alkoxymethyl of 2–7 carbon atoms, alkanoyloxymethyl of 2–7 carbon atoms, alkoxy of 1–6 carbon atoms, alkylthio of 1–6 carbon atoms, hydroxy, trifluoromethyl, cyano, nitro, carboxy, carboalkoxy of 2–7 carbon atoms, carboalkyl of 2–7 carbon atoms, phenoxy, phenyl, thiophenoxy, benzoyl, benzyl, amino, alkylamino of 1–6 carbon atoms, dialkylamino of 2 to 12 carbon atoms, phenylamino, benzylamino, alkanoylamino of 1–6 carbon atoms, alkenoylamino of 3–8 carbon atoms, alkynoylamino of 3–8 carbon atoms, carboxyalkyl of 2–7 carbon atoms, carboalkoxyalky of 3–8 carbon atoms, aminoalkyl of 1–5 carbon atoms, N-alkylaminoalkyl of 2–9 carbon atoms, N,N-dialkylaminoalkyl of 3–10 carbon atoms, N-alkylaminoalkoxy of 2–9 carbon atoms, N,N-dialkylaminoalkoxy of 3–10 carbon atoms, mercapto, and benzoylamino; provided that L can be an unsubstituted phenyl ring only when m>0 and T is not —CH$_2$NH— or —CH$_2$O—; or L is a 5- or 6-membered heteroaryl ring where the heteroaryl ring contains 1 to 3 heteroatoms selected from N, O, and S, with the proviso that the heteroaryl ring does not contain O—O, S—S, or S—O bonds, and where the heteroaryl ring is optionally mono- or di-substituted with a substituent selected from the group consisting of halogen, oxo, thio, alkyl of 1–6 carbon atoms, alkenyl of 2–6 carbon atoms, alkynyl of 2–6 carbon atoms, azido, hydroxyalkyl of 1–6 carbon atoms, halomethyl, alkoxymethyl of 2–7 carbon atoms, alkanoyloxymethyl of 2–7 carbon atoms, alkoxy of 1–6 carbon atoms, alkylthio of 1–6 carbon atoms, hydroxy, trifluoromethyl, cyano, nitro, carboxy, carboalkoxy of 2–7 carbon atoms, carboalkyl of 2–7 carbon atoms, phenoxy, phenyl, thiophenoxy, benzoyl, benzyl, amino, alkylamino of 1–6 carbon atoms, dialkylamino of 2 to 12 carbon atoms, phenylamino, benzylamino, alkanoylamino of 1–6 carbon atoms, alkenoylamino of 3–8 carbon atoms, alkynoylamino of 3–8 carbon atoms, carboxyalkyl of 2–7 carbon atoms, carboalkoxyalky of 3–8 carbon atoms, aminoalkyl of 1–5 carbon atoms, N-alkylaminoalkyl of 2–9 carbon atoms, N,N-dialkylaminoalkyl of 3–10 carbon atoms, N-alkylaminoalkoxy of 2–9 carbon atoms, N,N-dialkylaminoalkoxy of 3–10 carbon atoms, mercapto, and benzoylamino;

Z is —NH—, —O—, —S—, or —NR—;

R is alkyl of 1–6 carbon atoms, or carboalkyl of 2–7 carbon atoms;

$G_1$, $G_2$, $R_1$, and $R_4$ are each, independently, hydrogen, halogen, alkyl of 1–6 carbon atoms, alkenyl of 2–6 carbon atoms, alkynyl of 2–6 carbon atoms, alkenyloxy of 2–6 carbon atoms, alkynyloxy of 2–6 carbon atoms, hydroxymethyl, halomethyl, alkanoyloxy of 1–6 carbon atoms, alkenoyloxy of 3–8 carbon atoms, alkynoyloxy of 3–8 carbon atoms, alkanoyloxymethyl of 2–7 carbon atoms, alkenoyloxymethyl of 4–9 carbon atoms, alkynoyloxymethyl of 4–9 carbon atoms, alkoxymethyl of 2–7 carbon atoms, alkoxy of 1–6 carbon atoms, alkylthio of 1–6 carbon atoms, alkylsulphinyl of 1–6 carbon atoms, alkylsulphonyl of 1–6 carbon atoms, alkylsulfonamido of 1–6 carbon atoms, alkenylsulfonamido of 2–6 carbon atoms, alkynylsulfonamido of 2–6 carbon atoms, hydroxy, trifluoromethyl, trifluoromethoxy, cyano, nitro, carboxy, carboalkoxy of 2–7 carbon atoms, carboalkyl of 2–7 carbon atoms, phenoxy, phenyl, thiophenoxy, benzoyl, amino, hydroxyamino, alkoxyamino of 1–4 carbon atoms, alkylamino of 1–6 carbon atoms, dialkylamino of 2 to 12 carbon atoms, N-alkylcarbamoyl, N,N-dialkylcarbamoyl, N-alkyl-N-alkenylamino of 4 to 12 carbon atoms, N,N-dialkenylamino of 6–12 carbon atoms, phenylamino, benzylamino,

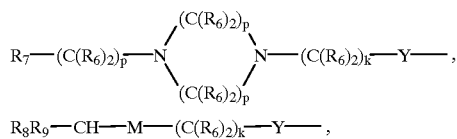

$R_7$—$(C(R_6)_2)_g$—Y—,
$R_7$—$(C(R_6)_2)_p$—M—$(C(R_6)_2)_k$—Y—,
or Het—$(C(R_6)_2)_q$—W—$(C(R_6)_2)_k$—Y—;

or R1 and R4 are as defined above and $G_1$ or $G_2$ or both are $R_2$—NH—;

or if any of the substituents $R_1$, $G_2$, $G_3$, or $R_4$ are located on contiguous carbon atoms then they may be taken together as the divalent radical —O—$C(R_6)_2$—O—;

Y is a divalent radical selected from the group consisting of

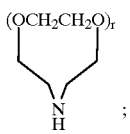

$R_7$ is —$NR_6R_6$, —$OR_6$, —J, —$N(R_6)_3^+$, or —$NR_6(OR_6)$;

M is >$NR_6$, —O—, >N—$(C(R_6)_2)_p NR_6R_6$, or >N—$(C(R_6)_2)_p$—$OR_6$;

W is >$NR_6$, —O— or is a bond;

Het is is selected from the group consisting of morpholine, thiomorpholine, thiomorpholine S-oxide, thiomorpholine S,S-dioxide, piperidine, pyrrolidine, aziridine, pyridine, imidazole, 1,2,3-triazole, 1,2,4-triazole, thiazole, thiazolidine, tetrazole, piperazine, furan, thiophene, tetrahydrothiophene, tetrahydrofuran, dioxane, 1,3-dioxolane, tetrahydropyran, and $$\underset{H}{N}\diagdown(OCH_2CH_2O)_r\diagup$$

wherein Het is optionally mono- or di-substituted on carbon or nitrogen with $R_6$, optionally mono- or di-substituted on carbon with hydroxy, —$N(R_6)_2$, or —$OR_6$, optionally mono or di-substituted on carbon with the mono-valent radicals —$(C(R_6)_2)_sOR_6$ or —$(C(R_6)_2)_sN(R_6)_2$, and optionally mono or di-substituted on a saturated carbon with divalent radicals —O— or —$O(C(R_6)_2)_sO$—;

$R_6$ is hydrogen, alkyl of 1–6 carbon atoms, alkenyl of 2–6 carbon atoms, alkynyl of 2–6 carbon atoms, cycloalkyl of 1–6 carbon atoms, carboalkyl of 2–7 carbon atoms, carboxyalkyl (2–7 carbon atoms), phenyl, or phenyl optionally substituted with one or more halogen, alkoxy of 1–6 carbon atoms, trifluoromethyl, amino, alkylamino of 1–3 carbon atoms, dialkylamino of 2–6 carbon atoms, nitro, cyano, azido, halomethyl, alkoxymethyl of 2–7 carbon atoms, alkanoyloxymethyl of 2–7 carbon atoms, alkylthio of 1–6 carbon atoms, hydroxy, carboxyl, carboalkoxy of 2–7 carbon atoms, phenoxy, phenyl, thiophenoxy, benzoyl, benzyl, phenylamino, benzylamino, alkanoylamino of 1–6 carbon atoms, or alkyl of 1–6 carbon atoms; with the proviso that the alkenyl or alkynyl moiety is bound to a nitrogen or oxygen atom through a saturated carbon atom;

$R_2$, is selected from the group consisting of

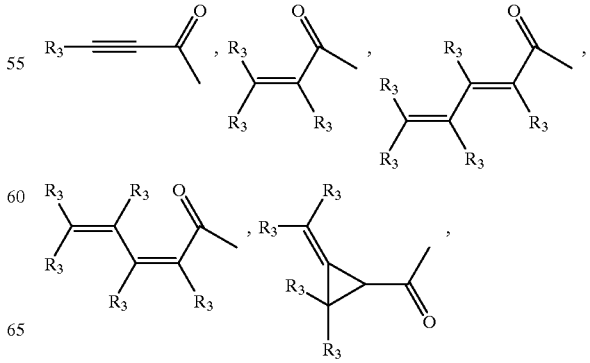

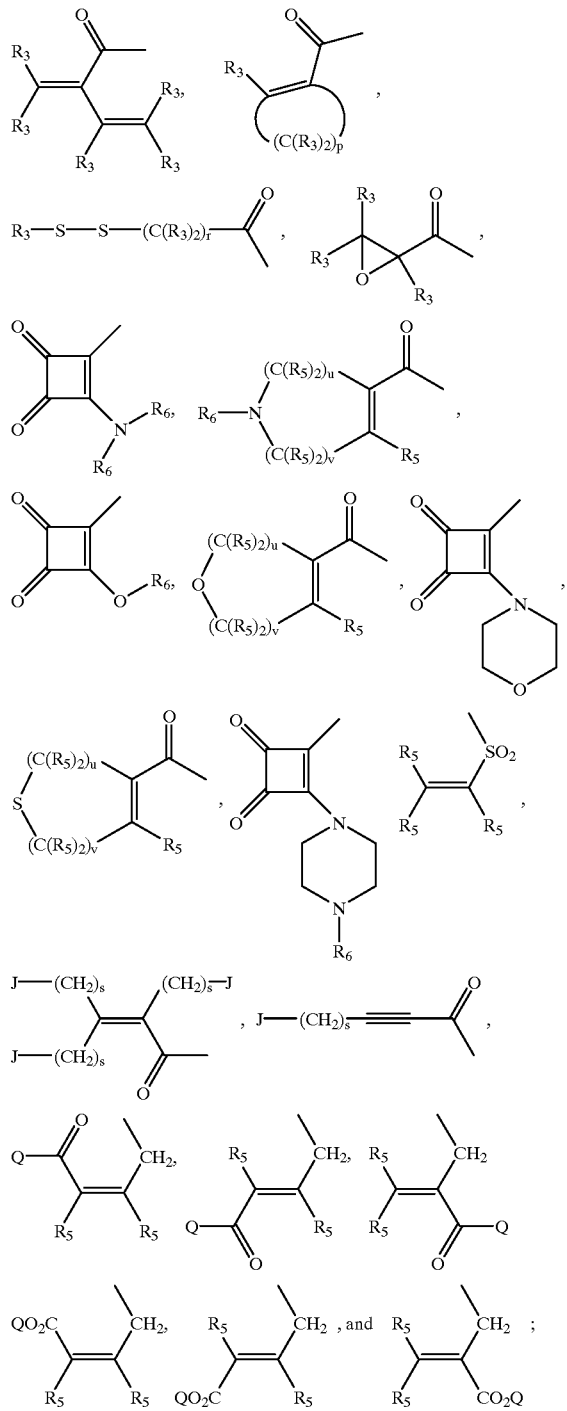

$R_3$ is independently hydrogen, alkyl of 1–6 carbon atoms, carboxy, carboalkoxy of 1–6 carbon atom, phenyl, carboalkyl of 2–7 carbon atoms,

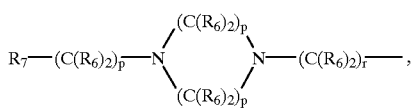

$R_7\text{—}(C(R_6)_2)_s\text{—}$,
$R_7\text{—}(C(R_6)_2)_p\text{—}M\text{—}(C(R_6)_2)_r\text{—}$, $R_8R_9\text{—}CH\text{—}$
$M\text{—}(C(R_6)_2)_r\text{—}$, or
$\text{Het-}(C(R_6)_2)_q\text{—}W\text{—}(C(R_6)_2)_r\text{—}$;

$R_5$ is indepently hydrogen, alkyl of 1–6 carbon atoms, carboxy, carboalkoxy of 1–6 carbon atoms, phenyl, carboalkyl of 2–7 carbon atoms,

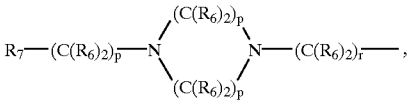

$R_7\text{—}(C(R_6)_2)_s\text{—}$,
$R_7\text{—}(C(R_6)_2)_p\text{—}M\text{—}(C(R_6)_2)_r\text{—}$, $R_8R_9\text{—}CH\text{—}$
$M\text{—}(C(R_6)_2)_r\text{—}$, or
$\text{Het-}(C(R_6)_2)_q\text{—}W\text{—}(C(R_6)_2)_r\text{—}$;

$R_8$, and $R_9$ are each, independently, $\text{—}(C(R_6)_2)_r NR_6R_6$, or $\text{—}(C(R_6)_2)_r\, OR_6$;

J is independently hydrogen, chlorine, fluorine, or bromine;

Q is alkyl of 1–6 carbon atoms or hydrogen;

a=0 or 1;
g=1–6;
k=0–4;
n is 0–1;
m is 0–3;
p=2–4;
q=0–4;
r=1–4;
s=1–6;
u=0–4 and v=0–4, wherein the sum of u+v is 2–4;

or a pharmaceutically acceptable salt thereof, provided that
when $R_6$ is alkenyl of 2–7 carbon atoms or alkynyl of 2–7 carbon atoms, such alkenyl or alkynyl moiety is bound to a nitrogen or oxygen atom through a saturated carbon atom;

and further provided that
when Y is $\text{—}NR_6\text{—}$ and $R_7$ is $\text{—}NR_6R_6$, $\text{—}N(R_6)_3^+$, or $\text{—}NR_6(OR_6)$, then g=2–6;

when M is —O— and $R_7$ is —$OR_6$ then p=1–4;

when Y is $\text{—}NR_6\text{—}$ then k=2–4;

when Y is —O— and M or W is —O— then k=1–4 when W is not a bond with Het bonded through a nitrogen atom then q=2–4 and when W is a bond with Het bonded through a nitrogen atom and Y is —O— or $\text{—}NR_6\text{—}$ then k=2–4.

The pharmaceutically acceptable salts are those derived from such organic and inorganic acids as: acetic, lactic, citric, tartaric, succinic, maleic, malonic, gluconic, hydrochloric, hydrobromic, phosphoric, nitric, sulfuric, methanesulfonic, and similarly known acceptable acids.

Preferred bicyclic aryl or bicyclic heteroaryl ring systems include naphthalene, 1,2,3,4-tetrahydronaphthalene, indane, 1-oxo-indane, 1,2,3,4-tetrahydroquinoline, naphthyridine, benzofuran, 3-oxo-1,3-dihydro-isobenzofuran, benzothiaphene, 1,1-dioxo-benzothiaphene, indole, 2,3-dihydroindole, 1,3-dioxo-2,3-dihydro-1H-isoindole, benzotriazole, 1H-indazole, indoline, benzopyrazole, 1,3-benzodioxole, benzooxazole, purine, phthalimide, coumarin, chromone, quinoline, terahydroquinoline, isoquinoline, benzimidazole, quinazoline, pyrido[2,3-b] pyridine, pyrido[3,4-b]pyrazine, pyrido[3,2-c]pyridazine, pyrido[3,4-b]pyridine, 1H-pyrazole[3,4-d]pyrimidine, 1,4-Benzodioxane, pteridine, 2(1H)-quinolone, 1(2H)- isoquinolone, 2-oxo-2,3-dihydro-benzthiazole, 1,2-methylenedioxybenzene, 2-oxindole, 1,4-benzisoxazine, benzothiazole, quinoxaline, quinoline-N-oxide, isoquinoline-N-oxide, quinoxaline-N-oxide, quinazoline-N-oxide, benzoazine, phthalazine, 1,4-dioxo-1,2,3,4-tetrahydro-phthalazine, 2-oxo-1,2-dihydro-quinoline, 2,4-dioxo-1,4-dihydro-2H-benzo[d][1,3]oxazine, 2,5-dioxo-2,3,4,5-tetrahydro-1H-benzo[e][1,4]diazepine, or cinnoline.

When L is a 5 or 6-membered heteroaryl ring, preferred heteroaryl rings include pyridine, pyrimidine, imidazole, thiazole, thiazolidine, pyrrole, furan, thiophene, oxazole, or 1,2,4-triazole.

Either or both rings of the bicyclic aryl or bicyclic heteroaryl group may be fully unsaturated, partially saturated, or fully saturated. An oxo substituent on the bicyclic aryl or bicyclic heteroaryl moiety means that one of the carbon atoms has a carbonyl group. An thio substituent on the bicyclic aryl or bicyclic heteroaryl moiety means that one of the carbon atoms has a thiocarbonyl group.

When L is a 5 or 6-membered heteroaryl ring, it may be fully unsaturated, partially saturated, or fully saturated. The heteroaryl ring can be bound to A via carbon or nitrogen. An oxo substituent on the heteroaryl ring means that one of the carbon atoms has a carbonyl group. An thio substituent on the heteroaryl ring means that one of the carbon atoms has a thiocarbonyl group.

The alkyl portion of the alkyl, alkoxy, alkanoyloxy, alkoxymethyl, alkanoyloxymethyl, alkylsulphinyl, alkylsulphonyl, alkylsulfonamido, carboalkoxy, carboalkyl, carboxyalkyl, carboalkoxyalkyl, alkanoylamino, N-alkylcarbamoyl, and N,N-dialkylcarbamoyl, N-alkylaminoalkoxy, N,N-dialkylaminoalkoxy include both straight chain as well as branched carbon chains. The alkenyl portion of the alkenyl, alkenoyloxymethyl, alkenyloxy, alkenylsulfonamido, substituents include both straight chain as well as branched carbon chains and one or more sites of unsaturation and all possible configurational isomers. The alkynyl portion of the alkynyl, alkynoyloxymethyl, alkynylsulfonamido, alkynyloxy, substituents include both straight chain as well as branched carbon chains and one or more sites of unsaturation. Carboxy is defined as a —$CO_2H$ radical. Carboalkoxy of 2–7 carbon atoms is defined as a —$CO_2R"$ radical, where R" is an alkyl radical of 1–6 carbon atoms. Carboxyalkyl is defined as a $HO_2C$—R'''— radical where R''' is a divalent alkyl radical of 1–6 carbon atoms. Carboalkoxyalkyl is defined as a $R"O_2C$—R'''— radical where R''' is a divalent akyl radical and where R"and R''' together have 2–7 carbon atoms. Carboalkyl is defined as a —COR" radical, where R" is an alkyl radical of 1–6 carbon atoms. Alkanoyloxy is defined as a —OCOR"radical, where R" is an alkyl radical of 1–6 carbon atoms. Alkanoyloxymethyl is defined as $R"CO_2CH_2$— radical, where R" is an alkyl radical of 1–6 carbon atoms. Alkoxymethyl is defined as $R"OCH_2$— radical, where R" is an alkyl radical of 1–6 carbon atoms. Alkylsulphinyl is defined as R"SO— radical, where R" is an alkyl radical of 1–6 carbon atoms. Alkylsulphonyl is defined as $R"SO_2$— radical, where R" is an alkyl radical of 1–6 carbon atoms. Alkylsulfonamido, alkenylsulfonamido, alkynylsulfonamido are defined as $R"SO2NH$— radical, where R" is an alkyl radical of 1–6 carbon atoms, an alkenyl radical of 2–6 carbon atoms, or an alkynyl radical of 2–6 carbon atoms, respectively. N-alkylcarbamoyl is defined as R"NHCO— radical, where R" is an alkyl radical of 1–6 carbon atoms. N,N-dialkylcarbamoyl is defined as R"R'NCO— radical, where R" is an alkyl radical of 1–6 carbon atoms, R' is an alkyl radical of 1–6 carbon atoms and R', and R" may be the same or different. When X is substituted, it is preferred that it is mono- , di- , or tri-substituted, with monosubstituted being most preferred. It is preferred that of the substituents R1 and R4, at least one is hydrogen and it is most preferred that both be hydrogen. It is also preferred that X is a phenyl ring, Z is —NH—, and n=0.

Het is a heterocycle, as defined above which may be optionally mono- or di-substituted with $R_6$ on carbon or nitrogen, optionally mono- or di-substituted on carbon with hydroxy, —$N(R_6)_2$, or —$OR_6$, optionally mono or di-substituted on carbon with with —$(C(R_6)_2)_sOR_6$ or —$(C(R_6)_2)_sN(R_6)_2$, and optionally mono or di-substituted on a saturated carbon with divalent —O— or —$O(C(R_6)_2)_sO$— (carbonyl and ketal groups, respectively); in some cases when Het is substituted with —O— (carbonyl), the carbonyl group can be hydrated. Het may be bonded to W when q=0 via a carbon atom on the heterocyclic ring, or when Bet is a nitrogen containing heterocycle which also contains a saturated carbon-nitrogen bond, such heterocycle may be bonded to carbon, via the nitrogen when W is a bond. When q=0 and Het is a nitrogen containing heterocycle which also contains an unsaturated carbon-nitrogen bond, that nitrogen atom of the heterocycle may be bonded to carbon when W is a bond and the resulting heterocycle will bear a positive charge. When Het is substituted with $R_6$, such substitution may be on a ring carbon, or in the case of a nitrogen containing heterocycle, which also contains a saturated carbon-nitrogen, such nitrogen may be substituted with $R_6$ or in the case of a nitrogen containing heterocycle, which also contains an unsaturated carbon-nitrogen, such nitrogen may be substituted with $R_6$ in with case the heterocycle will bear a positive charge. Preferred heterocycles include pyridine, 2,6-disubstituted morpholine, 2,5-disubstituted thiomorpholine, 2-substituted imidazole, substituted thiazole, N-substituted imidazole, N-substituted 1,4-piperazine, N-substituted piperadine, and N-substituted pyrrolidine.

The compounds of this invention may contain one or more asymmetric carbons atoms; in such cases, the compounds of this invention include the individual diasteromers, the racemates, and the individual R and S entantiomers thereof. Some of the compound of this invention may contain one or more double bonds; in such cases, the compounds of this invention include each of the possible configurational isomers as well as mixtures of these isomers. The preparation of the compounds and intermediates of this invention encompassed by Formula 5 is described below in Flowsheet 1 where Z, X, n, $R_1$, $G_2$, $G_1$, and $R_4$ are as described above. According to the sequence of reaction outlined in Flowsheet 1, a quinoline-3-carboxylic acid ester of Formula 2 is hydrolyzed with base to furnish a carboxylic acid of Formula 3. The carboxylic acid group of 3 is converted to an acyl imidazole by heating it with carbonyl-diimidazole in an inert solvent such as dimethylformamide (DMF) followed by the addition of ammonia to give the amide 4. Dehydration of the amide functional group with a dehydrating agent such as trifluoroacetic anhydride in pyridine, phosphorous pentoxide in an inert solvent, or the like gives the 3-cyano quinolines, 5, of this invention. In those cases where any of the intermediates have an asymmetric carbon atom, they can be used as the racemate or as the individual R or S entantiomers in which case the compounds of this invention will be in the racemic or R and S optically active forms, respectively. The quinoline-3-carboxylic acid esters of Formula 2, the quinoline-3-carboxylic acids of Formula 3, and the quinoline-3- carboxylic amides of Formula 4 needed to prepare the compounds of this invention are either already known to the art or can be prepared by procedures known in the art as detailed in the following references: Sarges, Reinhard; Gallagher, Andrea; Chambers, Timothy J.; Yeh, Li An, *J. Med. Chem.,* 36, 2828 (1993); Savini, Luisa; Massarelli, Paola; Pellerano, Cesare; Bruni, Giancarlo, *Farmaco,* 48(6), 805 (1993); Ife, Robert J.; Brown, Thomas H.; Keeling, David J.; Leach, Colin, *J. Med. Chem.,* 35, 3413 (1992); Hanifin, J. William; Capuzzi, Rosemary; Cohen, Elliott, *J. Med. Chem,* 12(5), 1096 (1969); Marecki, Paul E.; Bambury, Ronald E., *J. Pharm. Sci.,* 73(8), 1141 (1984); Pellerano, C.; Savini, L.; Massarelli, P.; Bruni, G.; Fiaschi, A. I., *Farmaco,* 45(3), 269, (1990); Marecki, Paul E.; Bambury, Ronald E., *J. Pharm. Sci.,* 73(8), 114 (1984); patent application WO 8908105; U.S. Pat. Nos. 4,343,804; 3,470,186.

FLOWSHEET 1

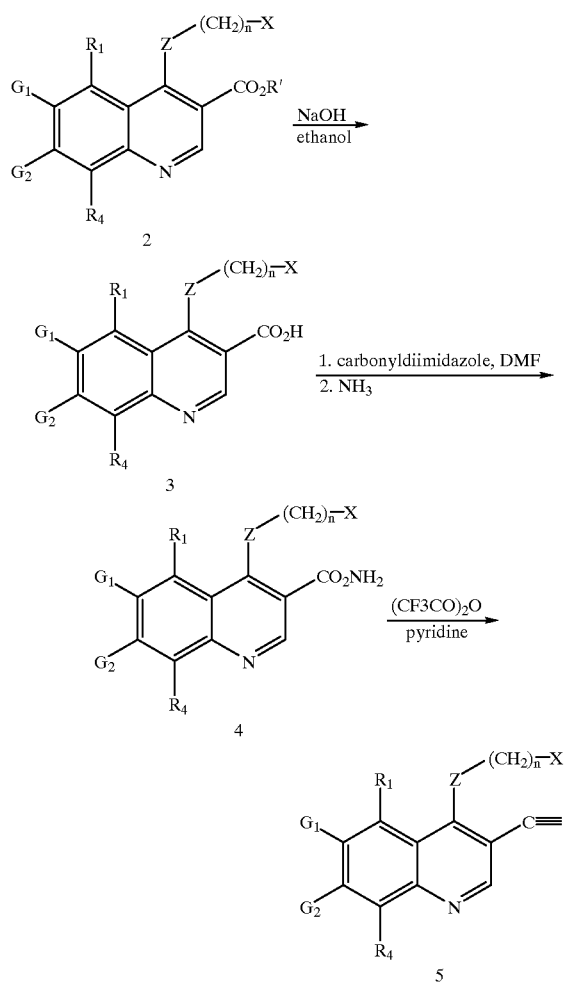

The preparation of the compounds of this invention encompassed by Formula 12 is described below in Flowsheet 2 where X, Z, n, $R_1$, $G_2$, $G_1$, and $R_4$ are as described above. The substituted aniline of Formula 6 is heated with or without a solvent with the reagent 7 to give intermediate 8 as a mixture of isomers. Thermolysis of 8 in a high boiling solvent such as diphenyl ether at 200–350° C. gives the 3-cyano quinolones of Formula 9; these intermediates may also exist in the 4-hydroxy quinoline tautomeric form. In those cases where $R_4$ is a hydrogen atom, the intermediates 9 may be formed as a mixture of two regioisomers. These isomers can be separated by methods well known in the art including, but not limited to, fractional crystallization and chromatographic methods. The separated isomers can then be converted separately to the compounds of the invention. Alternatively, the isomers can be separated at a later stage of the synthesis. Heating compounds 9 with or without solvent with a chlorinating agent such as phosphorous oxychloride or phosphorous pentachloride gives the 4-chloro-3-cyano quinolines of Formula 10. Condensation of 10 with a nucleophilic amine, aniline, mercaptan, thiophenol, phenol, or alcohol reagent of Formula 11 gives the 3-cyano quinolines intermediates of Formula 12; this condensation can be accelerated by heating the reaction mixture or by using basic catalysts such as trialkylamines, sodium hydride in an inert solvent, sodium or potassium alkoxides in an alcohol solvents, and the like. In those cases where the substituents may contribute an asymmetric carbon atom, the intermediates can be used as the racemate or as the individual R or S entantiomers in which case the compounds of this invention will be in the racemic or R and S optically active forms, respectively. In cases where the substituents may contribute more than one asymmetric carbon atoms, diasteriomers may be present; these can be separated by methods well known in the art including, but not limited to, fractional crystallization and chromatographic methods. In those cases where $R_1$, $G_2$, $G_1$, and $R_4$ moieties contain primary or secondary amino groups, the amino groups may first have to be used in protected form prior to reaction with reagent 7. Suitable protecting groups include, but are not limited to, tert-butoxycarbonyl (BOC) and benzyloxycarbonyl (CBZ) protecting groups. The former protecting group can be removed from the final products of Formula 12 by treatment with an acid such as trifluoroactic acid while the latter protecting group can be removed by catalytic hydrogenation. In those cases where the $R_1$, $G_2$, $G_1$, and $R_4$ moieties contain hydroxyl groups, the hydroxyl groups may first have to be used in protected form prior to reaction with reagent 7. Suitable protecting groups include, but are not limited to, t-butyldimethylsilyl, tetrahydropyranyl, or benzyl protecting groups. The first two protecting groups can be removed from the final products of formula 12 by treatment with an acid such as acetic acid or hydrochloric acid while the latter protecting group can be removed by catalytic hydrogenation.

FLOWSHEET 2

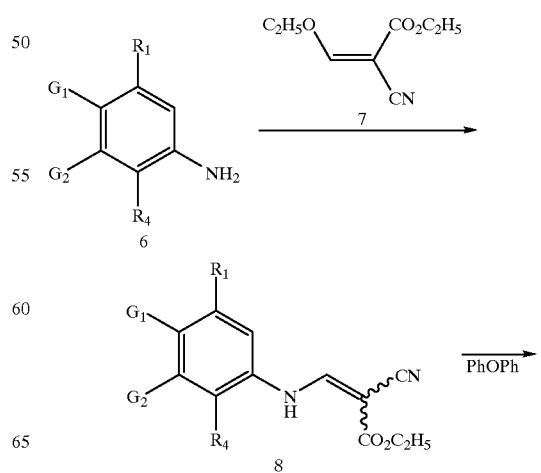

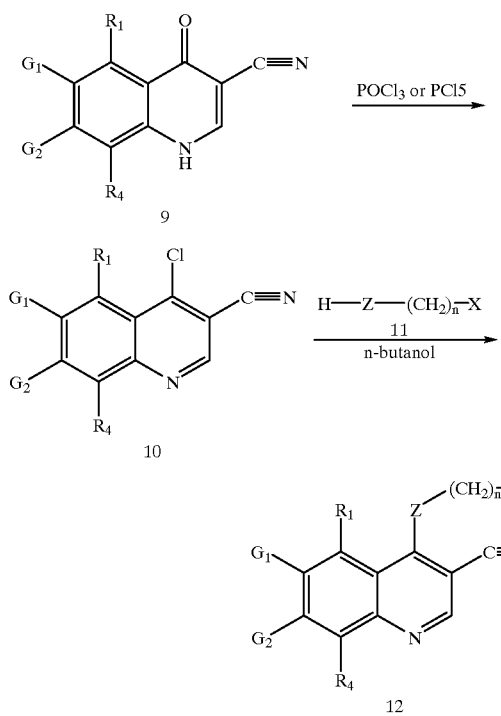

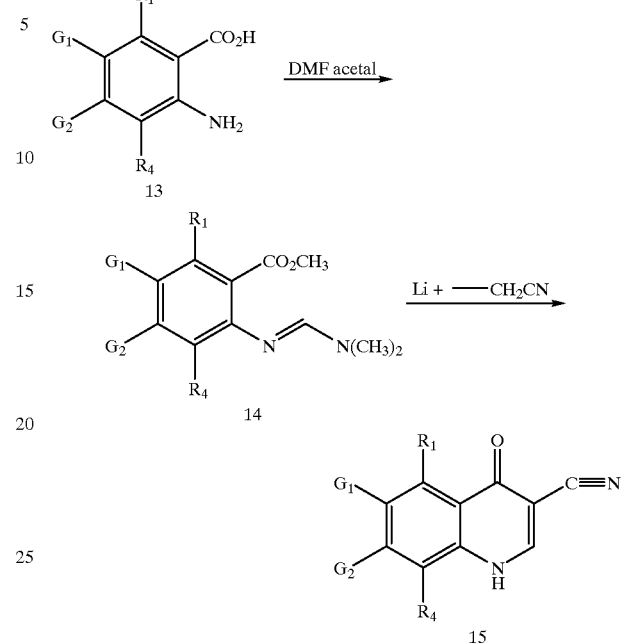

The preparation of intermediate 15 (identical to intermediate 9 of Flowsheet 2) can also be prepared as describe below in Flowsheet 3. Heating the substituted aniline of Formula 13 with dimethylformamide dimethyl acetal with or without a solvent gives intermediates for Formula 14. The reaction of 14 with the lithium anion of acetonitrile prepared using a base such as n-butyl lithium or the like in an inert solvent gives the 3-cyano quinolone, 15, or the 3-cyano-4-hydroxy quinoline tautomers thereof which can be converted to the compounds of this invention. In those cases where $R_1$, $G_2$, $G_1$, and $R_4$ moieties contain primary or secondary amino groups, the amino groups may first have to be used in protected form. Suitable protecting groups include, but are not limited to, tert-butoxycarbonyl (BOC) and benzyloxy-carbonyl (CBZ) protecting groups. The former protecting group can be removed from the final products of Formula 15 by treatment with an acid such as trifluoroactic acid while the latter protecting group can be removed by catalytic hydrogenation. In those cases where the $R_1$, $G_2$, $G_1$, and $R_4$ moieties contain hydroxyl groups, the hydroxyl groups may first have to be used in protected form. Suitable protecting groups include, but are not limited to, t-butyldimethylsilyl, tetrahydropyranyl, or benzyl protecting groups. The first two protecting groups can be removed from the final products of formula 15 by treatment with an acid such as acetic acid or hydrochloric acid while the latter protecting group can be removed by catalytic hydrogenation.

The preparation of the compounds of this invention encompassed by Formula 24 is described below in Flowsheet 4 wherein $R_1$, $G_2$, $R_4$, Z, n, and X are defined. $R_{10}$ is alkyl of 1–6 carbon atoms (preferably isobutyl). $R_2'$ is a radical selected from the group consisting of:

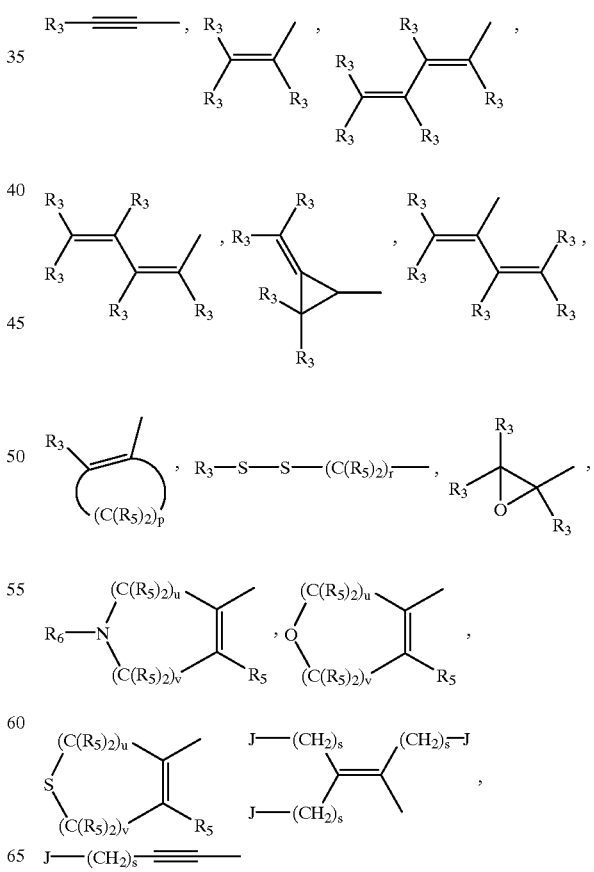

wherein $R_6$, $R_3$, $R_5$, J, s, r, u, and v are defined. According to the reactions outlined in Flowsheet 4, a 4-chloro-3-cyano-6-nitroquinoline, 16, can be reacted with an amine or aniline 17 by heating in an inert solvent such as tetrahydrofuran, butanol, or methoxyethanol to give compounds of Formula 20 where Z is —NH—. The reaction of 16 with a mercaptan or thiophenol 18 in an inert solvent can be accomplished using a base such as sodium hydride to give compounds of Formula 20 where Z is —S—. The reaction of 16 with a alcohol or phenol 19 in an inert solvent can be accomplished using a base such as sodium hydride to give compounds of Formula 20 where Z is —O—. Compounds of Formula 20 can be reduced to a 6-amino-3-cyano-quinoline, 21, using a reducing agent such as sodium hydrosulfite in a two phase system consisting of tetrahydrofuran and water in the presence of a small amount of phase transfer catalyst or by using iron in refluxing protic solvents containing acetic acid or ammonium chloride. Acylation of 21 with either an acid chloride of Formula 22 or a mixed anhydride of Formula 23 (which is prepared from the corresponding carboxylic acid) in an inert solvent such as tetrahydrofuran (THF) in the presence of an organic base such as pyridine, triethylamine, diisopropylethylamine, or N-methyl morpholine gives the compounds of this invention of Formula 24. In those cases where 22 or 23 have an asymmetric carbon atom, they can be used as the racemate or as the individual R or S entantiomers in which case the compounds of this invention will be in the racemic or R and S optically active forms, respectively. In those cases, where the $R_2'$ contains primary or secondary amino groups, the amino groups will first have to be protected prior to anhydride or acid chloride formation. Suitable protecting groups include, but are not limited to, tert-butoxycarbonyl (BOC) and benzyloxycarbonyl (CBZ) protecting groups. The former protecting group can be removed from the final products of Formula 24 by treatment with an acid such as trifluoroactic acid while the latter protecting group can be removed by catalytic hydrogenation. In those cases where the $R_2'$ contains hydroxyl groups, the hydroxyl groups may first have to be protected prior to anhydride or acid chloride formation. Suitable protecting groups include, but are not limited to, t-butyldimethylsilyl, tetrahydropyranyl, or benzyl protecting groups. The first two protecting groups can be removed from the final products of Formula 24 by treatment with an acid such as acetic acid or hydrochloric acid while the latter protecting group can be removed by catalytic hydrogenation. In those cases, in intermediates 17, 18, or 19 where X contains primary or secondary amino groups or hydroxyl groups, it may be necessary to protect these groups prior to the reaction with 16. The same amine or alcohol protecting groups describe above can be used and they can be removed from the products 24 as previously described.

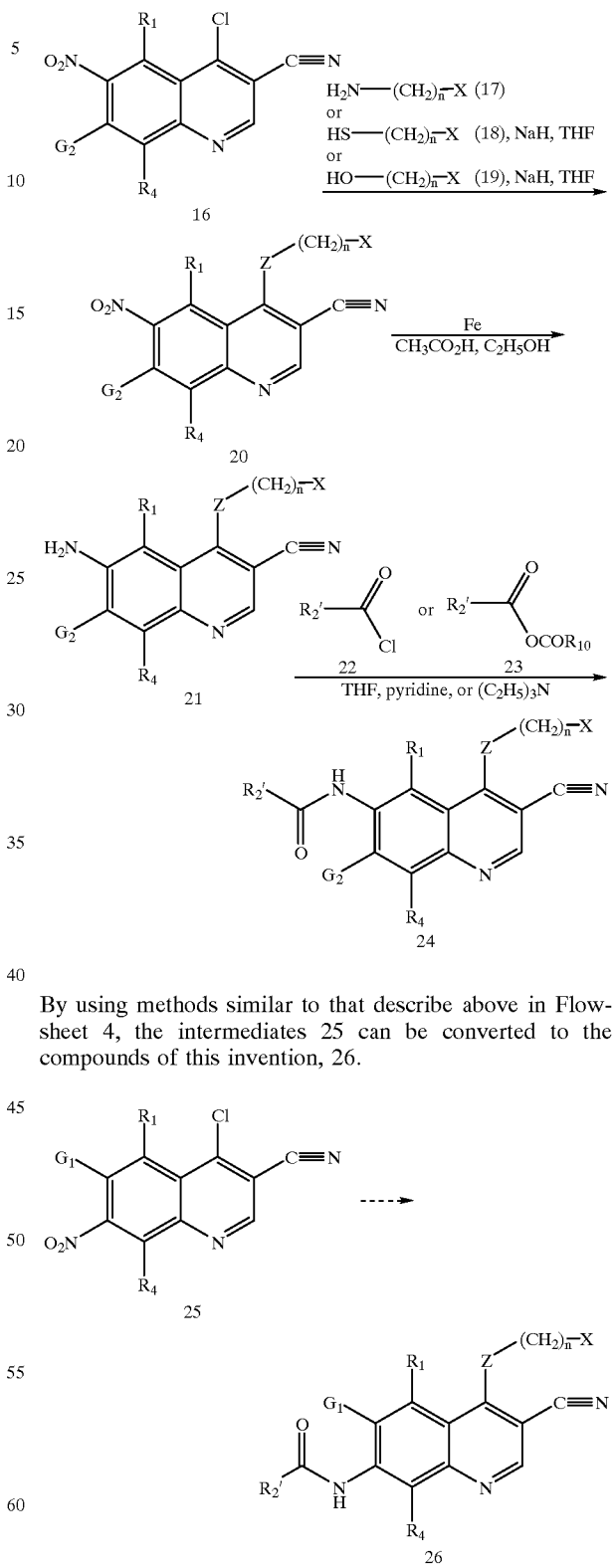

FLOWSHEET 4

By using methods similar to that describe above in Flowsheet 4, the intermediates 25 can be converted to the compounds of this invention, 26.

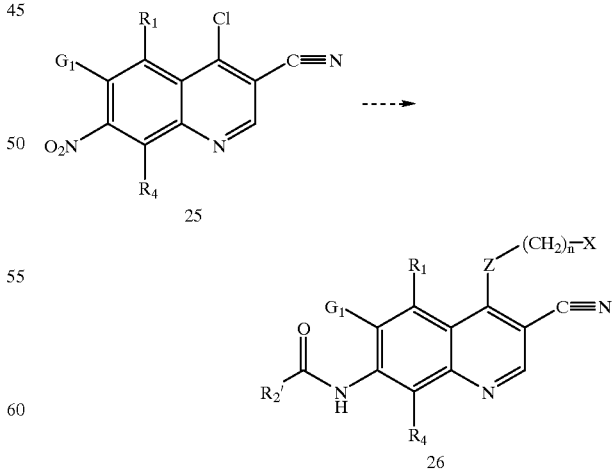

In order to prepare the compounds of this invention, certain amines are required. Some representative amines are shown below in List A wherein $R_6$, p, and r are as defined above. These amines are available commercially, are known in the chemical literature, or can be prepared by simple procedures that are well known in the art. In some cases, these amines may have an asymmetric carbon atoms; they can be used as the racemate or they can be resolved and used as the individual R or S entantiomers in which case the compounds of this invention will be in the racemic or optically active forms, respectively. Throughout this application in the Flowsheets shown below, these amines, and other similar amines, will be represented by the generic structure of the formula:

$(R')_2NH$, wherein this formula can represent a primary or secondary amine.

List A

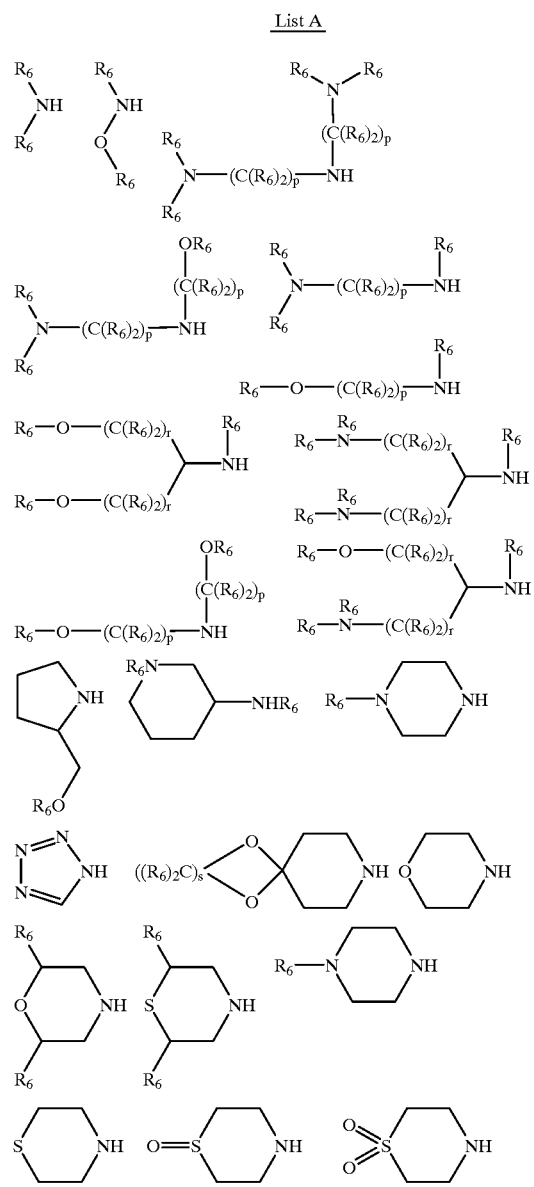

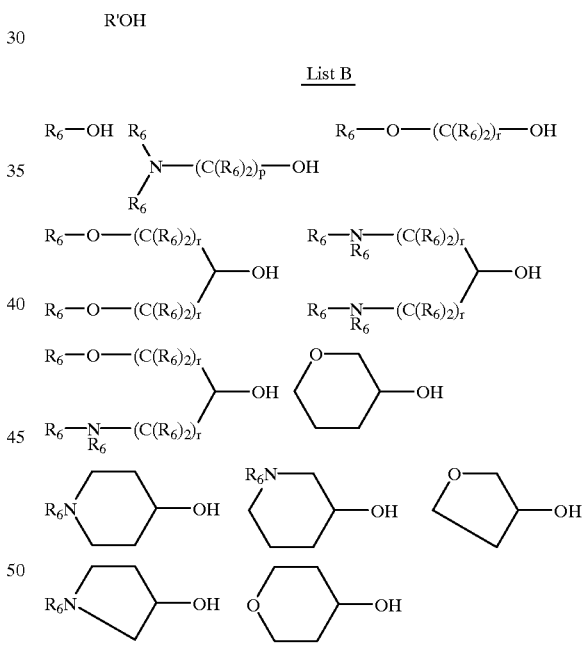

In order to prepare the compounds of this invention certain alcohols are required. Some representative alcohols are shown below in List B wherein $R_6$, p, and r are as defined above. These alcohols are available commercially, are known in the chemical literature, or can be prepared by simple procedures that are well known in the art. In some cases, these alcohols may have an asymmetric carbon atoms; they can be used as the racemate or they can be resolved and used as the individual R or S entantiomers in which case the compounds of this invention will be in the racemic or optically active forms, respectively. Throughout this application in the Flowsheets shown below, these alcohols, and other similar alcohols, will be represented by the generic structure of the formula:

R'OH

List B

In order to prepare some of the compounds of this invention certain mixed anhydrides of Formulas 31, 34, and 38 are required; these are prepared as outlined below in Flowsheet 5–6 wherein $R_6$, $R_{10}$, X, Z, n, and s are as defined above. J' is a halogen atom chlorine, bromine, or iodine, or is a toslyate (p-toluenesulfonate) or mesylate (methanesulfonate) group. The reaction of 27 with an amine of List A is accomplished by heating in an inert solvent such as tetrahydrofuran or N,N-dimethylformamide, or using potassium or cesium carbonate in acetone. The temperature and duration of the heating will depend on the reactivity of 27; longer reaction times and higher temperatures may be required when s is greater than 1. Treatment of 28 with an alkyl lithium reagent followed by quenching with an atmosphere of dry carbon dioxide furnishes the carboxylic acids of formula 29. These can be converted to mixed anhydrides of Formula 31 using a reagent such as isobutylchloroformate in an inert solvent such as tetrahydrofuran in the presence of a base such as N-methylmorpholine. These anhydrides can then be used to prepare the compounds of this invention as described above in Flowsheet 4. The reaction of 27 with an alcohol of List B is accomplished using sodium hydride or other non-nucleophic base such as potassium or cesium carbonate in an inert solvent such as tetrahydrofuran, acetone, or N,N-dimethylformamide. In some cases, the alcohol of List B can also be the solvent of the reaction. Treatment of 32 with an alkyl lithium reagent followed by quenching with an atmosphere of dry carbon dioxide furnishes the carboxylic acids of formula 33. These can be converted to mixed anhydrides Formula 34 using a reagent such as isobutylchloroformate in an inert solvent such as tetrahydrofuran in the presence of a base such as N-methylmorpholine. These anhydrides can then be used to prepare the compounds of this invention as described above in Flowsheet 4.

FLOWSHEET 5

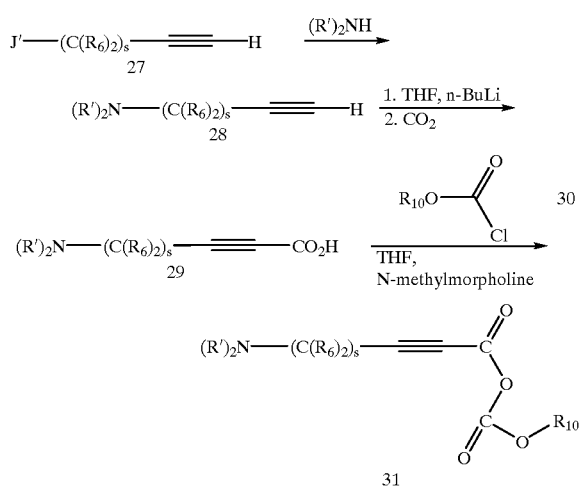

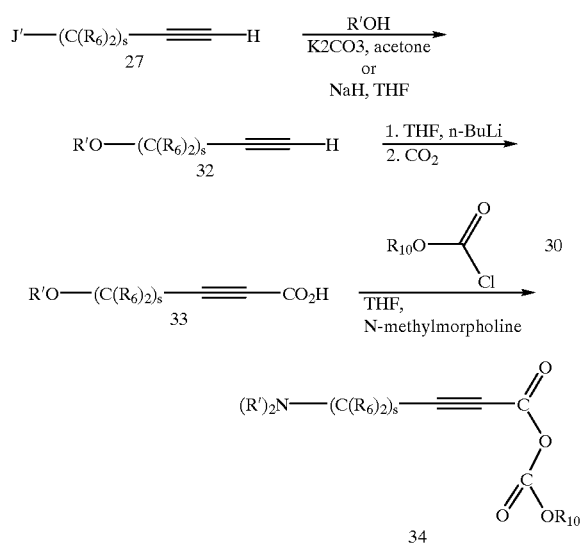

As outline in Flowsheet 6 below wherein $R_1$, $G_2$, $R_4$, $R_6$, $R_{10}$, X, Z, n, and s are as defined above, alcohols 35 can be protected with a t-butyl dimethysilyl protecting group by the reaction with the respective silyl chloride in methylene chloride in the presence of triethylamine and 4-N,N-dimethylamino pyridine (DMAP). The resulting protected alcohols, 36, are converted to the acetylenic Grignard reagents which, in turn, are maintained under an atmosphere of dry carbon dioxide to give the carboxylic acids 37. As described above these are converted to the mixed anhydrides 38 which on reaction with the 6-amino3-cyanoquinoline 39 gives 40. In the final step of the sequence, the silyl protecting group is removed by treating with acid in a protic solvent mixture to give the compounds represented by Formula 41.

FLOWSHEET 6

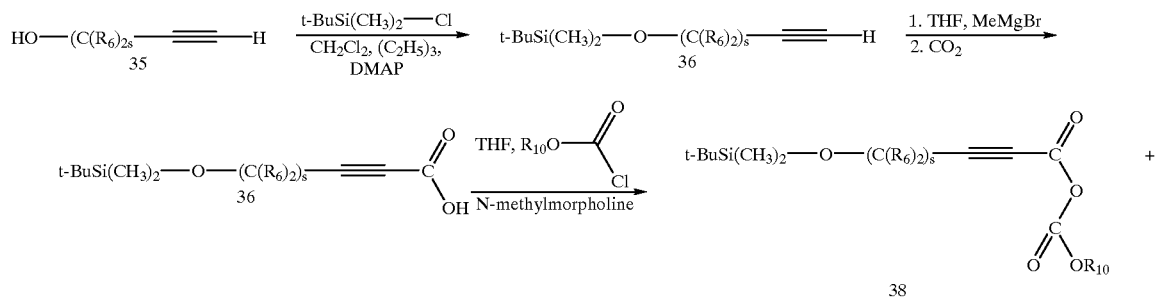

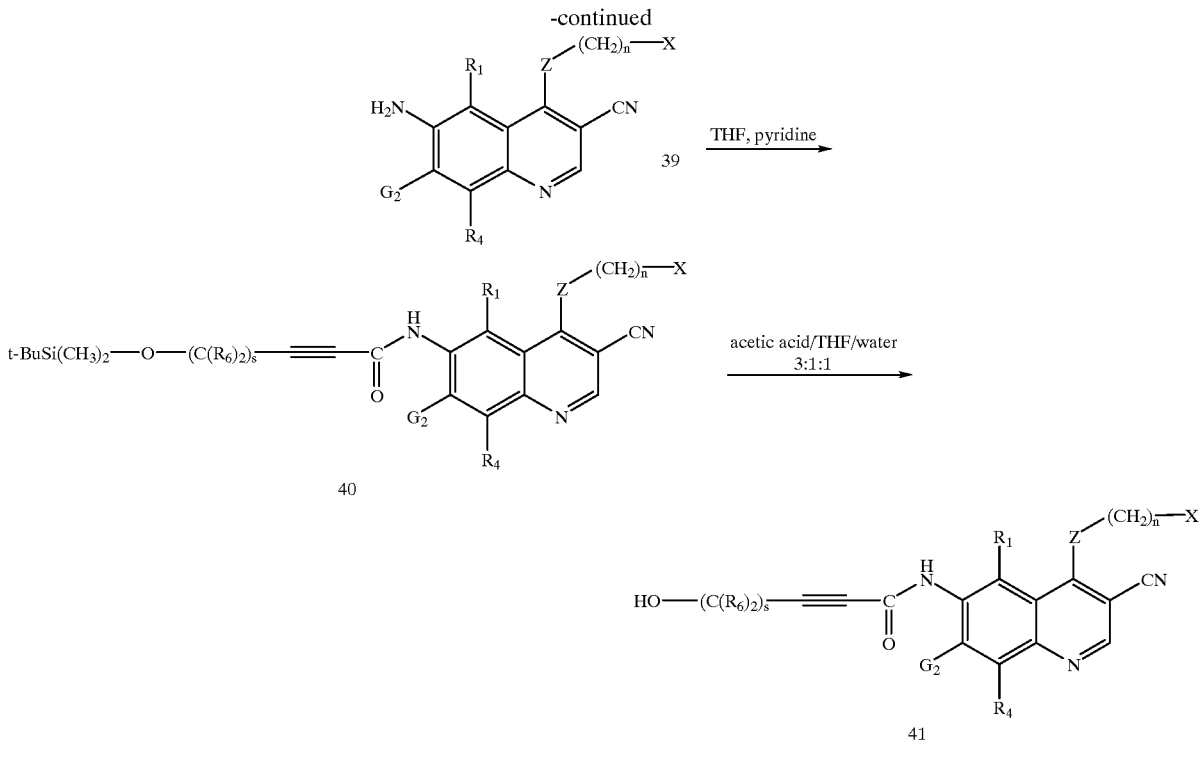

Compounds of this invention are also prepared as shown below in Flowsheet 7 wherein $R_1$, $G_2$, $R_4$, $R_6$, $R_{10}$, X, Z, n, and s are as defined above. J' is a halogen atom chlorine, bromine, or iodine, or is a toslyate or mesylate group. Treatment of 42 with an alkyl lithium reagent at low temperature followed by quenching with an atmosphere of dry carbon dioxide furnishes the carboxylic acids of formula 43. These can be converted to mixed anhydrides of Formula 44 using a reagent such as isobutylchloroformate in an inert solvent such as tetrahydrofuran in the presence of a base such as N-methylmorpholine. These anhydrides can then be used to prepare the compounds of this invention as by the reaction with the 6-amino-3-cyanoquinolines 45 described above in the Flowsheets. The reaction of 46 with an alcohol of List B is accomplished using sodium hydride or other non-nucleophic base in an inert solvent such as tetrahydrofuran or N,N-dimethylformamide to give the compounds of this invention represented by 47. In some cases, the alcohol of List B can also be the solvent of the reaction. The reaction of 46 with an amine of List A gives the compounds of this invention represented by 48 is accomplished by heating in an inert solvent such as tetrahydrofuran or N,N-dimethylformamide, or using potassium or cesium carbonate in acetone. The temperature and duration of the heating will depend on the reactivity of 46; longer reaction times and higher temperatures may be required when s is greater than 1.

FLOWSHEET 7

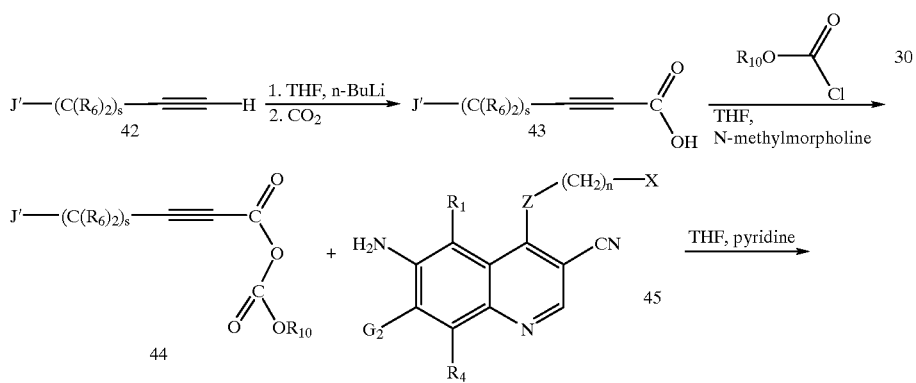

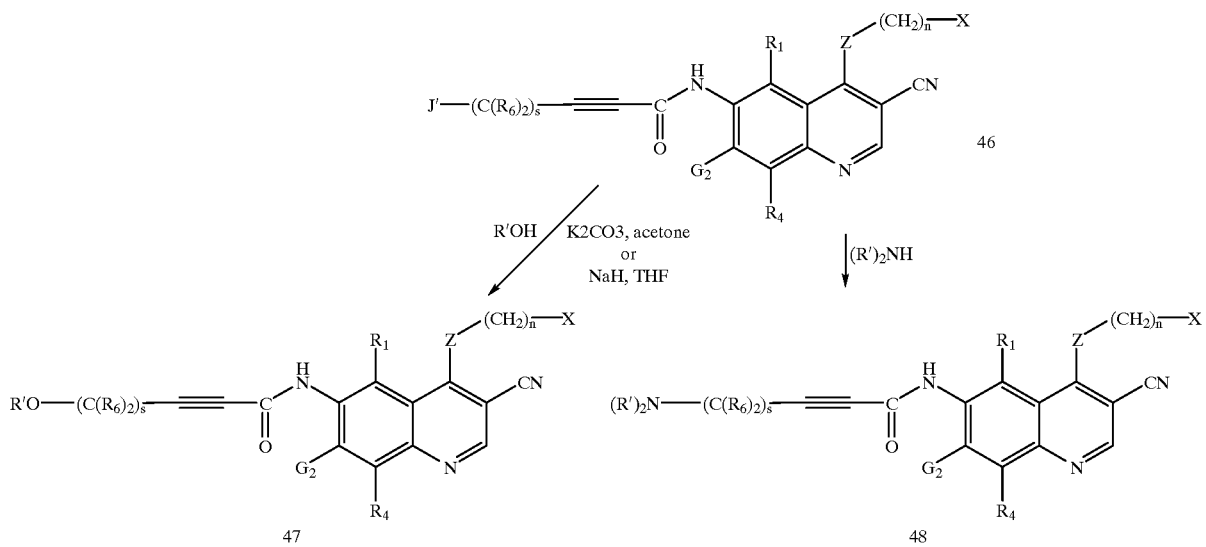

Using methods similar to that summarized above, 45b can be converted to 47b or 48b.

chlorides 51 and 56 and these anhydrides 55 and 59 can be used to prepare some of the compounds of this invention by

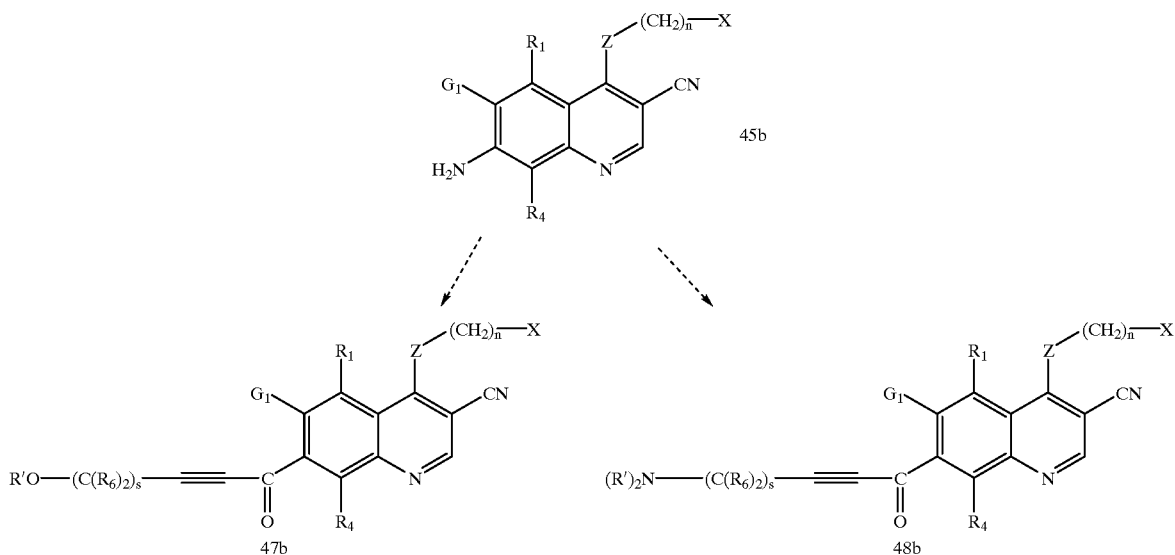

Other carboxylic acid chlorides and anhydrides needed to prepare some of the compounds of this invention are prepared as shown below in Flowsheet 8 wherein $R_6$, $R_3$, $R_{10}$, X, Z, J', n, and s are as defined above. Q' is an alkyl group of 1–6 carbon atoms. The esters 49, 53, or 57 can be hydrolyzed with a base such as barium hydroxide to give the respective carboxylic acid 50, 54, or 58. These acid can be converted to the respective carboxylic acid chlorides 51 or 56 by using oxalyl chloride and catalytic N,N-dimethylformamide in an inert solvent or respective mixed anhydrides 55 or 59 by using isobutyl chloroformate and an organic base such as N-methylmorpholine. The leaving group in compounds represented by Formula 52 can be displaced by the amines of List A or the alcohols of List B by using procedures previously described to give the intermediates 57 and 53, respectively. These carboxylic acid using the methods outlined herein above in the Flowsheets.

FLOWSHEET 8

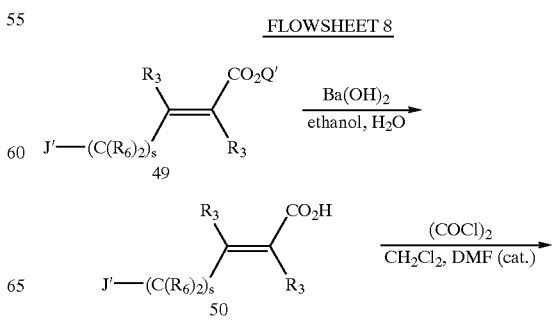

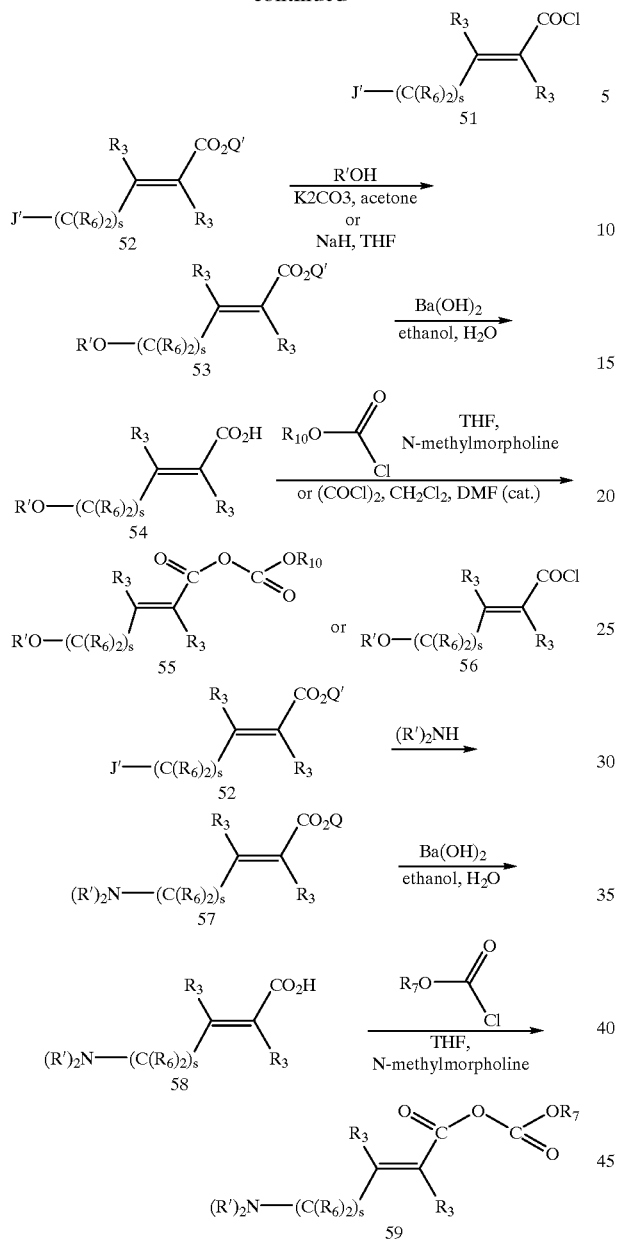

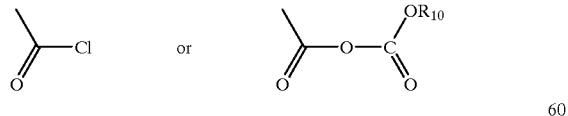

By using the methods identical to those outlined above in Flowsheet 8, it is possible to prepare the analogous carboxylic acid chlorides and anhydrides given below in List C wherein $R_6$, $R_3$, p, and s are as previously defined. G is the radical:

and A is the radical:

—N(R')$_2$, —OR', or —J' wherein —N(R')$_2$ is derived from the amines of List A, —OR' are derived from the alcohols of List B, and J' is a leaving group as defined previously. By making use of these carboxylic acid chlorides and anhydrides, by following the methods summarized in the above in Flowsheets, and by pursuing the details described in the examples given below, many of the compounds of this invention can be prepared.

LIST C

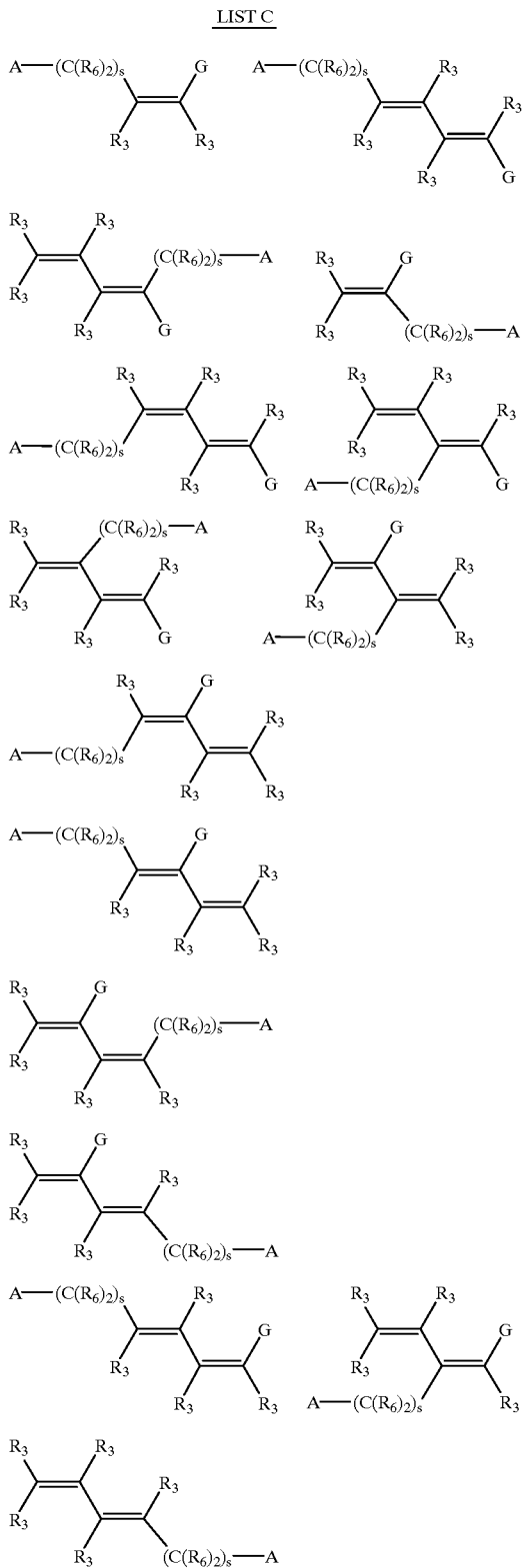

-continued

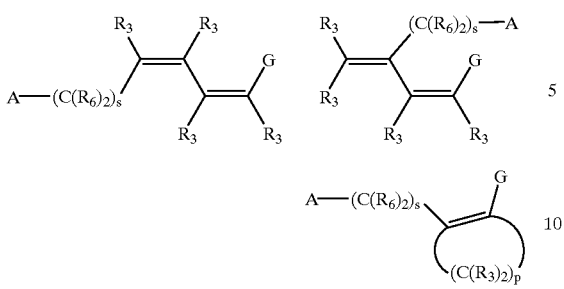

FLOWSHEET 9

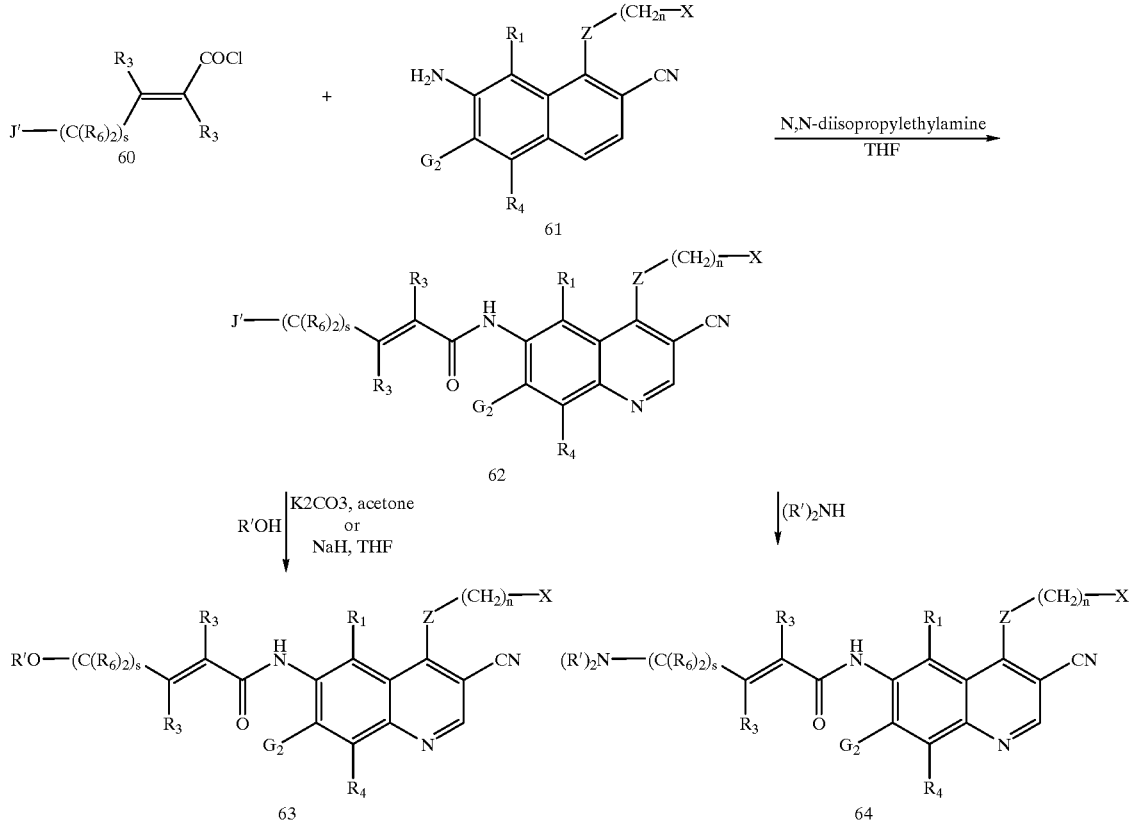

dimethylformamide. The temperature and duration of the heating will depend on the reactivity of 62; longer reaction times and higher temperatures may be required when s is greater than 1. In addition, by using this method, the carboxylic acid chlorides and mixed anhydrides listed in List C can be used to prepare the analogous compounds of this invention.

Compounds of this invention represented by Formulas 62–63 can be prepared as shown in Flowsheet 9 wherein $R_1$, $G_2$, $R_4$, $R_6$, $R_3$, $R_{10}$, X, Z, J', n, and s are as defined above. The reaction of the carboxylic acid chlorides 60 and the 6-amino-3-cyanoquinolines 61 using an organic base in an inert solvent gives the compounds of this invention represented by Formula 62. The reaction of 62 with an alcohol of List B is accomplished using sodium hydride or other non-nucleophic base such as potassium or cesium carbonate in an inert solvent such as tetrahydrofuran, acetone, or N,N-dimethylformamide to give the compounds of this invention represented by 63. In some cases, the alcohol of List B can also be the solvent of the reaction. The reaction of 62 with an amine of List A to give the compounds of this invention represented by 64 is accomplished by heating in an inert solvent such as tetrahydrofuran or N,N-dimethylformamide. By applying the methods summarized above, 61b can be converted to 63b and 64b via the intermediate 62b.

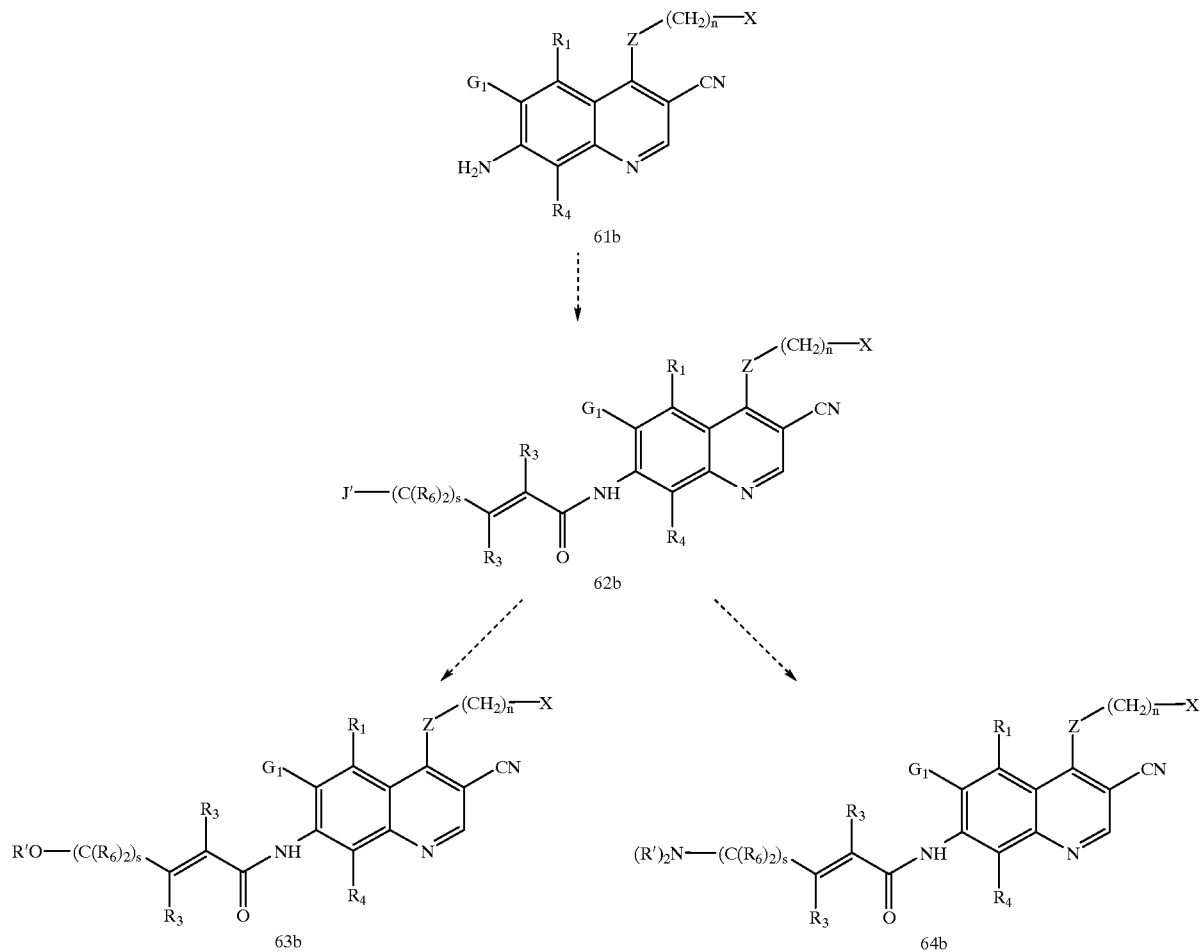

The reaction of 62 or 62b with a nitrogen containing heterocycle HET which also contains an unsaturated carbon-nitrogen bond is accomplished by refluxing in an inert solvent and gives the compounds of this invention 64c and 64d, respectively where the compound bears a positive charge. The counter anion J'— can be replaced with any other pharmaceutically acceptable anion using the appropriate ion exchange resin.

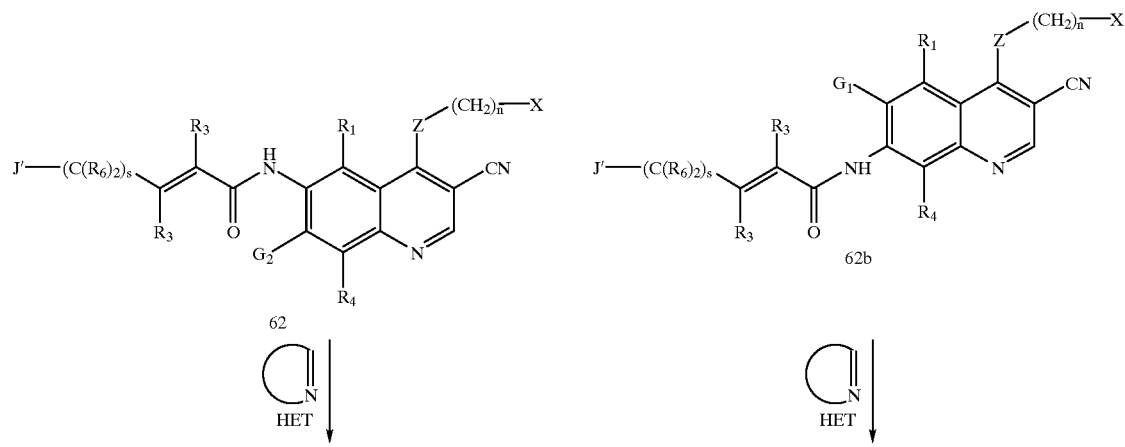

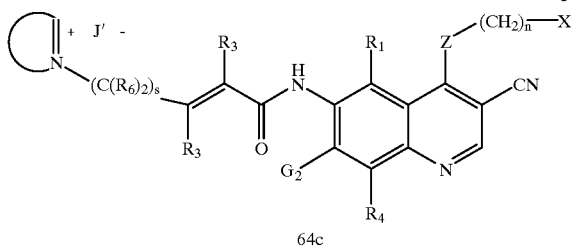
64c

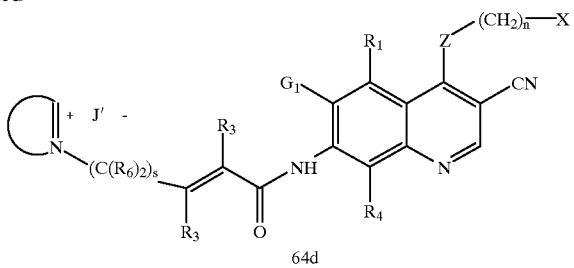
64d

Some of the compounds of this invention can be prepared as outline below in Flowsheet 10 wherein $R_1$, $G_2$, $R_3$, $R_4$, $R_6$, $R_{10}$, X, Z, J', n, and r are as defined above. The acetylenic alcohols 65 can be coupled to the halides, mesylates, or tosylates 66 using a base such as sodium hydride in an inert solvent such as tetrahydrofuran. The resulting acetylene, 67, is then treated with an alkyl lithium reagent at low temperature. Maintaining the reaction under an atmosphere of carbon dioxide then gives the carboxylic acids 68. These, in turn, are reacted with the 6-amino-3-cyanoquinolines, 69, via the mixed anhydrides to give the compounds of this invention represented by Formula 70. Alternatively, the intermediates 67 can be prepared starting with an alcohol 71 by first treating it with a base such as sodium hydride in an inert solvent such as tetrahydrofuran and then adding an acetylene 72 that has an appropriate leaving group. In a similar manner, the amino alcohols represented by the formula: $(R_6)_2N$—$(C(R_6)_2)_r$—OH by reacting with 72, and applying the chemistry of Flowsheet 10, can be converted to the compounds of this invention represented by the formulas:

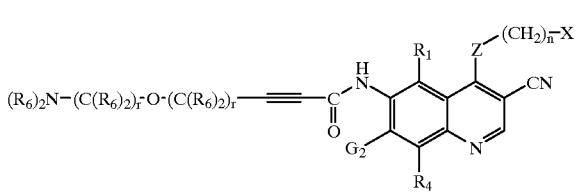

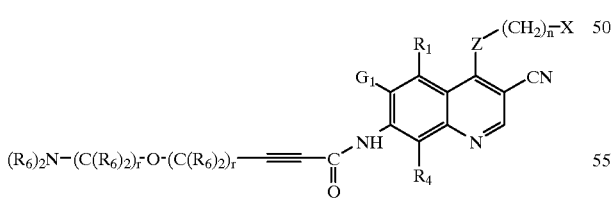

FLOWSHEET 10

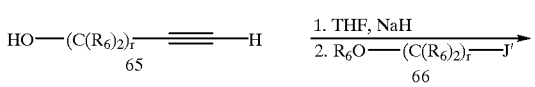

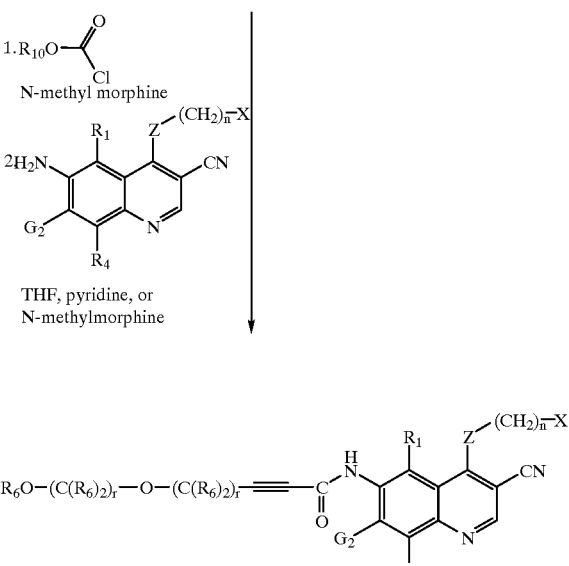

70

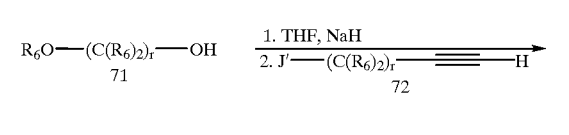

By applying similar methods as described above, 69b can be converted to the compounds of this invention represented by 70b.

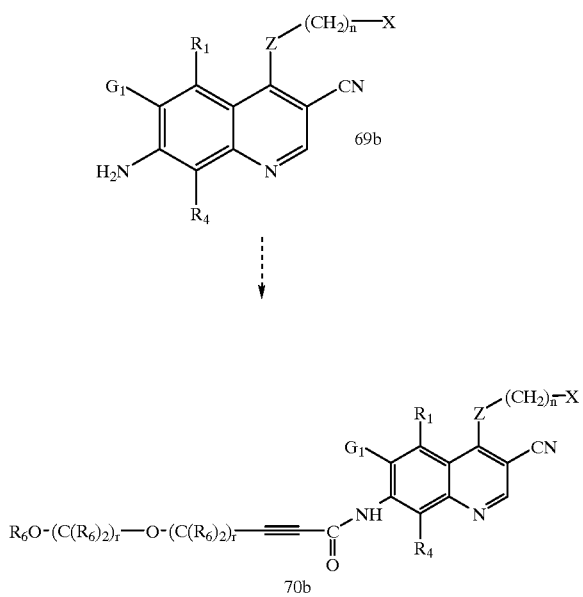

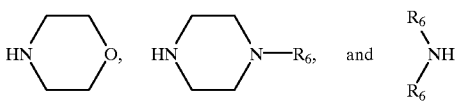

The compounds of this invention represented by Formula 76 and 77 are prepared as shown below in Flowsheet 11 wherein $R_1$, $R_3$, $R_4$, $R_6$, and n defined above and the amines $HN(R'')_2$ are selected from the group:

Refluxing 73 and 74 in an a solvent such as ethanol gives the intermediate 75 which can react with an amine in refluxing ethanol to give the compounds of this invention represented by Formula 76. Treating 75 with an excess of a sodium alkoxide in an inert solvent or a solvent from which the alkoxide is derived gives the compounds of this invention of Formula 77.

FLOWSHEET 11

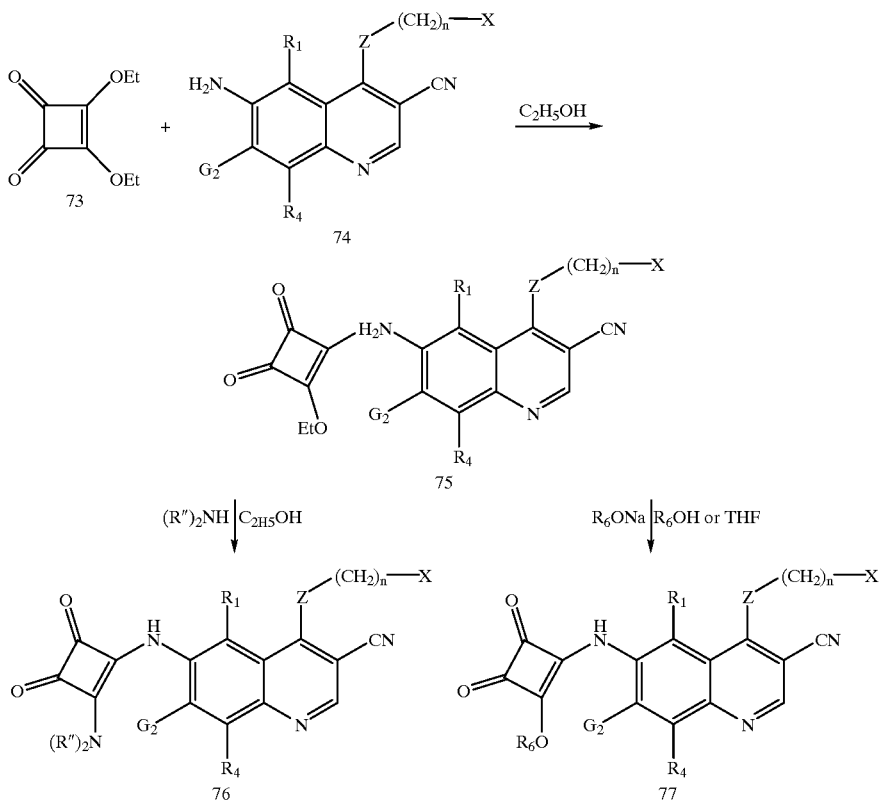

In a manner similar to that described above, 74b can be converted to 76b or 77b.

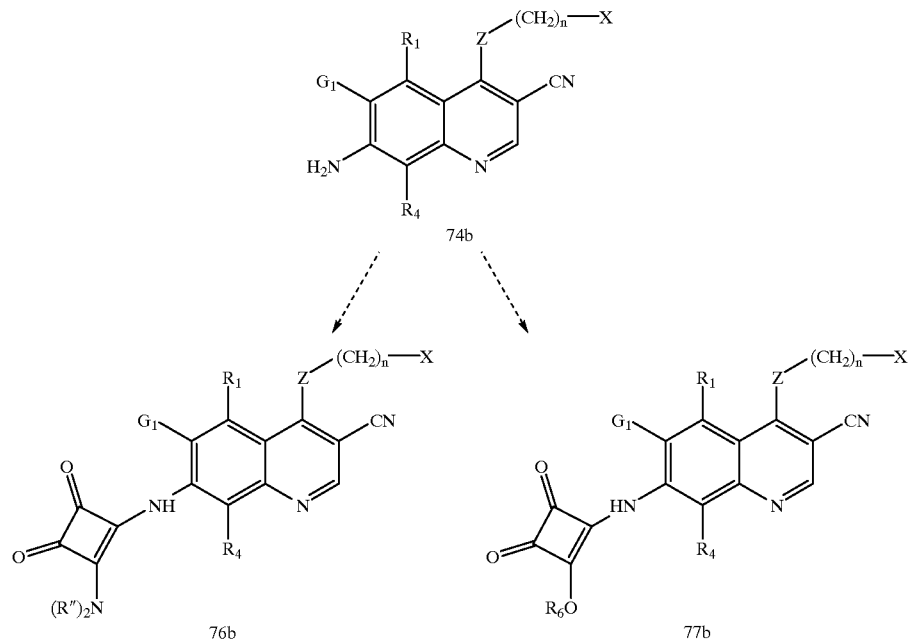

Compounds of this invention represented by Formula 83 can be prepared as shown in Flowsheet 12 wherein $R_1$, $G_2$, $R_4$, $R_6$, $R_3$, $R_{10}$, X, Z, n, and r are as defined above. The reaction of the mecapto carboxylic acids 78 with the reagents 79 give the compounds represented by Formula 80. Alternatively, 80 can be prepared from the mercaptan $R_3SH$ using the mercapto acid 78, triethylamine and 2,2'-dipyridyl disulfide. Mixed anhydride formation to give 81 followed by condensation with the 6-amino-3-cyanoquinolines 82 give the compounds of this invention.

FLOWSHEET 12

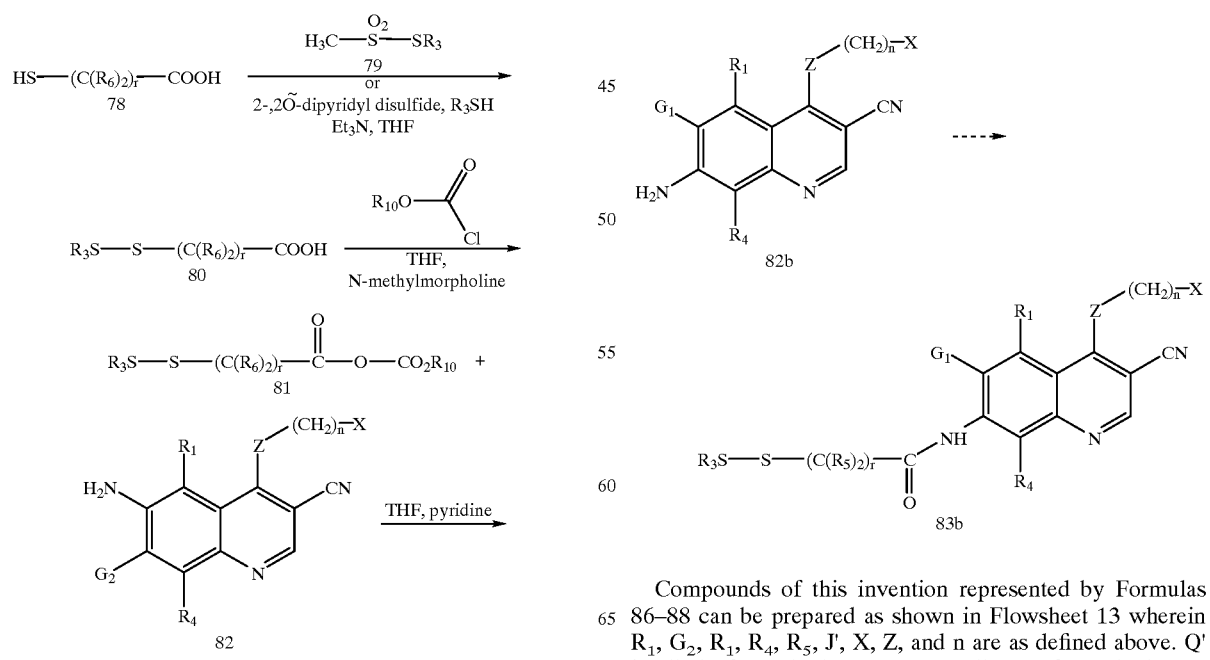

By applying similar methods as described above 82b can be converted to 83b.

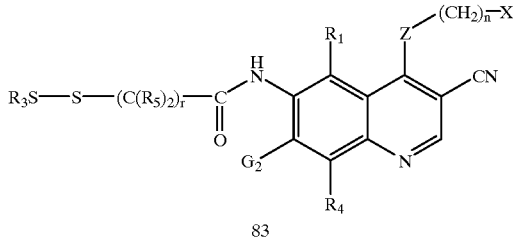

Compounds of this invention represented by Formulas 86–88 can be prepared as shown in Flowsheet 13 wherein $R_1$, $G_2$, $R_1$, $R_4$, $R_5$, J', X, Z, and n are as defined above. Q' is alkyl of 1–6 hydrogen atoms, alkoxy of 1–6 hydrogen atoms, hydroxy, or hydrogen. Akylation of 84 with the 6-amino-3-cyanoquinolines 85 can be accomplished by heating in an inert solvent such as N,N-dimethylformamide using a base such as potassium carbonate to give the compounds of this invention represented by the Formula 86. When Q' is alkoxy, the ester group can be hydrolyzed to an acid using a base such as sodium hydroxide in methanol. In a similar manner, by using intermediates 89 and 90, the compounds of this invention represented by Formulas 87 and 88 can be prepared, respectively.

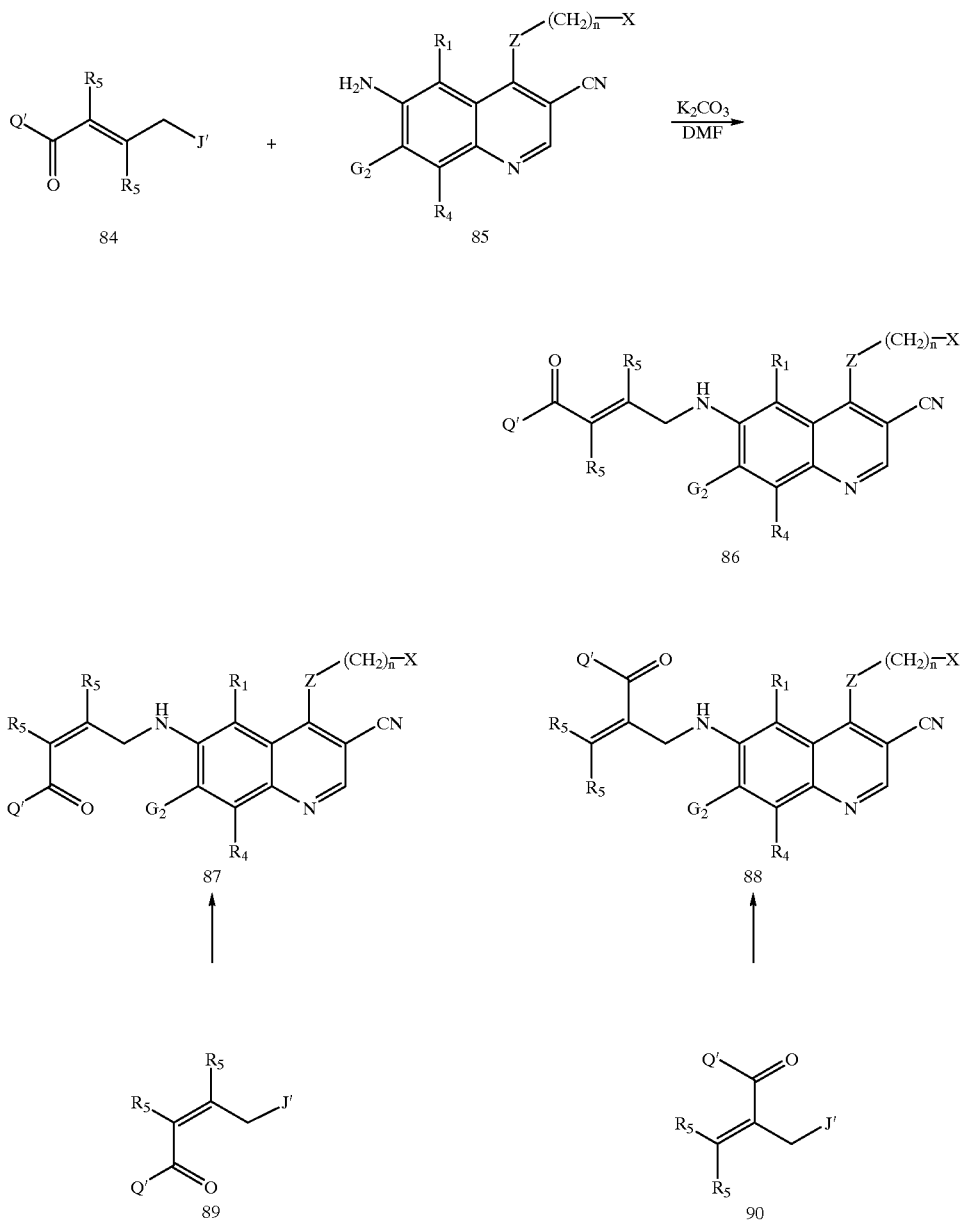

By apply similar methods as described above 85b can be converted to 86b–88b.
By

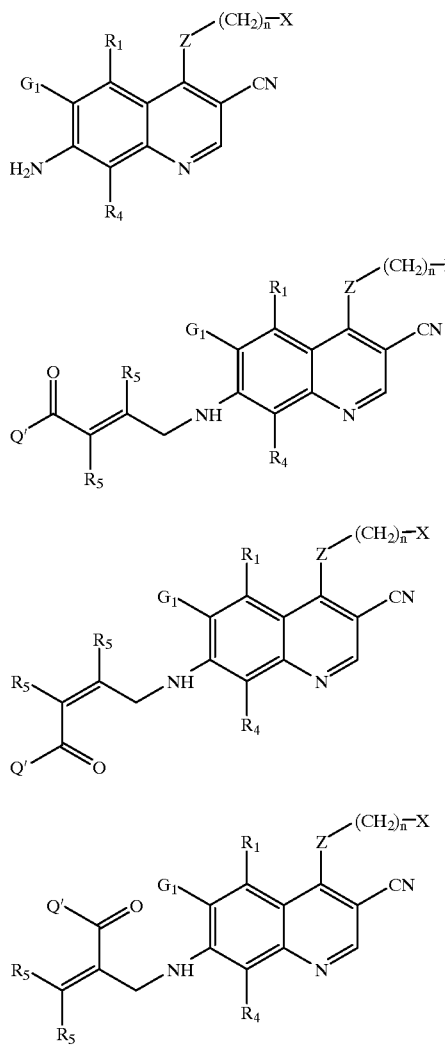

Compounds of this invention represented by Formula 93 can be prepared as shown in Flowsheet 14 wherein $R_1$, $G_2$, $R_1$, $R_4$, $R_5$, X, Z, and n are as defined above. The reaction of reagent 91 with the 6-amino-3-cyanoquinolines 92 is accomplished using an excess of an organic base such as triethylamine and an inert solvent such as tetrahydrofuran to give compounds of this invention represented by Formula 93.

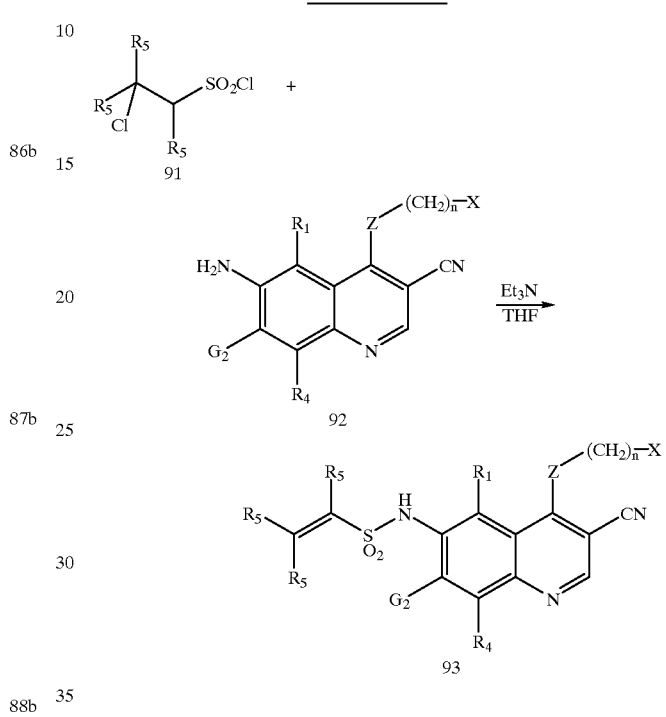

Compounds of this invention represented by Formula 96 can be prepared as shown in Flowsheet 15 wherein $R_1$, $G_1$, $R_1$, $R_4$, $R_5$, $R_6$, W, Het, X, Z, k, and n are as defined above by the Mitsunobu reaction of phenol 94 and an alcohol 95 in an inert solvent. Alternatively, the Mitsunobu reaction can be applied to compound 97 to give 98. This compound can be converted to 96 as described above in Flowsheet 4. The heterocycle can be introduced at the 6-position by using the corresponding compounds where $G_1$ is hydroxy and $G_2$ is located at the 7-position.

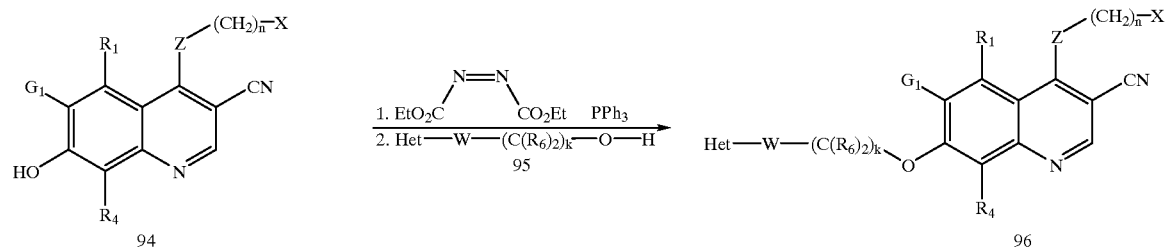

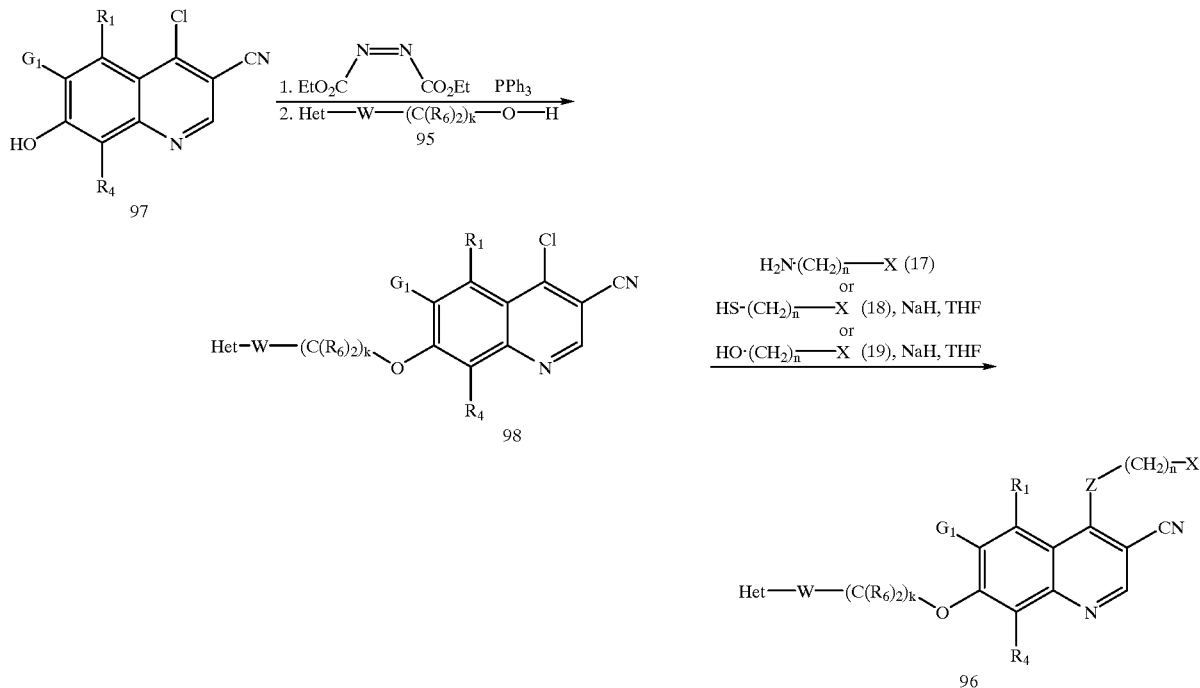

There are certain functional group manipulations that are useful to prepare the compounds of this invention that can be applied to various intermediate 3-cyanoquinolines as well as to the final compounds of this invention. These manipulations refer to the substituents $R_1$, $G_1$, $G_2$, or $R_4$ that are located on the 3-cyanoquinolines shown in the above Flowsheets. Some of these functional group manipulations are described below:

Where one or more of $R_1$, $G_1$, $G_2$, or $R_4$ is a nitro group, it can be converted to the corresponding amino group by reduction using a reducing agent such as iron in acetic acid or by catalytic hydrogenation. Where one or more of $R_1$, $G_1$, $G_2$, or $R_4$ is an amino group, it can be converted to the corresponding dialkyamino group of 2 to 12 carbon atoms by alkylation with at least two equivalents of an alkyl halide of 1 to 6 carbon atoms by heating in an inert solvent or by reductive alkylation using an aldehyde of 1 to 6 carbon atoms and a reducing agent such as sodium cyanoborohydride. Where one or more of $R_1$, $G_1$, $G_2$, or $R_4$ is a methoxy group, it can be converted to the corresponding hydroxy group by reaction with a demethylating agent such as boron tribromide in an inert solvent or by heating with pyridinium chloride with or without solvent. Where one or more of $R_1$, $G_1$, $G_2$, or $R_4$ is an amino group, it can be converted to the corresponding alkylsulfonamido, alkenylsulfonamido, or alkynylsulfonamido group of 2 to 6 carbon atoms by the reaction with an alkylsulfonyl chloride, alkenylsulfonyl chloride, or alkynylsulfonyl chloride, respectively, in an inert solvent using a basic catalyst such as triethylamine or pyridine. Where one or more of $R_1$, $G_1$, $G_2$, or $R_4$ is an amino group, it can be converted to the corresponding alkylamino group of 1 to 6 carbon atoms by alkylation with one equivalent of an alkyl halide of 1 to 6 carbon atoms by heating in an inert solvent or by reductive alkylation using an aldehyde of 1 to 6 carbon atoms and a reducing agent such as sodium cyanoborohydride in a protic solvent such as water or alcohol, or mixtures thereof. Where one or more of $R_1$, $G_1$, $G_2$, or $R_4$ is hydroxy, it can be converted to the corresponding alkanoyloxy, group of 1–6 carbon atoms by reaction with an appropriate carboxylic acid chloride, anhydride, or mixed anhydride in a inert solvent using pyridine or a trialkylamine as a catalyst. Where one or more of $R_1$, $G_1$, $G_2$, or $R_4$ is hydroxy, it can be converted to the corresponding alkenoyloxy group of 1–6 carbon atoms by reaction with an appropriate carboxylic acid chloride, anhydride, or mixed anhydride in an inert solvent using pyridine or a trialkylamine as a catalyst. Where one or more of $R_1$, $G_1$, $G_2$, or $R_4$ is hydroxy, it can be converted to the corresponding alkynoyloxy group of 1–6 carbon atoms by reaction with an appropriate carboxylic acid chloride, anhydride, or mixed anhydride in a inert solvent using pyridine or a trialkylamine as a catalyst. Where one or more of $R_1$, $G_1$, $G_2$, or $R_4$ is carboxy or a carboalkoxy group of 2–7 carbon atoms, it can be converted to the corresponding hydroxymethyl group by reduction with an appropriate reducing agent such as borane, lithium borohydride, or lithium aluminum hydride in a inert solvent; the hydroxymethyl group, in turn, can be converted to the corresponding halomethyl group by reaction in an inert solvent with a halogenating reagent such as phosphorous tribromide to give a bromomethyl group, or phosphorous pentachloride to give a chloromethyl group. The hydroxymethyl group can be acylated with an appropriate acid chloride, anhydride, or mixed anhydride in an inert solvent using pyridine or a trialkylamine as a catalyst to give the compounds of this invention with the corresponding alkanoyloxymethyl group of 2–7 carbon atoms, alkenoyloxymethyl group of 2–7 carbon atoms, or alkynoyloxymethyl group of 2–7 carbon atoms. Where one or more of $R_1$, $G_1$, $G_2$, or $R_4$ is a halomethyl group, it can be converted to an alkoxymethyl group of 2–7 carbon atoms by displacing the halogen atom with a sodium alkoxide in an inert solvent. Where one or more of $R_1$, $G_1$, $G_2$, or $R_4$ is a halomethyl group, it can be converted to an aminomethyl group, N-alkylaminomethyl group of 2–7 carbon atoms or N,N-dialkylaminomethyl group of 3–14 carbon atoms by displacing the halogen atom with ammonia, a primary, or secondary amine, respectively, in an inert solvent.

In addition to the methods described herein above, there a number of patent applications that describe methods that are useful for the preparation of the compounds of this invention. Although these methods describe the preparation of certain quinazolines, they are also applicable to the preparation of correspondingly substituted 3-cyanoquinolines. The chemical procedures described in the application WO-9633981 can be used to prepare the 3-cyanoquinoline intermediates used in this invention wherein $R_1$, $G_1$, $G_2$, or $R_4$ are alkoxyalkylamino groups. The chemical procedures described in the application WO-9633980 can be used to prepare the 3-cyanoquinoline intermediates used in this invention wherein $R_1$, $G_1$, $G_2$, or $R_4$ are aminoalkylalkoxy groups. The chemical procedures described in the application WO-9633979 can be used to prepare the 3-cyanoquinoline intermediates used in this invention wherein $R_1$, $G_1$, $G_2$, or $R_4$ are alkoxyalkylamino groups. The chemical procedures described in the application WO-9633978 can be used to prepare the 3-cyanoquinoline intermediates used in this invention wherein $R_1$, $G_1$, $G_2$, or $R_4$ are aminoalkylamino groups. The chemical procedures described in the application WO-9633977 can be used to prepare the 3-cyanoquinoline intermediates used in this invention wherein $R_1$, $G_1$, $G_2$, or $R_4$ are aminoalkylalkoxy groups. Although the above patent applications describe compounds where the indicated functional group have been introduced onto the 6-position of a quinazoline, the same chemistry can be used to introduce the same groups unto positions occupied by the $R_1$, $G_1$, $G_2$, and $R_4$ substituents of the compounds of this invention.

Representative compounds of this invention were evaluated in several standard pharmacological test procedures that showed that the compounds of this invention possess significant activity as inhibitors of protein tyrosine kinase and are antiproliferative agents. Based on the activity shown in the standard pharmacological test procedures, the compounds of this invention are therefore useful as antineoplastic agents. The test procedures used and results obtained are shown below.

Inhibition of Epidermal Growth Factor Receptor Kinase (EGF-R) Using Recombinant Enzyme Representative test compounds were evaluated for their ability to inhibit the phosphorylation of the tyrosine residue of a peptide substrate catalyzed by the enzyme epidermal growth factor receptor kinase. The peptide substrate (RR-SRC) has the sequence arg-arg-leu-ile-glu-asp-ala-glu-tyr-ala-ala-arg-gly. The enzyme used in this test procedure is the His-tagged cytoplasmic domain of EGFR. A recombinant baculovirus (vHcEGFR52) was constructed containing the EGFR cDNA encoding amino acids 645–1186 preceded by Met-Ala-(His)$_6$. Sf9 cells in 100 mm plates were infected at an moi of 10 pfu/cell and cells were harvested 48 h post infection. A cytoplasmic extract was prepared using 1% Triton X-100 and applied to Ni-NTA column. After washing the column with 20 mM imidazole, HcEGFR was eluted with 250 mM imidazole (in 50 mM Na$_2$HPO$_4$, pH 8.0, 300 mM NaCl). Fractions collected were dialyzed against 10 mM HEPES, pH 7.0, 50 mM NaCl, 10% glycerol, 1 ug/mL antipain and leupeptin and 0.1 mM Pefabloc SC. The protein was frozen in dry ice/methanol and stored −70° C.

Test compounds were made into 10 mg/mL stock solutions in 100% dimethylsulfoxide (DMSO). Prior to experiment, stock solutions were diluted to 500 uM with 100% DMSO and then serially diluted to the desired concentration with HEPES buffer (30 mM HEPES pH 7.4).

For the enzyme reaction, 10 uL of each inhibitor (at various concentrations) were added to each well of a 96-well plate. To this was added 3 uL of enzyme (1:10 dilution in 10 mM HEPES, pH 7.4 for final conc. of 1:120). This was allowed to sit for 10 min on ice and was followed by the addition of 5 ul peptide (80 uM final conc.), 10 ul of 4×Buffer (Table A), 0.25 uL $^{33}$P-ATP and 12 uL H$_2$O. The reaction was allowed to run for 90 min at room temperature and was followed by spotting the entire volume on to precut P81 filter papers. The filter discs were washed 2× with 0.5% phosphoric acid and radioactivity was measured using a liquid scintillation counter.

| Reagent | Final | 100 Rxns |
|---|---|---|
| 1 M HEPES (pH 7.4) | 12.5 mM | 50 uL |
| 10 mM Na$_3$VO$_4$ | 50 uM | 20 uL |
| 1M MnCl$_2$ | 10 mM | 40 uL |
| 1 mM ATP | 20 uM | 80 uL |
| $^{33}$P-ATP | 2.5 uCi | 25 uL |

The inhibition data for representative compounds of the invention are shown below in TABLE 1. The IC$_{50}$ is the concentration of test compound needed to reduce the total amount of phosphorylated substrate by 50%. The % inhibition of the test compound was determined for at least three different concentrations and the IC$_{50}$ value was evaluated from the dose response curve. The % inhibition was evaluated with the following formula:

% inhibition=100−[CPM(drug)/CPM(control)]×100 where CPM(drug) is in units of counts per minute and is a number expressing the amount of radiolabled ATP (γ-$^{33}$P) incorporated onto the RR-SRC peptide substrate by the enzyme after 90 minutes at room temperature in the presence of test compound as measured by liquid scintillation counting. CPM(control) is in units of counts per minute and was a number expressing the amount of radiolabled ATP (γ-$^{33}$P) incorporated into the RR-SRC peptide substrate by the enzyme after 90 minutes at room temperature in the absence of test compound as measured by liquid scintillation counting. The CPM values were corrected for the background counts produced by ATP in the absence of the enzymatic reaction. Where it was possible to determine an IC$_{50}$ value, this is reported in TABLE 1 otherwise the % inhibition at 0.5 μM concentration of test compound is shown in TABLE 1. Multiple entries for the same compound indicates that it was tested multiple times.

TABLE 1

Inhibition of EGF-R Kinase (recombinant enzyme)

| Example | IC$_{50}$ (μM) | % Inh @ 0.5 μM |
|---|---|---|
| 173 | 0.5 | |
| 172 | 0.09 | |
| 176 | 0.01 | |
| 96 | >10 | 6 |
| 97 | >10 | 7 |
| 101 | >1 | 27 |
| 111 | >1 | 10 |
| 148 | >1 | 11 |
| 115 | >0.5 | 49 |
| 167 | >1 | 0 |
| 126 | .45 | |
| 168 | >1 | 1 |
| 127 | >1 | 25 |

TABLE 1-continued

Inhibition of EGF-R Kinase (recombinant enzyme)

| Example | IC$_{50}$ (μM) | % Inh @ 0.5 μM |
|---|---|---|
| 144 | >1 | 14 |
| 149 | >1 | 9 |
| 156 | >1 | 34 |
| 141 | >1 | 5.5 |
| 142 | >1 | 24 |
| 130 | >1 | 5 |
| 129 | >1 | 6.7 |
| 131 | >1 | 0 |
| 150 | .0015 | |
| 150 | 0.004 | |
| 151 | >1 | 34 |
| 152 | >1 | 24 |
| 132 | >1 | 0 |
| 133 | >1 | 0 |
| 134 | >1 | 35 |
| 135 | >1 | 0 |
| 153 | >1 | 14 |
| 136 | >1 | 33 |
| 137 | 0.15 | |

Inhibition of Epithelial Cell Kinase (ECK)

In this standard pharmacological test procedure, a biotinylated peptide substrate is first immobilized on neutravidin-coated microtiter plates. The test drug, the Epithelial Cell Kinase (ECK), Mg$^{++}$, sodium vanadate (a protein tyrosine phosphatase inhibitor), and an appropriate buffer to maintain pH (7.2) are then added to the immobilized substrate-containing microtiter wells. ATP is then added to initiate phosphorylation. After incubation, the assay plates are washed with a suitable buffer leaving behind phosphorylated peptide which is exposed to horse radish peroxidase (HRP)-conjugated anti-phosphotyrosine monoclonal antibody. The antibody-treated plates are washed again and the HRP activity in individual wells is quantified as a reflection of degree of substrate phosphorylation. This nonradioactive format was used to identify inhibitors of ECK tyrosine kinase activity where the IC$_{50}$ is the concentration of drug that inhibits substrate phosphorylation by 50%. The results obtained for representative compounds of this invention are listed in TABLE 2. Multiple entries for a given compound indication it was tested multiple times.

Inhibition of Kinase Insert Domain Containing Receptor (KDR; the Catalytic Domain of the VEGF Receptor)

In this standard pharmacological test procedure, KDR protein is mixed, in the presence or absence of a inhibitor compound, with a substrate peptide to be phosphorylated (a copolymer of glutamic acid and tyrosine, E:Y: 4:1) and other cofactors such as Mg$^{++}$ and sodium vanadate (a protein tyrosine phosphatase inhibitor) in an appropriate buffer to maintain pH (7.2). ATP and a radioactive tracer (either P$^{32}$- or P$^{33}$-labeled ATP) is then add to initiate phosphorylation. After incubation, the radioactive phosphate associated with the acid-insoluble fraction of the assay mixture is then quantified as reflection of substrate phosphorylation. This radioactive format was used to identify inhibitors of KDR tyrosine kinase activity where the IC$_{50}$ is the concentration of drug that inhibits substrate phosphorylation by 50%. The results obtained for representative compounds of this invention are listed in TABLE 2. Multiple entries for a given compound indication it was tested multiple times.

Mitogen Activated Protein Kinase (MAPK) Assay

To evaluate inhibitors of the MAP (mitogen activated protein) kinase a two component coupled standard pharmacological test procedure, which measures phosphorylation of a serine/threonine residue in an appropriate sequence in the substrate in the presence and absence of a putative inhibitor, was used. Recombinant human MEK 1 (MAPKK) was first used to activate recombinant human ERK2 (MAPK) and the activated MAPK (ERK) was incubated with substrate (MBP peptide or MYC peptide) in the presence of ATP, Mg$^{+2}$ and radiolabeled $^{33}$P ATP. The phosphorylated peptide was captured on a P 81 phosphocellulose filter (paper filter or embedded in microtiter plate) washed and counted by scintillation methods.

The peptide substrates used in the assay are MBP, peptide substrate (APRTPGGRR), or synthetic Myc substrate, (KKFELLPTPPLSPSRR·5 TFA. The recombinant enzymes used were prepared as GST fusion proteins of human ERK 2 and human MEK 1. Inhibitor samples were prepared as 10×stocks in 10% DMSO and an appropriate aliquot was used to deliver either 10 ug/ml for a single point screening dose or 100, 10, 1, and 0.1 uM final concentration for a dose response curve. Final DMSO concentrations were less than or equal to 1%.

The reaction was run as follows in 50 mM Tris kinase buffer, pH 7.4 in a reaction volume of 50 ul. The appropriate volume of kinase buffer and inhibitor sample was added to the tube. Appropriate dilution of enzyme was delivered to give 2–5 ug recombinant MAPK (Erk ) per tube. The inhibitor was incubated with MAPK (Erk) for 30 min at 0 deg. C. Recombinant Mek (MAPKK) (0.5–2.5 ug) or fully activated Mek (0.05–0.1 units) was added to activate the Erk and incubated for 30 min at 30° C. Then substrate and gamma $^{33}$P ATP was were added to give a final concentration of 0.5–1 mM MBPP or 250–500 uM Myc; 0.2–0.5 uCi gamma P 33 ATP/tube; 50 μM ATP final concentration. Samples were incubated at 30° C. for 30 minutes and the reaction was stopped by adding 25 μl of ice cold 10% TCA. After samples were chilled on ice for 30 min, 20 μl of sample was transferred onto P 81 phosphocellulose filter paper or appropriate MTP with embedded P 81 filter. Filter papers or MTP were washed 2 times with a large volume of 1% acetic acid, then 2 times with water. The filters or MTP were briefly air dried before addition of scintillant and samples were counted in the appropriate scintillation counter set up for reading $^{33}$P isotope. Samples included a positive control (activated enzyme plus substrate); a no enzyme control; a no substrate control; samples with different concentrations of putative inhibitor; and samples with reference inhibitors (other active compounds or non-specific inhibitors such as staurosporine or K252 B).

The raw data was captured as cpm. Sample replicates were averaged and corrected for background count. Mean cpm data was tabulated by group and % inhibition by a test compound was calculated as (corrected cpm control-corrected. cpm sample/control)×100=% inhibition. If several concentrations of inhibitor were tested, IC$_{50}$ values (the concentration which gives 50% inhibition) were determined graphically from the dose response curve for % inhibition or by an appropriate computer program. The results obtained for representative compounds of this invention are listed in TABLE 2 where there may be separate entries for the same compound; this is an indication that the compound was evaluated more than one time.

TABLE 2

Inhibition of Kinase insert Domain containing Receptor (KDR), Epithelial Cell Kinase (Eck), and Mitogen Activated Protein Kinase (Mek-Erk)

| Example | KDR μM | Eck μM | Mek-Erk μM |
|---|---|---|---|
| 96 | 8.0214 | >53.476 | 2 |
|  |  |  | <1 |
|  |  |  | 0.8 |
| 97 | >2.5610 | >2.561 | 55 |
| 98 | 52.9872 | >2.649 | 2.5 |
|  | 2.6494 |  | <1 |
|  |  |  | 0.4 |
|  |  |  | <0.1 |
| 99 | 21.4247 |  | <1 |
|  |  |  | <1 |
|  |  |  | 0.08 |
|  |  |  | 0.05 |
|  |  |  | 0.08 |
|  |  |  | 0.3 |
|  |  |  | 0.07 |
|  |  |  | 0.08 |
|  |  |  | <1 |
|  |  |  | 0.2 |
|  |  |  | 0.3 |
|  |  |  | <1 |
|  |  |  | 0.2 |
|  |  |  | <1 |
|  |  |  | 0.2 |
|  |  |  | 0.15 |
|  |  |  | 0.25 |
|  |  |  | 0.25 |
|  |  |  | 0.15 |
|  |  |  | 0.8 |
|  |  |  | <1 |
|  |  |  | <1 |
|  |  |  | 0.2 |
|  |  |  | 0.2 |
|  |  |  | 0.3 |
|  |  |  | 0.4 |
|  |  |  | 1.1 |
|  |  |  | 0.4 |
|  |  |  | 0.25 |
|  |  |  | 0.4 |
|  |  |  | 0.05 |
|  |  |  | 0.2 |
|  |  |  | 0.006 |
|  |  |  | 0.04 |
|  |  |  | 0.1 |
|  |  |  | 0.1 |
|  |  |  | 0.2 |
|  |  |  | 0.4 |
|  |  |  | <0.001 |
|  |  |  | 0.06 |
|  |  |  | 0.06 |
|  |  |  | 0.09 |
|  |  |  | <0.001 |
|  |  |  | 0.09 |
|  |  |  | 0.4 |
| 100 | >72.2892 | >48.193 | >100 |
|  |  |  | 3.5 |
|  |  |  | >100 |
| 101 | 5.3706 | >53.706 | 0.8 |
|  |  |  | <1 |
|  |  |  | 0.001 |
|  |  |  | <0.001 |
| 102 | 14.1123 | >56.449 | 10 |
|  |  |  | 0.5 |
|  |  |  | 0.1 |
|  |  |  | 1 |
|  |  |  | 1 |
|  |  |  | 0.5 |
| 103 |  | >53.419 | 1.5 |
|  |  |  | 0.5 |
|  |  |  | <1 |
|  |  |  | <0.001 |
| 104 | >74.5527 | >49.702 | 35 |
| 105 | 76.6479 | >51.099 |  |
| 106 | 23.0734 | >46.147 | 1.1 |
|  |  |  | 0.2 |
| 107 | >71.8735 | >47.916 |  |
| 108 | >80.3428 | >2.678 |  |
|  | >2.6781 |  |  |
| 109 | 23.9006 | >47.801 | >100 |
|  |  |  | >100 |
| 110 | >77.4393 | 0.155 | >100 |
|  | >25.8131 | 0.036 | 50 |
| 111 | >77.0416 | >51.361 | >100 |
|  |  |  | >100 |
| 112 | >71.1744 | >47.450 | >100 |
| 113 | 8.6630 |  |  |
| 115 | 5.5648 | >27.824 | 25 |
|  | >2.7824 | >2.782 |  |
| 119 | 1.5504 | 22.148 |  |
|  | 2.2148 | >2.215 |  |
| 125 |  |  | 35 |
| 126 | 8.3565 | >27.855 | >100 |
|  | >2.7855 | >2.786 |  |
|  | >2.7855 | >2.786 |  |
| 127 | >67.3428 | >44.895 | >100 |
| 128 | >79.9148 | >53.277 | >100 |
|  |  |  | 100 |
| 129 | >25.8790 | 25.879 | >100 |
| 130 | >26.5647 | >26.565 | >100 |
| 131 | >26.4262 | >26.426 | >100 |
| 132 | >28.0594 | >28.059 | 90 |
| 133 | >28.0594 | >28.059 | 90 |
| 134 | >28.0594 | >28.059 | >100 |
| 135 | 26.8538 | 0.537 | >100 |
| 136 | >29.0377 | 0.871 | 1.8 |
|  | >2.9038 |  | 3 |
| 137 | 28.9553 | >2.896 | 1.1 |
|  | >2.8955 |  | 2 |
| 138 | >86.8634 | >28.954 | >100 |
|  | >2.8954 | >2.895 |  |
| 139 | 21.8093 | >2.181 | 15 |
|  | >2.1809 |  |  |
| 140 | 21.7623 | 2.176 | 22 |
|  |  | 2.1762 | 15 |
| 141 | 63.4242 | >31.712 | 1.1 |
|  |  |  | 3 |
|  |  |  | 3 |
|  |  |  | 2 |
| 142 | 94.8392 | >31.613 | 30 |
| 143 | 47.5682 | >31.712 | 6 |
|  | >3.1712 | >3.171 | 6 |
|  |  |  | 2 |
| 144 | >94.8392 | >31.613 | >100 |
|  | 94.8392 |  | >100 |
| 146 |  |  | 3 |
| 147 |  |  |  |
| 148 | >95.1363 | >63.424 | >100 |
| 149 | >94.8392 | >31.613 | >100 |
|  |  |  | >100 |
| 150 | 0.5808 | >29.038 | <1 |
|  |  |  | 2 |
|  |  |  | 0.8 |
|  |  |  | 0.3 |
| 151 | 28.9550 | >28.955 | 20 |
| 152 | >0.0000 | >27.825 | >100 |
| 153 | >28.0594 | >28.059 | >100 |
| 154 | 12.8256 | 0.770 | 0.5 |
|  | >2.5651 |  | <0.1 |
| 155 |  |  | 4 |
| 156 | >79.7071 | >26.569 | 35 |
|  |  |  | 35 |
| 171 |  |  | <1 |
|  |  |  | 0.001 |
|  |  |  | 0.0025 |
|  |  |  | <0.001 |

TABLE 2-continued

Inhibition of Kinase insert Domain containing Receptor (KDR), Epithelial Cell Kinase (Eck), and Mitogen Activated Protein Kinase (Mek-Erk)

| Example | KDR $\mu$M | Eck $\mu$M | Mek-Erk $\mu$M |
|---|---|---|---|
| 166 | >2.5391 | 0.762 | |
| 167 | 24.8472 | 0.025 | 8 |
|  | 2.4847 | >2.485 | |
| 168 | 4.4995 | >22.497 | <1 |
|  |  |  | 3 |

Inhibition of Cancer Cell Growth as Measured by Cell Number

Human tumor cell lines were plated in 96-well plates (250 $\mu$l/well, 1–6×10$^4$ cells/ml) in RPMI 1640 medium, containing 5% FBS (Fetal Bovine Serum). Twenty four hours after plating, test compounds were added at five log concentrations (0.01–100 mg/ml) or at lower concentrations for the more potent compounds. After 48 hours exposure to test compounds, cells were fixed with trichloroacetic acid, and stained with Sulforhodamine B. After washing with trichloroacetic acid, bound dye was solubilized in 10 mM Tris base and optical density was determined using plate reader. Under conditions of the assay the optical density is proportional to the number of cells in the well. IC$_{50}$s (concentrations causing 50% inhibition of cell growth) were determined from the growth inhibition plots. The test procedure is described in details by Philip Skehan et. al, *J.Natl. Canc. Inst.*, 82, 1107–1112 (1990). These data are shown below in TABLE 3. Information about some of the cell lines used in these test procedures is available from the American Type Tissue Collection: Cell Lines and Hybridomas, 1994 Reference Guide, 8th Edition.

In Vivo Inhibition of the Growth of Human Colon Carcinoma SW620

Representative compounds of this invention (listed below) were evaluated in an in vivo standard pharmacological test procedure which measured its ability to inhibit the growth of human epidermoid tumors. Human colon carcinoma SW620 cells (American Type Culture Collection, Rockville, Md. #CCL-227) were grown in vitro as described above. BALB/c nu/nu female mice (Charles River, Wilmington, Mass.) were used in this in vivo standard pharmacological test procedure. A unit of 7×10$^6$ cells were injected SC into mice. When tumors attained a mass of between 80 and 120 mg, the mice were randomized into treatment groups (day zero). Mice were treated IP once a day on days 1 through 20 post staging with doses of either 30, 10, 3 or 1 mg/kg/dose of the compound to be evaluated in 0.2% Klucel. Control animals received vehicle only. Tumor mass was determined every 7 days [(length×width$^2$)/2] for 28 days post staging. Relative tumor growth (Mean tumor mass on days 7, 14, 21, and 28 divided by the mean tumor mass on day zero) is determined for each treatment group. Statistical analysis (Student-t-test) of log relative tumor growth compares treated verses control group. A p-value (p$\leq$0.05) indicates a statistically significant reduction in relative tumor growth of treated group compared to the vehicle control.

The compound of Example 99 was evaluated for its ability to inhibit the growth of human colon carcinoma in vivo using the standard pharmacological test procedure described above. The results obtained are shown in Table 4.

TABLE 3

Inhibition of Cancer Cell Growth as Measured by Cell Number (IC$_{50}$ $\mu$g/mL)

| Ex. | MDA-MB-435 | A431 | SK-BR3 | A2780 | DDP | SW620 | 3T3 | 3T3/c-erbb2 |
|---|---|---|---|---|---|---|---|---|
| 99 | 0.020 | 0.025 | 0.016 | 0.032 | 0.036 | 0.033 | | |
| 100 | 0.067 | 0.369 | 0.429 | 0.270 | 0.249 | 0.325 | | |
| 101 | 0.073 | 0.216 | 0.18 | 0.231 | 0.313 | 0.326 | | |
| 101 | 0.365 | 0.123 | 0.0374 | | | 0.286 | 1.53 | 0.933 |
| 102 | 0.490 | 1.309 | 0.780 | 1.491 | 3.054 | 2.18 | | |
| 103 | 0.309 | 1.611 | 0.767 | 2.391 | 2.690 | 2.637 | | |
| 104 | 0.021 | 0.049 | 0.034 | 0.044 | 0.107 | 0.207 | | |
| 105 | 0.235 | 0.270 | 0.281 | | | 0.411 | 0.853 | 0.375 |
| 106 | 2.045 | 1.961 | >5 | | | >5 | >5 | >5 |
| 107 | >5 | >5 | >5 | | | >5 | >5 | >5 |
| 108 | 0.352 | 0.342 | 0.294 | | | <.0005 | 0.525 | 0.198 |
| 109 | >5 | >5 | >5 | | | 2.922 | >5 | 4.616 |
| 110 | 0.0280 | 0.0244 | 0.0281 | | | 0.0181 | 0.0923 | 0.0311 |
| 111 | 3.404 | >5 | >5 | | | 1.565 | >5 | 3.301 |
| 112 | 0.0033 | 0.257 | 0.336 | | | 0.146 | 0.392 | 0.251 |
| 115 | 0.0359 | 0.0368 | 0.0220 | | | 0.0212 | 0.344 | 0.0267 |
| 126 | 2.626 | 0.786 | 2.094 | | | 4.313 | 3.219 | 4.801 |
| 127 | >5 | >5 | >5 | | | >5 | >5 | >5 |

TABLE 4

In Vivo Inhibition of the Growth of Human Colon Carcinonia SW620 (9791CD-186) in Mice by the Compound of Example 99. Relative Tumor Growth

| a<br>Drug Treatment<br>mg/kg/dose | b<br>Day 7 | c<br>% T/C | d<br>(p) | b<br>Day 14 | c<br>% T/C | d<br>(p) | b<br>Day 21 | c<br>% T/C | d<br>(p) | e<br>S/T |
|---|---|---|---|---|---|---|---|---|---|---|
| Klucel (Placebo) | 4.10 | | | 11.59 | | | 11.23 | | | 13/15 |
| Example 99 (30 IP) | 1.81 | 44 | <0.01 | 3.85 | 33 | <0.01 | 4.44 | 40 | 0.02 | 4/5 |
| Example 99 (10 IP) | 3.69 | 90 | 0.37 | 7.88 | 68 | 0.18 | 9.75 | 87 | 0.36 | 5/5 |
| Example 99 (3 IP) | 3.80 | 93 | 0.62 | 12.53 | 108 | 0.78 | 16.47 | 147 | 0.54 | 5/5 | a Compound administered on days 1 through 20 IP b Relative Tumor Growth = $\dfrac{\text{Mean Tumor Mass on Day 7, 14, 21}}{\text{Mean Tumor Mass on Day 0}}$ c % T/C = $\dfrac{\text{Relative Tumor Growth of Treated Group}}{\text{Relative Tumor Growth of Placebo Group}} \times 100$ d Statistical analysis (Student-t-test) of Log Relative Tumor Growth. A p-value (p = 0.05) indicates a statistically significant reduction in Relative Tumor Growth of Treated Group, compared to Placebo Control.

e S/T = No. Survivors/No. Treated on Day +21 post tumor staging.

As shown in Table 4, the compound of Example 99 inhibited tumor growth; for example at 30 mg/kg (administered i.p. during days 1–20), tumor growth was inhibited by 56% at day 7, 67% at day 14, and 60% at day 21.

Based on the results obtained for representative compounds of this invention, the compounds of this invention are antineoplastic agents which are useful in treating, inhibiting the growth of, or eradicating neoplasms. In particular, the compounds of this invention are useful in treating, inhibiting the growth of, or eradicating neoplasms that express EGFR such as those of the breast, kidney, bladder, mouth, larynx, esophagus, stomach, colon, ovary, or lung. In addition, the compounds of this invention are useful in treating, inhibiting the growth of, or eradicating neoplasms of the breast that express the receptor protein produced by the erbB2 (Her2) oncogene. Based on the results obtained, the compounds of this invention are also useful in the treatment of polycystic kidney disease.

The compounds of this invention may formulated neat or may be combined with one or more pharmaceutically acceptable carriers for administration. For example, solvents, diluents and the like, and may be administered orally in such forms as tablets, capsules, dispersible powders, granules, or suspensions containing, for example, from about 0.05 to 5% of suspending agent, syrups containing, for example, from about 10 to 50% of sugar, and elixirs containing, for example, from about 20 to 50% ethanol, and the like, or parenterally in the form of sterile injectable solution or suspension containing from about 0.05 to 5% suspending agent in an isotonic medium. Such pharmaceutical preparations may contain, for example, from about 0.05 up to about 90% of the active ingredient in combination with the carrier, more usually between about 5% and 60% by weight.

The effective dosage of active ingredient employed may vary depending on the particular compound employed, the mode of administration and the severity of the condition being treated. However, in general, satisfactory results are obtained when the compounds of the invention are administered at a daily dosage of from about 0.5 to about 1000 mg/kg of body weight, optionally given in divided doses two to four times a day, or in sustained release form. The total daily dosage is projected to be from about 1 to 1000 mg, preferably from about 2 to 500 mg. Dosage forms suitable for internal use comprise from about 0.5 to 1000 mg of the active compound in intimate admixture with a solid or liquid pharmaceutically acceptable carrier. This dosage regimen may be adjusted to provide the optimal therapeutic response. For example, several divided doses may be administered daily or the dose may be proportionally reduced as indicated by the exigencies of the therapeutic situation.

The compounds of this invention may be administered orally as well as by intravenous, intramuscular, or subcutaneous routes. Solid carriers include starch, lactose, dicalcium phosphate, microcrystalline cellulose, sucrose arid kaolin, while liquid carriers include sterile water, polyethylene glycols, non-ionic surfactants and edible oils such as corn, peanut and sesame oils, as are appropriate to the nature of the active ingredient and the particular form of administration desired. Adjuvants customarily employed in the preparation of pharmaceutical compositions may be advantageously included, such as flavoring agents, coloring agents, preserving agents, and antioxidants, for example, vitamin E, ascorbic acid, BHT and BHA.

The preferred pharmaceutical compositions from the standpoint of ease of preparation and administration are solid compositions, particularly tablets and hard-filled or liquid-filled capsules. Oral administration of the compounds is preferred.

In some cases it may be desirable to administer the compounds directly to the airways in the form of an aerosol.

The compounds of this invention may also be administered parenterally or intraperitoneally. Solutions or suspensions of these active compounds as a free base or pharmacologically acceptable salt can be prepared in water suitably mixed with a surfactant such as hydroxy-propylcellulose. Dispersions can also be prepared in glycerol, liquid polyethylene glycols and mixtures thereof in oils. Under ordinary conditions of storage and use, these preparation contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), suitable mixtures thereof, and vegetable oils.

For the treatment of cancer, the compounds of this invention can be administered in combination with other antitumor substances or with radiation therapy. These other substances or radiation treatments can be given at the same or at different times as the compounds of this invention. These combined therapies may effect synergy and result in improved efficacy. For example, the compounds of this invention can be used in combination with mitotic inhibitors such as taxol or vinblastine, alkylating agents such as cisplatin or cyclophosamide, antimetabolites such as 5-fluorouracil or hydroxyurea, DNA intercalators such as adriamycin or bleomycin, topoisomerase inhibitors such as etoposide or camptothecin, antiangiogenic agents such as angiostatin, and antiestrogens such as tamoxifen.

The preparation of representative examples of the compounds of this invention is described below.

EXAMPLE 1

1,4-Dihydro-7-methoxy-4-oxo-quinoline-3-carbonitrile

A mixture of 30.2 g (245.2 mmol) of 3-methoxy aniline and 41.5 g (245.2 mmol) of ethyl(ethoxymethylene)cyanoacetate was heated in the absence of solvent to 140° C. for 30 minutes. To the resulting oil was added 1200 ml of Dowtherm. The solution was refluxed with stirring under nitrogen for 22 hours. The mixture was cooled to room temperature and solid was collected and washed with hexanes. The solid was recrystallized from acetic acid to give 17 g of 1,4-dihydro-7-methoxy-4-oxo-quinoline-3-carbonitrile: mass spectrum (electrospray, m/e): M+H 200.9.

EXAMPLE 2

1,4-Dihydro-7-methoxy-6-nitro-4-oxo-quinoline-3-carbonitrile

To a suspension of 10 g (49.6 mmol) of 1,4-dihydro-7-methoxy-4-oxo-quinoline-3-carbonitrile in 160 ml of trifluroacetic anhydride was added 6 g (74.9 mmol) of ammonium nitrate over a period of 3 hours. The mixture was stirred an additional two hours. Excess anhydride was removed at reduced pressure at 45° C. The residue was stirred with 500 ml of water. The solid was collected and washed with water. The solid was dissolved in 1000 ml of boiling acetic acid and the solution was treated with decolorizing charcoal. The mixture was filtered and concentrated to a volume of 300 ml. Cooling gave a solid which was collected giving 5.4 g of 1,4-dihydro-7-methoxy-6-nitro-4-oxo-quinoline-3-carbonitrile as a brown solid: mass spectrum (electrospray, m/e): M+H 246.

EXAMPLE 3

4-Chloro-7-methoxy-6-nitro-quinoline-3-carbonitrile

A mixture of 5.3 g (21.6 mmol) of 1,4-dihydro-7-methoxy-6-nitro-4-oxo-quinoline-3-carbonitrile and 9 g (43.2 mmol) of phosphorous pentachloride was heated at 165° C. for 2 hours. The mixture was diluted with hexanes and the solid was collected. The solid was dissolved in 700 ml ethyl acetate and washed with cold dilute sodium hydroxide solution. The solution was dried over magnesium sulfate and filtered through a pad of silica gel giving 5.2 g of 4-chloro-7-methoxy-6-nitro-quinoline-3-carbonitrile as a tan solid.

EXAMPLE 4

2-Cyano-3-(4-nitrophenylamino)acrylic Acid Ethyl Ester

4-Nitroaniline (60.0 g, 0.435 mol) and ethyl (ethoxymethylene) cyanoacetate (73.5 g, 0.435 mol) were mixed mechanically in a flask. The mixture was heated at 100° C. for 0.5 h after it had melted and resolidified. A 114 g portion of the crude product was recrystallized from dimethylformamide to give 44.2 g of yellow crystals; mp 227–228.5° C.

EXAMPLE 5

1,4-Dihydroquinoline-6-Nitro-4-oxo-3-carbonitrile

A slurry of 25.0 g (95.8 mmol) of 2-cyano-3-(4-nitrophenylamino)acrylic acid ethyl ester in 1.0 L of Dowtherm A was heated at 260° C. under $N_2$ for 12.5 h. The cooled reaction was poured into 1.5 L of hexane. The product was collected, washed with hexane and hot ethanol and dried in vacuo. There was obtained 18.7 g of brown solid. An analytical sample was obtained by recrystallization from dimethylformamide/ethanol: mass spectrum (electrospray, m/e): M+H 216.

EXAMPLE 6

4-Chloro-6-nitro-quinoline-3-carbonitrile

A mixture of 31.3 g (0.147 mol) of 6-nitro-4-oxo-1,4-dihydro-quinoline-3-carbonitrile and 160 mL of phosphorous oxychloride was refluxed for 5.5 h. The phosphorous oxychloride was removed in vacuo and the residue was poured over ice and neutralized with sodium bicarbonate. The product was collected, washed with water and dried in vacuo (50° C.). There was obtained 33.5 g of tan solid; solid: mass spectrum (electrospray, m/e): M+H 234.

EXAMPLE 7

2-Cyano-3-(2-methyl-4-nitrophenyl)acrylic Acid Ethyl Ester

A mixture of 2-methyl-4-nitroaniline (38.0 g, 250 mmol), ethyl (ethoxymethylene)cyanoacetate (50.8 g, 300 mmol), and 200 ml of toluene was refluxed for 24 h, cooled, diluted with 1:1 ether-hexane, and filtered. The resulting white solid was washed with hexane-ether and dried to give 63.9 g, mp 180–210° C.

EXAMPLE 8

1,4-Dihydroquinoline-8-methyl-6-nitro-3-carbonitrile

A stirred mixture of 64 g (230 mmol) of 2-cyano-3-(2-methyl-4-nitrophenyl)acrylic acid ethyl ester and 1.5 L of Dowtherm A was heated at 260° C. for 12 h, cooled, diluted with hexane, and filtered. The grey solid thus obtained was washed with hexane and dried to give 51.5 g, mp 295–305° C.

EXAMPLE 9

4-Chloro-8-methyl-6-nitro-quinoline-3-carbonitrile

A stirred mixture of 1,4-dihydroquinoline-8-methyl-6-nitro-3-carbonitrile (47 g, 200 mmol) and 200 ml of phosphorous oxychloride was refluxed for 4 h. The phosphorous oxychloride was removed in vacuo, and the residue was stirred with methylene chloride at 0° C. and treated with a slurry of ice and sodium carbonate. The organic layer was separated and washed with water. The solution was dried and concentrated to a volume of 700 ml. The product was precipitated by the addition of hexane and cooling to 0° C. The white solid was filtered off and dried to give 41.6 g, mp 210–212° C.

EXAMPLE 10

7-Ethoxy-4-hydroxy-quinoline-3-carbonitrile

A mixture of 10 g (73 mmol) of 3-ethoxy aniline and 12.3 g (73 mmol) of ethyl (ethoxymethylene) cyanoacetate was heated in 90 ml of Dowther at 140° C. for 7 hours. To this mixture was added 250 ml of Dowther. The solution was stirred and refluxed under nitrogen for 12 hours with periodically distilling out the eliminated ethanol. The mixture was cooled to room temperature and the solid was collected and washed with hexane. The crude solid was treated with boiling ethanol and then filtered to give 9.86 g of brown solid: mass spectrum (electrospray, m/e): M+H 214.7.

EXAMPLE 11

7-Ethoxy-4-hydroxy-6-nitro-quinoline-3-carbonitrile

To a suspension of 5 g (23 mmol) of 7-Ethoxy-4-hydroxy-quinoline-3-carbonitrile in 75 ml of trifluroacetic anhydride was added 5.5 g (69 mmol) of ammonium nitrate over a period of 6 hours at room temperature. Excess anhydride was removed at reduced pressure at 45° C. The residue was stirred with 300 ml of water. The solid was collected and treated with boiling ethanol to give 3.68 g of tin solid: mass spectrum (electrospray, m/e) M+H 259.8.

EXAMPLE 12

4-Chloro-7-ethoxy-6-nitro-quinoline-3-carbonitrile

A mixture of 3.45 g (13 mmol) of 7-Ethoxy-4-hydroxy-6-nitro-quinoline-3-carbonitrile, 5.55 g (26 mmol) of phosphorous pentachloride, and 10 ml of phosphorous oxychloride was refluxed for 3 hours. The mixture was diluted with hexane and the solid was collected. The solid was dissolved in 500 ml of ethyl acetate and washed with cold diluted sodium hydroxide solution. The solution was dried over magnesium sulfate and filtered through a pad of silica gel. The solvent was removed giving 2.1 g of beige solid: mass spectrum (electrospray, m/e) M+H 277.7.

EXAMPLE 13

8-Methoxy-4-hydroxy-6-nitro-quinoline-3-carbonitrile

A mixture of 12.6 g (75 mmol) of 2-methoxy-4-nitro aniline and 12.7 g (75 mmol) of ethyl (ethoxymethylene) cyanoacetate was heated in 100 ml of Dowther at 120° C. for overnight and 180° C. for 20 hours. To this mixture was added 300 ml of Dowther. The solution was stirred and refluxed under nitrogen for 12 hours with periodically distilling out the eliminated ethanol. The mixture was cooled to room temperature and the solid was collected and washed with hexane. The crude solid was treated with boiling ethanol and then filtered to give 12 g of brown solid: mass spectrum (electrospray, m/e): M+H 245.8.

EXAMPLE 14

4-Chloro-8-methoxy-6-nitro-quinoline-3-carbonitrile

A mixture of 4 g (16 mmol) of 8-Methoxy-4-hydroxy-6-nitro-quinoline-3-carbonitrile, 6.66 g (32 mmol) of phosphorous pentachloride, and 15 ml of phosphorous oxychloride was refluxed for 2.5 hours. The mixture was diluted with hexane and the solid was collected. The solid was dissolved in 500 ml of ethyl acetate and washed with cold diluted sodium hydroxide solution. The solution was dried over magnesium sulfate and filtered through a pad of silica gel. The solvent was removed giving 2.05 g of tan solid: mass spectrum (electrospray, m/e) M+H 263.7.

EXAMPLE 15

4-Chloro-but-2-yanoic acid

Propargyl chloride (2 mL, 26.84 mmol) was dissolved in 40 mL of tetrahydrofuran under nitrogen and cooled to −78° C. After addition of n-butyllithium (5.4 mL, 13.42 mmol, 2.5 M in n-hexane) and stirred for 15 min, a stream of dry carbon dioxide was passed through it at −78° C. for two hours. The reaction solution was filtered and neutralized with 3.5 mL of 10% sulfuric acid. After evaporation of the solution, the residue was extracted with ether. The ether solution was washed with saturated brine solution, and dried over sodium sulfate. After evaporation of the dry ether solution, 0.957 g (60 %) of an oil product was obtained: ESMS m/z 116.6 (M−H$^+$).

EXAMPLE 16

4-Dimethylamino-but-2-ynoic acid n-Butyl lithium in hexane (96 mL, 2.5 M in n-hexane) was slowly added to 1-dimethylamino-2-propyne (20 g, 240 mmol) in 100 mL of tetrahydrofuran under nitrogen. The mixture was stirred for 1 h at −78° C., then dry carbon dioxide was pass through overnight. The resulting solution was poured into water and washed with ethyl acetate. The aqueous layer was evaporated under reduced pressure to give the crude acid. The dry acid was dissolved in methanol, and the insoluble salt was removed via filtration. The filtrate was collected and dried in vacuo to give 15.6 g of 4-dimethylamino-but-2-ynoic acid: mass spectrum (m/e) :M−H 126.

EXAMPLE 17

Bis-(2-methoxy-ethyl)-prop-2-ynyl-amine

Propargyl bromide (17.8 g, 150 mmol) was added dropwise to a mixture of bis(2-methoxy-ethyl)amine (20 g, 150 mmol) and cesium carbonate (49 g, 150 mmol) in 350 mL of acetone. The mixture was stirred overnight under nitrogen at room temperature. The inorganic salts were then filtered off, and the solvent was removed. The residue was dissolved in saturated sodium bicarbonate solution and extracted with ethyl acetate. The organic extracts were then evaporated to give 20 g of bis-(2-methoxy-ethyl)-prop-2-ynyl-amine: mass spectrum (m/e): M+H 172.

EXAMPLE 18

4-[Bis-(2-methoxy-ethyl)-amino]-but-2-ynoic acid n-Butyl lithium in hexane (42 mL, 2.5 M in n-hexane) was slowly added to bis-(2-methoxy-ethyl)-prop-2-ynyl-amine (18 g, 105 mmol) in 80 mL of tetrahydrofuran under nitrogen. The mixture was stirred for 1 h at −78° C., then dry carbon dioxide was passed through overnight. The resulting solution was poured into water and washed with ethyl acetate. The aqueous layer was evaporated under reduced pressure to give the crude acid. The dry acid was dissolved in methanol, and the insoluble salt was removed via filtration. The filtrate was collected and dried in vacuo to give 18 g of 4-[bis-(2-methoxy-ethyl)-amino]-but-2-ynoic acid: mass spectrum (m/e):M−H 214.

EXAMPLE 19

1-Methyl-4-prop-2-ynyl-piperazine

Propargyl bromide (23.8 g, 200 mmol) was added dropwise to a mixture of 1-methyl-piperazine (20 g, 200 mmol) and cesium carbonate (65 g, 200 mmol) in 350 mL of acetone. The mixture was stirred overnight under nitrogen at room temperature. The inorganic salts were then filtered off, and the solvent was removed. The residue was dissolved in saturated sodium bicarbonate solution and extracted with ethyl acetate. The organic extracts were then evaporated to give 7.5 g of 1-methyl-4-prop-2-ynyl-piperazine: mass spectrum (m/e): M+H 139.

EXAMPLE 20

4-(4-Methyl-piperazin-1-yl)-but-2-ynoic acid n-Butyl lithium in hexane (17.2 mL, 2.5 M in n-hexane) was slowly added to 1-methyl-4-prop-2-ynyl-piperazine (6.0 g, 43.5 mmol) in 40 mL of tetrahydrofuran under nitrogen. The mixture was stirred for 1 hr at −78° C., then dry carbon dioxide was passed through overnight. The resulting solution was poured into water and washed with ethyl acetate. The aqueous layer was evaporated under reduced pressure to give the crude acid. The dry acid was dissolved in methanol, and the insoluble salt was removed via filtration. The filtrate was collected and dried in vacuo to give 7 g of 4-(4-methyl-piperazin-1-yl)-but-2-ynoic acid: mass spectrum (m/e):M−H 181.

EXAMPLE 21

(2-Methoxy-ethyl)-methyl-prop-2-ynyl-amine

Propargyl bromide (26.8 g, 225 mmol) was added dropwise to a mixture of N-(2-methoxyethyl)methyl amine (20 g, 225 mmol) and cesium carbonate (73 g, 225 mmol) in 350 mL of acetone. The mixture was stirred overnight under nitrogen at room temperature. The inorganic salts were then filtered off, and the solvent was removed. The residue was dissolved in saturated sodium bicarbonate solution and extracted with ethyl acetate. The organic extracts were then evaporated to give 14 g of (2-methoxy-ethyl)-methyl-prop-2-ynyl-amine: mass spectrum (m/e): M+H 127.

EXAMPLE 22

4-[(2-Methoxy-ethyl)-methyl-amino]-but-2-ynoic acid n-Butyl lithium in hexane (37.8 mL, 2.5 M in n-hexane) was slowly added to (2-methoxy-ethyl)-methyl-prop-2-ynyl-amine (12.0 g, 94.5 mmol) in 90 mL of tetrahydrofuran under nitrogen. The mixture was stirred for 1 hr at −78° C., then dry carbon dioxide was passed through overnight. The resulting solution was poured into water and washed with ethyl acetate. The aqueous layer was evaporated under reduced pressure to give the crude acid. The dry acid was dissolved in methanol, and the insoluble salt was removed via filtration. The filtrate was collected and dried in vacuo to give 15 g of 4-[(2-methoxy-ethyl)-methyl-amino]-but-2-ynoic acid: mass spectrum (m/e): M−H 170.

EXAMPLE 23

Allyl-methyl-prop-2-ynyl-amine

Propargyl bromide (33.4 g, 281 mmol) was added dropwise to a mixture of isopropyl-methyl-amine (20 g, 281 mmol) and cesium carbonate (90 g, 281 mmol) in 350 mL of acetone. The mixture was stirred overnight under nitrogen at room temperature. The inorganic salts were then filtered off, and the solvent was removed. The residue was dissolved in saturated sodium bicarbonate solution and extracted with ethyl acetate. The organic extracts were then evaporated to give 4.6 g of allyl-methyl-prop-2-ynyl-amine: mass spectrum (m/e): M+H 110.

EXAMPLE 24

4-(Allyl-methyl-amino)-but-2-ynoic acid n-Butyl lithium in hexane (16.4 mL, 2.5 M in n-hexane) was slowly added to allyl-methyl-prop-2-ynyl-amine (4.5 g, 46 mmol) in 50 mL of tetrahydrofuran under nitrogen. The mixture was stirred for 1 hr at −78° C., then dry carbon dioxide was passed through overnight. The resulting solution was poured into water and washed with ethyl acetate. The aqueous layer was evaporated under reduced pressure to give the crude acid. The dry acid was dissolved in methanol, and the insoluble salt was removed via filtration. The filtrate was collected and dried in vacuo to give 4.1 g of 4-(allyl-methyl-amino)-but-2-ynoic acid: mass spectrum (m/e): M−H 152.

EXAMPLE 25

4-Methoxymethoxy-but-2-ynoic acid

To a suspension of 8.2 g of 60% sodium hydride in mineral oil in 271 mL of tetrahydrofuran at 0° C. with stirring under nitrogen was added dropwise 10 g of propargyl alcohol over 15 min. The mixture was stirred an additional 30 min. To the stirred mixture at 0° C. was added 15.8 g of chloromethylmethyl ether. Stirring was continued at room temperature over night. The mixture was filtered and the solvent was removed from the filtrate. The residue was distilled (35–38° C., 4 mm) giving 8.5 g of a liquid. The distillate was dissolved in 200 mL of ether. The solution was stirred under nitrogen and cooled to −78° C. as 34.1 mL of 2.5 molar n-butyl lithium in hexanes was added over 15 min. Stirring was continued for another 1.5 hr. Dry carbon dioxide was allowed to pass over the surface of the stirring reaction mixture as it warmed from −78° C. to room temperature. The mixture was stirred under a carbon dioxide atmosphere over night. The mixture was poured into a mixture of 14 mL of hydrochloric acid and 24 mL of water. The organic layer was separated and dried over magnesium sulfate. The solvent was removed and the residue was maintained at 100° C. at 4 mm for 1 hr giving 10.4 g 4-Methoxymethoxy-but-2-ynoic acid.

EXAMPLE 26

4-Bromo crotonic acid

After the method of Braun [Giza Braun, J. Am. Chem. Soc. 52, 3167 (1930)], 11.76 mL (17.9 grams 0.1 moles) of methyl 4-bromo crotonate in 32 mL of ethanol and 93 mL of water was cooled to −11° C. The reaction was stirred vigorously, and 15.77 g (0.05 moles) of finely powdered barium hydroxide was added portionwise over a period of about an hour. Cooling and vigorous stirring were continued for about 16 hours. The reaction mixture was then extracted with 100 mL of ether. The aqueous layer was treated with 2.67 mL (4.91 g; 0.05 moles) of concentrated sulfuric acid. The resulting mixture was extracted with 3–100 mL portions of ether. The combined ethereal extracts were washed with 50 mL of brine, then dried over sodium sulfate. The solution was taken to an oil in vacuo. This oil was taken up in about 400 mL of boiling heptane, leaving a gum. The heptane solution was separated and boiled down to about 50 mL. Cooling gave 3.46 g of product.

EXAMPLE 27

4-(2-Methoxy-ethoxy)-but-2-ynoic acid

To a suspension of 6.04 g (151 mmol) of 60% sodium hydride in 200 ml of tetrahydrofuran at 0° C. was add 10 g (131.4 mmol) of 2-methoxyethanol dropwise over 15 min. After 1 hr, 19.54 g (131.4 mmol) of 80% propargyl bromide was added dropwise. After stirring 17 hr at room temperature, the mixture was filtered and the solvent was remove. The residue was distilled (48–51° C., 4mm) to give 11.4 g of a colorless liquid. This was dissolved in 250 ml of ether and cooled to −78° C. with stirring under nitrogen. To this solution was added 39.95 ml (99.9 mmol) of 2.5M n-butyl lithium solution in hexanes dropwise over 15 min. After 1.5 hr, dry carbon dioxide was bubbled in as the mixture slowly warmed to room temperature. The mixture was maintained in a carbon dioxide atmosphere overnight. To the mixture was added 100 ml of 3N hydrochloric acid and solid sodium chloride. The organic layer was separated and dried over magnesium sulfate. The solvent was removed and the residue was maintained under vacuum giving 11.4 g of the title compound.: mass spectrum (electrospray, m/e, negative mode): M−H 156.8.

EXAMPLE 28

4-(Methoxymethoxy)-but-2-ynoic acid

To a suspension of 8.2 g (205 mmol) of 60% sodium hydride in 271 ml of tetrahydrofuran was added dropwise at 0° C. with stirring 10.0 g (178.4 mmol) of propargyl alcohol. After 30 min, 15.8 g (196.2 mmol) of chloromethylmethyl ether was added. After stirring over the weekend at room temperature, the mixture was filtered and the solvent was remove. The residue was distilled (35–38° C., 4 mm) to give 8.54 g of a colorless liquid. This was dissolved in 200 ml of ether and cooled to −78° C. with stirring under nitrogen. To this solution was added 34.1 ml (85.3 mmol) of 2.5M n-butyl lithium solution in hexanes dropwise over 15 min. After 1.5 hr, dry carbon dioxide was bubbled in as the mixture slowly warmed to room temperature. The mixture was maintained in a carbon dioxide atmosphere overnight. To the mixture was added 14 ml of hydrochloric acid in 24 ml water. The organic layer was separated and dried over magnesium sulfate. The solvent was removed and the residue was maintained under vacuum giving 10.4 g of the title compound as a liquid.

EXAMPLE 29

4-((2S)-2-methoxymethylpyrrolidin-1-yl)butynoic Acid n-Butyllithium solution in hexane (35.9 mmol) was added over 10 min to a solution of 5.49 g (35.9 mmol) of (2S)-2-methoxymethyl-1-prop-2-ynylpyrrolidine in 100 mL of THF at −78° C. under $N_2$. After stirring cold for 1 h, $CO_2$ was bubbled into the solution as it slowly came to 25° C. After stirring overnight, 100 mL of water was added, the reaction was extracted with ethyl acetate and the extracts were discarded. The reaction was adjusted to pH 7 with 20% $H_2SO_4$ and solvent was removed. The residue was slurried with methanol and filtered. The filtrate was evaporated and dried in vacuo to give 7.06 g of 4-((2S)-2-methoxymethylpyrrolidin-1-yl)butynoic acid as a brown foam: mass spectrum (electrospray, m/e): M+H 198.0.

EXAMPLE 30

(2S)-2-Methoxymethyl-1-prop-2-ynylpyrrolidine

A mixture of 4.82 g (41.9 mmol) of S-2-(methoxymethyl) pyrrolidine, 13.7 g (41.9 mmol) of cesium carbonate and 5.00 g (41.9 mmol) of propargyl bromide in 80 mL of acetone was stirred at 25° C. overnight. The reaction was filtered and solvent was removed from the filtrate. The residue was diluted with a small amount of water and satd $NaHCO_3$ and extracted with ether. The extract was treated with Darco, dried and evaporated to give 5.93 g of (2S)-2-methoxymethyl-1-prop-2-ynylpyrrolidine as a yellow orange oil: mass spectrum (electrospray, m/e): 153.8.

EXAMPLE 31

4-(1,4-Dioxa-8-azaspiro[4,5]dec-8-yl)but-2-ynoic Acid n-Butyllithium in hexane (55.8 mmol) was added dropwise to a solution of 10.1 g (55.8 mmol) of 3-(1,4-dioxa-8-azaspiro[4,5]dec-8-yl)but-2-yne in 185 mL of THF at −78° C. under $N_2$. After stirring at −78° C. for 1 h, $CO_2$ was bubbled into the solution as it slowly came to 25° C. After stirring overnight, the reaction was diluted with 150 mL of water, extracted with ethyl acetate and the extracts were discarded. The solution was adjusted to pH 6 with 2 M sulfuric acid and evaporated. The residue was slurried with methanol and filtered. The filtrate was evaporated and dried in vacuo to give 4.5 g of 4-(1,4-dioxa-8-azaspiro[4,5]dec-8-yl)but-2-ynoic acid as a brown amorphous solid: mass spectrum electrospray, m/e): M+H 225.8.

EXAMPLE 32

3-(1,4-Dioxa-8-azaspiro[4,5]dec-8-yl)but-2-yne

A mixture of 10.0 g (69.9 mmol) of 1,4-dioxa-8-azaspiro [4,5]decane, 22.8 g (69.9 mmol) of cesium carbonate and 8.32 g (69.9 mmol) of propargyl bromide in 165 mL of acetone was stirred overnight at 25° C. The reaction was filtered and the filtrate was evaporated to dryness. A small amount of water and satd $NaHCO_3$ was added to the residue and it was extracted with ether. The ethereal extracts were treated with Darco, dried and evaporated to give 10.8 g of 3-(1,4-dioxa-8-azaspiro[4,5]dec-8-yl)but-2-yne as a yellow orange oil: mass spectrum (electrospray, m/e): M+H 181.8.

EXAMPLE 33

Methyl 4-benzyloxy-2-(dimethylaminomethyleneamino)-5-methoxybenzoate

A stirred mixture of 70.0 g (244 mmol) of methyl 2-amino-4-benzyloxy-5-methoxybenzoate (Phytochemistry 1976, 15, 1095) and 52 ml of dimethylformamide dimethyl acetal was heated at 100° C. for 1.5 h, cooled, and evaporated directly under high vacuum to give 81.3 g of off-white solid, mp 134–140° C.; NMR (CDCl$_3$) d 3.01 (s, Me$_2$N).

EXAMPLE 34

7-benzyloxy-4-hydroxy-6-methoxy-quinoline-3-carbonitrile

To a stirred solution of 26.9 ml of n-butyllithium (2.5 M in hexane) in 50 ml of THF at −78° C. was added a 3.51 ml of acetonitrile in 20 ml of THF during 10 min. After stirring at −78° C. for 30 min, the mixture was treated with 10 g of methyl 4-benzyloxy-2-(dimethylaminomethyleneamino)-5-methoxybenzoate in 20 ml of THF during 5 min. After 15 min at −78° C. the stirred mixture was warmed to 0° C. for a further 30 min. It was then treated with 5 ml of acetic acid, warmed to 25° C. and stirred for 30 min. The mixture was evaporated to dryness, and diluted with aqueous sodium bicarbonate. The resulting off-white solid was filtered, washed with water, ethyl acetate and ether. After drying, 4.5 g of 7-benzyloxy-4-hydroxy-6-methoxy-quinoline-3-carbonitrile was obtained as an off-white solid, dec>255° C.; mass spectrum (electrospray, m/e) M+H 307.

EXAMPLE 35

7-benzyloxy-4-chloro-6-methoxy-quinoline-3-carbonitrile

To a stirred suspension of 1 g of 7-benzyloxy-4-hydroxy-6-methoxy-quinoline-3-carbonitrile in 10 ml of methylene chloride was added 5 ml of oxalyl chloride (2M in methylene chloride), and 2 drops of N,N-dimethylformamide. The mixture was refluxed for 20 min and to it was slowly added aqueous sodium bicarbonate until the bubbling ceased. Following separation of the layers, the organic layer was evaporated to a small volume, then passed through a plug of magnesol. Elution with 50 ml methylene chloride, followed by evaporation provided 0.6 g of 7-benzyloxy-4-chloro-6-methoxy-quinoline-3-carbonitrile as a pale yellow solid, mp 282–284° C.; mass spectrum (electrospray, m/e) M+H 325.

EXAMPLE 36

4-chloro-7-hydroxy-6-methoxy-quinoline-3-carbonitrile

A stirred suspension of 0.54 g of 7-benzyloxy-4-chloro-6-methoxy-quinoline-3-carbonitrile in 10 ml of methylene chloride was cooled to 0° C. To this was added 10 ml of boron trichloride (1M in methylene chloride). The mixture darkened as it warmed to room temperature and a solid precipitated out. After stirring for 1 hour, no further reaction was observed. The solid (unreacted starting material) was filtered off, the remaining solution was cooled to 0° C. and quenched by the dropwise addition of methanol. Following evaporation of the solvent, the residue was dissolved in methylene chloride/methanol/acetone. Purification of this residue was carried out using silica gel chromatography, eluting with a solvent gradient of 1 to 5 percent methanol/methylene chloride, to provide 0.075 g of 4-chloro-7-hydroxy-6-methoxy-quinoline-3-carbonitrile as a yellow solid, dec>245° C.; mass spectrum (electrospray, m/e) M+H 235.2.

EXAMPLE 37

4-chloro-6-methoxy-7-(3-pyridin-4-yl-propoxy)-quinoline-3-carbonitrile

A mixture of 0.070 g of 4-chloro-7-hydroxy-6-methoxy-quinoline-3-carbonitrile, 0.062 g of 3-(4-pyridyl)-1-propanol and 0.235 g of triphenylphosphine in 3 ml of methylene chloride under nitrogen was cooled to 0° C. To this was added 0.14 ml of diethyl azodicarboxylate dropwise. After 30 minutes, the reaction mixture was warmed to room temperature and further stirred for 2 hours. The mixture was concentrated down to 1 ml and purified by silica gel chromatography, eluting with a solvent gradient of 1 to 2 percent methanol/methylene chloride, to provide 0.090 g of 4-chloro-6-methoxy-7-(3-pyridin-4-yl-propoxy)-quinoline-3-carbonitrile as an off-white gum.

EXAMPLE 38

4-Chloro-7-methoxy-quinoline-3-carbonitrile

A mixture of 4.0 g (20 mmol) of 1,4-dihydro-7-methoxy-4-oxo-quinoline-3-carbonitrile and 8.3 g (40 mmol) of phosphorous pentachloride was heated at 165° C. for 3 hours. The mixture was diluted with hexanes and the solid was collected. The solid was mixed with brine and dilute sodium hydroxide solution and extracted several times with a mixture of tetrahydrofuran and ethyl acetate. The solution was dried over magnesium sulfate and filtered through a pad of silica gel giving 3.7 g of 4-chloro-7-methoxy-quinoline-3-carbonitrile as a white solid: mass spectrum (electrospray, m/e): M+H 218.9.

EXAMPLE 39

3-Carbethoxy-4-hydroxy-6,7-dimethoxyquinoline

A mixture of 30.6 g of 4-aminoveratrole and 43.2 g of diethyl ethoxymethylenemalonate was heated at 100 for 2 h and at 165° C. for 0.75 h. The intermediate thus obtained was dissolved in 600 ml of diphenyl ether, and the resulting solution was heated at reflux temperature for 2 h, cooled, and diluted with hexane. The resulting solid was filtered, washed with hexane followed by ether, and dried to provide the title compound as a brown solid, mp 275–285° C.

EXAMPLE 40

3-Carbethoxy-4-chloro-6,7-dimethoxylquinoline

A mixture of 28.8 g of 3-carbethoxy-4-hydroxy-6,7-dimethoxyquinoline and 16.6 ml of phosphorous oxychloride was stirred at 110° C. for 30 min, cooled to 0° C., and treated with a mixture of ice and ammonium hydroxide. The resulting grey solid was filtered, washed with water and ether, and dried, mp 147–150° C.

EXAMPLE 41

Ethyl 2-cyano-3-(3,4-dimethoxyphenylamino)acrylate

A mixture of 7.66 g of 4-aminoveratrole, 8.49 g of ethyl ethoxymethylenecyanoacetate, and 20 ml of toluene was heated at 100° C. for 90 min. The toluene was evaporated to give a solid, mp 150–155° C.

EXAMPLE 42

1,4-Dihydro-6,7-dimethoxy-4-oxo-quinoline-3-carbonitrile

A mixture of 40 g of ethyl 2-cyano-3-(3,4-dimethoxyphenylamino)acrylate and 1.2 L of Dowtherm® A was refluxed for 10 h, cooled, and diluted with hexane. The resulting solid was filtered, washed with hexane followed by dichloromethane, and dried; mp 330–350° C. (dec).

EXAMPLE 43

4-Chloro-6,7-dimethoxy-quinoline-3-carbonitrile

A stirred mixture of 20 g of 1,4-dihydro-6,7-dimethoxy-4-oxo-quinoline-3-carbonitrile and 87 ml of phosphorous oxychloride was refluxed for 2 h, cooled, and evaporated free of volatile matter. The residue was stirred at 0° C. with dichloromethane-water as solid sodium carbonate was added until the aqueous layer was pH 8. The organic layer was separated, washed with water, dried and concentrated. Recrystallization from dichloromethane gave a solid, mp 220–223° C.

EXAMPLE 44

Methyl 2-(dimethylaminomethyleneamino)benzoate

To a stirred solution of 7.56 g of methyl anthranilate in 50 ml of dimethylformamide at 0° C. was added 5.6 ml of phosphorous oxychloride during 15 m. The mixture was heated at 55 for 45 m, cooled to 0, and diluted with dichloromethane. The mixture was basified at 0° C. by slow addition of cold 1N NaOH to pH 9. The dichloromethane layer was separated, washed with water, dried and concentrated to an oil.

EXAMPLE 45

1,4-Dihydro-4-oxo-quinoline-3-carbonitrile

A stirred mixture of 1.03 g of methyl 2-(dimethylaminomethyleneamino)benzoate, 0.54 g of sodium methoxide, 1.04 ml of acetonitrile, and 10 ml of toluene was refluxed for 18 h. The mixture was cooled, treated with water, and brought to pH 3 by addition of dilute HCl. The resulting solid was extracted with ethyl acetate. The extract was washed with water, dried and evaporated. The residue was recrystallized from ethanol to give a solid, mp 290–300° C.

EXAMPLE 46

4-(3-Chloro-propoxy)-5-methoxy-benzoic acid methyl ester

A mixture of 102.4 g (411.7 mmol) of 3-chloropropyl p-toluene sulfonate, 75 g (411.7 mmol) of 4-hydroxy-5-methoxy-benzoic acid methyl ester, 75.7 g (547.5 mmol) of potassium carbonate, and 1.66 g (4.1 mmol) of methyl-tricapryl ammonium chloride in 900 ml of acetone was stirred rapidly at reflux for 18 hr. The mixture was filtered and the solvent was removed giving 106 g of the tile compound after recrystallization from a chloroform-hexane mixture.

EXAMPLE 47

4-(2-Chloro-ethoxy)-5-methoxy-benzoic acid methyl ester

By using an identical method as in Example 46, 77 g of 4-hydroxy-5-methoxy-benzoic acid methyl ester, 99.2 g of 2-chloroethyl p-toluene sulfonate, 77.7 g of potassium carbonate, and 1.7 g (4.1 mmol) of methyl-tricapryl ammonium chloride was converted to 91.6 g of the title compound: mass spectrum (electrospray, m/e,): M+H 245.0

EXAMPLE 48

4-(3-Chloro-propoxy)-5-methoxy-2-nitro-benzoic acid methyl ester

To a solution of 100 g (386.5 mmol) 4-(3-chloro-propoxy)-5-methoxy-benzoic acid methyl ester in 300 ml acetic acid was added dropwise 100 ml of 70% nitric acid. The mixture was heated to 50° C. for 1 hr and then poured into ice water. The mixture was extracted with chloroform. The organic solution was washed with dilute sodium hydroxide and then dried over magnesium sulfate. The solvent was removed. Ether was added an the mixture was stirred until solid was deposited. The solid was collected by filtration giving 98 g of 4-(3-Chloro-propoxy)-5-methoxy-2-nitro-benzoic acid methyl ester as white crystals: mass spectrum (electrospray, m/e,): M+H 303.8; 2M+NH$_4$ 623.9.

EXAMPLE 49

4-(2-Chloro-ethoxy)-5-methoxy-2-nitro-benzoic acid methyl ester

By using an identical method as in Example 48, 85 g of 4-(2-Chloro-ethoxy)-5-methoxy-benzoic acid methyl ester was nitrated to give 72 g of the title compound: mass spectrum (electrospray, m/e): 2M+NH$_4$ 595.89

EXAMPLE 50

2-Amino-4-(3-chloro-propoxy)-5-methoxy-benzoic acid methyl ester

A mixture of 91 g (299.6 mmol) of 4-(3-chloro-propoxy)-5-methoxy-2-nitro-benzoic acid methyl ester and 55.2 g (988.8 mmol) of iron was mechanically stirred at reflux in a mixture containing 60.1 g ammonium chloride, 500 ml water, and 1300 ml methanol for 5.5 hr. The mixture was concentrated and mixed with ethyl acetate. The organic solution was washed with water and saturated sodium bicarbonate. The solution was dried over magnesium sulfate and filtered through a short column of silica gel. The solvent was removed and the residue mixed with 300 ml of ether-hexane 2:1. After standing 73.9 g of the title compound was obtained as a pink solid: mass spectrum (electrospray, m/e): 2M–HCl+H 511.0; M+H 273.8

EXAMPLE 51

2-Amino-4-(2-chloro-ethoxy)-5-methoxy-benzoic acid methyl ester

A mixture of 68.2 g (235.4 mmol) of 4-(2-chloro-ethoxy)-5-methoxy-2-nitro-benzoic acid methyl ester and 52.6 g (941.8 mmol) of iron was mechanically stirred at reflux in a mixture containing 62.9 g ammonium chloride, 393 ml water, and 1021 ml methanol for 15 hr. The mixture was concentrated and mixed with ethyl acetate. The organic solution was washed with water and saturated sodium bicarbonate. The solution was dried over magnesium sulfate and filtered through a short column of silica gel. The solution was concentrated to 200 ml and diluted with 250 of hot hexane. After standing 47.7 g of the title compound was obtained as a solid : mass spectrum (electrospray, m/e) M+H 259.8.

EXAMPLE 52

7-(2-Chloro-ethoxy)-4-hydroxy-6-methoxy-quinoline-3-carbonitrile

A mixture of 25 g (96.3 mmol) of 2-amino-4-(2-chloro-ethoxy)-5-methoxy-benzoic acid methyl ester and 17.2 g (144.4 mmol) of dimethyformamide dimethyacetal was heated to reflux for 1.5 hr. Excess reagents were removed at reduced pressure leaving 30.3 g of a residue which was dissolved in 350 ml of tetrahydrofuran. In a separate flask, to a stirred solution of 80.9 ml of 2.5M n-butyl lithium in hexane in 300 ml of tetrahydrofuran at −78° C. was added dropwise 8.3 g (202.1 mmol) of acetonitrile over 40 min. After 30 min, the above solution of amidine was added dropwise over 45 min at −78° C. After 1 hr, 27.5 ml of acetic acid was added and the mixture was allow to warm to room temperature. The solvent was removed and water was added. Solid was collected by filtration and washed with water and ether. After drying in vacumn, 18.5 g of the title compound was obtained as a tan powder: mass spectrum (electrospray, m/e) M+H 278.8.

EXAMPLE 53

7-(3-Chloro-propoxy)-4-hydroxy-6-methoxy-quinoline-3-carbonitrile

By using the method of example 52 and starting with 6.01 g of the corresponding amidine, 1.58 g of acetonitrile, and 15.35 ml of n-butyl lithium solution, 3.7 g of the title compound was obtained as a tan powder: mass spectrum (electrospray, m/e) M+H 292.8; 2M+H 584.2

EXAMPLE 54

7-(3-Chloro-propoxy)-4-chloro-6-methoxy-quinoline-3-carbonitrile

A mixture of 3.5 g (12 mmol) of 7-(3-chloro-propoxy)-4-hydroxy-6-methoxy-quinoline-3-carbonitrile and 28 ml of phosphorous oxychloride was refluxed for 1.5 hr. Excess reagent was removed at reduced pressure. The residue was mixed with ice cold dilute sodium hydroxide and ethyl acetate. The mixture was extracted with a combination of ethyl acetate and tetrahydrofuran. The combined extracts were washed with a saturated solution of sodium bicarbonate, dried over magnesium sulfate, and filter through a short column of silica gel. Solvents were removed giving 3.2 g of the title compound as a pink solid that is used with additional purification.

EXAMPLE 55

7-(2-Chloro-ethoxy)-4-chloro-6-methoxy-quinoline-3-carbonitrile

A solution of 8 g (28.7 mmol) of 7-(2-Chloro-ethoxy)-4-hydroxy-6-methoxy-quinoline-3-carbonitrile and 18.2 g (143.5 mmol) of oxalyl chloride in 80 ml of methylene chloride containing 0.26 g of dimethylformamide was stirred at reflux for 2.5 hr. The solvent was removed. The residue was mixed with cold dilute sodium hydroxide and extracted several time with ethyl acetate and tetrahydrofuran. The combined extracts were dried over magnesium sulfate and the solution was passed through a short silica gel column. The solvents were removed giving 6.0 g of the title compound as an off-white solid that is used without additional purification.

EXAMPLE 56

4-Chloro-6-ethoxy-7-methoxyquinoline-3-carbonitrile

A mixture of 7.95 g (32.6 mmol) of 6-ethoxy-7-methoxy-4-oxo-1,4-dihydroquinoline-3-carbonitrile and 50 mL of phosphorous oxychloride was refluxed for 3 h 40 min. The phosphorous oxychloride was removed in vacuo and the residue was slurried with ice water. Solid $NaHCO_3$ was added (pH8) and the product was collected by filtration, washed well with water and dried in vacuo (40° C.). The yield was 7.75 g of 4-chloro-6-ethoxy-7-methoxyquinoline-3-carbonitrile as a tan solid: mass spectrum (electrospray, m/e): M+H 262.8, 264.8.

EXAMPLE 57

6-Ethoxy-7-methoxy-4-oxo-1,4-dihydroquinoline-3-carbonitrile

A solution of 10.2 g (45.3 mmol) of methyl 2-amino-5-ethoxy-4-methoxy benzoate and 10.8 g (90.7 mmol) of dimethylformamide dimethyl acetal in 50 mL of dimethyl-formamide was refluxed for 3 h. Volatile material was removed and the residue was azeotroped with toluene and dried in vacuo to give the formamidine as a purple syrup. n-Butyllithium (100 mmol) in hexane was diluted with 60 mL of tetrahydrofuran at −78° C. A solution of 4.18 g (102 mmol) of acetonitrile in 80 mL of tetrahydrofuran was added over 15 min and the solution was stirred for 20 min. The crude formamidine was dissolved in 80 mL of tetrahydrofuran and added dropwise to the cold solution over 0.5 h. After stirring for 2 h, the reaction was quenched at −78° C. with 13 mL of acetic acid. It was allowed to warm to room temperature and volatile material was removed in vacuo. The residue was slurried with water and the crude product was collected by filtration washed with water and dried. This material was then washed with chloroform and dried to give 7.95 g of 6-ethoxy-7-methoxy-4-oxo-1,4-dihydroquinoline-3-carbonitrile as yellow crystals: mass spectrum (electrospray, m/e): M−H 243.2.

EXAMPLE 58

Methyl 2-Amino-5-ethoxy-4-methoxybenzoate

A mixture of 17.0 g (66.7 mmol) of methyl 5-ethoxy-4-methoxy-2-nitrobenzoate, 13.1 g (233 mmol) of powdered iron and 17.7 g (334 mmol) of ammonium chloride in 95 mL of water and 245 mL of methanol was refluxed for 4.5 h. An additional 13.1 g of iron was added followed by refluxing for 2.5 h. Then an additional 13.1 g of iron and 17.7 g of ammonium chloride was added and refluxing was continued for 12 h. The reaction was filtered through Celite and methanol was removed from the filtrate. The filtrate was extracted with chloroform and the extracts were treated with Darco, evaporated and dried in vacuo (50° C.). The yield was 11.0 g of methyl 2-amino-5-ethoxy-4-methoxybenzoate as tan crystals: mass spectrum (electrospray, m/e): M+H 225.9.

EXAMPLE 59

Methyl 5-Ethoxy-4-methoxy-2-nitrobenzoate

A mixture of 15.0 g (74.1 mmol) of methyl 3-ethoxy-4-methoxybenzoate in 45 mL of acetic acid was treated with 15 mL of conc nitric acid dropwise over 12 min. The reaction was kept at 55° C. for 45 min, cooled to 25° C. and poured into ice water. The product was extracted into methylene chloride and the extracts were washed with water and dil sodium hydroxide, dried and evaporated. The yield was 17.8 g of methyl 5-ethoxy-4-methoxy-2-nitrobenzoate as yellow crystals: mass spectrum (electrospray, m/e): M+H 256.0.

EXAMPLE 60

Methyl 3-Ethoxy-4-methoxybenzoate

A mixture of 24.3 g (134 mmol) of methyl 3-hydroxy-4-methoxybenzoate, 36.8 g (267 mmol) of anhyd potassium carbonate and 31.4 g (201 mmol) of ethyl iodide in 500 mL of dimethylformamide was stirred at 100° C. for 5.5 h. An additional amount of ethyl iodide (31.4 g) and potassium carbonate (18.4 g) was added and heating was continued for 2 h more. The reaction was filtered and volatile material was removed from the filtrate in vacuo. The residue was slurried with water and filtered to collect the product which was washed with water and dried. Recrystallization from heptane gave 15.6 g of methyl 3-ethoxy-4-methoxybenzoate as white crystals: mass spectrum (electrospray, m/e): M+H 210.9.

EXAMPLE 61

Methyl 3-Hydroxy-4-methoxybenzoate

A solution of 30.8 g (183 mmol) of 3-hydroxy-4-methoxybenzoic acid and 6 mL of conc sulfuric acid in 600 mL of methanol was refluxed overnight. Most of the solvent was removed and the remaining solution was poured into 600 mL of water containing 25 g of sodium bicarbonate. The product was extracted into ether, treated with Darco, dried and evaporated. The yield was 31.8 g of methyl 3-hydroxy-4-methoxybenzoate as pale yellow crystals.

EXAMPLE 62

N'-[2-Carbethoxy-4,5-bis(2-methoxyethoxy)phenyl]-N,N-dimethylformamidine

To a stirred solution of 15.7 g (50 mmol) of ethyl 2-amino-4,5-bis(2-methoxyethoxy)benzoate (WO-96130347) in 50 ml of DMF at 0° C. was added phosphorous oxychloride (5.6 ml, 60 mmol) during 15 m. The resulting solution was heated at 55° C. for 45 m, cooled, diluted with methylene chloride, and treated at 0° C. with 200 ml of N/1 sodium hydroxide during 2 m. The organic layer was separated and washed at 0° C. with water. The solution was dried and evaporated with added toluene present to give 18.4 g of amber oil; NMR (CDCl$_3$) δ 3.02 (s, Me$_2$N).

EXAMPLE 63

1,4-Dihydroquinoline-5,6-bis(2-methoxyethoxy)-3-carbonitrile

To a stirred solution of n-butylllithium (44 ml of 2.5 M in hexane; 110 mmol) in 65 ml of THF at −78° C. was added a solution of acetonitrile (5.85 ml, 112 mmol) in 110 ml of THF during 10 m. After stirring at −78° C. for 15 m, the mixture was treated with a solution of N'-[2-carbethoxy-4,5-bis(2-methoxyethoxy)phenyl]-N,N-dimethylformamidine in 75 ml of THF during 20 m. After 30 m at −78° C. the stirred mixture was treated with acetic acid (14.3 ml, 250 mmol). The mixture was warmed to 25° C. and stirred for 2 h. The mixture was evaporated to dryness, and diluted with water. The resulting white solid was filtered, washed with water, and dried to give 10.7 g; mass spectrum (electrospray, m/e) M+H 319.2.

EXAMPLE 64

4-Chloro-5,6-bis(2-methoxyethoxy)-quinoline-3-carbonitrile

A stirred mixture of 1,4-dihydroquinoline-5,6-bis(2-methoxyethoxy)-3-carbonitrile 9.68 g, 30.4 mmol) and 30 ml of phosphorous oxychloride was refluxed for 1.5 h. The resulting solution was concentrated under vacuum, and the residue was stirred with methylene chloride at 0° C. as ice-water and sodium carbonate were added until pH of mixture was 8–9. The organic layer was separated, washed with water, dried and concentrated to give a tan solid; mass spectrum (electrospray, m/e) M+H 337.1, 339.1.

EXAMPLE 65

Methyl 4-methoxy-3-(3-morpholin-4-yl-propoxy))benzoate

A stirred mixture of methyl isovanillate (22.6 g, 124 mmol), N-(3-chloropropyl)-morpholine (25.4 g, 155 mmol), potassium carbonate (18.8 g, 136 mmol), tetrabutylammonium iodide (0.92 g, 2.5 mmol), and 248 ml of 2-butanone was refluxed for 20 h. The 2-butanone was evaporated off, and the residue was stirred with water at 0° C. The resulting white solid was filtered off, washed successively with water and hexane, and dried; mp 90–94° C.

EXAMPLE 66

Methyl 4-methoxy-5-(3-morpholin-4-yl-propoxy))-2-nitrobenzoate

To a stirred solution of methyl 4-methoxy-3-(3-morpholin-4-yl-propoxy))benzoate (30.9 g, 100 mmol) in 100 ml of acetic acid at 25° C. was added 50 ml of 70% nitric acid during 30 m. The solution was heated to 45° C. at which point the reaction started and was self-sustaining at that temperature. After a total of 1.5 h at 45–50° C. the mixture was cooled to 0° C., treated with ice-water and 240 g (1.75 mol) of potassium carbonate, and extracted with ethyl acetate. The extract was washed with water, dried, and concentrated to give a yellow solid, mp 78–82° C.

EXAMPLE 67

Methyl 2-amino-4-methoxy-5-(3-morpholin-4-yl-propoxy))benzoate

A solution of methyl 4-methoxy-3-(3-morpholin-4-yl-propoxy))-2-nitrobenzoate (32.5 g, 91.7 mmol) in 110 ml of methanol and 220 ml of ethyl acetate was hydrogenated at 55 psi in the presence of 2.0 g of 10% Pd on carbon catalyst at 25° C. After 4 h the mixture was filtered, and the filtrate was evaporated to dryness. The residue was recrystallized from acetone-hexane to give a tan solid, mp 78–82° C.

EXAMPLE 68

Ethyl 2-(dimethylaminomethyleneamino)-4-methoxy-5-(3-morpholin-4-yl-propoxy))benzoate A mixture of methyl 2-amino-4-methoxy-5-(3-morpholin-4-yl-propoxy))benzoate (6.49 g, 20 mmol) and dimethylformamide dimethyl acetal (4.25 ml, 30 mmol) was heated at 100° C. for 1.5 h. All volatile materials were evaporated off directly at 70° C. to give a syrup; mass spectrum (electrospray, m/e) M+H 380.5.

EXAMPLE 69

1,4-Dihydroquinoline-7-methoxy-6-(3-morpholin-4-yl-propoxy))-4-oxo-3-carbonitrile To a stirred solution of n-butylllithium (17.6 ml of 2.5 M in hexane; 44 mmol) in 26 ml of THF at −78° C. was added a solution of acetonitrile (1.85 ml, 45 mmol) in 44 ml of THF during 10 m. After stirring at −78° C. for 15 m, the mixture was treated with a solution of ethyl 2-(dimethylaminomethyleneamino)-4-methoxy-5-(3- morpholin-4-yl-propoxy))benzoate (7.6 g, 20 mmol) in 30 ml of THF during 20 m. After 90 m at −78° C. the mixture was treated with carbon dioxide while warming slowly to 25° C. and then evaporated to dryness. The residue was partitioned with n-butanol (200 ml) and half-saturated NaCl solution (40 ml). The organic layer was separated, washed with saturated NaCl solution, and evaporated to dryness. The resulting solid was triturated successively with boiling acetone and methanol, filtered, and dried to give a tan solid, mp 255–260° C.

EXAMPLE 70

4-Chloro-7-methoxy-6-(3-morpholin-4-yl-propoxy))-quinoline-3-carbonitrile

A stirred mixture of 1,4-Dihydroquinoline-7-methoxy-6-(3-morpholin-4-yl-propoxy))-4-oxo-3-carbonitrile (4.75 g, 13.8 mmol), 0.10 ml of DMF, and 55 ml of thionyl chloride was refluxed for 3 h. Volatile matter was removed by evaporation at 30° C., and the residue was stirred at 0° C. with a mixture of methylene chloride and water containing potassium carbonate to give pH 9–10. The organic layer was separated, washed with water, dried and concentrated to give a brown solid; mass spectrum (electrospray, m/e) M+H 362.4, 364.4.

EXAMPLE 71

4-Chloro-7-ethoxy-6-methoxy-quinoline-3-carbonitrile

Mixed 122 mg (0.50 mmol) 7-ethoxy-1,4-dihydro-6-methoxy-4-oxo-quinoline-3-carbonitrile and 2.0 ml methylene chloride under $N_2$ and kept temperature near 25° C. Added 218 µl (2.5 mmol) oxalyl chloride and 10 µl (0.125 mmol) DMF. Stirred overnight, diluted with chloroform and stirred in saturated sodium bicarbonate until basic. Separated layers and dried organics with magnesium sulfate, stripped solvent and dried in vacuo, giving 117 mg of tan solid: mass spectrum (electrospray m/e): M+H=262.8, 264.8.

EXAMPLE 72

7-Ethoxy-1,4-dihydro-6-methoxy-4-oxo-quinoline-3-carbonitrile

Added 54.0 ml (135 mmol) n-butyl lithium to 150 ml THF and chilled to −78° C. under $N_2$. Added dropwise over 20 minutes 7.05 ml (135 mmol) acetonitrile in 200 ml THF. Stirred 15 minutes and added a solution of 17.99 g (64.2 mmol) methyl 4-ethoxy-5-methoxy-2-(dimethylaminomethyleneamino)benzoate in 150 ml THF dropwise over 20 minutes. Let stir for 0.5 hour at −78° C. Added 11.0 ml (193 mmol) acetic acid and warmed gradually to 25° C. After 2.5 hours, stripped solvent, slurried residue with water, collected solids and dried in vacuo, giving 13.025 g of yellow solid: mass spectrum (electrospray m/e): M+H=245.2.

EXAMPLE 73

Methyl 4-ethoxy-5-methoxy-2-(dimethylaminomethyleneamino)benzoate

A mixture of 15.056 g ( 66.9 mmol) methyl 2-amino-4-ethoxy-5-methoxybenzoate and 14.1 ml (100 mmol) N,N-dimethylformamide dimethylacetal was heated to 100° C. under $N_2$. At 4.5 hours added 4.7 ml (33.3 mmol) more DMF/DMA and removed heat at 5 hours. Stripped solvent, azeotroped with toluene, and dried in vacuo, giving 18.211 g of grey-brown solid: mass spectrum (electrospray m/e): M+H=281.3.

EXAMPLE 74

Methyl 2-amino-4-ethoxy-5-methoxybenzoate

A mixture of 24.110 g (94.5 mmol) methyl 4-ethoxy-5-methoxy-2-nitrobenzoate, 15.81 g (283 mmol) iron powder, 25.28 g (472 mmol) ammonium chloride, 135 ml water, and 350 ml methanol was heated to reflux under $N_2$. At both 3 and 5.5 hours added the same amount of iron and ammonium chloride. Removed heat at 6.5 hours, added ethyl acetate and saturated sodium bicarbonate, filtered through celite and separated layers. Washed organic layer with saturated sodium bicarbonate, dried with magnesium sulfate, stripped solvent, and dried in vacuo, giving 17.594 g of pink solid: mass spectrum (electrospray m/e): M+H= 226.2.

EXAMPLE 75

Methyl 4-ethoxy-5-methoxy-2-nitrobenzoate

Dissolved 5.00g (23.7 mmol) methyl 4-ethoxy-3-methoxybenzoate in 25 ml acetic acid under $N_2$ and added 6.1 ml (95.1 mmol) 69% nitric acid dropwise over 30 minutes. Heated to 50° C. for 1.5 hours and poured onto ice bath. Extracted with chloroform, washed with dilute sodium hydroxide solution and filtered through magnesium sulfate. Stripped solvent and dried in vacuo, giving 5.268 of off-white solid: mass spectrum (electrospray m/e): M+H=255.8.

EXAMPLE 76

Methyl 4-ethoxy-3-methoxybenzoate

A mixture of 25.0 g (137 mmol) methyl vanillate, 38.87 g (274 mmol) potassium carbonate, 500 ml DMF, and 16.5 ml (206 mmol) ethyl iodide was heated to 100° C. under $N_2$. At 2.5 hours, cooled and removed solids. Stripped solvent, and partitioned between water and methylene chloride. Stripped solvent and dried in vacuo, giving 25.85 g of white solid: mass spectrum (EI m/e): M=210.0.

EXAMPLE 77

7-Ethoxy-4-hydroxy-quinoline-3-carbonitrile

A mixture of 10 g (73 mmol) of 3-ethoxy aniline and 12.3 g (73 mmol) of ethyl (ethoxymethylene) cyanoacetate was heated in 90 ml of Dowther at 140° C. for 7 hours. To this mixture was added 250 ml of Dowther. The solution was stirred and refluxed under nitrogen for 12 hours with periodically distilling out the eliminated ethanol. The mixture was cooled to room temperature and the solid was collected and washed with hexane. The crude solid was treated with boiling ethanol and then filtered to give 9.86 g of brown solid: mass spectrum (electrospray, m/e): M+H 214.7.

EXAMPLE 78

7-Ethoxy-4-hydroxy-6-nitro-quinoline-3-carbonitrile

To a suspension of 5 g (23 mmol) of 7-Ethoxy-4-hydroxy-quinoline-3-carbonitrile in 75 ml of trifluroacetic anhydride was added 5.5 g (69 mmol) of ammonium nitrate over a period of 6 hours at room temperature. Excess anhydride was removed at reduced pressure at 45° C. The residue was stirred with 300 ml of water. The solid was collected and treated with boiling ethanol to give 3.68 g of tin solid: mass spectrum (electrospray, m/e) M+H 259.8.

EXAMPLE 79

4-Chloro-7-ethoxy-6-nitro-quinoline-3-carbonitrile

A mixture of 3.45 g (13 mmol) of 7-Ethoxy-4-hydroxy-6-nitro-quinoline-3-carbonitrile, 5.55 g (26 mmol) of phosphorous pentachloride, and 10 ml of phosphorous oxychloride was refluxed for 3 hours. The mixture was diluted with hexane and the solid was collected. The solid was dissolved in 500 ml of ethyl acetate and washed with cold diluted sodium hydroxide solution. The solution was dried over magnesium sulfate and filtered through a pad of silica gel. The solvent was removed giving 2.1 g of beige solid: mass spectrum (electrospray, m/e) M+H 277.7.

EXAMPLE 80

8-Methoxy-4-hydroxy-6-nitro-quinoline-3-carbonitrile

A mixture of 12.6 g (75 mmol) of 2-methoxy-4-nitro aniline and 12.7 g (75 mmol) of ethyl (ethoxymethylene) cyanoacetate was heated in 100 ml of Dowther at 120° C. for overnight and 180° C. for 20 hours. To this mixture was added 300 ml of Dowther. The solution was stirred and refluxed under nitrogen for 12 hours with periodically distilling out the eliminated ethanol. The mixture was cooled to room temperature and the solid was collected and washed with hexane. The crude solid was treated with boiling ethanol and then filtered to give 12 g of brown solid: mass spectrum (electrospray, m/e): M+H 245.8.

EXAMPLE 81

4-Chloro-8-methoxy-6-nitro-quinoline-3-carbonitrile

A mixture of 4 g (16 mmol) of 8-Methoxy-4-hydroxy-6-nitro-quinoline-3-carbonitrile, 6.66 g (32 mmol) of phosphorous pentachloride, and 15 ml of phosphorous oxychloride was refluxed for 2.5 hours. The mixture was diluted with hexane and the solid was collected. The solid was dissolved in 500 ml of ethyl acetate and washed with cold diluted sodium hydroxide solution. The solution was dried over magnesium sulfate and filtered through a pad of silica gel. The solvent was removed giving 2.05 g of tan solid: mass spectrum (electrospray, m/e) M+H 263.7.

EXAMPLE 82

4-Hydroxy-6,7,8-trimethoxy-quinoline-3-carbonitrile

A mixture of 4.82 g of methyl 3,4,5-trimethoxyanthranilate in 20 ml of N,N-dimethylformamide dimethyl acetal was refluxed for 18 hours and concentrated in vacuo. The crude amidine product was used in the next step without further purification.

To 25 ml of tetrahydrofuran at −78° C. was added 17.6 ml of 2.5M n-butyllithium in hexanes. Then 2.35 ml of acetonitrile in 45 ml of tetrahydrofuran was added dropwise. The mixture was stirred at −78° C. for 15 minutes. Then a solution of the crude amidine in 30 ml of tetrahydrofuran was added dropwise. The mixture was stirred at −78° C. for 30 minutes, then 5.7 ml of acetic acid was added. The mixture was warmed to room temperature, and 100 ml of water was added. The product was collected, washed with water, and dried to give 4.14 g of 4-hydroxy-6,7,8-trimethoxy-quinoline-3-carbonitrile as a solid, mp 280° C. (decomposed); mass spectrum (electrospray, m/e): M+H 261.2.

EXAMPLE 83

4-Chloro-6,7,8-trimethoxy-quinoline-3-carbonitrile

A stirred mixture of 1.30 g of 4-hydroxy-6,7,8-trimethoxy-quinoline-3-carbonitrile, 10 ml of phosphorous oxychloride, and 1 drop of N,N-dimethylformamide was refluxed for 10 minutes and evaporated free of volatile matter. The residue was stirred with 20 ml of 5% methyl alcohol in ethyl acetate. The product was collected and dried to give 1.12 g of 4-chloro-6,7,8-trimethoxy-quinoline-3-carbonitrile as a solid, mp 161–163° C.; mass spectrum (EI, m/e): M 278.0452.

EXAMPLE 84

2-(Dimethylamino-methyleneamino)-3,6-dimethoxy-benzoic acid methylester

A mixture of 3.46 g of 2-amino-3,6-dimethoxybenzoic acid (Manouchehr Azadi-Ardakani and Timothy W. Wallace, Tetrahedron, Vol. 44, No. 18, pp. 5939 to 5952, 1988) in 20 ml of N,N-dimethylformaide dimethyl acetal was refluxed for 18 hours and concentrated in vacuo. To the residue was added 180 ml of ethyl acetate. The mixture was filtered, and 200 ml of hexanes was added to the filtrate. The mixture was then concentrated to 100 ml. The product was collected and dried to give 3.25 g of 2-(dimethylamino-methyleneamino)-3,6-dimethoxy-benzoic acid methylester as a solid, mp 81–83° C.; mass spectrum (EI, m/e): M 266.1263.

EXAMPLE 85

4-Hydroxy-5,8-dimethoxy-quinoline-3-carbonitrile

To 12.5 ml of tetrahydrofuran at −78° C. was added 8.8 ml of 2.5M n-butyllithium in hexanes. Then 1.18 ml of acetonitrile in 25 ml of tetrahydrofuran was added dropwise. The mixture was stirred at −78° C. for 15 minutes. Then a solution of 2-(dimethylamino-methyleneamino)-3,6-dimethoxy-benzoic acid methylester in 62 ml of tetrahydrofuran was added dropwise. The mixture was stirred at −78° C. for 10 minutes, then warmed to room temperature in 15 minutes. Acetic acid (3 ml) was added, followed by 200 ml of water. The product was collected, washed with water, and dried to give 1.57 g of 4-hydroxy-5,8-dimethoxy-quinoline-3-carbonitrile as a solid, mp 300–305° C.; mass spectrum (EI, m/e): M 230.0685.

EXAMPLE 86

4-Chloro-5,8-dimethoxy-quinoline-3-carbonitrile

A stirred mixture of 1.30 g of 4-hydroxy-5,8-dimethoxy-quinoline-3-carbonitrile, 10 ml of phosphorous oxychloride, and 2 drops of N,N-dimethylformamide was refluxed for 10 minutes and evaporated free of volatile matter. The residue was stirred with 50 ml of water. The product was collected and dried to give 1.74 g of 4-chloro-5,8-dimethoxy-quinoline-3-carbonitrile as a solid, mp 165–167° C.; mass spectrum (EI, m/e): M 248.0346.

EXAMPLE 87

Methyl 2-(dimethylaminomethyleneamino)-4,5-diethoxybenzoate

To a stirred solution of methyl 2-amino-4,5-diethoxybenzoate (4.79 g, 20 mmol) in 20 ml of DMF at 0°

C. was added phosphorous oxychloride (2.24 ml, 24 mmol) during 15 m. The mixture was warmed to 55° C. and stirred for 45 m. The resulting solution was diluted with methylene chloride, cooled to 0° C., and treated with 80 ml of pre-cooled N/1 sodium hydroxide during 5 m. The organic layer was separated and washed at 0° C. with with water. The solution was dried and concentrated to give an amber oil; NMR (CDCl$_3$) δ3.00(s, Me$_2$N).

EXAMPLE 88

1.4-Dihydroquinoline-6,7-diethoxy-4-oxo-3-carbonitrile

To a stirred solution of n-butylllithium (17.6 ml of 2.5 M in hexane; 44 mmol) in 25 ml of THF at –78° C. was added a solution of acetonitrile (2.35 ml, 45 mmol) in 44 ml of THF during 10 m. After stirring at –78° C. for 15 m, the mixture was treated with a solution of ethyl 2-(dimethylaminomethyleneamino)-4,5-diethoxybenzoate (5.83 g, 19.8 mmol) in 30 ml of THF during 30 m. After 30 m at –78° C. the mixture was treated with 5.7 ml (100 mmol) of acetic acid and evaporated to dryness. The residue was stirred in water, and the resulting precipitate was filtered off, washed with water, and dried to give 4.01 g of off-white solid; NMR (DMSO-d$_6$) d 8.58(s, 2-H).

EXAMPLE 89

4-Chloro-6,7-diethoxy-quinoline-3-carbonitrile

In the manner of Example 64 treatment of 1,4-dihydroquinoline-6,7-diethoxy-4-oxo-3-carbonitrile with phosphorous oxychloride gave the title compound as a pink solid, mp 170–175° C.

EXAMPLE 90

2-(Dimethylamino-methyleneamino)-3-methoxy-benzoic acid methyl ester

A reaction mixture of 5.0 g (29.9 mmol) of 2-amino-3-methoxy-benzoic acid in 25.0 mL of DMF-DMA was heated at 100–105° C. for 2.5 hr, and then the solvent was removed to give a red-purple viscous oil. After standing in a refrigerator, the oil solidified to give 5.8 g of the product as a red-purple solid in 82.8% yield, mass spectrum (electrospray, m/e): M+H 236.9

EXAMPLE 91

1,4-Dihydro-8-methoxy-4-oxo-quinoline-3-carbonitrile

To 35.0 mL of THF was added 26.6 mL (66.4 mmol ) of n-BuLi solution during 5 min at –78° C. To the stirred solution was added a solution of 3.55 mL (67.9 mmol) of CH$_3$CN in 65 mL of THF during 10 min which time the solution became white suspension, and then continued to stir for 15 min at –78° C. To the suspension was added a solution of 5.8 g (24.5 mmol) of 2-(Dimethylamino-methyleneamino)-3-methoxy-benzoic acid methyl ester in 45 mL of THF during 30 min, and then continued to stir 30 min at –78° C. during which time the mixture gradually became clear. The solution was quenched with 8.5 mL of HOAc. The resulting thick slurry was stirred and warmed to room temperature. After most of the solvent was evaporated, the residue was diluted with cold water. The separate solid was collected by filtration and washed with water. After drying in vacuo, this afforded 3.8 g of the product as an off white solid in 77.6% of yield, m.p. 270° C. (dec.), mass spectrum (electrospray, m/e): M+H 201.1

EXAMPLE 92

4-Chloro-8-methoxy-quinoline-3-carbonitrile

A mixture of 3.8 g (19 mmol) of 1,4-dihydro-8-methoxy-4-oxo-quinoline-3-carbonitrile and 40 mL of phosphorous oxochloride and 5 drops of DMF was refluxed for 0.5 hours. The mixture was evaporated to dryness and diluted with hexanes. The solid was collected and mixed with cold dilute sodium carbonate solution and extracted several times with ethyl acetate. The organic layer was dried over sodium sulfate and filtered through a pad of silica gel. Removal of the solvent gave 3.8 g of 4-chloro-8-methoxy-quinoline-3-carbonitrile as an off white solid in 91% yield, mass spectrum (electrospray, m/e): M+H 219.1.

EXAMPLE 93

4-Chloro-7-methoxy-quinoline-3-carbonitrile

In the manner of Example 64 treatment of 1,4-dihydroquinolin-7-methoxy-4-oxo-3-carbonitrile with phosphorous oxychloride gave the title compound as a tan solid; mass spectrum (electrospray, m/e) M+H 219.2, 221.2.

EXAMPLE 94

7-benzyloxy-4-hydroxy-6-methoxy-quinoline-3-carbonitrile

To a stirred solution of 26.9 ml of n-butyllithium (2.5 M in hexane) in 50 ml of THF at –78° C. was added a 3.51 ml of acetonitrile in 20 ml of THF during 10 min. After stirring at –78° C. for 30 min, the mixture was treated with 10 g of L17741-150 (B. Floyd) in 20 ml of THF during 5 min. After 15 min at –78° C. the stirred mixture was warmed to 0° C. for a further 30 min. It was then treated with 5 ml of acetic acid, warmed to 25° C. and stirred for 30 min. The mixture was evaporated to dryness, and diluted with aqueous sodium bicarbonate. The resulting off-white solid was filtered, washed with water, ethyl acetate and ether. After drying, 4.5 g of 7-benzyloxy-4-hydroxy-6-methoxy-quinoline-3-carbonitrile was obtained as an off-white solid, dec >255° C.; mass spectrum (electrospray, m/e) M+H 307.

EXAMPLE 95

7-benzyloxy-4-chloro-6-methoxy-quinoline-3-carbonitrile

To a stirred suspension of 1 g of 7-benzyloxy-4-hydroxy-6-methoxy-quinoline-3-carbonitrile in 10 ml of methylene chloride was added 5 ml of oxalyl chloride (2M in methylene chloride), and 2 drops of N,N-dimethylformamide. The mixture was refluxed for 20 min and to it was slowly added aqueous sodium bicarbonate until the bubbling ceased. Following separation of the layers, the organic layer was evaporated to a small volume, then passed through a plug of magnesol. Elution with 50 ml methylene chloride, followed by evaporation provided 0.6 g of 7-benzyloxy-4-chloro-6-methoxy-quinoline-3-carbonitrile as a pale yellow solid, mp 282–284° C.; mass spectrum (electrospray, m/e) M+H 325.

EXAMPLE 96

4-(2,3-Dihydro-1H-indol-6-ylamino)-6,7-diethoxy-quinoline-3-carbonitrile

A solution of 400 mg (1.44 mM) of 4-chloro-6,7-diethoxy-quinoline-3-carbonitrile and 258 mg (1.88 mM) of 6-Aminoindoline dihydrochloride salt in 10 ml of ethanol was refluxed for 3 hours. To the warm solution was added 1 ml of 1M sodium carbonate and the sample was heated for 5 minutes at 100° C., then poured into 300 ml of ice water. The solid was collected, washed with water followed by ether and dried under vacuum at 80° C. The solid was dissolved in 50/50 methanol/chloroform and dried onto silica gel and purified by chromatography using a gradient of 20% to 50% acetone in hexane to yield 496 mg of the title compound as a tan solid: mass spectrum (electrospray, m/e): M+H 375.1, mp=121–124° C.

EXAMPLE 97

4-(Benzothiazol-6-ylamino)-6,7-diethoxy-quinoline-3-carbonitrile HCl Salt

A solution of 500 mg (1.8 mM) of 4-chloro-6,7-diethoxy-quinoline-3-carbonitrile and 353 mg (2.35 mM) of 6-aminobenzothiozole in 15 ml of ethanol was refluxed for 3 hours. To the warm solution was added 2 drops of concentrated HCl and the sample was heated for 5 minutes at 100° C., then the solid was isolated by filtration. The solid was taken up into 20 ml of ethanol and digested for 1 hour. The hot solution was filtered and the isolated solid was washed with ethanol and dried under vacuum at 80° C. to yield 666 mg of 4-(benzothiazol-6-ylamino)-6,7-diethoxy-quinoline-3-carbonitrile HCl Salt as a tan solid: mass spectrum (electrospray, m/e): M+H 391.0, mp=285–287° C.

EXAMPLE 98

4-(Benzo[1,3]dioxol-5-ylamino)-6,7-diethoxy-quinoline-3-carbonitrile

A solution of 400 mg (1.44 mM) of 4-chloro-6,7-diethoxy-quinoline-3-carbonitrile and 258 mg (1.88 mM) of 3,4-(methylenedioxy) aniline in 10 ml of ethanol was refluxed for 3 hours. To the warm solution was added 1 ml of 1M sodium carbonate and the sample was heated for 5 minutes at 100° C., then poured into 300 ml of ice water. The solid was collected, washed with water followed by ether and dried under vacuum at 80° C. to yield 526 mg of 4-(Benzo[1,3]dioxol-5-ylamino)-6,7-diethoxy-quinoline-3-carbonitrile as a tan solid: mass spectrum (electrospray, m/e): M+H 378.0, mp=200–203° C.

EXAMPLE 99

6.7-Diethoxy-4-(1H-indazol-6-ylamino)-quinoline-3-carbonitrile

A solution of 400 mg (1.44 mM) of 4-chloro-6,7-diethoxy-quinoline-3-carbonitrile and 250 mg (1.88 mM) of 6-aminoindazole in 10 ml of ethanol was refluxed for 3 hours. To the warm solution was added 1 ml of 1M sodium carbonate and the sample was heated for 5 minutes at 100° C., then poured into 300 ml of ice water. The solid was collected, washed with water followed by ether and dried under vacuum at 80° C. to yield 448 mg of 6,7-Diethoxy-4-(1H-indazol-6-ylamino)-quinoline-3-carbonitrile as a tan solid: mass spectrum (electrospray, m/e): M+H 374.1, mp=143–145° C.

EXAMPLE 100

6,7-Diethoxy-4-(4-methyl-2-oxo-2H-chromen-7-ylamino)-quinoline-3-carbonitrile

A solution of 400 mg (1.44 mM) of 4-chloro-6,7-diethoxy-quinoline-3-carbonitrile and 330 mg (1.88 mM) of 7-Amino-4-methyl-coumarin in 15 ml of 2-methoxyethanol was refluxed for 3 hours. To the warm solution was added 1 ml of 1M sodium carbonate and the sample was heated for 5 minutes at 100° C., then poured into 300 ml of ice water. The solid was collected, washed with water followed by ether and dried under vacuum at 80° C. to yield 431 mg of 6,7-Diethoxy-4-(4-methyl-2-oxo-2H-chromen-7-ylamino)-quinoline-3-carbonitrile as a tan solid: mass spectrum (electrospray, m/e): M+H 416.0, mp=282–284° C.

EXAMPLE 101

6,7-Diethoxy-4-(1H-indol-6-ylamino)-quinoline-3-carbonitrile

A solution of 964 mg (3.50 mM) of 4-chloro-6,7-diethoxy-quinoline-3-carbonitrile and 830 mg (6.29 mM) of 6-Aminoindole in 5 ml of 2-methoxyethanol was refluxed for 3 hours. To the warm solution was added 1 ml of 1M sodium carbonate and the sample was heated for 5 minutes at 100° C., then poured into 300 ml of ice water. The solid was collected, washed with water followed by ether and dried under vacuum at 80° C. to yield 712 mg of 6,7-Diethoxy-4-(1H-indol-6-ylamino)-quinoline-3-carbonitrile as a yellow solid: mass spectrum (electrospray, m/e): M+H 373.0, mp=128–130° C.

EXAMPLE 102

6,7-Dimethoxy-4-(1H-indazol-6-ylamino)-quinoline-3-carbonitrile

A solution of 500 mg (2.00 mM) of 4-chloro-6,7-dimethoxy-quinoline-3-carbonitrile and 975 mg (2.61 mM) of 6-aminoindazole in 15 ml of 2-methoxyethanol was refluxed for 3 hours. To the warm solution was added 1 ml of 1M sodium carbonate and the sample was heated for 5 minutes at 100° C., then poured into 300 ml of ice water. The solid was collected, washed with water followed by ether and dried under vacuum at 80° C. to yield 738 mg of the title compound as a tan solid: mass spectrum (electrospray, m/e): M+H 345.9, mp=180–183° C.

EXAMPLE 103

4-(1H-Benzotriazol-5-ylamino)-6,7-diethoxy-quinoline-3-carbonitrile

A solution of 1.07 mg (3.87 mM) of 4-chloro-6,7-diethoxy-quinoline-3-carbonitrile and 675 mg (5.00 mM) of 5-Aminobenzotriazole in 15 ml of 2-methoxyethanol was refluxed for 3 hours. To the warm solution was added 1 ml of 1M sodium carbonate and the sample was heated for 5 minutes at 100° C., then poured into 300 ml of ice water. The solution was made acetic by addition of concentrated HCl and the solid was collected, washed with water followed by ether and dried under vacuum at 80° C. The solid was taken up into 200 ml of methanol and 500 μl of 5 N sodium hydroxide and boiled for 20 minutes. To this heterogeneous mixture was added 100 ml of glacial acetic acid and the volume was reduced to a total of 100 ml by boiling. To the room temperature mixture, 500 ml of ice cold water was added and the solid was collected, washed with water followed by ether and dried under vacuum at 80° C. to yield 738 mg of Name as a brown solid: mass spectrum (electrospray, m/e): M+H 375.0, mp=Decomposed at 115° C.

EXAMPLE 104

4-(1,3-Dioxo-2,3-dihydro-1H-isoindol-5-ylamino)-6,7-diethoxy-quinoline-3-carbonitrile A solution of 400 mg (1.44 mM) of 4-chloro-6,7-diethoxy-quinoline-3-carbonitrile and 305 mg (1.88 mM) of 4-Aminophthalimide in 10 ml of ethanol was refluxed for 3 hours. To the warm solution was added 1 ml of 1M sodium carbonate and the sample was heated for 5 minutes at 100° C., then poured into 300 ml of ice water. The solid was collected, washed with water followed by ether and dried under vacuum at 80° C. to yield 348 mg of 4-(1,3-Dioxo-2,3-dihydro-1H-isoindol-5-ylamino)-6,7-diethoxy-quinoline-3-carbonitrile as a yellow solid: mass spectrum (electrospray, m/e): M+H 402.9, mp=248–251° C.

EXAMPLE 105

4-(2,3-Dihydro-benzo[1,4]dioxin-6-ylamino)-6,7-diethoxy-quinoline-3-carbonitrile A solution of 400 mg (1.44 mM) of 4-chloro-6,7-diethoxy-quinoline-3-carbonitrile and 232 mg (1.54 mM) of 1,4-Benzodioxane-6-amine in 15 ml of 2-methoxyethanol was refluxed for 3 hours. To the warm solution was added 1 ml of 1M sodium carbonate and the sample was heated for 5 minutes at 100° C., then poured into 300 ml of ice water. The solid was collected, washed with water followed by ether and dried under vacuum at 80° C. to yield 526 mg of 4-(2,3-Dihydro-benzo[1,4]dioxin-6-ylamino)-6,7-diethoxy-quinoline-3-carbonitrile as a yellow solid: mass spectrum (electrospray, m/e): M+H 402.9, mp=225–227° C.

EXAMPLE 106

4-(1H-Indazol-6-ylamino)-6,7-bis-(2-methoxy-ethoxy)-quinoline-3-carbonitrile A solution of 400 mg (1.19 mM) of 4-chloro-6,7-(2-methoxyethoxy)-quinoline-3-carbonitrile and 174 mg (1.31 mM) of 6-Aminoindazole in 12 ml of 2-methoxyethanol was refluxed for 3 hours. To the warm solution was added 1 ml of 1M sodium carbonate and the sample was heated for 5 minutes at 100° C., then poured into 300 ml of ice water. The solid was collected, washed with water followed by ether and dried under vacuum at 80° C. to yield 362 mg of 4-(1H-Indazol-6-ylamino)-6,7-bis-(2-methoxy-ethoxy)-quinoline-3-carbonitrile as a orange solid: mass spectrum (electrospray, m/e): M+H 434.0, mp=105–110° C.

EXAMPLE 107

4-(1,4-Dioxo-1,2,3,4-tetrahydro-phthalazin-6-ylamino)-6,7-diethoxy-quinoline-3-carbonitrile A solution of 400 mg (1.44 mM) of 4-chloro-6,7-diethoxy-quinoline-3-carbonitrile and 273 mg (1.54 mM) of 4-Aminophthalhydrazide Hydrate in 15 ml of 2-methoxyethanol was refluxed for 3 hours. To the warm solution was added 1 ml of 1M sodium carbonate and the sample was heated for 5 minutes at 100° C., then poured into 300 ml of ice water. The solution was made acetic by addition of concentrated HCl and the solid was collected, washed with water followed by ether and dried under vacuum at 80° C. The solid was taken up into 200 ml of methanol and 500 µl of 5 N sodium hydroxide and boiled for 20 minutes. To this heterogeneous mixture was added 100 ml of glacial acetic acid and the volume was reduced to a total of 100 ml by boiling. To the room temperature mixture, 500 ml of ice cold water was added and the solid was collected, washed with water followed by ether and dried under vacuum at 80° C. The solid was digested in 400 ml of ethanol until the volume had been reduced to 150 ml. The hot solution was filtered and the solid was washed with ethanol and to dried under vacuum at 80° C. yield 121 mg of the title compound as a white solid: mass spectrum (electrospray, m/e): M+H 418.0, mp=>270° C.

EXAMPLE 108

6,7-Diethoxy-4-(indan-5-ylamino)-quinoline-3-carbonitrile

A solution of 400 mg (1.44 mM) of 4-chloro-6,7-diethoxy-quinoline-3-carbonitrile and 205 mg (1.54 mM) of 5-Aminoindan in 12 ml of 2-methoxyethanol was refluxed for 3 hours. To the warm solution was added 1 ml of 1M sodium carbonate and the sample was heated for 5 minutes at 100° C., then poured into 300 ml of ice water. The solid was collected, washed with water followed by ether and dried under vacuum at 80° C. The brown solid was dissolved digested in 200 ml of ethanol and the volume was reduced to 100 ml. The solid was isolated from the warm solution and washed with ethanol followed by ether and dried under vacuum at 80° C. to yield 435 mg of 6,7-Diethoxy-4-(indan-5-ylamino)-quinoline-3-carbonitrile as a brown solid: mass spectrum (electrospray, m/e): M+H 374.0, mp=85–88° C.

EXAMPLE 109

4-(2,4-Dioxo-1,4-dihydro-2H-benzo[d][1,31]oxazin-6-ylamino)-6,7-diethoxy-quinoline-3-carbonitrile A solution of 400 mg (1.44 mM) of 4-chloro-6,7-diethoxy-quinoline-3-carbonitrile, 274 mg (1.54 mM) of 5-Aminoisatoic Anhydride and 161 mg (1.44 mM) of pyridine hydrochloride in 15 ml of 2-methoxyethanol was refluxed for 3 hours. The hot solution was filtered and the solid was washed with ethanol and to dried under vacuum at 60° C. yield 482 mg of the HCl salt of 4-(2,4-Dioxo-1,4-dihydro-2H-benzo[d][1,3]oxazin-6-ylamino)-6,7-diethoxy-quinoline-3-carbonitrile as a gray solid: mass spectrum (electrospray, m/e): M+H 418.9, mp=>270° C.

EXAMPLE 110

6,7-Diethoxy-4-(1-oxo-indan-5-ylamino)-quinoline-3-carbonitrile

A solution of 400 mg (1.44 mM) of 4-chloro-6,7-diethoxy-quinoline-3-carbonitrile, 227 mg (1.54 mM) of 6-Amino-1-Indanone and 161 mg (1.44 mM) of pyridine hydrochloride in 12 ml of 2-methoxyethanol was refluxed for 3 hours. To the warm solution was added 1 ml of 1M sodium carbonate and the sample was heated for 5 minutes at 100° C., then poured into 300 ml of ice water. The solid was collected, washed with water followed by ether and dried under vacuum at 80° C. to yield 483 mg of 6,7-Diethoxy-4-(1-oxo-indan-5-ylamino)-quinoline-3-carbonitrile as a white solid: mass spectrum (electrospray, m/e): M+H 388.0, mp=Decomposed at 263° C.

EXAMPLE 111

6,7-Diethoxy-4-(3-oxo-1,3-dihydro-isobenzofuran-5-ylamino)-quinoline-3-carbonitrile A solution of 400 mg (1.44 mM) of 4-chloro-6,7-diethoxy-quinoline-3-carbonitrile, 230 mg (1.54 mM) of 6-Aminophthalide and 161 mg of pyridine hydrochloride in 12 ml of 2-methoxyethanol was refluxed for 3 hours. To the warm solution was added 1 ml of 1M sodium carbonate and the sample was heated for 5 minutes at 100° C., then poured into 300 ml of ice water. The solid was collected, washed with water followed by ether and dried under vacuum at 80°

C. to yield 535 mg of 6,7-Diethoxy-4-(3-oxo-1,3-dihydro-isobenzofuran-5-ylamino)-quinoline-3-carbonitrile as a white solid: mass spectrum (electrospray, m/e): M+H 390.1, mp=280–284° C.

EXAMPLE 112

4-(1,1-Dioxo-1H-benzo[b]thiophen-6-ylamino)-6,7-diethoxy-quinoline-3-carbonitrile A solution of 400 mg (1.44 mM) of 4-chloro-6,7-diethoxy-quinoline-3-carbonitrile, 230 mg (1.54 mM) of 6-Amino-1,1-dioxobenzo[b]thiophene and 161 mg of pyridine hydrochloride in 12 ml of 2-methoxyethanol was refluxed for 6 hours. To the warm solution was added 1 ml of 1M sodium carbonate and the sample was heated for 5 minutes at 100° C., then poured into 300 ml of ice water. The solid was collected, washed with water followed by ether and dried under vacuum at 80° C. The solid was dissolved in acetone and dried onto silica gel under high vacuum. Purification of the compound was obtained by chromatography using a gradient of 30% to 50% acetone in hexane. The first of the three components of the mixture isolated from the column was the desired product. Removal of the solvent by evaporation yielded 69 mg of 4-(1,1-Dioxo-1H-benzo[b]thiophen-6-ylamino)-6,7-diethoxy-quinoline-3-carbonitrile as a yellow solid: mass spectrum (electrospray, m/e): M+H 421.9, mp=155–160° C.

EXAMPLE 113

4-(2,3-Dihydro-1 H-indol-6-ylamino)-6,7-methoxy-quinoline-3-carbonitrile

A solution of 400 mg (1.61 mM) of 4-chloro-6,7-methoxy-quinoline-3-carbonitrile and 366 mg (1.77 mM) of 6-aminoindoline dihydrochloride in 12 ml of 2-methoxyethanol was refluxed for 3 hours. The warm solution was filtered to isolate the resulting solid which was then washed with water followed by ether and dried under vacuum at 80° C. The solid was dissolved in 1 to 1 methanol and chloroform and dried onto silica gel under high vacuum. Purification of the compound was obtained by chromatography using a gradient of 30% to 60% acetone in hexane. The first of the three components of the mixture isolated from the column was the desired product. The column fractions were reduced to a volume of 10 ml and then diluted with 250 ml of hexane. The resulting solid was isolated, washed with hexane and dried under vacuum at 80° C. to give 16 mg of 4-(2,3-Dihydro-1H-indol-6-ylamino)-6,7-methoxy-quinoline-3-carbonitrile as a tan solid: mass spectrum (electrospray, m/e): M+H 347.0, mp=Decomposed at 175° C.

EXAMPLE 114

4-(1H-Indol-5-ylamino)-6-nitro-quinoline-3-carbonitrile

A mixture of 5.00 g (21.5 mmol) 4-chloro-6-nitro-3-quinolinecarbonitrile, 200 ml ethanol, and 3.40 g (25.8 mmol) 5-aminoindole was heated to reflux under $N_2$ for 3.5 hours. Removed heat, made basic with saturated sodium bicarbonate and stripped solvents, azeotroping with ethanol. Collected solids and washed with hexane, then water. Dissolved solids in 200 ml ethyl acetate, added Darco and filtered. Stripped solvent and dried in vacuo overnight (50° C.). Washed twice more with ether to removed starting material aminoindole. 4.372 g of red-brown solid: mass spectrum (m/e electrospray): M+H=330.2.

EXAMPLE 115

7-Ethoxy-4-(indazol-6-ylamino)-6-methoxy-quinoline-3-carbonitrile

A mixture of 500 mg (1.90 mmol) 4-chloro-7-ethoxy-6-methoxy-quinoline-3-carbonitrile, 30 ml ethanol, and 304 mg (2.28 mmol) 6-aminoindazole was heated to reflux under $N_2$. Removed heat at 4 hours and made basic with saturated sodium bicarbonate. Stripped solvents, slurried residue with hexane, collected solids and dried. Washed with water and dried in vacuo, giving 546 mg of tan solid: mass spectrum (electrospray m/e): M+H=359.9.

EXAMPLE 116

7-Benzyloxy-4-chloro-6-methoxy-quinoline-3-carbonitrile

A total of 500 mg (1.63 mM) of 7-benzyloxy-4hydroxy-6-methoxy-quinoline-3-carbonitrile was taken up into 3 ml of oxalyl chloride (2M in $CHCl_3$) and allowed to stand for 15 min followed by refluxing for 1 h. The solution was allowed to cool and then diluted with 300 mg of hexane to give a green solid. The solid was isolated and washed with excess hexane and dried under vacuum at 40° C. to yield 586 mg of 7-benzyloxy-4-chloro-6-methoxy-quinoline-3-carbonitrile as the hydrogen chloride salt. This compound was taken immediately on for the next step.

EXAMPLE 117

7-Benzyloxy-4-(2,3-dihydro-1H-indol-6-ylamino)-6-methoxy-quinoline-3-carbonitrile A solution of 586 mg (1.60 mM) of 7-benzyloxy-4-chloro-6-methoxy-quinoline-3-carbonitrile, 560 mg (1.70 mM) of 6-Aminoindolin dihydrchloride salt and 208 mg (1.80 mM) of pyridine hydrochloride in 13 ml of 2-methoxyethanol was refluxed for 3 hours. The reaction was allowed to cool to room temperature and the resulting solid was isolated and washed with excess ethanol and dried under vacuum at 80° C. The resulting solid was digested in 300 ml of ethanol and the volume was reduced to 100 ml. The solid was isolated from the hot solution and the digestion process was repeated a second time. The solid was once again isolated from the hot solution to yield 206 mg of 7-benzyloxy-4-(2,3-dihydro-1H-indol-6-ylamino)-6-methoxy-quinoline-3-carbonitrile as a tan solid.

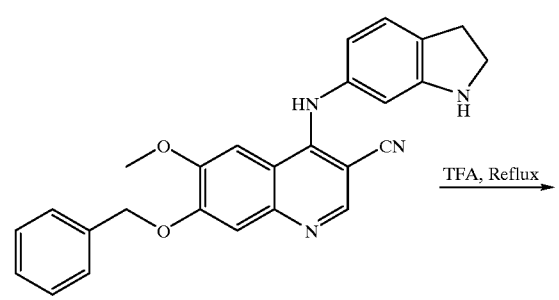

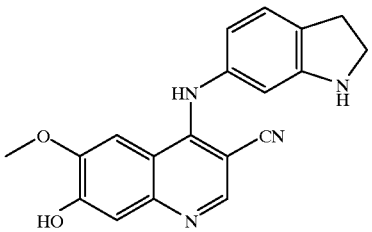

EXAMPLE 118

4-(2,3-Dihydro-1H-indol-6-ylamino)-7-hydroxy-6-methoxy-quinoline-3-carbonitrile To 5 ml of trifluoroacetic acid was added 206 mg 7-benzyloxy-4-(2,3-dihydro-1H-indol-6-ylamino)-6-methoxy-quinoline-3-carbonitrile and the reaction was refluxed for 1.5 h. The TFA was removed under vacuum and the resulting film was dissolved in 7 ml of methanol followed by the addition of 50 ml of ice cold saturated sodium bicarbonate. The solution was allowed to stand at 10° C. for 1 h. The resulting solid was isolated, washed with excess water and dried under vacuum at 80° C. to yield 107 mg of 4-(2,3-dihydro-1H-indol-6-ylamino)-7-hydroxy-6-methoxy-quinoline-3-carbonitrile. This compound was taken directly on to the next step without purification.

EXAMPLE 119

4-(2,3-Dihydro-1H-indol-6-ylamino)-6-methoxy-7-(3-pyridin-4-yl-propoxy)-quinoline-3-carbonitrile To a 0° C. solution consisting of 2 ml of chloroform, 1 ml of tetrahydrofurane, 167 mg (0.64 mM) of triphenyl phosphine, 52 μl (0.40 mM) of 4-hydroxypropylpyridine and 107 mg (0.32 mM) of the 4-(2,3-dihydro-1H-indol-6-ylamino)-7-hydroxy-6-methoxy-quinoline-3-carbonitrile, was slowly added 101 μL (0.64 mM) of DEAD. The reaction was allowed to run at 0° C. for 15 min and then allowed to warm to room temperature. The heterogeneous solution was allowed to stir at room temperature for 7 hour. TCL and ES MS showed no signs of product formation. An additional 1 ml of chloroform and 500 mL of tetrahydrofurane was added and the reaction was refluxed for 14 hours. Once again no signs of product formation were seen. The volume of the reaction was reduced to 1 ml by heating and then brought up to 4 ml by addition of tetrahydrofurane. Once the reaction had cooled to room temperature, and additional 80 mg (0.32 mM) of triphenyl phosphine, 25 μl (0.20 mM) of 4-hydroxypropylpyridine was added followed by the slow addition of 50 μL (0.32 mM) of DEAD. The reaction quickly turned to a clear brown solution. After six hours at room temperature, TLC and the mass spectrum showed the reaction was complete. To the reaction mixture was added 10 ml of 1N HCl followed by 20 ml of water. The solution was extracted five time with 25 ml portions of chloroform. The water layer was allowed to stand for three hours at room temperature and the resulting brown solid was isolated by filtration. The filtrate was treated with solid sodium bicarbonate until a yellow solid fell from solution. The precipitate was isolated and washed with excess water followed by 1 ml of diethyl ether and dried under vacuum at 80° C. to give 57 mg of 4-(2,3-dihydro-1H-indol-6-ylamino)-6-methoxy-7-(3-pyridin-4-yl-propoxy)-quinoline-3-carbonitrile as a yellow solid: mass spectrum (electrospray, m/e): 452.3 M+H, 226.7 M+2H/2, mp=100–105° C.

EXAMPLE 120

2,3-Dihydro-benzo[1,4]dioxine-6-carboxylic acid methyl ester

A solution of 19.6 g (109 mmol) of 2,3-dihydro-benzo[1,4]dioxine-6-carboxylic acid (*J. Chem. Soc.*, 3445, 1957) in 400 mL of MeOH containing 4 mL of $H_2SO_4$ was refluxed overnight. Sodium bicarbonate (18 g) was added, the solvent was removed and the residue was triturated several times with $Et_2O$. The washes were combined, filtered through anhyd $MgSO_4$ and evaporated to yield 20.7 g of the title compound as a pale yellow oil: mass spectrum (electron impact, m/e): 194.

EXAMPLE 121

7-Nitro-2,3-dihydro-benzo[1,4]dioxine-6-carboxylic acid methyl ester

Nitric Acid (18 mL) was added dropwise to a solution of 15.0 g (77.3 mmol) of 2,3-dihydro-benzo[1,4]dioxine-6-carboxylic acid methyl ester in 45 mL of HOAc. The solution was heated at 60° C. for 1.5 h. An additional 9 mL of $HNO_3$ was then added and heating was continued for 1.5 h at 70° C. The reaction was poured into ice-$H_2O$ and the solid product was collected, washed well with $H_2O$ and dried. Recrystallization from heptane-toluene yielded 16.8 g of the title compound as yellow crystals: mass spectrum (electron impact, m/e): 239.

EXAMPLE 122

7-Amino-2,3-dihydro-benzo[1.4]dioxine-6-carboxylic acid methyl ester

A mixture of 12.0 g (50.2 mmol) of 7-nitro-2,3-dihydro-benzo[1,4]dioxine-6-carboxylic acid methyl ester, 11.2 g (201 mmol) of powdered Fe and 13.3 g (257 mmol) of $NH_4Cl$ in 175 ml of MeOH and 70 mL of $H_2O$ was refluxed for 5.5 h. An additional 11.2 g of Fe and 13.3 g of $NH_4Cl$ was added and the mixture was heated for 5.5 h more. Finally, 5.5 g of Fe and 6.5 g of $NH_4Cl$ was added and the mixture was heated for 4 h. The cooled reaction was filtered through Celite, the pad was washed well with MeOH and the filtrate and washings were combined. The solvent was removed and the residue was slurried in $H_2O$ and collected. The crude product was filtered through silica ($CHCl_3$) to give 9.5 g of the title compound as tan crystals: mass spectrum (electrospray, m/e): M+H 209.9.

EXAMPLE 123

9-Oxo-2,3,6,9-tetrahydro-[1,4]dioxino[2,3-g]quinoline-8-carbonitrile

A solution of 9.71 g (46.5 mmol) of 7-amino-2,3-dihydro-benzo[1,4]dioxine-6-carboxylic acid methyl ester and 11.1 g (92.9 mmol) of dimethylformamide dimethyl acetal in 45 mL of DMF was refluxed under $N_2$ for 6 h. Volatile material was removed and the residue was azeotroped with toluene and dried in vacuo to give the formamidine as a purple syrup. n-Butyllithium (102 mmol) in hexane was diluted with 70 mL of THF at −78° C. under $N_2$. A solution of 4.31 g (105 mmol) of acetonitrile in 85 mL of THF was added over 15 min and the solution was stirred for 25 min. The crude formamidine was dissolved in 90 mL of THF and added dropwise to the cold solution over 0.5 h. After stirring for 1.25 h, the reaction was quenched at −78° C. with 13.4 mL of acetic acid. It was allowed to warm to room temperature and volatile material was removed in vacuo. The residue was slurried with H$_2$O and the crude product was collected by filtration, washed with H$_2$O and dried. The solid material was boiled with MeOH, collected and dried in vacuo (50° C.) to yield 7.62 g of the title compound as a tan powder: mass spectrum (electrospray, m/e): M+H 228.8.

EXAMPLE 124

9-chloro-2,3-dihydro[1,4]dioxino[2,3-g]quinoline-8-carbonitrile

A mixture of 7.06 g (31.0 mmol) of WAY 170839 and 35 mL of POCl$_3$ was refluxed for 3.5 h. The POCl$_3$ was removed and ice-H$_2$O was added followed by solid NaHCO$_3$ to pH 8. The product was collected, washed well with H$_2$O and dried in vacuo to yield 7.42 g of 9-chloro-2,3-dihydro [1,4]dioxino[2,3-g]quinoline-8-carbonitrile as a tan solid: mass spectrum (electrospray, m/e): M+H 246.8.

EXAMPLE 125

9-(1H-Indazol-6-ylamino)-2,3-dihydro[1,4]dioxino[2,3-g]quinoline-8-carbonitrile

A mixture of 1.00 g (4.07 mmol) of 9-chloro-2,3-dihydro [1,4]dioxino[2,3-g]quinoline-8-carbonitrile and 0.649 g (4.88 mmol) of 6-aminoindazole in 25 mL of EtOH was refluxed under N$_2$ for 5.7 h. Satd NaHCO$_3$ was added and the solvent was removed. The residue was slurried with H$_2$O, filtered, washed with H$_2$O and cold EtOH and dried. The crude product was boiled with EtOH, filtered and dried in vacuo (50° C.) to yield 1.06 g of 9-(1H-indazol-6-ylamino)-2,3-dihydro[1,4]dioxino[2,3-g]quinoline-8-carbonitrile as tan crystals: mass spectrum (electrospray, m/e): M+H 344.3.

EXAMPLE 126

6-Ethoxy-4-(1H-indazol-6-ylamino)-7-methoxyquinoline-3-carbonitrile

A mixture of 1.00 g (3.82 mmol) of 4-chloro-6-ethoxy-7-methoxyquinoline-3-carbonitrile and 0.609 g (4.58 mmol) of 6-aminoindazole in 20 mL of EtOH was refluxed under N$_2$ for 8 h. Satd NaHCO$_3$ was added, solvent was removed and the residue was azeotroped twice with EtOH. The solid was slurried with cold EtOH, collected, washed twice with H$_2$O and dried. Recrystallization from EtOH yielded 0.646 g of 6-ethoxy-4-(1H-indazol-6-ylamino)-7-methoxyquinoline-3-carbonitrile as tan crystals: mass spectrum (electrospray, m/e): M+H 359.9.

EXAMPLE 127

6,7-Diethoxy-4-(1-methyl-2,5-dioxo-2,3,4,5-tetrahydro-1H-benzo[e][1,4]diazepin-7-ylamino)-quinoline-3-carbonitrile A mixture of 0.5 g (1.8 mmol) of 4-chloro-6,7-diethoxy-quinoline-3-carbonitrile, 0.35 g (1.8 mmol) of 7-amino-1-methyl-2,5-dioxo-2,3,4,5-tetrahydro-1H-benzo[e][1,4] diazepine, and 0.21 g of pyridine hydrochloride was refluxed in ethoxyethanol for 5 hr. The solvent was removed at reduced pressure. The residue was stirred with ammonium hydroxide and the insoluble material was collected to give 0.8 g of title compound as a a tan solid. crystals: mass spectrum (electrospray, m/e): M+H 446.0.

EXAMPLE 128

4-(1H-Indazol-6-ylamino)-6,7,8-trimethoxy-quinoline-3-carbonitrile

A mixture of 0.279 g of 4-chloro-6,7,8-trimethoxy-quinoline-3-carbonitrile, 0.147 g of 6-aminoindazole, 0.020 of pyridine hydrochloride, and 15 ml of ethoxyethanol was stirred under nitrogen, at reflux temperature for 1 hour. The mixture was cooled and added to 100 ml of water. To this mixture was added sodium carbonate to pH 9. The product was collected, washed with water, and dried to give 0.332 g of 4-(1H-indazol-6-ylamino)-6,7,8-trimethoxy-quinoline-3-carbonitrile as a solid, mp 243–245° C.; mass spectrum (EI, m/e): M 375.1331.

EXAMPLE 129

6,7-Dimethoxy-4-(4-methyl-2-oxo-1,2-dihydro-quinolin-7-ylamino)-quinoline-3- carbonitrile A mixture of 0.249 g of 4-chloro-6,7-dimethoxy-quinolin-3-carbonitrile, 0.174 g of carbostyril 124, 0.020 g of pyridine hydrochloride, and 10 ml of ethoxyethanol was stirred under nitrogen, at reflux temperature for 30 minutes. The mixture was cooled and added to 40 ml of water. To this mixture was added sodium carbonate to pH 9. The product was collected, washed with water, and dried to give 0.356 g of 6,7-dimethoxy-4-(4-methyl-2-oxo-1,2-dihydro-quinolin-7-ylamino)-quinoline-3-carbonitrile as a solid, mp>300° C.; mass spectrum (electrospray, m/e): M+H 387.1446.

EXAMPLE 130

6,7-Dimethoxy-4-(2-methyl-benzothiazol-5-ylamino)-quinoline-3-carbonitrile

A mixture of 0.249 g of 4-chloro-6,7-dimethoxy-quinolin-3-carbonitrile, 0.237 g of 5-amino-2-methylbenzothiazole dihydrocholride, 0.158 g of pyridine, and 10 ml of ethoxyethanol was stirred under nitrogen, at reflux temperature for 20 minutes. The mixture was cooled and added to 40 ml of water. To this mixture was added sodium carbonate to pH 9. The product was collected, washed with water, and dried to give 0.356 g of 6,7-dimethoxy-4-(2-methyl-benzothiazol-5-ylamino)-quinoline-3-carbonitrile as a solid, mp 118–120° C.; mass spectrum (EI, m/e): M 376.0973.

EXAMPLE 131

6,7-Dimethoxy-4-(2-oxo-2,3-dihydro-benzothiazol-6-ylamino)-quinoline-3-carbonitrile A mixture of 0.249 g of 4-chloro-6,7-dimethoxy-quinolin-3-carbonitrile, 0.166 g of 6-amino-2-benzothiazolinone, 0.020 g of pyridine hydrochloride, and 10 ml of ethoxyethanol was stirred under nitrogen, at reflux temperature for 20 minutes. The mixture was cooled and added to 40 ml of water. To this mixture was added sodium carbonate and concentrated hydrochloric acid to adjust pH to 7. The product was collected, washed with water, and dried to give 0.326 g of 6,7-dimethoxy-4-(2-oxo-2,3-dihydro-benzothiazol-6-ylamino)-quinoline-3-carbonitrile as a solid, mp 285–287° C.; mass spectrum (electrospray, m/e): M+H 379.0858.

EXAMPLE 132

6,7-Dimethoxy-4-(quinolin-5-ylamino)-quinoline-3-carbonitrile

A mixture of 0.249 g of 4-chloro-6,7-dimethoxy-quinolin-3-carbonitrile, 0.288 g of 5-aminoquinoline, 0.020 g of pyridine hydrochloride, and 10 ml of ethoxyethanol was heated under nitrogen in a sealed tube at 200° C. for 2 hours. The mixture was cooled and added to 100 ml of water. To this mixture was added sodium carbonate to pH 9. The product was collected, washed with water, and dried to give 0.132 g of 6,7-dimethoxy-4-(quinolin-5-ylamino)-quinoline-3-carbonitrile as a solid, mp 115° C. (decomposed); mass spectrum (EI, m/e): M 356.1276.

EXAMPLE 133

4-(Isoquinolin-5-ylamino)-6,7-dimethoxy-quinoline-3-carbonitrile

A mixture of 0.249 g of 4-chloro-6,7-dimethoxy-quinolin-3-carbonitrile, 0.288 g of 5-aminoisoquinoline, 0.020 g of pyridine hydrochloride, and 10 ml of ethoxyethanol was heated under nitrogen in a sealed tube at 200° C. for 2 hours. The mixture was cooled and added to 100 ml of water. To this mixture was added sodium carbonate to pH 9. The product was collected, washed with water, and dried to give 0.100 g of 4-(isoquinolin-5-ylamino)-6,7-dimethoxy-quinoline-3-carbonitrile as a solid, mp 140° C. (decomposed); mass spectrum (EI, m/e): M 356.1279.

EXAMPLE 134

6,7-Dimethoxy-4-(quinolin-8-ylamino)-quinoline-3-carbonitrile

A mixture of 0.249 g of 4-chloro-6,7-dimethoxy-quinolin-3-carbonitrile, 0.288 g of 8-aminoquinoline, 0.020 g of pyridine hydrochloride, and 10 ml of ethoxyethanol was heated under nitrogen in a sealed tube at 200° C. for 2 hours. The mixture was cooled and added to 100 ml of water. To this mixture was added sodium carbonate to pH 9. The product was collected, washed with water, and dried to give 0.167 g of 6,7-dimethoxy-4-(quinolin-8-ylamino)-quinoline-3-carbonitrile as a solid, mp 150° C. (decomposed); mass spectrum (EI, m/e): M 356.1271.

EXAMPLE 135

4-(8-Hydroxy-quinolin-5-ylamino)-6,7-dimethoxy-quinoline-3-carbonitrile

A mixture of 0.249 g of 4-chloro-6,7-dimethoxy-quinolin-3-carbonitrile, 0.233 g of 5-amino-8-hydroxyquinoline dihydrocholride, 0.158 g of pyridine, and 10 ml of ethoxyethanol was stirred under nitrogen, at reflux temperature for 2 hours. The mixture was cooled and added to 40 ml of water. To this mixture was added sodium carbonate and concentrated hydrochloric acid to adjust pH to 7. The product was collected, washed with water, and dried to give 0.210 g of 4-(8-hydroxy-quinolin-5-ylamino)-6,7-dimethoxy-quinoline-3-carbonitrile as a solid, mp 150° C. (decomposed); mass spectrum (EI, m/e): M 372.1228.

EXAMPLE 136

4-(1H-Indol-4-ylamino)-6,7-dimethoxy-quinoline-3-carbonitrile

A mixture of 0.249 g of 4-chloro-6,7-dimethoxy-quinolin-3-carbonitrile, 0.132 g of 4-aminoindole, 0.020 g of pyridine hydrochloride, and 10 ml of ethoxyethanol was stirred under nitrogen, at reflux temperature for 2 hours. The mixture was cooled and added to 40 ml of water. To this mixture was added sodium carbonate and concentrated hydrochloric acid to adjust pH to 7. The product was collected, washed with water, and dried to give 0.249 g of 4-(1H-indol-4-ylamino)-6,7-dimethoxy-quinoline-3-carbonitrile as a solid, mp 260° C. (decomposed); mass spectrum (EI, m/e): M 344.1282.

EXAMPLE 137

4-(1H-Indazol-5-ylamino)-6,7-dimethoxy-quinoline-3-carbonitrile

A mixture of 0.249 g of 4-chloro-6,7-dimethoxy-quinolin-3-carbonitrile, 0.132 g of 5-aminoindazole, 0.020 g of pyridine hydrochloride, and 10 ml of ethoxyethanol was stirred under nitrogen, at reflux temperature for 2 hours. The mixture was cooled and added to 40 ml of water. To this mixture was added sodium carbonate and concentrated hydrochloric acid to adjust pH to 7. The product was collected, washed with water, and dried to give 0.252 g of 4-(1H-indazol-5-ylamino)-6,7-dimethoxy-quinoline-3-carbonitrile as a solid, mp 290–295° C.; mass spectrum (EI, m/e): M 345.1217.

EXAMPLE 138

4-(1H-Indazol-6-ylamino)-5,8-dimethoxy-quinoline-3-carbonitrile

A mixture of 0.148 g of 4-chloro-5,8-dimethoxy-quinolin-3-carbonitrile, 0.093 g of 6-aminoindazole, and 5 ml of ethoxyethanol was stirred under nitrogen, at reflux temperature for 30 minutes. The mixture was cooled and added to 50 ml of water. To this mixture was added sodium carbonate to pH 9. The product was collected, washed with water, dried, and washed with 10 ml of hexanes-ethyl acetate (4:1) to give 0.189 g of 4-(1H-indazol-6-ylamino)-5,8-dimethoxy-quinoline-3-carbonitrile as a solid, mp 302–305° C.; mass spectrum (EI, m/e): M 345.1223.

EXAMPLE 139

4-(1H-Indazol-6-ylamino)-7-methoxy-6-(3-morpholine-4-yl-propoxy)-quinoline-3-carbonitrile hydrochloride A mixture of 0.362 g of 4-chloro-7-methoxy-6-(3-morpholin-4-yl-propoxy))-quinoline-3-carbonitrile, 0.267 g of 6-aminoindazole, and 10 ml of ethoxyethanol was stirred under nitrogen, at reflux temperature for 30 minutes. The mixture was cooled and added to 50 ml of a mixture of ethyl acetate/acetone/methyl alcohol (5:5:2). The product was collected, washed with water, dried, and washed with 10 ml of hexanes-ethyl acetate (4:1) to give 0.189 g of 4-(1H-indazol-6-ylamino)-7-methoxy-6-(3-morpholin-4-yl-propoxy)-quinoline-3-carbonitrile hydrochloride as a solid, mp 100° C. (decomposed); mass spectrum (electrospray, m/e): M+H 459.2146.

EXAMPLE 140

4-(3H-Benzotriazol-5-ylamino)-7-methoxy-6-(3-morpholin-4-yl-proloxy)-quinoline-3-carbonitrile hydrochloride A mixture of 0.362 g of 4-chloro-7-methoxy-6-(3-morpholin-4-yl-propoxy))-quinoline-3-carbonitrile, 0.268 g of 5-aminobenzotriazole, and 10 ml of ethoxyethanol was stirred under nitrogen, at reflux temperature for 30 minutes. The mixture was cooled and added to 50 ml of a mixture of ethyl acetate/acetone/methyl alcohol (5:5:2). The product was collected, washed with water, dried, and washed with 10 ml of hexanes-ethyl acetate (4:1) to give 0.142 g of 4-(3H-benzotriazol-6-ylamino)-7-methoxy-6-(3-morpholin-4-yl-propoxy)-quinoline-3-carbonitrile hydrochloride as a solid, mp 260° C. (decomposed); mass spectrum (electrospray, m/e): M+H 460.2096.

EXAMPLE 141

4-(1H-Indazol 6-ylamino)-6-methoxy-quinoline-3-carbonitrile

To a suspension of 218.6 mg (1.0 mmol) of 4-chloro-6-methoxy-3-quinolinecarbonitrile and 159.8 mg (1.2 mmol)

of 6-aminoindazole in 10 mL of 2-ethoxyethanol was added 115.6 mg (1.0 mmol) of pyridine hydrochloride. The resulting reaction mixture was refluxed for 1 hr. After cooling, most of solvent was evaporated off and the residue was diluted with ether. The precipitate was collected by filtration and was taken into water. The aqueous suspension was neutralized to PH 7–8 by addition of sat. sodium carbonate aqueous solution and stirred for 15 min. The separated solid was filtered off and washed with water and ether. After drying in vacuo, 297.5 mg (94.3%) of the product was obtained as a deep yellow solid, m.p.>250° C., mass (electrospray, m/e): M+H 315.8. HRCIMS m/z: cacld 315.112 for $C_{18}H_{13}N_5O$ (M+), obsd 315.1124

EXAMPLE 142

4-(3H-Benzotriazol-5-ylamino)-6-methoxy-quinoline-3-carbonitrile

Using an analogous procedure to that described in Example 141, 218.6 mg (1 mmol) of 4-chloro-6-methoxy-3-quinolinecarbonitrile in 10 mL of 2-ethoxyethanol and in the presence of 115.6 mg (1 mmol) of pyridine hydrochloride was reacted with 161.0 mg (1.2 mmol) of 5-aminobenzotriazole to give 302.9 mg (95.8%) of the product as a yellow solid, m.p.>250° C., mass (electrospray, m/e): M+H 316.9. HRCIMS calcd: 316.107 for $C_{17}H_{12}N_6O$ (M+), obsd 316.1081

EXAMPLE 143

4-(1H-Indazol-6-ylamino)-7-methoxy-quinoline-3-carbonitrile

Using an analogous procedure to that described in Example 141, 200.0 mg (0.914 mmol) of 4-chloro-7-methoxy-3-quinolinecarbonitrile in 10 mL of 2-ethoxyethanol and in the presence of 105.6 mg (0.914 mmol) of pyridine hydrochloride was reacted with 147.8 mg (1.1 mmol) of 6-aminoindazole to give 280.0 mg (97.3%) of the product as a deep yellow solid, m.p.>250° C., mass (electrospray, m/e): M+H 315.9. HRCIMS: calcd 315.112 for $C_{18}H_{13}N_5O$ (M+), obsd 315.1124.

EXAMPLE 144

4-(3H-benzotriazol-5-ylamino)-7-methoxy-quinoline-3-carbinitile

Using an analogous procedure to that described in Example 141, 218.6 mg (1.0 mmol) of 4-chloro-7-methoxy-3-quinolinecarbonitrile in 10 mL of 2-ethoxyethanol and in the presence of 115.6 mg (1.0 mmol) of pyridine hydrochloride was reacted with 161.0 mg (1.2 mmol) of 5-aminobenzotriazole to give 231.0 mg (73.1%) of the product as a light brown solid, m.p.>250° C., mass (electrospray, m/e): M+H 316.9 HRCIMS: calcd 316.107 for $C_{17}H_{12}N_6O$ (M+), obsd 316.1063.

EXAMPLE 145

7-Hydroxy-4-(1H-indazol-6-ylamino)-quinoline-3-carbonitrile

A reaction mixture of 1.74 g (5.52 mmol) of 4-(1H-Indazol-6-ylamino)-7-methoxy-quinoline-3-carbonitrile and 15.3 g of pyridine hydrochloride was heated at 200–210° C. for 1.5 hr. After cooling, the mixture was taken into 3% $NH_4OH$ aqueous solution. The precipitate was collected by filtration and washed with water. Drying in vacuo afforded 1.66 g (63.8%) of the product as deep brown solid, m.p.>250° C., mass (electrospray, m/e): M+H 301.9. HRCIMS: calcd 302.1042 for $C_{17}H_{11}N_5O$ (M+) obsd 302.1079.

EXAMPLE 146

4-(1H-Indol-5-ylamino)-7-methoxy-quinoline-3-carbonitrile

Using an analogous procedure to that described in Example 141, 1.0 g (4.57 mmol) of 4-chloro-7-methoxy-3-quinolinecarbonitrile, 724.8 mg (5.48 mmol) of 5-aminoindole and 528.3 mg (4.57 mmol) of 5-aminoindole in 35 mL of 2-ethoxyethanol was heated at 120° C. for 2 hr. The work up gave 1.38 g of the product as a greenish gray solid, m.p.>250° C., mass (electrospray, m/e): M+H 314.9 HRCIMS: calcd 314.117 for $C_{19}H_{14}N_4O$ (M+), obsd 314.1135.

EXAMPLE 147

7-Hydroxy-4-(3H-benzotrizol-5-ylamino)-quinoline-3-carbonitrile

Using an analogous procedure to that described in Example 145, 1.45 g (4.58 mmol) of 4-(3H-benzotrizol-5-ylamino)-7-methoxy-quinoline-3-carbonitrile and 10 g of pyridine hydrochloride was heated for 1 hr. The work up gave 1.04 g (75.4%) of the product as a dark brown solid, m.p.>250° C., mass (electrospray, m/e): M+H 303.3. HRCIMS: calcd 301.0838 for $C_{16}H_{10}N_6O$ (M+), obsd 301.0833.

EXAMPLE 148

4-(1H-Indazol-6-ylamino)-8-methoxy-quinoline-3-carbonitrile

Using an analogous procedure to that described in Example 141, 328.0 mg (1.5 mmol) of 4-chloro-8-methoxy-3-quinolinecarbonitrile, 219.7 mg (1.65 mmol) of 6-aminoindazole and 105.6 mg (173.3 mmol) of pyridine hydrochloride in 15 mL of 2-ethoxyethanol was heated at 100° C. for 2 hr. The work up gave 373.8 mg (79%) of the product as a yellow solid, m.p. 242° C. (dec.), mass (electrospray, m/e): M+H 315.9. HRCIMS: calcd 315.112 for $C_{18}H_{13}N_5O$ (M+), obsd 315.1126.

EXAMPLE 149

4-(3H-benzotriazol-5-ylamino)-8-methoxy-quinoline-3-carbonitrile

Using an analogous procedure to that described in Example 141, 218.6 mg (1 mmol) of 4-chloro-8-methoxy-3-quinolinecarbonitrile, 161.0 mg (1.2 mmol) of 5-aminobenzotriazole and 115.6 mg (1 mmol) of pyridine hydrochloride in 10 mL of 2-ethoxyethanol was heated at 100° C. for 1 hr. The work up gave 213.5 mg (67.6%) of the product as a yellow solid, m.p.>250 C., mass (electrospray, m/e): M+H 316.9. HRCIMS: calcd 316.107 for $C_{17}H_{12}N_6O$ (M+), obsd 316.1079.

EXAMPLE 150

4-(1H-Indol-5-ylamino)-6,7-Dimethoxy-quinoline-3-carbonitrile

Using an analogous procedure to that described in Example 141, 248.7 mg (1 mmol) of 4-chloro-6,7- dimethoxy-3-quinolinecarbonitrile, 158.6 mg (1.2 mmol) of 5-aminoindole and 115.6 mg (1 mmol) of pyridine hydrochloride in 10 mL of 2-ethoxyethanol was refluxed for 0.5 hr. The work up gave 338.7 mg (98.5%) of the product as a yellow solid, m.p.>250° C., mass (electrospray, m/e): M+H 344.9. HRCIMS: calcd 344.127 for $C_{20}H_{16}N_4O_2$ ($M^+$), obsd 344.1277.

EXAMPLE 151

4-(1H-Benzoimidazol-5-ylamino)-6,7-dimethoxy-quinoline-3-carbonitrile

Using an analogous procedure to that described in Example 150, 248.7 mg (1 mmol) of 4-chloro-6,7-dimethoxy-3-quinolinecarbonitrile, 159.8 mg (1.2 mmol) of 5-aminobenzimdazole and 115.6 mg (1 mmol) of pyridine hydrochloride in 10 mL of 2-ethoxyethanol was refluxed for 1 hr. The work up gave 233.6 mg (67.7%) of the product as a brown solid, m.p. 230°0 C. (dce.), mass (electrospray, m/e): M+H 345.9. HRCIMS: calcd 346.1304 for $C_{19}H_{15}N_5O_2$ ($M^+$), obsd 346.1325.

EXAMPLE 152

6,7-Dimethoxy-4-(2-methyl-1H-benzoimidazol-5-ylamino)-quinoline-3-carbonitrile

Using an analogous procedure to that described in Example 150, 248.7 mg (1 mmol) of 4-chloro-6,7-dimethoxy-3-quinolinecarbonitrile, 294.4 mg (2.0 mmol) of 2-methyl-5-aminobenzimidazol and 115.6 mg (1 mmol) of pyridine hydrochloride in 10 mL of 2-ethoxyethanol was refluxed for 4 hr. The work up gave 220.2 mg (61.3%) of the product as a sand color solid, m.p. 207° C. (dce.), mass (electrospray, m/e): M+H 359.9. HRCIMS: calcd 359.138 for $C_{20}H_{17}N_5O_2$ ($M^+$), obsd 359.1403.

EXAMPLE 153

6,7-Dimethoxy-4-(quinoline-6-ylamino)-quinoline-3-carbonitrile

Using an analogous procedure to that described in Example 150, 248.7 mg (1 mmol) of 4-chloro-6,7-dimethoxy-3-quinolinecarbonitrile, 173.8 mg (1.2 mmol) of 6-aminoquinoline and 115.6 mg (1 mmol) of pyridine hydrochloride in 15 mL of 2-ethoxyethanol was refluxed for 6 hr. The work up gave 212.5 mg (59.5%) of the product as a orange solid, m.p. 241–243° C., mass (electrospray, m/e): M+H 356.8. HRCIMS: calcd 356.127 for $C_{20}H_{17}N_5O_2$ ($M^+$), obsd 356.1275.

EXAMPLE 154

4-(4-Chloro-naphthalen-1-ylamino)-6,7-Dimethoxy-quinoline-3-carbonitrile

Using an analogous procedure to that described in Example 150, 248.7 mg (1 mmol) of 4-chloro-6,7-dimethoxy-3-quinolinecarbonitrile, 213.2 mg (1.2 mmol) of 1-amino-4-chloronaphthalenen and 115.6 mg (1 mmol) of pyridine hydrochloride in 12 mL of 2-ethoxyethanol was refluxed for overnight. The work up gave 290.1 mg (74.4%) of the product as a yellowish green solid, m.p.>250° C., mass (electrospray, m/e): M+H 390.2. HRCIMS: calcd 389.093 for $C_{22}H_{16}N_3O_2Cl$($M^+$), obsd 389.0938.

EXAMPLE 155

6,7-Dimethoxy-4-(5,6,7,8,-tetrahydro-naphthalen-1-ylamino)-quinoline-3-carbonitrile Using an analogous procedure to that described in Example 150, 248.7 mg (1 mmol) of 4-chloro-6,7-dimethoxy-3-quinolinecarbonitrile, 176.7 mg (1.2 mmol) of 1-amino-5,6,7,8-tetrahydronaphthalene and 115.6 mg (1 mmol) of pyridine hydrochloride in 12 mL of 2-ethoxyethanol was refluxed for 2 hr. The work up gave 195.1 mg (54.3%) of the product as a yellow solid, m.p. 248° C. (dec.), mass (electrospray, m/e): M+H 360.1. HRCIMS: calcd 359.163 for $C_{22}H_{16}N_3O_2Cl$($M^+$), obsd 359.1632.

EXAMPLE 156

4-(3H-Benzotriazol-5-ylamino)-6,7,8-Trimethoxy-quinoline-3-carbonitrile

Using an analogous procedure to that described in Example 150, 278.7 mg (1 mmol) of 4-chloro-6,7-dimethoxy-3-quinolinecarbonitrile, 161.3 mg (1.2 mmol) of 5-aminobenzotriazole and 115.6 mg (1 mmol) of pyridine hydrochloride in 10 mL of 2-ethoxyethanol was refluxed for 10 min. The work up gave 246.3 mg (65.4%) of the product as a yellow solid, m.p. 205° C. (dec.), mass (electrospray, m/e): M+H 376.9. HRCIMS: calcd 376.128 for $C_{19}H_{16}N_6O_3$ ($M^+$), obsd 376.1264.

EXAMPLE 157

4-(1H-Indazol-6-ylamino)-6-methoxy-7-[2-(4-methyl-piperazin-1-yl)-ethoxy]-quinoline-3-carbonitrile A reaction mixture of 196.5 mg (0.5 mmol) of the 7-(2-chloro-ethoxy)-4-(1H-indazol-6-ylamino)-6-methoxy-quinoline-3-carbonitrile, 500.9 mg (5 mmol) of 1-methylpiperazine and 74.5 mg (0.5 mmol) of sodium iodide in 10 mL of DME was heated at 135° C. for 15 hr under $N_2$ in a sealed tube. After cooling, the solvent was removed and the residue was taken into 15 mL of brine. The aqueous solution was extracted with 15% methanol/methylene chloride. The organic solvent was dried over $Na_2SO_4$ and filtered. Removal of the solvent gave the crude product solid. Purification of the crude product on preparative TLC (developing solvent: 15% methanol/methylene chloride) to give a yellow foam solid. Trituration of the foam solid with ether yielded 117.9 mg (51.6%) of the product as a yellow solid, m.p. 179° C. (dec.), mass (electrospray, m/e): M+H 458.0.

EXAMPLE 158

7-{2-[(2-hydroxy-ethyl)-amino]-ethoxy}-4(1H-indazol-6-ylamino)-6-methoxy -quinoline-3-carbonitrile Using an analogous procedure to that described in Example 157, 196.5 mg (0.5 mmol) of the 7-(2-chloro-ethoxy)-4-(1H-indazol-6-ylamino)-6-methoxy-quinoline-3-carbonitrile, 375.6 mg (5.0 mmol) of 2-(methylamino)-ethanol and 75.0 mg (0.5 mmol) of sodium iodide in 5 mL of DME was heated at 135° C. for 15 hr. The work up gave 116.4 mg (54.0%) of the product as a yellow solid, m.p. 179° C. (dec.), mass (electrospray, m/e): M+H 433.0.

EXAMPLE 159

7-{2-[Bis-(2-hydroxy-ethyl)-amino]-ethoxy}-4-(1H-indazol-6-ylamino)-6-methoxy-quinoline-3-carbonitrile Using an analogous procedure to that described in Example 157, 196.5 mg (0.5 mmol) of the 7-(2-chloro-ethoxy)-4-(1H-indazol-6-ylamino)-6-methoxy-quinoline-3- carbonitrile, 525.7 mg (5.0 mmol) of diethanolamine and 75.0 mg (0.5 mmol) of sodium iodide in 6 mL of DME was heated at 135° C. for 15 hr. The work up gave 109.1 mg (47.2%) of the product as a yellow solid, m.p. 150° C. (dec.), mass (electrospray, m/e): M+H 463.0.

EXAMPLE 160

7-[2-(4-Hydroxy-piperidin-1-yl)-ethoxy]-4-(-indazol-6-ylamino)-6-methoxy-quinoline-3-carbonitrile Using an analogous procedure to that described in Example 157, 196.5 mg (0.5 mmol) of the 7-(2-chloroethoxy)-4-(1H-indazol-6-ylamino)-6-methoxy-quinoline-3-carbonitrile, 505.8 mg (5.0 mmol) of 4-hydroxypiperidine and 75.0 mg (0.5 mmol) of sodium iodide in 5 mL of DME was heated at 135° C. for 16 hr. The work up gave 97.9 mg (42.8%) of the product as a off white solid, m.p. 174° C. (dec.), mass (electrospray, m/e): M+H 459.0.

EXAMPLE 161

7-{2-[(4-(2-Hydroxy-ethyl)-piperazin-1-yl)-ethoxy]-4-(1H-indazol-6-ylamino)-6-methoxy-quinoline-3-carbonitrile Using an analogous procedure to that described in Example 157, 196.5 mg (0.5 mmol) of the 7-(2-chloroethoxy)-4-(1H-indazol-6-ylamino)-6-methoxy-quinoline-3-carbonitrile, 651.0 mg (5.0 mmol) of 1-(2-hydroxyethyl)piperazine and 75.0 mg (0.5 mmol) of sodium iodide in 5 mL of DME was heated at 135° C. for 16 hr. The work up gave 90.5 mg (37.1%) of the product as a yellow solid, m.p. 174° C. (dec.), mass (electrospray, m/e): M+H 488.0.

EXAMPLE 162

7-[2-(1,4Dioxa-8-aza-spiro[4,5]dec-8-yl)-ethoxy]-4-(1H-indazol-6-ylamino)-6-methoxy-quinoline-3-carbonitrile Using an analogous procedure to that described in Example 157, 196.5 mg (0.5 mmol) of the 7-(2-chloroethoxy)-4-(1H-indazol-6-ylamino)-6-methoxy-quinoline-3-carbonitrile, 716.0 mg (5.0 mmol) of 1,4-dioxa-8-azapiro[4,5]decane and 75.0 mg (0.5 mmol) of sodium iodide in 5 mL of DME was heated at 135° C. for 16 hr. The work up gave 173.1 mg (69.2%) of the product as aoff white solid, m.p. 245° C. (dec.), mass (electrospray, m/e): M+H 501.0.

EXAMPLE 163

4-(1H-Indazol-6-ylamino)-6-methoxy-7-(2-thiomorpholin-4-yl-ethoxy)-quinoline-3-carbonitrile Using an analogous procedure to that described in Example 157, 173.0 mg (0.44 mmol) of the 7-(2-chloroethoxy)-4-(1H-indazol-6-ylamino)-6-methoxy-quinoline-3-carbonitrile, 454.0 mg (4.4 mmol) of thiomopholine and 66.0 mg (0.44 mmol) of sodium iodide in 4 mL of DME was heated at 135° C. for 16 hr. The work up gave 108.4 mg (53.5%) of the product as a light yellow solid, m.p. 213–215° C., mass (electrospray, m/e): M+H 461.0.

EXAMPLE 164

7-[2-([1,3]Dioxolan-2-ylmethyl-methyl-amino)-ethoxy]-4-(1H-indazol-6-ylamino)-6-methoxy-quinoline-3-carbonitrile Using an analogous procedure to that described in Example 157, 173.0 mg (0.44 mmol) of the 7-(2-chloroethoxy)-4-(1H-indazol-6-ylamino)-6-methoxy-quinoline-3-carbonitrile, 515.5 mg (4.4 mmol) of 2-([1,3]-dioxolan-2-ylmethyl-methylamine and 66.0 mg (0.44 mmol) of sodium iodide in 4 mL of DME was heated at 135° C. for 16 hr. The work up gave 136.1 mg (65.2%) of the product as a yellow solid, m.p. 185–187° C., mass (electrospray, m/e): M+H 475.1

EXAMPLE 165

7-[2-(3,4-Dihydro-1H-isoquinolin-2-yl)-ethoxy]-4-(1H-indazol-6-ylamino)-6-methoxy-quinoline-3-carbonitrile Using an analogous procedure to that described in Example 157, 173.0 mg (0.44 mmol) of the 7-(2-chloroethoxy)-4-(1H-indazol-6-ylamino)-6-methoxy-quinoline-3-carbonitrile, 586.0 mg (4.4 mmol) of 1,2,3,4-tetrahydroisoquinoline and 66.0 mg (0.44 mmol) of sodium iodide in 4 mL of DME was heated at 135° C. for 16 hr. The work up gave 109.3 mg (50.6%) of the product as a yellow solid, m.p. 170–173° C., mass (electrospray, m/e): M+H 491.0

EXAMPLE 166

7-(2-Chloroethoxy)-4-(1H-indazol-6-ylamino)-6-methoxyquinoline-3-carbonitrile

A mixture of 0.50 g (1 equivalent) of 7-(2-chloro-ethoxy)-4-chloro-6-methoxy-quinoline-3-carbonitrile, 0.25 g (1.1 equivalents) of 6-aminoindazole, 0.22 g (1.1 equivalents) of pyridine hydrochloride and 15 ml of 2-methoxyethanol was heated in 120° C. oil bath for 2 hours. The reaction progress was monitored by thin layer chromatography (acetone/hexane 1:1). After 2 hours, the reaction mixture was cooled to room temperature; a total of 25 ml of 1M sodium bicarbonate was added and the reaction was stirred for 1 hour. The resultant precipitate was collected, washed with water and dried in vacuo at 60° C. overnight to give 0.645 g (97%) of the desired product. :mass spectrum (electrospray m/e): M+H=393.9 (M+H)$^+$; Analysis calculated for $C_{20}H_{16}ClN_5O_2$: 2 $H_2O$: Calculated C:55.88; H:4.69; N:16.29; Found C:55.63; H:4.78; N:15.24

EXAMPLE 167

7-(2-Dimethylaminoethoxy)-4-(1H-indazol-6-ylamino)-6-methoxyquinoline-3-carbonitrile A mixture of 0.67 g (1 equivalent) of 7-(2-chloroethoxy)-4-(1H-indazol-6-ylamino)-6-methoxyquinoline-3-carbonitrile, 0.097 g (0.4 equivalent) of sodium iodide and 15 ml of 2M dimethylamine in tetrahydrofuran was heated at 135° C. for 14 hours in a sealed tube. The reaction mixture was diluted with ethyl acetate, washed with saturated sodium bicarbonate, the organic layer was dried over magnesium sulfate and concentrated to give 0.50 g. The crude product was purified by chromatography (Silica Gel: ethyl acetate, ethyl acetate/methyl alcohol/triethylamine 6:4:0.1) to give 0.312 g (46%) of pure product. MP 218–219° C. mass spectrum (electrospray m/e): M+H=402.9.

EXAMPLE 168

4-(1H-Indazol-6-ylamino)-6-methoxy-7-(2-morpholine-4-yl-ethoxy)quinoline-3-carbonitrile The title compound was prepared by the procedure of Example 167 using 0.616 g of 7-(2-chloroethoxy)-4-(1H- indazol-6-ylamino)-6-methoxyquinoline-3-carbonitrile, 0.094 g of sodium iodide and 2.03 ml of morpholine to give after purification by chromatography (Silica Gel: ethyl acetate, ethyl acetate/methyl alcohol/triethyl amine 6:4:0.1) 0.196 g (28%) of the desired product. MP 133–135° C. :mass spectrum (electrospray m/e): M+H=445.0.

EXAMPLE 169

4-(3H-Benzotriazol-5-ylamino)-7-(2-chloroethoxy)-6-methoxyquinoline-3-carbonitrile The title compound was prepared by the procedure of Example 166 using 0.442 g of 7-(2-chloro-ethoxy)-4-chloro-6-methoxy-quinoline-3-carbonitrile, 0.22 g 5-amino benzotriazole, 0.190 g of pyridine hydrochloride and 15 ml of 2-methoxyethanol to give 0.48 g (82%) of the desired product :mass spectrum (electrospray m/e): M+H=394.8.

EXAMPLE 170

7-(3-Chloropropoxy)-4-(1H-indazol-6-ylamino)-6-methoxyquinoline-3-carbonitrile

The title compound was prepared by the procedure of Example 166 using 0.311 g of 7-(3-chloro-propoxy)-4-chloro-6-methoxy-quinoline-3-carbonitrile, 0.147 g of 6-aminoimidazole, 0.128 g of pyridine hydrochloride and 12 ml of ethoxyethanol to give 0.367 g (90%) of the desired product. MP 280–285° C. mass spectrum (electrospray m/e): M+H=407.9.

EXAMPLE 171

4-(1H-Indazole-6-ylamino)-6-methoxy-7-(3-morpholin-4-ylpropoxy)quinoline-3-carbonitrile The title compound was prepared by the procedure of Example 167 using 0.408 g of (3-chloropropoxy)-4-(1H-indazol-6-ylamino)-6-methoxyquinoline-3-carbonitrile, 1.4 ml of morpholine, 0.060 g of sodium iodide and 12 ml of ethylene glycol dimethyl ether to give 0.255 g (56%) of the desired product. MP 143–145° C.; HRMS: $C_{25}H_{26}N_6O_3$: m/z 458.2084; δ(mu)−1.7

EXAMPLE 172

4[3-Chloro-4-(1-methyl-2-imidazolylthio)phenylamino]-6,7-diethoxy-3-quinolinecarbonitrile In the manner of Example 141 reaction of 4-chloro-6,7-diethoxy-3-quinolinecarbonitrile with 3-chloro-4-(1-methyl-2-imidazolylthio)aniline (WO-9615118) gave the title compound as a tan solid, mp 285–290° C.

EXAMPLE 173

4-[3-Chloro-4-(1-methyl-2-imidazolylthio)phenylamino]-6,7-dimethoxy-3-quinolinecarbonitrile In the manner of Example 141 reaction of 4-chloro-6,7-dimethoxy-3-quinolinecarbonitrile with 3-chloro-4-(1-methyl-2-imidazolylthio)aniline (WO-9615118) gave the title compound as a white solid, mp 302–307° C.

EXAMPLE 174

4-[3-Chloro-4-(1-methyl-1H-imidazol-2-ylsulfanyl)-phenylamino]-6-nitro-quinoline-3-carbonitrile A mixture of 5.00 g (21.5 mmol) 4-chloro-6-nitro-3-quinolinecarbonitrile, 250 ml ethanol, and 6.18 g (25.8 mmol) 3-chloro-4-(1-methyl-1H-imidazol-2-ylsulfanyl)-aniline (WO-9615118) was heated to reflux under $N_2$. Removed heat at 3½ hours and made basic with a solution of saturated sodium bicarbonate. Stripped solvents and azeotroped with ethanol. Slurried residue with hexane and collected solids. Washed with water, dried in vacuo. Boiled solids in hexane to remove excess aniline, air dried. Boiled in 2 L ethyl acetate, and because of extreme insolubility, collected solids and dried in vacuo, giving 5.90 g of yellow solid: mass spectrum (electrospray m/e): M+H=437.2, 439.1.

EXAMPLE 175

6-Amino-4-[3-chloro-4-(1-methyl-1H-imidazol-2-ylsulfanyl)-phenylamino]-quinoline-3-carbonitrile A mixture of 5.734 g (13.1 mmol) 4-[3-chloro-4-(1-methyl-1H-imidazol-2-ylsulfanyl)-phenylamino]-6-nitro-quinoline-3-carbonitrile, 250 ml ethanol, and 14.83 g (65.6 mmol) tin chloride dihydrate was heated to reflux under $N_2$. Removed heat at 2½ hours and added a large volume of ice water. Made basic with sodium bicarbonate and stirred for 2 hours. With mixture still basic, extracted with chloroform, stirred organic layer with Darco, dried with sodium sulfate and filtered. Stripped solvent and dried in vacuo, giving 2.86 g of yellow-brown solid: mass spectrum (electrospray m/e): M+H=407.3, 409.3.

EXAMPLE 176

N-{4-[3-Chloro-4-(1-methyl-1H-imidazol-2-ylsulfanyl)-phenylamino]-3-cyano-quinolin-6-yl}-acrylamide Dissolved most of 1.00 g (2.46 mmol) 6-amino-4-[3-chloro-4-(1-methyl-1H-imidazol-2-ylsulfanyl)-phenylamino]-quinoline-3-carbonitrile in 3.5 ml hot DMF, added 12 ml THF and chilled to 0° C. Added 377 μl triethyl amine and 225 μl (2.70 mmol) acryloyl chloride. Removed ice bath at 15 minutes and stripped solvent at 2 hours. Slurried residue in water, collected solids and air dried overnight. Boiled in ethyl acetate, collected solids and dried in vacuo, giving 670 mg of yellow-brown solid: mass spectrum (electrospray m/e): M+H=461.1, 462.2.

EXAMPLE 177

6-Amino-4-(1H-indol-5-ylamino)-quinoline-3-carbonitrile

Covered 200 mg of 10% Palladium on carbon with 75 ml ethanol. Added 2.00 g (6.07 mmol) 4-(1H-indol-5-ylamino)-6-nitro-quinoline-3-carbonitrile and 477 μl (15.2 mmol) hydrazine. Heated to reflux under $N_2$ for 2 hours. Filtered hot through celite and washed through with hot methanol. Removed solvent and dried in vacuo (50° C.), giving 1.89 g brown solid: mass spectrum (m/e electrospray): M+H=300.2.

EXAMPLE 178

3-chloro-4-(1,3-thiazol-2-ylsulfanyl)aniline

To a suspension of 3.8 g sodium hydride (60% in mineral oil) in 100 ml of dimethylformamide was added slowly a solution of 10.0 g of 2-mercapto thiazole in 100 ml of dimethylformamide. After 15 min a solution of 15.0 g 3-chloro-4-fluoro nitrobenzene in 50 ml of dimethylformamide was added. After 4 hrs, the mixture was poured into water. The resulting solid was collected, washed with water, and dried in vacuum. This material was mechanically stirred at reflux in a mixture of 830 ml of methanol, 230 ml of water, 37.0 g of ammonium chloride, and 30.1 g of iron powder for 4 hrs. The boiling mixture was filtered. The solvent was removed from the filtrate and the residue was extracted with hot ethyl acetate. The ethyl acetate solution was filtered through a short silica gel column. The solvent was removed and the residue was recrystallized from ether hexane giving 17.7 g of an off white solid.: mass spectrum electrospray, m/e): M+H 243.1.

By using a procedure similar that that described above, the following intermediates needed to prepare some of the compounds of this invention can be made.

3-chloro-4-(1H-imidazol-1-yl)aniline
2-[(4-amino-2-chlorophenyl)sulfanyl]-4(3H)-quinazolinone
N-(4-amino-2-chlorophenyl)-N-(3-pyridinylmethyl) acetamide
2-chloro-N~1~-[5-(trifluoromethyl)-1,3,4-thiadiazol-2-yl]-1,4-benzenediamine
3-chloro-4-[(4,6-dimethyl-2-pyrimidinyl)sulfanyl]aniline
3-chloro-4-[(4-methyl-2-pyrimidinyl)sulfanyl]aniline
4-[(4-phenyl-1,3-thiazol-2-yl)sulfanyl]-3-(trifluoromethyl) aniline
4-[(4-phenyl-1,3-thiazol-2-yl)sulfanyl]-3-(chloro)aniline

EXAMPLE 179

1-(2-chloro-4-aminobenzyl)-1H-imidazole

A solution of 10 g of 4-bromomethyl-3-chloro nitrobenzene and 5.44 g of imidazole in 125 ml of tetrahydrofuran was refluxed for 4 hrs. The solvent was removed and the residue was dissolved in ethyl acetate. The solution was washed with water and dried over magnesium sulfate. The solvent was removed and the residue was extracted several times with ether. The ether extracts were diluted with two volumes of hexanes. 1-(2-Chloro-4-nitrobenzyl)-1H-imidazole (4.3 g) crystallized as a white solid. A 4 g portion of this material was mechanically stirred at reflux with 153 ml of methanol, 52 ml of water, 8.1 g of ammonium chloride, and 6.6 g of iron powder for 2 hrs. The hot mixture was filtered and solids were washed with hot methanol-tetrahydrofuran mixtures. Solvents were removed from the combined filtrates. The residue was extracted several times with hot ethyl acetate, The ethyl acetate solution was treat with magnesium sulfate and activated charcoal. Filtering and removing the solvent gave the 3.9 g of the title compound.

By using the methods described in Examples 1–179 above and the methods described in the patent applications WO-98/43960 and WO-99/09016, the compounds of this invention listed in Table 5 were prepared.

TABLE 5

| Example | Compound | m.p. (° C.) | mass spectrum |
|---|---|---|---|
| 180 | 4-(2-Hydroxy-naphthalen-1-ylamino)-6,7-dimethoxy-quinoline-3-carbonitrile | 240 dec | 371.9 (M + H) |
| 181 | 4-(2,3-Dihydro-benzo[1, 4]dioxin-6-ylamino)-6,7 dimethoxy-quinoline-3-carbonitrile | 200–201 | 364.0 (M + H) |
| 182 | 4-(2-Mercapto-benzothiazol-6-ylamino)-6,7-dimethoxy quinoline-3-carbonitrile | >255 dec | 394.8 (M + H) |
| 183 | 4-(6-Hydroxy-naphthalen-1-ylamino)-6,7-dimethoxy quinoline-3-carbonitrile | 205 dec | 372.0 (M + H) |
| 184 | 4-(1H-Indazol-6-ylamino)-5-methoxy-quinoline 3 carbonitrile | >260 | 315.8 (M + H) |
| 185 | 4-(2-chloro-5-methoxyanilino)-5-methoxyquinoline 3 carbonitrile | 185–187 | 339.9 (M + H) |
| 186 | 4-[(2-Amino-4-chlorophenyl)amino]-6,7-dimethoxy 3 quinolinecarbonitrile | 215 dec | 354.9 (M + H) |
| 187 | 4-[(3-hydroxy-2-naphthyl)amino]-6,7-dimethoxy 3 quinolinecarbonitrile | 277–282 dec | 372.2 (M + H) |
| 188 | 4-{3-chloro-4-[(1-methyl-1H-imidazol-2-yl)sulfanyl]anilino}-7-methoxy-6-nitro-3-quinolinecarbonitrile | | 467.2 (M + H) |
| 189 | 6-amino-4-{3-chloro-4-[(1-methyl-1H-imidazol 2 yl)sulfanyl]anilino}-7-methoxy-3-quinolinecarbonitrile | | 437.0 (M + H) |
| 190 | (E)-N-(4-{3-chloro-4-[(1-methyl-1H-imidazol-2 yl)sulfanyl]anilino}-3-cyano-7-methoxy-6-quinolinyl) 4 (dimethylamino)-2-butenamide | | 548.1 (M + H), 274.7 (M + 2H)$^{+2}$ |
| 191 | 4-[3-chloro-4-(1,3-thiazol-2-ylsulfanyl)anilino]-7-methoxy-6-nitro-3-quinolinecarbonitrile | | 470.0 (M + H) |
| 192 | 6-amino-4-[3-chloro-4-(1,3-thiazol-2-ylsulfanyl)anilino]-7-methoxy-3-quinolinecarbonitrile | | 440.1 (M + H) |
| 193 | (E)-N-{4-[3-chloro-4-(1,3-thiazol-2-ylsulfanyl)anilino]-3-cyano-7-methoxy-6--quinolinyl}-4-(dimethylamino) 2-butenamide | | 551.1 (M + H), 276.2 (M + 2H)$^{+2}$ |
| 194 | 4-[3-chloro-4-(1H-imidazol-1-yl)anilino]-7-methoxy-6-nitro-3-quinolinecarbonitrile | | 421.3 (M + H), 211.1 (M + 2H)$^{+2}$ |
| 195 | 6-amino-4-[3-chloro-4-(1H-imidazol-1-yl)anilino]-7-methoxy-3-quinolinecarbonitrile | | 391.2 (M + H), 196.2 (M + 2H)$^{+2}$ |
| 196 | (E)-N-{4-[3-chloro-4-(1H-imidazol-1-yl)anilino]-3-cyano-7-methoxy-6-quinolinyl}-4-(dimethylamino)-2-butenamide | | 502.4 (M + H), 251.7 (M + 2H)$^{+2}$ |
| 197 | 4-{3-chloro-4-[(4-oxo-3,4-dihydro-2-quinazolinyl)sulfanyl]anilino}-7-methoxy-6-nitro-3-quinolinecarbonitrile | | 531.2 (M + H), 266.2 (M + 2H)$^{+2}$ |

TABLE 5-continued

| Example | Compound | m.p. (° C.) | mass spectrum |
|---|---|---|---|
| 198 | 6-amino-4-{3-chloro-4-[(4-oxo-3,4-dihydro-2-quinazolinyl)sulfanyl]anilino}-7-methoxy-3-quinolinecarbonitrile | | 501.3 (M + H), 251.1 (M + 2H)$^{+2}$ |
| 199 | (E)-N-(4-{3-chloro-4-[(4-oxo-3,4-dihydro-2-quinazolinyl)sulfanyl]anilino}-3-cyano-7-methoxy-6-quinolinyl)-4-(dimethylamino)-2-butenamide | | 612.4 (M + H), 306.7 (M + 2H)$^{+2}$ |
| 200 | 6-methoxy-7-[3-(4-morpholinyl)propoxy]-4-[4-(4-pyridinylmethyl)anilino]-3-quinolinecarbonitrile | 139–141 | 510.2 (M + H), 255.7 (M + 2H)$^{+2}$ |
| 201 | 6-methoxy-7-[3-(4-morpholinyl)propoxy]-4-[4-(3-pyridinylmethyl)anilino]-3-quinolinecarbonitrile | 112–114 | 510.3 (M + H), |
| 202 | 6-methoxy-7-[3-(4-morpholinyl)propoxy]-4-[4-(2-pyridinylmethyl)anilino]-3-quinolinecarbonitrile | 168–170 | 510.2 (M + H), 255.7 (M + 2H)$^{+2}$ |
| 203 | (E)-N-(4-{4-[acetyl(3-pyridinylmethyl)amino]-3-chloroanilino}-3-cyano-7-methoxy-6-quinolinyl)-4-(dimethylamino)2-butenamide | | 584.1 (M + H), 292.7 (M + 2H)$^{+2}$ |
| 204 | N-{2-chloro-4-[(3-cyano-7-methoxy-6-nitro-4-quinolinyl)amino]phenyl}-N-(3--pyridinylmethyl)acetamide | | 503.1 (M + H), 252.1 (M + 2H)$^{+2}$ |
| 205 | N-{4-[(6-amino-3-cyano-7-methoxy-4-quinolinyl)amino]-2-chlorophenyl}-N-(3-pyridinylmethyl)acetamide | | 473.1 (M + H), 237.2 (M + 2H)$^{+2}$ |
| 206 | N-(4-{[6-(acetylamino)-3-cyano-7-methoxy-4-quinolinyl]amino}-2-chlorophenyl)-N-(3-pyridinylmethyl)acetamide | | 515.1 (M + H) |
| 207 | 4-[3chloro-4-(1,3-dimethyl-2,4,6-trioxohexahydro-5 pyrimidinyl)anilino]-7-methoxy-6-nitro-3-quinolinecarbonitrile | 270–272 | 509.2(M + H) |
| 208 | 4-{3-chloro-4-[(4-phenyl-1,3-thiazol-2-yl)sulfanyl]anilino}-7-methoxy-6-nitro-3-quinolinecarbonitrile | 256–262 | 546.2 (M + H) |
| 209 | 6-methoxy-7-[3-(4-morpholinyl)propoxy]-4-[4-(3-thienylmethyl)anilino]-3-quinolinecarbonitrile | 152–153 | 515.3 (M + H), 258.3 (M + 2H)$^{+2}$ |
| 210 | 6-methoxy-7-[3-(4-morpholinyl)propoxy]-4-[4-(2-thienylmethyl)anilino]-3-quinolinecarbonitrile | 152–154 | 515.3 (M + H), |
| 211 | 6-methoxy-4-(4-phenoxyanilino)-7-[2-(2H-1, 2, 3-triazol 2-yl)ethoxy]-3-quinolinecarbonitrile | 154–155 | 479.3 (M + H) |
| 212 | 6-methoxy-4-(4-phenoxyanilino)-7-[2-(1H-1, 2, 3-triazol 1-yl)ethoxy]-3-quinolinecarbonitrile | 188–189 | 479.3 (M + H) |
| 213 | 4-(4-benzylanilino)-6-methoxy-7-[2-(2H-1, 2, 3-triazol-2-yl)ethoxy]-3-quinolinecarbonitrile | 167–170 | 477.4 (M + H) |
| 214 | 4-(4-benzylanilino)-6-methoxy-7-[2-(2H-1, 2, 3-triazol-1-yl)ethoxy]-3-quinolinecarbonitrile | | 477.5 (M + H) |
| 215 | 6-methoxy-7-[3-(4-morpholinyl)propoxy]4-[4-(2-pyndinyloxy)anilino]-3-quinolinecarbonitrile | 127–130 | 512.6 (M + H), 256.8 (M + 2H)$^{+2}$ |
| 216 | 4-{3-chloro-4-[(1-methyl-1H-imidazol-2-yl)sulfanyl]anilino}-6-methoxy-7-[3-(4-morpholinyl)propoxy]-3-quinolinecarbonitrile | 234–235 | 565.4 (M + H), 283.5 (M + 2H)$^{+2}$ |
| 217 | 4[4-(2-furylmethyl)anilino]-6-methoxy-7-[3,(4-morpholinyl)propoxy]-3-quinolinecarbonitrile | 149–151 | 499.5 (M + H), 250.3 (M + 2H)$^{+2}$ |
| 218 | 6-methoxy-7-[3-(4-morpholinyl)propoxy]-4-]4-(tetrahydro-2-furanylmethyl)anilino]-3-quinolinecarbonitrile | 132–134 | 503.4 (M + H), 252.4 (M + H)$^{+2}$ |
| 219 | 4-[4-(3-furylmethyl)anilino]-6-methoxy-7-[3-(4-morpholinyl)propoxy]-3-quinolinecarbonitrile | 163–165 | 499.5 (M + H), 250.3 (M + 2H)$^{+2}$ |
| 220 | 6-methoxy-7-[3-(4-morpholinyl)propoxy]-4-[4-(tetrahydro-3-furanylmethyl)anilino]-3-quinolinecarbonitrile | 123–125 | 503.4 (M + H), 252.2 (M + 2H)$^{+2}$ |
| 221 | 4-(3-chloro-4-{[5-(trifluoromethyl)-1,3,4-thiadiazol-2-yl]amino}anilino)-7-ethoxy-6-nitro-3-quinolinecarbonitrile | | 536.1 (M + H) |
| 222 | (E)-N[4-(3-chloro-4-{[5-(trifluoromethyl)-1,3,4-thiadiazol-2-yl]amino}anilino)-3-cyano-7-ethoxy-6-quinolinyl]-4-(dimethylamino)-2-butenamide | | 617.3 (M + H), 309.3 (M + 2H)$^{+2}$ |
| 223 | 4-[3-chloro-4-(4-pyridinyloxy)anilino]-7-ethoxy-6-nitro-3-quinolinecarbonitrile | | 462.2 (M + H), 231.6 (M + 2H)$^{+2}$ |
| 224 | 6-amino-4-[3-chloro-4-(4-pyridinyloxy)anilino]-3-cyano-ethoxy-3-quinolinecarbonitrile | | 543.4 (M + H), 216.6 (M + 2H)$^{+2}$ |
| 225 | (E)-N-·4-[3-chloro-4-(4-pyridinyloxy)anilino]-3-cyano-7-ethoxy-6-quinolinyl}-4-(dimethylamino)-2-butenamide | | 543.3 (M + H), 272.2 (M + 2H)$^{+2}$ |
| 226 | 4-{3-chloro-4-[(3-pyridinylmethyl)amino]anilino}-7-methoxy-6-nitro-3-quinolinecarbonitrile | | 461.3 (M + H), |
| 227 | 6-amino-4-}3-chloro-4-[(4-phenyl-1,3-thiazol-2-yl)sulfanyl]anilino}-7-methoxy-3-quinolinecarbonitrile | 166–172 | 516.2 (M + H) |
| 228 | 6-amino-4-(3-chloro-4-{[5-(trifluoromethyl)-1,3,4-thiadiazol-2-yl]amino}anilino)-7-ethoxyl-3-quinolinecarbonitrile | | 506.4 (M + H) |

TABLE 5-continued

| Example | Compound | m.p. (° C.) | mass spectrum |
|---|---|---|---|
| 229 | 6-methoxy-7-[3-(4-morpholinyl)propoxy]-4-[4-(2-phenylethyl)anilino]-3-quinolinecarbonitrile | 106–108 | 523.5 (M + H), |
| 230 | (E)-N-(4-{3-chloro-4-[(4-phenyl-1,3-thiazol-2-yl)sulfanyl]anilino}-3-cyano-7-methoxy-6-quinolinyl)-4-(dimethylamino)-2-butenamide | 154–157 | 627.3 (M + H), 314.3 (M + 2H)$^{+2}$ |
| 231 | 4-[3-chloro-4-(1H-imidazol-1-yl)anilino]-6-methoxy-7-[3-(4-morpholinyl)propoxy]-3-quinolinecarbonitrile | 130–133 | 519.3 (M + H), 260.3 (M + 2H)$^{+2}$ |
| 232 | 6-methoxy-7-[3-(4-morpholinyl)propoxy]-4-[4-(3-pyridinyloxy)anilino]-3-quinolinecarbonitrile | 135–137 | 512.2 (M + H), |
| 233 | 4-[3-chloro-4-(4-pyridinyloxy)anilino]-6-methoxy-7-[3-(4-morpholinyl)propoxy]-3-quinolinecarbonitrile | 174 dec | 546.1 (M + H), 273.8 (M + 2H)$^{+2}$ |
| 234 | 6-methoxy-7-[3-(4-morpholinyl)propoxy]-4-[4-(4-pyridinyloxy)anilino]-3-quinolinecarbonitrile | 129–131 | 512.1 (M + H), 256.8 (M + 2H)$^{+2}$ |
| 235 | 4-[2-chloro-4-(1,3-thiazol-2-ylsulfanyl)anilino]-6-methoxy-7-[3-(4-morpholinyl)propoxy]-3-quinolinecarbonitrile | 122 | 568.0 (M + H), 284.7 (M + 2H)$^{+2}$ |
| 236 | N-[2-chloro-4-({3-cyano-6-methoxy-7-[3-(4-morpholinyl)propoxy]-4-quinolinyl}amino)phenyl]-N-(3-pyridinylmethyl)acetamide | 120 dec | 601.1 (M + H), 301.3 (M + 2H)$^{+2}$ |
| 237 | 6-methoxy-7-[3-(4-morpholinyl)propoxy]-4-[4-(1H-tetraazol-5-ylmethyl)anilino]-3-quinolinecarbonitrile | 208 dec | 501.2 (M + H), 251.0 (M + 2H)$^{+2}$ |
| 238 | 6-methoxy-7[3-(4-morpholinyl)propoxy]-4-[4-(2H-1,2,3-triazol-2-ylmethyl)anilino]-3-quinolinecarbonitrile | 186–187 | 500.3 (M + H), 250.8 (M + 2H)$^{+2}$ |
| 239 | 6-methoxy-7[3-(4-morpholinyl)propoxy]-4-[4-(2H-1,2,3-triazol-2-ylmethyl)anilino]-3-quinolinecarbonitrile | 200–201 | 500.2 (M + H), 250.7 (M + 2H)$^{+2}$ |
| 240 | 4-(2,4-dichloro-5-methoxyanilino)-6-methoxy-7-[2-(2H-1,2,3-triazol-2-yl)ethoxy]-3-quinolinecarbonitrile | 223–226 | 485.1 (M + H) |
| 242 | 4-(2,4-dichloro-5-methoxyanilino)-6-methoxy-7-[2-(2H-1,2,3-triazol-2-yl)ethoxy]-3-quinolinecarbonitrile | 196–197 | 485.1 (M + H) |
| 242 | 7-ethoxy-6-nitro-4[4[(4-phenyl-1,3-thiazol-2-yl)sulfanyl]-3-(trifluoromethyl)anilino]-3-quinolinecarbonitrile | | 594.0 (M + H) |
| 243 | 6-amino-7-ethoxy-4[4[(4-phenyl-1,3-thiazol-2-yl)sulfanyl]-3-(trifluoromethyl)anilino]-3-quinolinecarbonitrile | | 564.0 (M + H) |
| 244 | (E)-N-{3-cyano-7-ethoxy-4[4[(4-phenyl-1,3-thiazol-2-yl)sulfanyl]-3-(trifluoromethyl)anilino]6-quinolinyl}-4-(dimethylamino)_-2-butenamide | | 675.0 (M + H), 338.3 (M + 2H)$^{+2}$ |
| 245 | 4[3-chloro-4-(1H-imidazol-1-ylmethyl)anilino]-7-ethoxy-6-nitro-3-quinolinecarbonitrile | | 449.1 (M + H), 225.2 (M + 2H)$^{+2}$ |
| 246 | 6-amino-4[3-chloro-4-1H-imidazol-1-ylmethyl)anilino]-7-ethoxy-3-quinolinecarbonitrile | | 419.2 (M + H), 210.3 (M + 2H)$^{+2}$ |
| 247 | (E)-N-{4[3-chloro-4-(1H-imidazol-1-ylmethyl)anilino]-3-cyano-7-ethoxy-6-quinolinyl}-4-(dimethylamino)-2-butenamide | | 530.2 (M + H), 265.8 (M + 2H)$^{+2}$ |
| 248 | 4-{3-chloro-4[(4-methyl-2-pyrimidinyl)sulfanyl]anilino}-7-ethoxy-6-nitro-3-quinolinecarbonitrile | | 493.0 (M + H) |
| 249 | 6-amino-4-{3-chloro-4-(4-methyl-2-pyrimidinyl)sulfanyl]anilino}-7-ethoxy-3-quinolinecarbonitrile | | 463.1 (M + H) |
| 250 | (E)-N-(4-{3-chloro-4[(4-methyl-2-pyrimidinyl)sulfanyl]anilino}-3-cyano-7-ethoxy-6-quinolinyl)-4-(dimethylamino)-2-butenamide | | 574.1 (M + H), 287.8 (M + 2H)$^{+2}$ |
| 251 | 4-{3-chloro-4[(4,6-dimethyl-2-pyrimidinyl)sulfanyl]anilino}-7-ethoxy-6-nitro-3-quinolinecarbonitrile | | 507.1 (M + H) |
| 252 | 6-amino-4-{3-chloro-4[(4,6-dimethyl-2-pyrimidinyl)sulfanyl]anilino}-7-ethoxy-3-quinolinecarbonitrile | | 477.1 (M + H) |
| 253 | (E)-N-(4-{3-chloro-4[(4,6-dimethyl-2-pyrimidinyl)sulfanyl]anilino}-3-cyano-7-ethoxy-6-quinolinyl)-4-(dimethylamino)-2-butenamide | | 588.1 (M + H), 294.8 (M + 2H)$^{+2}$ |
| 254 | 4-[4-(1H-imidazol-2-ylmethyl)anilino]-6-methoxy-7-[3-(4-morpholinyl)propoxy]-3-quinolinecarbonitrile | 156–158 | 499.3 (M + H), 250.3 (M + 2H)$^{+2}$ |
| 255 | 6-methoxy-7[3-(4-morpholinyl)propoxy]-4[4-(1H-tetraazol-1-ylmethyl)anilino]-3-quinolinecarbonitrile | 180 dec | 501.3 (M + H), 251.3 (M + 2H)$^{+2}$ |
| 256 | 6-methoxy-7[3-(4-morpholinyl)propoxy]-4-[4-(2H-tetraazol-2-ylmethyl)anilino]-3-quinolinecarbonitrile | 123 dec | 501.2 (M + H), 251.3 (M + 2H)$^{+2}$ |
| 257 | 4-{3-chloro-4[(4,6-dimethyl-2-pyrimidinyl)sulfanyl]anilino}-6-methoxy-7-[3-(4-morpholinyl)propoxy]-3-quinolinecarbonitrile | 110–113 | 591.1 (M + H), 296.2 (M + 2H)$^{+2}$ |
| 258 | 4-{3-chloro-4[(4-methyl-2-pyrimidinyl)sulfanyl]anilino}-6-methoxy-7-[3-(4-morpholinyl)propoxy]-3-quinolinecarbonitrile | 10–113 | 577.1 (M + H), 289.2 (M + 2H)$^{+2}$ 577.1 (M + H), 289.2 (M + 2H)$^{+2}$ |

TABLE 5-continued

| Example | Compound | m.p. (° C.) | mass spectrum |
|---|---|---|---|
| 259 | (E)-N[4-(3-chloro-4-{[2-(phenylsulfanyl)acetyl]amino}anilino)-3-cyano-7-methoxy-6-quinolinyl]-4-(dimethylamino)-2-butenamide | 194–198 | 601.3 (M + H), 301.1 (M + 2H)$^{+2}$ |
| 260 | 4-[4-(2,6-dimethoxyphenoxy)anilino]-6-methoxy-7-[3-(4-morpholinyl)propoxy]-3-quinolinecarbonitrile | 160–162 | 571.4 (M + H) |
| 261 | 6-methoxy-4-[4-(3-methoxyphenoxy)anilino]-7-[3-(4 morpholinyl)propoxy]-3-quinolinecarbonitrile | 132–134 | 541.5 (M + H) |
| 262 | 6-methoxy-4-{4[(1-methyl-1H-imidazol-2-yl)sulfanyl]anilino}-7[3-(4-morpholinyl)propoxy]-3-quinolinecarbonitrile | 208–210 | 531.4 (M + H) |
| 263 | (E)-N-{4[3-chloro-4-(1,3-thiazol-2-ylsulfanyl)anilino]-3-cyano-7-methoxy-6-quinolinyl}-4[(2-methoxyethyl)(methyl)anilino]-2-butenamide | | 595.1 (M + H), 298.1 (M + 2H)$^{+2}$ |
| 264 | (E)-N-(4-{3-chloro-4[(5-phenyl-1,3-thiazol-2-yl)sulfanyl]anilino}-3-cyano-7-methoxy-6-quinolinyl)-4-(dimethylamino)-2-butenamide | | 627.1 (M + H), 314.1 (M + 2H)$^{+2}$ |
| 265 | (E)-N-(4-{3-chloro-4[(4-phenyl-1,3-thiazol-2-yl)sulfanyl]anilino}-3-cyano-7-'ethoxy-6-quinolinyl)-4-(dimethylamino)-2-butenamide | | 641.3 (M + H) 321.2 (M + 2H)$^{+2}$ |
| 266 | 4-{3-chloro-4[(4,6-dimethyl-2-pyrimidinyl)sulfanyl]anilino}-6,7-dimethoxy-3-quinolinecarbonitrile | 173–176 | 478.4#(M + H) |
| 267 | 6,7-dimethoxy-4-({6[(4-phenyl-1,3-thiazol-2 yl)sulfanyl]-3-pyridnyl}amino)-3-quinolinecarbonitrile | 250 (dec) | 498.3 (M + H) |
| 268 | 4-{3-chloro-4-[(1-methyl-1H-imidazol-2-yl)sulfanyl]anilino}-6-methoxy-7[3-(2H-1,2,3-triazol-2-yl)propoxy]-3-quinolinecarbonitrile | 232–234 | 547.3 (M + H) |
| 269 | 4-{3-chloro-4-[(1-methyl-1H-imidazol-2-yl)sulfanyl]anilino}-6-methoxy-7-[3-(1H-1,2,3-triazol-1-yl)propoxy]-3-quinolinecarbonitrile | 208–210 | 547.3 (M + H) |

What is claimed is:

1. A compound of formula 1 having the structure:

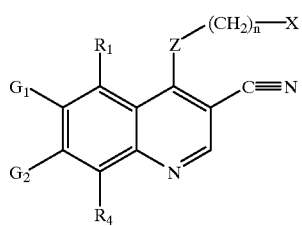

wherein:

X is a bicyclic aryl or bicyclic heteroaryl ring system of 8 to 12 atoms where the bicyclic heteroaryl ring contains 1 to 4 heteroatoms selected from N, O, and S with the proviso that the bicyclic heteroaryl ring does not contain O—O, S—S, or S—O bonds and where the bicyclic aryl or bicyclic heteroaryl ring may be optionally mono- di-, tri, or tetra-substituted with a substituent selected from the group consisting of halogen, oxo, thio, alkyl of 1–6 carbon atoms, alkenyl of 2–6 carbon atoms, alkynyl of 2–6 carbon atoms, azido, hydroxyalkyl of 1–6 carbon atoms, halomethyl, alkoxymethyl of 2–7 carbon atoms, alkanoyloxymethyl of 2–7 carbon atoms, alkoxy of 1–6 carbon atoms, alkylthio of 1–6 carbon atoms, hydroxy, trifluoromethyl, cyano, nitro, carboxy, carboalkoxy of 2–7 carbon atoms, carboalkyl of 2–7 carbon atoms, phenoxy, phenyl, thiophenoxy, benzoyl, benzyl, amino, alkylamino of 1–6 carbon atoms, dialkyl amino of 2 to 12 carbon atoms, phenylamino, benzylamino, alkanoylamino of 1–6 carbon atoms, alkenoylamino of 3–8 carbon atoms, alkynoylamino of 3–8 carbon atoms, carboxyalkyl of 2–7 carbon atoms, carboalkoxyalky of 3–8 carbon atoms, aminoalkyl of 1–5 carbon atoms, N-alkylaminoalkyl of 2–9 carbon atoms, N,N-dialkylaminoalkyl of 3–10 carbon atoms, N-alkylaminoalkoxy of 2–9 carbon atoms, N,N-dialkylaminoalkoxy of 3–10 carbon atoms, mercapto, and benzoylamino; or X is a radical having the formula:

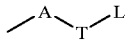

wherein

A is a pyridinyl, pyrimidinyl, or phenyl ring; wherein the pyridinyl, pyrimidinyl, or phenyl ring may be optionally mono- or di-substituted with a substituent selected from the group consisting of halogen, alkyl of 1–6 carbon atoms, alkenyl of 2–6 carbon atoms, alkynyl of 2–6 carbon atoms, azido, hydroxyalkyl of 1–6 carbon atoms, halomethyl, alkoxymethyl of 2–7 carbon atoms, alkanoyloxymethyl of 2–7 carbon atoms, alkoxy of 1–6 carbon atoms, alkylthio of 1–6 carbon atoms, hydroxy, trifluoromethyl, cyano, nitro, carboxy, carboalkoxy of 2–7 carbon atoms, carboalkyl of 2–7 carbon atoms, phenoxy, phenyl, thiophenoxy, benzoyl, benzyl, amino, alkylamnino of 1–6 carbon atoms, dialkylamino of 2 to 12 carbon atoms, phenylamino, benzylamino, alkanoylamino of 1–6 carbon atoms, alkenoylamino of 3–8 carbon atoms, alkynoylamino of 3–8 carbon atoms, carboxyalkyl of 2–7 carbon atoms, carboalkoxyalky of 3–8 carbon atoms, aminoalkyl of 1–5 carbon atoms, N-alkylaminoalkyl of 2–9 carbon atoms, N,N-dialkylaminoalkyl of 3–10 carbon atoms, N-alkylaminoalkoxy of 2–9 carbon atoms, N,N-dialkylaminoalkoxy of 3–10 carbon atoms, mercapto, and benzoylamino;

T is bonded to a carbon of A and is:
—NH(CH$_2$)$_m$—, —O(CH$_2$)$_m$—, —S(CH$_2$)$_m$—, —NR(CH$_2$)$_m$—, —(CH$_2$)$_m$— —(CH$_2$)$_m$NH—, —(CH$_2$)$_m$O—, —(CH$_2$)$_m$S—, or —(CH$_2$)$_m$NR—;

L is an unsubstituted phenyl ring or a phenyl ring mono-, di-, or tri-substituted with a substituent selected from the group consisting of halogen, alkyl of 1–6 carbon atoms, alkenyl of 2–6 carbon atoms, alkynyl of 2–6 carbon atoms, azido, hydroxyalkyl of 1–6 carbon atoms, halomethyl, alkoxymethyl of 2–7 carbon atoms, alkanoyloxymethyl of 2–7 carbon atoms, alkoxy of 1–6 carbon atoms, alkylthio of 1–6 carbon atoms, hydroxy, trifluoromethyl, cyano, nitro, carboxy, carboalkoxy of 2–7 carbon atoms, carboalkyl of 2–7 carbon atoms, phenoxy, phenyl, thiophenoxy, benzoyl, benzyl, amino, alkylamino of 1–6 carbon atoms, dialkylamino of 2 to 12 carbon atoms, phenylamino, benzylamino, alkanoylamino of 1–6 carbon atoms, alkenoylamino of 3–8 carbon atoms, alkynoylamino of 3–8 carbon atoms, carboxyalkyl of 2–7 carbon atoms, carboalkoxyalky of 3–8 carbon atoms, aminoalkyl of 1–5 carbon atoms, N-alkylaminoalkyl of 2–9 carbon atoms, N,N-dialkylaminoalkyl of 3–10 carbon atoms, N-alkylaminoalkoxy of 2–9 carbon atoms, N,N-dialkylaminoalkoxy of 3–10 carbon atoms, mercapto, and benzoylamino; provided that L can be an unsubstituted phenyl ring only when m>0 and T is not —CH$_2$NH— or —CH$_2$O—; or L is a 5- or 6-membered heteroaryl ring where the heteroaryl ring contains 1 to 3 heteroatoms selected from N, O, and S, with the proviso that the heteroaryl ring does not contain O—O, S—S, or S—O bonds, and where the heteroaryl ring is optionally mono- or di-substituted with a substituent selected from the group consisting of halogen, oxo, thio, alkyl of 1–6 carbon atoms, alkenyl of 2–6 carbon atoms, alkynyl of 2–6 carbon atoms, azido, hydroxyalkyl of 1–6 carbon atoms, halomethyl, alkoxymethyl of 2–7 carbon atoms, alkanoyloxymethyl of 2–7 carbon atoms, alkoxy of 1–6 carbon atoms, alkylthio of 1–6 carbon atoms, hydroxy, trifluoromethyl, cyano, nitro, carboxy, carboalkoxy of 2–7 carbon atoms, carboalkyl of 2–7 carbon atoms, phenoxy, phenyl, thiophenoxy, benzoyl, benzyl, amino, alkylamino of 1–6 carbon atoms, dialkylamino of 2 to 12 carbon atoms, phenylamino, benzylamino, alkanoylamino of 1–6 carbon atoms, alkenoylamino of 3–8 carbon atoms, alkynoylamino of 3–8 carbon atoms, carboxyalkyl of 2–7 carbon atoms, carboalkoxyalky of 3–8 carbon atoms, aminoalkyl of 1–5 carbon atoms, N-alkylaminoalkyl of 2–9 carbon atoms, N,N-dialkylaminoalkyl of 3–10 carbon atoms, N-alkylaminoalkoxy of 2–9 carbon atoms, N,N-dialkylaminoalkoxy of 3–10 carbon atoms, mercapto, and benzoylamino;

Z is —NH—, —O—, —S—, or —NR—;

R is alkyl of 1–6 carbon atoms, or carboalkyl of 2–7 carbon atoms;

G$_1$, G$_2$, R$_1$, and R$_4$ are each, independently, hydrogen, halogen, alkyl of 1–6 carbon atoms, alkenyl of 2–6 carbon atoms, alkynyl of 2–6 carbon atoms, alkenyloxy of 2–6 carbon atoms, alkynyloxy of 2–6 carbon atoms, hydroxymethyl, halomethyl, alkanoyloxy of 1–6 carbon atoms, alkenoyloxy of 3–8 carbon atoms, alkynoyloxy of 3–8 carbon atoms, alkanoyloxymethyl of 2–7 carbon atoms, alkenoyloxymethyl of 4–9 carbon atoms, alkynoyloxymethyl of 4–9 carbon atoms, alkoxymethyl of 2–7 carbon atoms, alkoxy of 1–6 carbon atoms, alkylthio of 1–6 carbon atoms, alkylsulphinyl of 1–6 carbon atoms, alkylsulphonyl of 1–6 carbon atoms, alkylsulfonamido of 1–6 carbon atoms, alkenylsulfonamido of 2–6 carbon atoms, alkynylsulfonamido of 2–6 carbon atoms, hydroxy, trifluoromethyl, trifluoromethoxy, cyano, nitro, carboxy, carboalkoxy of 2–7 carbon atoms, carboalkyl of 2–7 carbon atoms, phenoxy, phenyl, thiophenoxy, benzyl, amino, hydroxyamino, alkoxyamino of 1–4 carbon atoms, alkylamino of 1–6 carbon atoms, dialkylamino of 2 to 12 carbon atoms, N-alkylcarbamoyl, N,N-dialkylcarbamoyl, N-alkyl-N-alkenylamino of 4 to 12 carbon atoms, N,N-dialkenylamino of 6–12 carbon atoms, phenylamino, benzylamino,

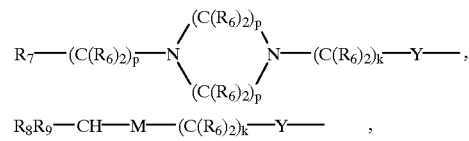

R$_7$—(C(R$_6$)$_2$)$_g$—Y—, R$_7$—(C(R$_6$)$_2$)$_p$—M—(C(R$_6$)$_2$)$_k$—Y—, or Het-(C(R$_6$)$_2$)$_q$—W—(C(R$_6$)$_2$—Y—;

or R1 and R4 are as defined above and G$_1$ or G$_2$ or both are R$_2$—NH—;

or if any of the substituents R$_1$, G$_2$, G$_3$, or R$_4$ are located on contiguous carbon atoms then they may be taken together as the divalent radical —O—C(R$_6$)$_2$—O—;

Y is a divalent radical selected from the group consisting of

—(CH$_2$)$_a$—, —O—, and —N(R$_6$)—;

R$_7$ is —NR$_6$R$_6$, —OR$_6$, —J, —N(R$_6$)$_3$$^+$, or —NR$_6$(OR$_6$);

M is >NR$_6$, —O—, >N—(C(R$_6$)$_2$)$_p$NR$_6$R$_6$, or >N—(C(R$_6$)$_2$)$_p$—OR$_6$;

W is >NR$_6$, —O— or is a bond;

Het is is selected from the group consisting of morpholine, thiomorpholine, thiomorpholine S-oxide, thiomorpholine S,S-dioxide, piperidine, pyrrolidine, aziridine, pyridine, imidazole, 1,2,3-triazole, 1,2,4-triazole, thiazole, thiazolidine, tetrazole, piperazine, furan, thiophene, tetrahydrothiophene, tetrahydrofuran, dioxane, 1,3-dioxolane, tetrahydropyran, and

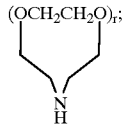

wherein Het is optionally mono- or di-substituted on carbon or nitrogen with R$_6$, optionally mono- or di-substituted on carbon with hydroxy, —N(R$_6$)$_2$, or —OR$_6$, optionally mono or di-substituted on carbon with the mono-valent radicals —(C(R$_6$)$_2$)$_s$OR$_6$ or —(C(R$_6$)$_2$)$_s$N(R$_6$)$_2$, and optionally mono or di-substituted on a saturated carbon with divalent radicals —O— or —O(C(R$_6$)$_2$)$_s$O—;

R$_6$ is hydrogen, alkyl of 1–6 carbon atoms, alkenyl of 2–6 carbon atoms, alkynyl of 2–6 carbon atoms, cycloalkyl of 1–6 carbon atoms, carboalkyl of 2–7 carbon atoms, carboxyalkyl (2–7 carbon atoms), phenyl, or phenyl optionally substituted with one or more halogen, alkoxy of 1–6 carbon atoms, trifluoromethyl, amino, alkylamino of 1–3 carbon atoms, dialkylamino of 2–6 carbon atoms, nitro, cyano, azido, halomethyl, alkoxymethyl of 2–7 carbon atoms, alkanoyloxymethyl of 2–7 carbon atoms, alkylthio of 1–6 carbon atoms, hydroxy, carboxyl, carboalkoxy of 2–7 carbon atoms, phenoxy, phenyl, thiophenoxy, benzoyl, benzyl, phenylamino, benzylamino, alkanoylamino of 1–6 carbon atoms, or alkyl of 1–6 carbon atoms; with the proviso that the alkenyl or alkynyl moiety is bound to a nitrogen or oxygen atom through a saturated carbon atom;

$R_2$, is selected from the group consisting of

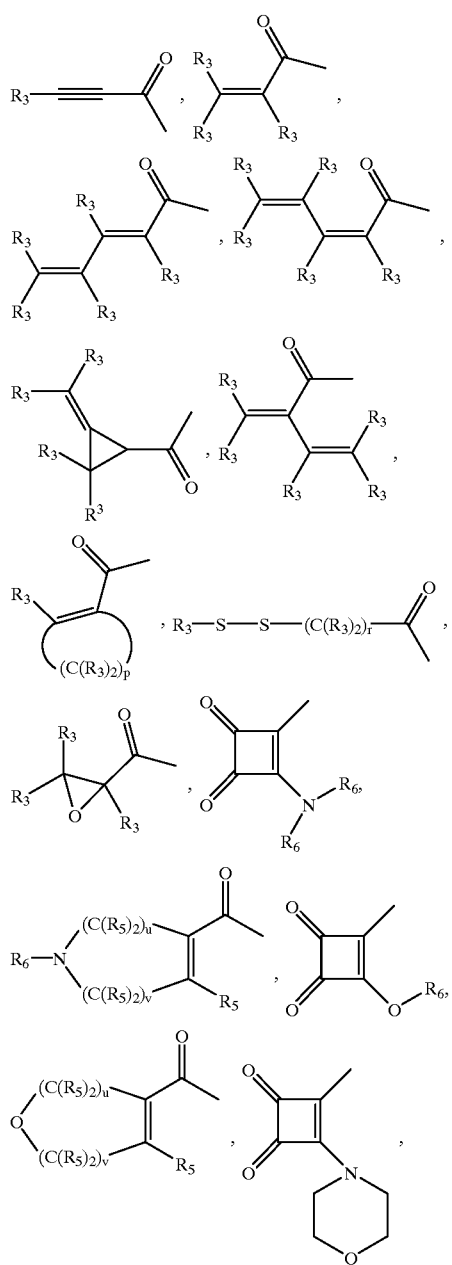

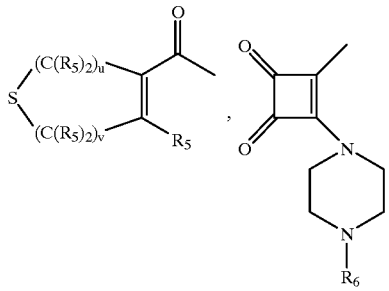

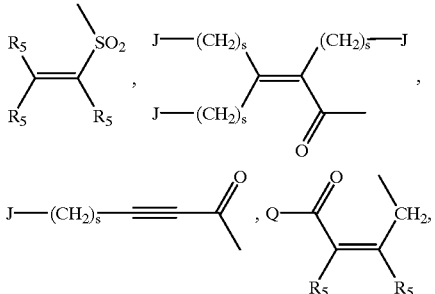

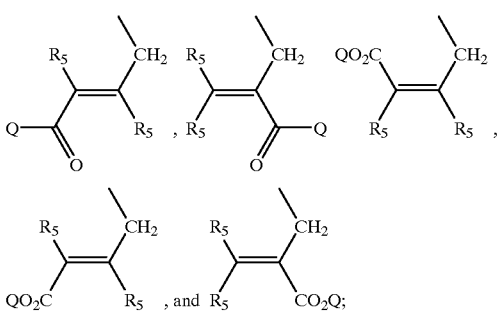

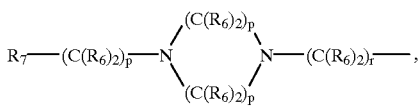

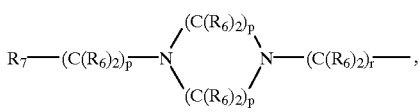

$R_3$ is independently hydrogen, alkyl of 1–6 carbon atoms, carboxy, carboalkoxy of 1–6 carbon atoms, phenyl, carboalkyl of 2–7 carbon atoms, $R_7$—$(C(R_6)_2)_p$—N$\begin{smallmatrix}(C(R_6)_2)_p\\(C(R_6)_2)_p\end{smallmatrix}$N—$(C(R_6)_2)_r$—, $R_7$—$(C(R_6)_2)_s$—, $R_7$—$(C(R_6)_2)_p$—M—$(C(R_6)_2)_r$—, $R_8R_9$—CH—M—$(C(R_6)_2)_r$—, or Het-$(C(R_6)_2)_q$—W—$(C(R_6)_2)_r$—;

$R_5$ is independently hydrogen, alkyl of 1–6 carbon atoms, carboxy, carboalkoxy of 1–6 carbon atoms, phenyl, carboalkyl of 2–7 carbon atoms, $R_7$—$(C(R_6)_2)_p$—N$\begin{smallmatrix}(C(R_6)_2)_p\\(C(R_6)_2)_p\end{smallmatrix}$N—$(C(R_6)_2)_r$—, $R_7$—$(C(R_6)_2)_s$—, $R_7$—$(C(R_6)_2)_p$—M—$(C(R_6)_2)_r$—, $R_8R_9$—CH—M—$(C(R_6)_2)_r$—, or Het-$(C(R_6)_2)_q$—W—$(C(R_6)_2)_r$—;

$R_8$, and $R_9$ are each, independently, —$(C(R_6)_2)_r$NR$_6$R$_6$, or —$(C(R_6)_2)_r$OR$_6$;

J is independently hydrogen, chlorine, fluorine, or bromine;

Q is alkyl of 1–6 carbon atoms or hydrogen;

a=0 or 1;

g=1–6;

k=0–4;

n is 0–1;

m is 0–3;

p=2–4;

q=0–4;

r=1–4;

s=1–6;

u=0–4 and v=0–4, wherein the sum of u+v is 2–4;

or a pharmaceutically acceptable salt thereof, provided that when $R_6$ is alkenyl of 2–7 carbon atoms or alkynyl of 2–7 carbon atoms, such alkenyl or alkynyl moiety is bound to a nitrogen or oxygen atom through a saturated carbon atom;

and further provided that when Y is —$NR_6$— and $R_7$ is —$NR_6R_6$, —$N(R_6)_3^+$, or —$NR_6(OR_6)$, then g=2–6;

when M is —O— and $R_7$ is —$OR_6$ then p=1–4;

when Y is —$NR_6$— then k=2–4;

when Y is —O— and M or W is —O— then k=1–4 when W is not a bond with Het bonded through a nitrogen atom then q=2–4 and when W is a bond with Het bonded through a nitrogen atom and Y is —O— or —$NR_6$— then k=2–4.

2. The compound according to claim 1 wherein Z is —NH— and n=0 or a pharmaceutically acceptable salt thereof.

3. The compound according to claim 2 wherein X is substituted or unsubstituted bicyclic aryl or bicyclic heteroaryl ring system, or a pharmaceutically acceptable salt thereof.

4. The compound according to claim 2 wherein X is the radical:

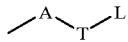

and A is a phenyl ring, or a pharmaceutically acceptable salt thereof.

5. The compound according to claim 3 wherein $R_1$ and $R_4$ are hydrogen or a pharmaceutically acceptable salt thereof.

6. The compound according to claim 4 wherein $R_1$ and $R_4$ are hydrogen or a pharmaceutically acceptable salt thereof.

7. The compound according to claim 3 wherein the bicyclic aryl or bicyclic heteroaryl ring system is selected from the group consisting of naphthaline, 1,2,3,4-tetrahydronaphthaline, indane, 1-oxo-indane, 1,2,3,4-tetrahydroquinoline, naphthyridine, benzofuran, 3-oxo-1,3-dihydro-isobenzofuran, benzothiaphene, 1,1-dioxo-benzothiaphene, indole, 2,3-dihydroindole, 1,3-dioxo-2,3-dihydro-1H-isoindole, benzotriazole, 1H-indazole, indoline, benzopyrazole, 1,3-benzodioxole, benzooxazole, purine, phthalimide, coumarin, chromone, quinoline, terahydroquinoline, isoquinoline, benzimidazole, quinazoline, pyrido[2,3-b]pyridine, pyrido[3,4-b]pyrazine, pyrido[3,2-c]pyridazine, pyrido[3,4-b]pyridine, 1H-pyrazole[3,4-d]pyrimidine, 1,4-Benzodioxane, pteridine, 2(1H)-quinolone, 1(2H)-isoquinolone, 2-oxo-2,3-dihydro-benzthiazole, 1,2-methylenedioxybenzene, 2-oxindole, 1,4-benzisoxazine, benzothiazole, quinoxaline, quinoline-N-oxide, isoquinoline-N-oxide, quinoxaline-N-oxide, quinazoline-N-oxide, benzoazine, phthalazine, 1,4-dioxo-1,2,3,4-tetrahydro-phthalazine, 2-oxo-1,2-dihydro-quinoline, 2,4-dioxo-1,4-dihydro-2H-benzo[d][1,3]oxazine, 2,5-dioxo-2,3,4,5-tetrahydro-1H-benzo[e][1,4]diazepine, and cinnoline or a pharmaceutically acceptable salt thereof.

8. The compound according to claim 4 wherein L is 5 or 6-membered heteroaryl ring or a pharmaceutically acceptable salt thereof.

9. The compound according to claim 8 wherein the heteroaryl ring is selected from the group consisting of pyridine, pyrimidine, imidazole, thiazole, thiazolidine, pyrrole, furan, thiophene, oxazole, and 1,2,4-triazole or a pharmaceutically acceptable salt thereof.

10. The compound according to claim 4 wherein L is a substituted phenyl ring or a pharmaceutically acceptable salt thereof.

11. The compound according to claim 1, which is:

a) 4-(2,3-dihydro-1H-indol-6-ylamino)-6,7-diethoxy-quinoline-3-carbonitrile or a pharmaceutically acceptable salt thereof;

b) 4-(benzothiazol-6-ylamino)-6,7-diethoxy-quinoline-3-carbonitrile or a pharmaceutically acceptable salt thereof;

c) 4-(benzo[1,3]dioxol-5-ylamino)-6,7-diethoxy-quinoline-3-carbonitrile or a pharmaceutically acceptable salt thereof;

d) 6,7-diethoxy-4-(1H-indazol-6-ylamino)-quinoline-3-carbonitrile or a pharmaceutically acceptable salt thereof;

e) 6,7-diethoxy-4-(4-methyl-2-oxo-2H-chromen-7-ylamino)-quinoline-3-carbonitrile or a pharmaceutically acceptable salt thereof;

f) 6,7-diethoxy-4-(1H-indol-6-ylamino)-quinoline-3-carbonitrile or a pharmaceutically acceptable salt thereof;

g) 6,7-dimethoxy-4-(1H-indazol-6-ylamino)-quinoline-3-carbonitrile or a pharmaceutically acceptable salt thereof;

h) 4-(1,3-dioxo-2,3-dihydro-1H-isoindol-5-ylamino)-6,7-diethoxy-quinoline-3-carbonitrile or a pharmaceutically acceptable salt thereof;

i) 4-(2,3-dihydro-benzo[1,4]dioxin-6-ylamino)-6,7-diethoxy-quinoline-3-carbonitrile or a pharmaceutically acceptable salt thereof;

j) 4-(1H-indazol-6-ylamino)-6,7-bis-(2-methoxy-ethoxy)-quinoline-3-carbonitrile or a pharmaceutically acceptable salt thereof;

k) 4-(1,4-dioxo-1,2,3,4-tetrahydro-phthalazin-6-ylamino)-6,7-diethoxy-quinoline-3-carbonitrile or a pharmaceutically acceptable salt thereof;

l) 6,7-diethoxy-4-(indan-5-ylamino)-quinoline-3-carbonitrile or a pharmaceutically acceptable salt thereof;

m) 4-(2,4-dioxo-1,4-dihydro-2H-benzo[d][1,3]oxazin-6-ylamino)-6,7-diethoxy-quinoline-3-carbonitrile or a pharmaceutically acceptable salt thereof;

n) 6,7-diethoxy-4-(3-oxo-1,3-dihydro-isobenzofuran-5-ylamino)-quinoline-3-carbonitrile or a pharmaceutically acceptable salt thereof;

o) 4-(1,1-dioxo-1H-benzo[b]thiophen-6-ylamino)-6,7-diethoxy-quinoline-3-carbonitrile or a pharmaceutically acceptable salt thereof;

p) 4-(2,3-dihydro-1H-indol-6-ylamino)-6,7-dimethoxy-quinoline-3-carbonitrile or a pharmaceutically acceptable salt thereof;

q) 7-ethoxy-4-(indazol-6-ylamino)-6-methoxy-3-quinolinecarbonitrile or a pharmaceutically acceptable salt thereof;

r) 4-(2,3-dihydro-1H-indol-6-ylamino)-6-methoxy-7-(3-pyridin-4-yl-propoxy)-quinoline-3-carbonitrile or a pharmaceutically acceptable salt thereof;

s) 9-(1H-indazol-6-ylamino)-2,3-dihydro[1,4]dioxino[2,3-g]quinoline-8-carbonitrile or a pharmaceutically acceptable salt thereof;

t) 6,7-diethoxy-4-(1-methyl-2,5-dioxo-2,3,4,5-tetrahydro-1H-benzo[e][1,4]diazepin-7-ylamino)-quinoline-3-carbonitrile or a pharmaceutically acceptable salt thereof;
u) 4-(1H-indazol-6-ylamino)-6,7,8-trimethoxy-quinoline-3-carbonitrile or a pharmaceutically acceptable salt thereof;
v) 6,7-dimethoxy-4-(4-methyl-2-oxo-1,2-dihydro-quinolin-7-ylamino)-quinoline-3-carbonitrile
w) 6,7-dimethoxy-4-(2-methyl-benzothiazol-5-ylamino)-quinoline-3-carbonitrile
x) 6,7-dimethoxy-4-(2-oxo-2,3-dihydro-benzothiazol-6-ylamino)-quinoline-3-carbonitrile or a pharmaceutically acceptable salt thereof;
y) 6,7-dimethoxy-4-(quinolin-5-ylamino)-quinoline-3-carbonitrile or a pharmaceutically acceptable salt thereof;
z) 4-(isoquinolin-5-ylamino)-6,7-dimethoxy-quinoline-3-carbonitrile or a pharmaceutically acceptable salt thereof;
aa) 6,7-dimethoxy-4-(quinolin-8-ylamino)-quinoline-3-carbonitrile or a pharmaceutically acceptable salt thereof;
bb) 4-(8-hydroxy-quinolin-5-ylamino)-6,7-dimethoxy-quinoline-3-carbonitrile or a pharmaceutically acceptable salt thereof;
cc) 4-(1H-indol-4-ylamino)-6,7-dimethoxy-quinoline-3-carbonitrile or a pharmaceutically acceptable salt thereof;
dd) 4-(1H-indazol-5-ylamino)-6,7-dimethoxy-quinoline-3-carbonitrile or a pharmaceutically acceptable salt thereof;
ee) 4-(1H-Indazol-6-ylamino)-5,8-dimethoxy-quinoline-3-carbonitrile or a pharmaceutically acceptable salt thereof;
ff) 4-(1H-indazol-6-ylamino)-7-methoxy-6-(3-morpholin-4-yl-propoxy)-quinoline-3-carbonitrile or a pharmaceutically acceptable salt thereof;
gg) 4-(3H-benzotriazol-5-ylamino)-7-methoxy-6-(3-morpholin-4-yl-propoxy)-quinoline-3-carbonitrile or a pharmaceutically acceptable salt thereof;
hh) 4-(1H-indazol 6-ylamino)-6-methoxy-quinoline-3-carbonitrile or a pharmaceutically acceptable salt thereof;
ii) 4-(3H-benzotriazol-5-ylamino)-6-methoxy-quinoline-3-carbonitrile or a pharmaceutically acceptable salt thereof;
jj) 4-(1H-indazol-6-ylamino)-7-methoxy-quinoline-3-carbonitrile or a pharmaceutically acceptable salt thereof;
kk) 4-(3H-benzotriazol-5-ylamino)-7-methoxy-quinoline-3-carbinitile or a pharmaceutically acceptable salt thereof;
ll) 7-hydroxy-4-(1H-indazol-6-ylamino)-quinoline-3-carbonitrile or a pharmaceutically acceptable salt thereof;
mm) 4-(1H-indol-5-ylamino)-7-methoxy-quinoline-3-carbonitrile or a pharmaceutically acceptable salt thereof;
nn) 7-hydroxy-4-(3H-benzotrizol-5-ylamino)-quinoline-3-carbonitrile or a pharmaceutically acceptable salt thereof;
oo) 4-(1H-indazol-6-ylamino)-8-methoxy-quinoline-3-carbonitrile or a pharmaceutically acceptable salt thereof;
pp) 4-(3H-benzotriazol-5-ylamino)-8-methoxy-quinoline-3-carbonitrile or a pharmaceutically acceptable salt thereof;
qq) 4-(1H-indol-5-ylamino)-6,7-Dimethoxy-quinoline-3-carbonitrile or a pharmaceutically acceptable salt thereof;
rr) 4-(1H-benzoimidazol-5-ylamino)-6,7-dimethoxy-quinoline-3-carbonitrile or a pharmaceutically acceptable salt thereof;
ss) 6,7-dimethoxy-4-(2-methyl-1H-benzoimidazol-5-ylamino)-quinoline-3-carbonitrile or a pharmaceutically acceptable salt thereof;
tt) 6,7-dimethoxy-4-(quinoline-6-ylamino)-quinoline-3-carbonitrile or a pharmaceutically acceptable salt thereof;
uu) 4-(4-chloro-naphthalen-1-ylamino)-6,7-Dimethoxy-quinoline-3-carbonitrile or a pharmaceutically acceptable salt thereof;
vv) 6,7-dimethoxy-4-(5,6,7,8,-tetrahydro-naphthalen-1-ylamino)-quinoline-3-carbonitrile or a pharmaceutically acceptable salt thereof;
ww) 4-(3H-benzotriazol-5-ylamino)-6,7,8-Trimethoxy-quinoline-3-carbonitrile or a pharmaceutically acceptable salt thereof;
xx) 4-(1H-indazol -6-ylamino)-6-methoxy-7-[2-(4-methyl-piperazin-1-yl)-ethoxy]-quinoline-3-carbonitrile or a pharmaceutically acceptable salt thereof;
yy) 7-{2-[(2-hydroxy-ethyl)-amino]-ethoxy}-4(1H-indazol-6-ylamino)-6-methoxy-quinoline-3-carbonitrile or a pharmaceutically acceptable salt thereof;
zz) 7-{2-[bis-(2-hydroxy-ethyl)-amino]-ethoxy}-4-(1H-indazol-6-ylamino)-6-methoxy-quinoline-3-carbonitrile or a pharmaceutically acceptable salt thereof;
aaa) 7-[2-(4-hydroxy-piperidin-1-yl)-ethoxy]-4-(-indazol-6-ylamino)-6-methoxy-quinoline-3-carbonitrile or a pharmaceutically acceptable salt thereof;
bbb) 7-{2-[(4-(2-hydroxy-ethyl)-piperazin-1-yl)-ethoxy]-4-(1H-indazol-6-ylamino)-6-methoxy-quinoline-3-carbonitrile or a pharmaceutically acceptable salt thereof;
ccc) 7-[2-(1,4dioxa-8-aza-spiro[4,5]dec-8-yl)-ethoxy]-4-(1H-indazol-6 -ylamino)-6-methoxy-quinoline-3-carbonitrile or a pharmaceutically acceptable salt thereof;
ddd) 7-[2-([1,3]dioxolan-2-ylmethyl-methyl-amino)-ethoxy]-4-(1H-indazol-6-ylamino)-6-methoxy-quinoline-3-carbonitrile
eee) 7-[2-(3,4-dihydro-1H-isoquinolin-2-yl)-ethoxy]-4-(1H-indazol-6-ylamino)-6-methoxy-quinoline-3-carbonitrile or a pharmaceutically acceptable salt thereof;
fff) 4-(1H-indazol-6-ylamino)-6-methoxy-7-(2-thiomorpholin-4-yl-ethoxy)-quinoline-3-carbonitrile or a pharmaceutically acceptable salt thereof;
ggg) 7-(2-chloroethoxy)-4-(1H-indazol-6-ylamino)-6-methoxyquinoline-3-carbonitrile or a pharmaceutically acceptable salt thereof;
hhh) 7-(2-dimethylaminoethoxy)-4-(1H-indazol-6-ylamino)-6-methoxyquinoline-3-carbonitrile or a pharmaceutically acceptable salt thereof;
iii) 4-(1H-indazol-6-ylamino)-6-methoxy-7-(2-morpholin-4-yl-ethoxy)quinoline-3-carbonitrile or a pharmaceutically acceptable salt thereof;
jjj) 4-(3H-benzotriazol-5-ylamino)-7-(2-chloroethoxy)-6-methoxyquinoline-3-carbonitrile or a pharmaceutically acceptable salt thereof;
kkk) 7-(3-chloropropoxy)-4-(1H-indazol-6-ylamino)-6-methoxyquinoline-3-carbonitrile or a pharmaceutically acceptable salt thereof;
lll) 4-(1H-indazole-6-ylamino)-6-methoxy-7-(3-morpholin-4-ylpropoxy)quinoline-3-carbonitrile or a pharmaceutically acceptable salt thereof;
mmm) 4-[3-chloro-4-(1-methyl-2-imidazolylthio)phenylamino]-6,7-diethoxy-3-quinolinecarbonitrile or a pharmaceutically acceptable salt thereof;
nnn) 4-[3-chloro-4-(1-methyl-2-imidazolylthio)phenylamino]-6,7-dimethoxy-3-quinolinecarbonitrile or a pharmaceutically acceptable salt thereof;
ooo) 6-amino-4-[3-chloro-4-(1-methyl-1H-imidazol-2-ylsulfanyl)-phenylamino]-quinoline-3-carbonitrile or a pharmaceutically acceptable salt thereof;
ppp) N-{4-[3-chloro-4-(1-methyl-1H-imidazol-2-ylsulfanyl)-phenylamino]-3-cyano-quinolin-6-yl}-acrylamide or a pharmaceutically acceptable salt thereof;
qqq) 6-amino-4-(1H-indol-5-ylamino)-quinoline-3-carbonitrile or a pharmaceutically acceptable salt thereof;
rrr) 4-(1H-indol-5-ylamino)-6-nitro-quinoline-3-carbonitrile or a pharmaceutically acceptable salt thereof;
sss) 4-(2-Hydroxy-naphthalen-1-ylamino)-6,7-dimethoxy-quinoline-3-carbonitrile or a pharmaceutically acceptable salt thereof;

ttt) 4-(2,3-Dihydro-benzo[1,4]dioxin-6-ylamino)-6,7-dimethoxy-quinoline-3-carbonitrile or a pharmaceutically acceptable salt thereof;

uuu) 4-(2-Mercapto-benzothiazol-6-ylamino)-6,7-dimethoxy-quinoline-3-carbonitrile or a pharmaceutically acceptable salt thereof;

vvv) 4-(6-Hydroxy-naphthalen-1-ylamino)-6,7-dimethoxy-quinoline-3-carbonitrile or a pharmaceutically acceptable salt thereof;

www) 4-(1H-Indazol-6-ylamino)-5-methoxy-quinoline-3-carbonitrile or a pharmaceutically acceptable salt thereof;

xxx) 4-(2-chloro-5-methoxyanilino)-5-methoxyquinoline-3-carbonitrile or a pharmaceutically acceptable salt thereof;

yyy) 4-[(2-Amino-4-chlorophenyl)amino]-6,7-dimethoxy-3-quinolinecarbonitrile or a pharmaceutically acceptable salt thereof;

zzz) 4-[(3-hydroxy-2-naphthyl)amino]-6,7-dimethoxy-3-quinolinecarbonitrile or a pharmaceutically acceptable salt thereof;

aaaa) 4-{3-chloro-4-[(1-methyl-1H-imidazol-2-yl)sulfanyl]anilino}-7-methoxy-6-nitro-3-quinolinecarbonitrile or a pharmaceutically acceptable salt thereof;

bbbb) 6-amino-4-{3-chloro-4-[(1-methyl-1H-imidazol-2-yl)sulfanyl]anilino}-7-methoxy-3-quinolinecarbonitrile or a pharmaceutically acceptable salt thereof;

cccc) (E)-N-(4-{3-chloro-4-[(1-methyl-1H-imidazol-2-yl)sulfanyl]anilino}-3-cyano-7-methoxy-6-quinolinyl)-4-(dimethylamino)-2-butenamide or a pharmaceutically acceptable salt thereof;

dddd) 4-[3-chloro-4-(1,3-thiazol-2-ylsulfanyl)anilino]-7-methoxy-6-nitro-3-quinolinecarbonitrile or a pharmaceutically acceptable salt thereof;

eeee) 6-amino-4-[3-chloro-4-(1,3-thiazol-2-ylsulfanyl)anilino]-7-methoxy-3-quinolinecarbonitrile or a pharmaceutically acceptable salt thereof;

ffff) (E)-N-{4-[3-chloro-4-(1,3-thiazol-2-ylsulfanyl)anilino]-3-cyano-7-methoxy-6-quinolinyl}-4-(dimethylamino)-2-butenamide or a pharmaceutically acceptable salt thereof;

gggg) 4-[3-chloro-4-(1H-imidazol-1-yl)anilino]-7-methoxy-6-nitro-3-quinolinecarbonitrile or a pharmaceutically acceptable salt thereof;

hhhh) 6-amino-4-[3-chloro-4-(1H-imidazol-1-yl)anilino]-7-methoxy-3-quinolinecarbonitrile or a pharmaceutically acceptable salt thereof;

iiii) (E)-N-{4-[3-chloro-4-(1H-imidazol-1-yl)anilino]-3-cyano-7-methoxy-6-quinolinyl}-4-(dimethylamino)-2-butenamide or a pharmaceutically acceptable salt thereof;

jjjj) 4-{3-chloro-4[(4-oxo-3,4-dihydro-2-quinazolinyl)sulfanyl]anilino}-7-methoxy-6-nitro-3-quinolinecarbonitrile or a pharmaceutically acceptable salt thereof;

kkkk) 6-amino-4-3-chloro-4-[(4-oxo-3,4-dihydro-2-quinazolinyl)sulfanyl]anilino)-7-methoxy-3-quinolinecarbonitrile or a pharmaceutically acceptable salt thereof;

llll) (E)-N-(4-{3-chloro-4-[(4-oxo-3,4-dihydro-2-quinazolinyl)sulfanyl]anilino}-3-cyano-7-methoxy-6-quinolinyl)-4-(dimethylamino)-2-butenamide or a pharmaceutically acceptable salt thereof;

mmmm) 6-methoxy-7-[3-(4-morpholinyl)propoxy]-4-[4-(4-pyridinylmethyl)anilino]-3-quinolinecarbonitrile or a pharmaceutically acceptable salt thereof;

nnnn) 6-methoxy-7-[3-(4-morpholinyl)propoxy]-4-[4-(3-pyridinylmethyl)anilino]-3-quinolinecarbonitrile or a pharmaceutically acceptable salt thereof;

oooo) 6-methoxy-7-[3-(4-morpholinyl)propoxy]-4-[4-(2-pyridinylmethyl)anilino]-3-quinolinecarbonitrile or a pharmaceutically acceptable salt thereof;

pppp) (E)-N-(4-{4-[acetyl(3-pyridinylmethyl)amino]-3-chloroanilino}-3-cyano-7-methoxy-6-quinolinyl)-4-(dimethylamino)-2-butenamide or a pharmaceutically acceptable salt thereof;

qqqq) N-(2-chloro-4-[(3-cyano-7-methoxy-6-nitro-4-quinolinyl)amino]phenyl}-N-(3-pyridinylmethyl)acetamide or a pharmaceutically acceptable salt thereof;

rrrr) N-{4-[(6-amino-3-cyano-7-methoxy-4-quinolinyl)amino]-2-chlorophenyl}-N-(3-pyridinylmethyl)acetamide or a pharmaceutically acceptable salt thereof;

ssss) N-(4-{[6-(acetylamino)-3-cyano-7-methoxy-4-quinolinyl]amino}-2-chlorophenyl)-N-(3-pyridinylmethyl)acetamide or a pharmaceutically acceptable salt thereof;

tttt) 4-[3-chloro-4-(1,3-dimethyl-2,4,6-trioxohexahydro-5-pyrimidinyl)anilino]-7-methoxy-6-nitro-3-quinolinecarbonitrile or a pharmaceutically acceptable salt thereof;

uuuu) 4-{3-chloro-4-[(4-phenyl-1,3-thiazol-2-yl)sulfanyl]anilino}-7-methoxy-6-nitro-3-quinolinecarbonitrile or a pharmaceutically acceptable salt thereof;

vvvv) 6-methoxy-7-[3-(4-morpholinyl)propoxy]-4-[4-(3-thienylmethyl)anilino]-3-quinolinecarbonitrile or a pharmaceutically acceptable salt thereof;

wwww) 6-methoxy-7-[3-(4-morpholinyl)propoxy]-4-[4-(2-thienylmethyl)anilino]-3-quinolinecarbonitrile or a pharmaceutically acceptable salt thereof;

xxxx) 6-methoxy-4-(4-phenoxyanilino)-7-[2-(2H-1,2,3-triazol-2-yl)ethoxy]-3-quinolinecarbonitrile or a pharmaceutically acceptable salt thereof;

yyyy) 6-methoxy-4-(4-phenoxyanilino)-7-[2-(1H-1,2,3-triazol-1-yl)ethoxy]-3-quinolinecarbonitrile or a pharmaceutically acceptable salt thereof;

zzzz) 4-(4-benzylanilino)-6-methoxy-7-[2-(2H-1,2,3-triazol-2-yl)ethoxy]-3-quinolinecarbonitrile or a pharmaceutically acceptable salt thereof;

aaaaa) 4-(4-benzylanilino)-6-methoxy-7-[2-(1H-1,2,3-triazol-1-yl)ethoxy]-3-quinolinecarbonitrile or a pharmaceutically acceptable salt thereof;

bbbbb) 6-methoxy-7-[3-(4-morpholinyl)propoxy]-4-[4-(2-pyridinyloxy)anilino]-3-quinolinecarbonitrile or a pharmaceutically acceptable salt thereof;

ccccc) 4-{3-chloro-4-[(1-methyl-1H-imidazol-2-yl)sulfanyl]anilino}-6-methoxy-7-[3-(4-morpholinyl)propoxy]-3-quinolinecarbonitrile or a pharmaceutically acceptable salt thereof;

ddddd) 4-[4-(2-furylmethyl)anilino]-6-methoxy-7-[3-(4-morpholinyl)propoxy]-3-quinolinecarbonitrile or a pharmaceutically acceptable salt thereof;

eeeee) 6-methoxy-7-[3-(4-morpholinyl)propoxy]-4-[4-(tetrahydro-2-furanylmethyl)anilino]-3-quinolinecarbonitrile or a pharmaceutically acceptable salt thereof;

fffff) 4-[4-(3-furylmethyl)anilino]-6-methoxy-7-[3-(4-morpholinyl)propoxy]-3-quinolinecarbonitrile or a pharmaceutically acceptable salt thereof;

ggggg) 6-methoxy-7-[3-(4-morpholinyl)propoxy]-4-[4-(tetrahydro-3-furanylmethyl)anilino]-3-quinolinecarbonitrile or a pharmaceutically acceptable salt thereof;

hhhhh) 4-(3-chloro-4-{[5-(trifluoromethyl)-1,3,4-thiadiazol-2-yl]amino}anilino)-7-ethoxy-6-nitro-3-quinolinecarbonitrile or a pharmaceutically acceptable salt thereof;

iiiii) (E)-N-[4-(3-chloro-4-{[5-(trifluoromethyl)-1,3,4-thiadiazol-2-yl]amino}anilino)-3-cyano-7-ethoxy-6-quinolinyl]-4-(dimethylamino)-2-butenamide or a pharmaceutically acceptable salt thereof;

jjjjj) 4-[3-chloro-4-(4-pyridinyloxy)anilino]-7-ethoxy-6-nitro-3-quinolinecarbonitrile or a pharmaceutically acceptable salt thereof;

kkkkk) 6-amino-4-[3-chloro-4-(4-pyridinyloxy)anilino]-7-ethoxy-3-quinolinecarbonitrile or a pharmaceutically acceptable salt thereof;

lllll) (E)-N-{3-[3-chloro-4-(4-pyridinyloxy)anilino]-3-cyano-7-ethoxy-6-quinolinyl}-4-(dimethylamino)-2-butenamide or a pharmaceutically acceptable salt thereof;

mmmmm) 4-{3-chloro-4-[(3-pyridinylmethyl)amino]anilino}-7-methoxy-6-nitro-3-quinolinecarbonitrile or a pharmaceutically acceptable salt thereof;

nnnnn) 6-amino-4-{3-chloro-4-[(4-phenyl-1,3-thiazol-2-yl)sulfanyl]anilino}-7-methoxy-3-quinolinecarbonitrile or a pharmaceutically acceptable salt thereof;

ooooo) 6-amino-4-(3-chloro-4-{[5-(trifluoromethyl)-1,3,4-thiadiazol-2-yl]amino}anilino)-7-ethoxy-3-quinolinecarbonitrile or a pharmaceutically acceptable salt thereof;

ppppp) 6-methoxy-7-[3-(4-morpholinyl)propoxy]-4-[4-(2-phenylethyl)anilino]-3-quinolinecarbonitrile or a pharmaceutically acceptable salt thereof;

qqqqq) (E)-N-(4-{3-chloro-4-[(4-phenyl-1,3-thiazol-2-yl)sulfanyl]anilino}-3-cyano-7-methoxy-6-quinolinyl)-4-(dimethylamino)-2-butenamide or a pharmaceutically acceptable salt thereof;

rrrrr) 4-[3-chloro-4-(1H-imidazol-1-yl)anilino]-6-methoxy-7-[3-(4-morpholinyl)propoxy]-3-quinolinecarbonitrile or a pharmaceutically acceptable salt thereof;

sssss) 6-methoxy-7-[3-(4-morpholinyl)propoxy]-4-[4-(3-pyridinyloxy)anilino]-3-quinolinecarbonitrile or a pharmaceutically acceptable salt thereof;

ttttt) 4-[3-chloro-4-(4-pyridinyloxy)anilino]-6-methoxy-7-[3-(4-morpholinyl)propoxy]-3-quinolinecarbonitrile or a pharmaceutically acceptable salt thereof;

uuuuu) 6-methoxy-7-[3-(4-morpholinyl)propoxy]-4-[4-(4-pyridinyloxy)anilinol-3-quinolinecarbonitrile or a pharmaceutically acceptable salt thereof;

vvvvv) 4-[2-chloro-4-(1,3-thiazol-2-ylsulfanyl)anilino]-6-methoxy-7-[3-(4-morpholinyl)propoxy]-3-quinolinecarbonitrile or a pharmaceutically acceptable salt thereof;

wwwww) N-[2-chloro-4-({3-cyano-6-methoxy-7-[3-(4-morpholinyl)propoxy]-4-quinolinyl}amino)phenyl]-N-(3-pyridinylmethyl)acetamide or a pharmaceutically acceptable salt thereof;

xxxxx) 6-methoxy-7-[3-(4-morpholinyl)propoxy]-4-[4-(1H-tetraazol-5-ylmethyl)anilino]-3-quinolinecarbonitrile or a pharmaceutically acceptable salt thereof;

yyyyy) 6-methoxy-7-[3-(4-morpholinyl)propoxy]-4-[4-(2H-1,2,3-triazol-2-ylmethyl)anilino]-3-quinolinecarbonitrile or a pharmaceutically acceptable salt thereof;

zzzzz) 6-methoxy-7-[3-(4-morpholinyl)propoxy]-4-[4-(1H-1,2,3-triazol-1-ylmethyl)anilino]-3-quinolinecarbonitrile or a pharmaceutically acceptable salt thereof;

aaaaaa) 4-(2,4-dichloro-5-methoxyanilino)-6-methoxy-7-[2-(2H-1,2,3-triazol-2-yl)ethoxy]-3-quinolinecarbonitrile or a pharmaceutically acceptable salt thereof;

bbbbbb) 4-(2,4-dichloro-5-methoxyanilino)-6-methoxy-7-[2-(1H-1,2,3-triazol-1-yl)ethoxy]-3-quinolinecarbonitrile or a pharmaceutically acceptable salt thereof;

cccccc) 7-ethoxy-6-nitro-4-[4-[(4-phenyl-1,3-thiazol-2-yl)sulfanyl]-3-(trifluoromethyl)anilino]-3-quinolinecarbonitrile or a pharmaceutically acceptable salt thereof;

dddddd) 6-amino-7-ethoxy-4-[4-[(4-phenyl-1,3-thiazol-2-yl)sulfanyl]-3-(trifluoromethyl)anilino]-3-quinolinecarbonitrile or a pharmaceutically acceptable salt thereof;

eeeeee) (E)-N-{3-cyano-7-ethoxy-4-[4-[(4-phenyl-1,3-thiazol-2-yl)sulfanyl]-3-(trifluoromethyl)anilino]-6-quinolinyl}-4-(dimethylamino)-2-butenamide or a pharmaceutically acceptable salt thereof;

ffffff) 4-[3-chloro-4-(1H-imidazol-1-ylmethyl)anilino]-7-ethoxy-6-nitro-3-quinolinecarbonitrile or a pharmaceutically acceptable salt thereof;

gggggg) 6-amino-4-[3-chloro-4-(1H-imidazol-1-ylmethyl)anilino]-7-ethoxy-3-quinolinecarbonitrile or a pharmaceutically acceptable salt thereof;

hhhhhh) (E)-N-{4-[3-chloro-4-(1H-imidazol-1-ylmethyl)anilino]-3-cyano-7-ethoxy-6-quinolinyl}-4-(dimethylamino)-2-butenamide or a pharmaceutically acceptable salt thereof;

iiiiii) 4-{3-chloro-4-[(4-methyl-2-pyrimidinyl)sulfanyl]anilino}-7-ethoxy-6-nitro-3-quinolinecarbonitrile or a pharmaceutically acceptable salt thereof;

jjjjjj) 6-amino-4-{3-chloro-4-[(4-methyl-2-pyrimidinyl)sulfanyl]anilino}-7-ethoxy-3-quinolinecarbonitrile or a pharmaceutically acceptable salt thereof;

kkkkkk) (E)-N-(4-{3-chloro-4-[(4-methyl-2-pyrimidinyl)sulfanyl]anilino}-3-cyano-7-ethoxy-6-quinolinyl)-4-(dimethylamino)-2-butenamide or a pharmaceutically acceptable salt thereof;

llllll) 4-{3-chloro-4-[(4,6-dimethyl-2-pyrimidinyl)sulfanyl]anilino}-7-ethoxy-6-nitro-3-quinolinecarbonitrile or a pharmaceutically acceptable salt thereof;

mmmmmm) 6-amino-4-{3-chloro-4-[(4,6-dimethyl-2-pyrimidinyl)sulfanyl]anilino}-7-ethoxy-3-quinolinecarbonitrile or a pharmaceutically acceptable salt thereof;

nnnnnn) (E)-N-(4-{3-chloro-4-[(4,6-dimethyl-2-pyrimidinyl)sulfanyl]anilino}-3-cyano-7-ethoxy-6-quinolinyl)-4-(dimethylamino)-2-butenamide or a pharmaceutically acceptable salt thereof;

oooooo) 4-[4-(1H-imidazol-2-ylmethyl)anilino]-6-methoxy-7-[3-(4-morpholinyl)propoxy]-3-quinolinecarbonitrile or a pharmaceutically acceptable salt thereof;

pppppp) 6-methoxy-7-[3-(4-morpholinyl)propoxy]-4-[4-(1H-tetraazol-1-ylmethyl)anilino]-3-quinolinecarbonitrile or a pharmaceutically acceptable salt thereof;

qqqqqq) 6-methoxy-7-[3-(4-morpholinyl)propoxy]-4-[4-(2H-tetraazol-2-ylmethyl)anilino]-3-quinolinecarbonitrile or a pharmaceutically acceptable salt thereof;

rrrrrr) 4-{3-chloro-4-[(4,6-dimethyl-2-pyrimidinyl)sulfanyl]anilino}-6-methoxy-7-[3-(4-morpholinyl)propoxy]-3-quinolinecarbonitrile or a pharmaceutically acceptable salt thereof;

ssssss) 4-{3-chloro-4-[(4-methyl-2-pyrimidinyl)sulfanyl]anilino}-6-methoxy-7-[3-(4-morpholinyl)propoxy]-3-quinolinecarbonitrile or a pharmaceutically acceptable salt thereof;

tttttt) (E)-N-[4-(3-chloro-4-{[2-(phenylsulfanyl)acetyl]amino}anilino)-3-cyano-7-methoxy-6-quinolinyl]-4-(dimethylamino)-2-butenamide or a pharmaceutically acceptable salt thereof;

uuuuuu) 4-[4-(2,6-dimethoxyphenoxy)anilino]-6-methoxy-7-[3-(4-morpholinyl)propoxy]-3-quinolinecarbonitrile or a pharmaceutically acceptable salt thereof;

vvvvvv) 6-methoxy-4-[4-(3-methoxyphenoxy)anilino]-7-[3-(4-morpholinyl)propoxy]-3-quinolinecarbonitrile or a pharmaceutically acceptable salt thereof;

wwwwww) 6-methoxy-4-{4-[(1-methyl-1H-imidazol-2-yl)
sulfanyl]anilino}-7-[3-(4-morpholinyl)propoxy]-3-
quinolinecarbonitrile or a pharmaceutically acceptable
salt thereof;

xxxxxx) (E)-N-{4-[3-chloro-4-(1,3-thiazol-2-ylsulfanyl)
anilino]-3-cyano-7-methoxy-6-quinolinyl}-4-[(2-
methoxyethyl)(methyl)amino]-2-butenamide or a pharmaceutically acceptable salt thereof;

yyyyyy) (E)-N-(4-{3-chloro-4-[(5-phenyl-1,3-thiazol-2-yl)
sulfanyl]anilino}-3-cyano-7-methoxy-6-quinolinyl)-4-
(dimethylamino)-2-butenamide or a pharmaceutically
acceptable salt thereof;

zzzzzz) (E)-N-(4-{3-chloro-4-[(4-phenyl-1,3-thiazol-2-yl)
sulfanyl]anilino}-3-cyano-7-'ethoxy-6-quinolinyl)-4-
(dimethylamino)-2-butenamide or a pharmaceutically
acceptable salt thereof;

aaaaaaa) 4-{3-chloro-4-[(4,6-dimethyl-2-pyrimidinyl)
sulfanyl]anilino}-6,7-dimethoxy-3-quinolinecarbonitrile
or a pharmaceutically acceptable salt thereof;

bbbbbbb) 6,7-dimethoxy-4-({6-[(4-phenyl-1,3-thiazol-2-yl)
sulfanyl]-3-pyridinyl}amino)-3-quinolinecarbonitrile or a
pharmaceutically acceptable salt thereof; or ccccccc) 4-{3-chloro-4-[(1-methyl-1H-imidazol-2-yl)
sulfanyl]anilino}-6-methoxy-7-[3-(1H-1,2,3-triazol-1-yl)
propoxy]-3-quinolinecarbonitrile or a pharmaceutically
acceptable salt thereof.

12. A method of treating, inhibiting the growth of, or eradicating neoplasms in a mammal in need thereof which comprises administering to said mammal an effective amount of a compound of formula 1 having the structure

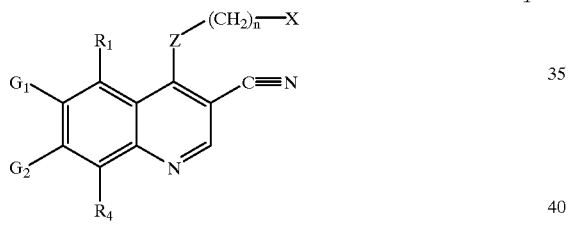

wherein:

X is a bicyclic aryl or bicyclic heteroaryl ring system of 8 to 12 atoms where the bicyclic heteroaryl ring contains 1 to 4 heteroatoms selected from N, O, and S with the proviso that the bicyclic heteroaryl ring does not contain O—O, S—S, or S—O bonds and where the bicyclic aryl or bicyclic heteroaryl ring may be optionally mono- di-, tri, or tetra-substituted with a substituent selected from the group consisting of halogen, oxo, thio, alkyl of 1–6 carbon atoms, alkenyl of 2–6 carbon atoms, alkynyl of 2–6 carbon atoms, azido, hydroxyalkyl of 1–6 carbon atoms, halomethyl, alkoxymethyl of 2–7 carbon atoms, alkanoyloxymethyl of 2–7 carbon atoms, alkoxy of 1–6 carbon atoms, alkylthio of 1–6 carbon atoms, hydroxy, trifluoromethyl, cyano, nitro, carboxy, carboalkoxy of 2–7 carbon atoms, carboalkyl of 2–7 carbon atoms, phenoxy, phenyl, thiophenoxy, benzoyl, benzyl, amino, alkylamino of 1–6 carbon atoms, dialkylamino of 2 to 12 carbon atoms, phenylamino, benzylamino, alkanoylamino of 1–6 carbon atoms, alkenoylamino of 3–8 carbon atoms, alkynoylamino of 3–8 carbon atoms, carboxyalkyl of 2–7 carbon atoms, carboalkoxyalky of 3–8 carbon atoms, aminoalkyl of 1–5 carbon atoms, N-alkylaminoalkyl of 2–9 carbon atoms, N,N-dialkylaminoalkyl of 3–10 carbon atoms, N-alkylaminoalkoxy of 2–9 carbon atoms, N,N-dialkylaminoalkoxy of 3–10 carbon atoms, mercapto, and benzoylamino; or X is a radical having the formula:

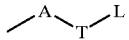

wherein

A is a pyridinyl, pyrimidinyl, or phenyl ring; wherein the pyridinyl, pyrimidinyl, or phenyl ring may be optionally mono- or di-substituted with a substituent selected from the group consisting of halogen, alkyl of 1–6 carbon atoms, alkenyl of 2–6 carbon atoms, alkynyl of 2–6 carbon atoms, azido, hydroxyalkyl of 1–6 carbon atoms, halomethyl, alkoxymethyl of 2–7 carbon atoms, alkanoyloxymethyl of 2–7 carbon atoms, alkoxy of 1–6 carbon atoms, alkylthio of 1–6 carbon atoms, hydroxy, trifluoromethyl, cyano, nitro, carboxy, carboalkoxy of 2–7 carbon atoms, carboalkyl of 2–7 carbon atoms, phenoxy, phenyl, thiophenoxy, benzoyl, benzyl, amino, alkylamino of 1–6 carbon atoms, dialkylamino of 2 to 12 carbon atoms, phenylamino, benzylamino, alkanoylamino of 1–6 carbon atoms, alkenoylamino of 3–8 carbon atoms, alkynoylamino of 3–8 carbon atoms, carboxyalkyl of 2–7 carbon atoms, carboalkoxyalky of 3–8 carbon atoms, aminoalkyl of 1–5 carbon atoms, N-alkylaminoalkyl of 2–9 carbon atoms, N,N-dialkylaminoalkyl of 3–10 carbon atoms, N-alkylaminoalkoxy of 2–9 carbon atoms, N,N-dialkylaminoalkoxy of 3–10 carbon atoms, mercapto, and benzoylamino;

T is bonded to a carbon of A and is:
—NH(CH$_2$)$_m$—, —O(CH$_2$)$_m$—, —S(CH$_2$)$_m$—, —NR(CH$_2$)$_m$—, —(CH$_2$)$_m$— —(CH$_2$)$_m$NH—, —(CH$_2$)$_m$O—, —(CH$_2$)$_m$S—, or —(CH$_2$)$_m$NR—;

L is an unsubstituted phenyl ring or a phenyl ring mono-, di-, or tri-substituted with a substituent selected from the group consisting of halogen, alkyl of 1–6 carbon atoms, alkenyl of 2–6 carbon atoms, alkynyl of 2–6 carbon atoms, azido, hydroxyalkyl of 1–6 carbon atoms, halomethyl, alkoxymethyl of 2–7 carbon atoms, alkanoyloxymethyl of 2–7 carbon atoms, alkoxy of 1–6 carbon atoms, alkylthio of 1–6 carbon atoms, hydroxy, trifluoromethyl, cyano, nitro, carboxy, carboalkoxy of 2–7 carbon atoms, carboalkyl of 2–7 carbon atoms, phenoxy, phenyl, thiophenoxy, benzoyl, benzyl, amino, alkylamino of 1–6 carbon atoms, dialkylamino of 2 to 12 carbon atoms, phenylamino, benzylamino, alkanoylamino of 1–6 carbon atoms, alkenoylamino of 3–8 carbon atoms, alkynoylamino of 3–8 carbon atoms, carboxyalkyl of 2–7 carbon atoms, carboalkoxyalky of 3–8 carbon atoms, aminoalkyl of 1–5 carbon atoms, N-alkylaminoalkyl of 2–9 carbon atoms, N,N-dialkylaminoalkyl of 3–10 carbon atoms, N-alkyliminoalkoxy of 2–9 carbon atoms, N,N-dialkylaminoalkoxy of 3–10 carbon atoms, mercapto, and benzoylamino; provided that L can be an unsubstituted phenyl ring only when m>0 and T is not —CH$_2$NH— or —CH$_2$O—; or L is a 5- or 6-membered heteroaryl ring where the heteroaryl ring contains 1 to 3 heteroatoms selected from N, O, and S, with the proviso that the heteroaryl ring does not contain O—O, S—S, or S—O bonds, and where the heteroaryl ring is optionally mono- or di-substituted with a substituent selected from the group consisting of halogen, oxo, thio, alkyl of 1–6 carbon atoms, alkenyl of 2–6 carbon atoms, alkynyl of 2–6 carbon atoms, azido, hydroxyalkyl of 1–6 carbon atoms, halomethyl, alkoxymethyl of 2–7 carbon atoms, alkanoyloxymethyl of 2–7 carbon atoms, alkoxy of 1–6 carbon atoms, alkylthio of 1–6 carbon atoms, hydroxy, trifluoromethyl, cyano, nitro, carboxy, carboalkoxy of 2–7 carbon atoms, carboalkyl of 2–7 carbon atoms, phenoxy, phenyl, thiophenoxy, benzoyl, benzyl, amino, alkylamino of 1–6 carbon atoms, dialkylamino of 2 to 12 carbon atoms, phenylamino, benzylamino, alkanoylamino of 1–6 carbon atoms, alkenoylamino of 3–8 carbon atoms, alkynoylamino of 3–8 carbon atoms, carboxyalkyl of 2–7 carbon atoms, carboalkoxyalky of 3–8 carbon atoms, aminoalkyl of 1–5 carbon atoms, N-alkylaminoalkyl of 2–9 carbon atoms, N,N-dialkylaminoalkyl of 3–10 carbon atoms, N-alkylaminoalkoxy of 2–9 carbon atoms, N,N-dialkylaminoalkoxy of 3–10 carbon atoms, mercapto, and benzoylamino;

Z is —NH—, —O—, —S—, or —NR—;

R is alkyl of 1–6 carbon atoms, or carboalkyl of 2–7 carbon atoms;

$G_1$, $G_2$, $R_1$, and $R_4$ are each, independently, hydrogen, halogen, alkyl of 1–6 carbon atoms, alkenyl of 2–6 carbon atoms, alkynyl of 2–6 carbon atoms, alkenyloxy of 2–6 carbon atoms, alkynyloxy of 2–6 carbon atoms, hydroxymethyl, halomethyl, alkanoyloxy of 1–6 carbon atoms, alkenoyloxy of 3–8 carbon atoms, alkynoyloxy of 3–8 carbon atoms, alkanoyloxymethyl of 2–7 carbon atoms, alkenoyloxymethyl of 4–9 carbon atoms, alkynoyloxymethyl of 4–9 carbon atoms, alkoxymethyl oi 2–7 carbon atoms, alkoxy of 1–6 carbon atoms, alkylthio of 1–6 carbon atoms, alkylsulphinyl of 1–6 carbon atoms, alkylsulphonyl of 1–6 carbon atoms, alkylsulfonamido of 1–6 carbon atoms, alkenylsulfonamido of 2–6 carbon atoms, alkynylsulfonamido of 2–6 carbon atoms, hydroxy, trifluoromethyl, trifluoromethoxy, cyano, nitro, carboxy, carboalkoxy of 2–7 carbon atoms, carboalkyl of 2–7 carbon atoms, phenoxy, phenyl, thiophenoxy, benzyl, amino, hydroxyamino, alkoxyamino of 1–4 carbon atoms, alkylamino of 1–6 carbon atoms, dialkylamino of 2 to 12 carbon atoms, N-alkylcarbamoyl, N,N-dialkylcarbamoyl, N-alkyl-N-alkenylamino of 4 to 12 carbon atoms, N,N-dialkenylamino of 6–12 carbon atoms, phenylamino, benzylamino,

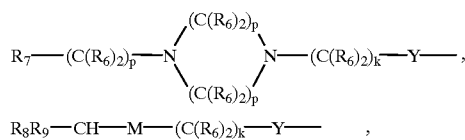

$R_7$—(C(R$_6$)$_2$)$_g$—Y—,
$R_7$—(C(R$_6$)$_2$)$_p$—M—(C(R$_6$)$_2$)$_k$—Y—,
or Het-(C(R$_6$)$_2$)$_q$—W—(C(R$_6$)$_2$)$_k$—Y—;

or R1 and R4 are as defined above and $G_1$ or $G_2$ or both are $R_2$—NH—;

or if any of the substituents $R_1$, $G_2$, $G_3$, or $R_4$ are located on contiguous carbon atoms then they may be taken together as the divalent radical —O—C(R$_6$)$_2$—O—;

Y is a divalent radical selected from the group consisting of

—(CH$_2$)$_a$—, —O—, and —N(R$_6$)—;

$R_7$ is —NR$_6$R$_6$, —OR$_6$, —J, —N(R$_6$)$_3^+$, or —NR$_6$(OR$_6$);

M is >NR$_6$, —O—, >N—(C(R$_6$)$_2$)$_p$NR$_6$R$_6$, or >N—(C(R$_6$)$_2$)$_p$—OR$_6$;

W is >NR$_6$, —O— or is a bond;

Het is is selected from the group consisting of morpholine, thiomorpholine, thiomorpholine S-oxide, thiomorpholine S,S-dioxide, piperidine, pyrrolidine, aziridine, pyridine, imidazole, 1,2,3-triazole, 1,2,4-triazole, thiazole, thiazolidine, tetrazole, piperazine, furan, thiophene, tetrahydrothiophene, tetrahydrofuran, dioxane, 1,3-dioxolane, tetrahydropyran, and

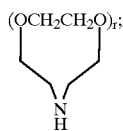

wherein Het is optionally mono- or di-substituted on carbon or nitrogen with $R_6$, optionally mono- or di-substituted on carbon with hydroxy, —N(R$_6$)$_2$, or —OR$_6$, optionally mono or di-substituted on carbon with the mono-valent radicals —(C(R$_6$)$_2$)$_s$OR$_6$ or —(C(R$_6$)$_2$)$_s$N(R$_6$)$_2$, and optionally mono or di-substituted on a saturated carbon with divalent radicals —O— or —O(C(R$_6$)$_2$)$_s$O—;

$R_6$ is hydrogen, alkyl of 1–6 carbon atoms, alkenyl of 2–6 carbon atoms, alkynyl of 2–6 carbon atoms, cycloalkyl of 1–6 carbon atoms, carboalkyl of 2–7 carbon atoms, carboxyalkyl (2–7 carbon atoms), phenyl, or phenyl optionally substituted with one or more halogen, alkoxy of 1–6 carbon atoms, trifluoromethyl, amino, alkylamino of 1–3 carbon atoms, dialkylamino of 2–6 carbon atoms, nitro, cyano, azido, halomethyl, alkoxymethyl of 2–7 carbon atoms, alkanoyloxymethyl of 2–7 carbon atoms, alkylthio of 1–6 carbon atoms, hydroxy, carboxyl, carboalkoxy of 2–7 carbon atoms, phenoxy, phenyl, thiophenoxy, benzoyl, benzyl, phenylamino, benzylamino, alkanoylamino of 1–6 carbon atoms, or alkyl of 1–6 carbon atoms; with the proviso that the alkenyl or alkynyl moiety is bound to a nitrogen or oxygen atom through a saturated carbon atom;

$R_2$, is selected from the group consisting of

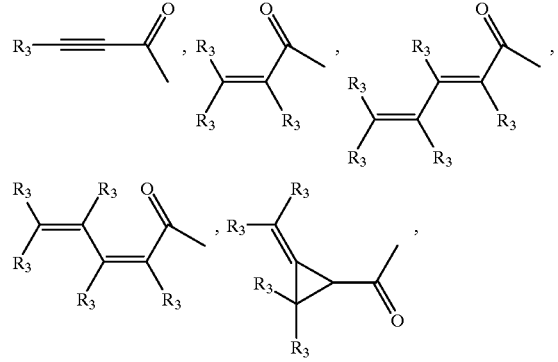

-continued

[chemical structures showing various R3, R5, R6 substituted compounds including ketones, disulfides, epoxides, cyclobutenediones, morpholine and piperazine derivatives]

R3 is independently hydrogen, alkyl of 1–6 carbon atoms, carboxy, carboalkoxy of 1–6 carbon atoms, phenyl, carboalkyl of 2–7 carbon atoms,

[structure: $R_7$—$(C(R_6)_2)_p$—N with $(C(R_6)_2)_p$ groups—N—$(C(R_6)_2)_r$—]

$R_7$—$(C(R_6)_2)_s$—,
$R_7$—$(C(R_6)_2)_p$—M—$(C(R_6)_2)_r$—, $R_8R_9$—CH—M—$(C(R_6)_2)_r$—,
or Het-$(C(R_6)_2)_q$—W—$(C(R_6)_2)_r$—;

$R_5$ is independently hydrogen, alkyl of 1–6 carbon atoms, carboxy, carboalkoxy of 1–6 carbon atoms, phenyl, carboalkyl of 2–7 carbon atoms,

[structure: $R_7$—$(C(R_6)_2)_p$—N with $(C(R_6)_2)_p$ groups—N—$(C(R_6)_2)_r$—]

$R_7$—$(C(R_6)_2)_s$—,
$R_7$—$(C(R_6)_2)_p$—M—$(C(R_6)_2)_r$—, $R_8R_9$—CH—M—$(C(R_6)_2)_r$—,
or Het-$(C(R_6)_2)_q$—W—$(C(R_6)_2)_r$—;

$R_8$, and $R_9$ are each, independently, —$(C(R_6)_2)_r$NR$_6$R$_6$, or —$(C(R_6)_2)_r$OR$_6$;

J is independently hydrogen, chlorine, fluorine, or bromine;

Q is alkyl of 1–6 carbon atoms or hydrogen;

a=0 or 1;
g=1–6;
k=0–4;
n is 0–1;
m is 0–3;
p=2–4;
q=0–4;
r=1–4;
s=1–6;
u=0–4 and v=0–4, wherein the sum of u+v is 2–4;

or a pharmaceutically acceptable salt thereof, provided that when $R_6$ is alkenyl of 2–7 carbon atoms or alkynyl of 2–7 carbon atoms, such alkenyl or alkynyl moiety is bound to a nitrogen or oxygen atom through a saturated carbon atom;

and further provided that when Y is —NR$_6$— and $R_7$ is —NR$_6$R$_6$, —N(R$_6$)$_3^+$, or —NR$_6$(OR$_6$), then g=2–6;

when M is —O— and $R_7$ is —OR$_6$ then p=1–4;

when Y is —NR$_6$— then k=2–4;

when Y is —O— and M or W is —O— then k=1–4 when W is not a bond with Het bonded through a nitrogen atom then q=2–4 and when W is a bond with Het bonded through a nitrogen atom and Y is —O— or —NR$_6$— then k=2–4.

13. The method according to claim 12 wherein the neoplasm is selected from the group consisting of breast, kidney, bladder, mouth, larynx, esophagus, stomach, colon, ovary, and lung.

14. A method of treating, inhibiting the progression of, or eradicating polycystic kidney disease in a mammal in need thereof which comprises administering to said mammal an effective amount of a compound of formula 1 having the structure

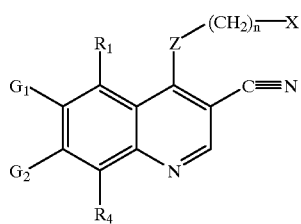

wherein:

X is a bicyclic aryl or bicyclic heteroaryl ring system of 8 to 12 atoms where the bicyclic heteroaryl ring contains 1 to 4 heteroatoms selected from N, O, and S with the proviso that the bicyclic heteroaryl ring does not contain O—O, S—S, or S—O bonds and where the bicyclic aryl or bicyclic heteroaryl ring may be optionally mono- di-, tri, or tetra-substituted with a substituent selected from the group consisting of halogen, oxo, thio, alkyl of 1–6 carbon atoms, alkenyl of 2–6 carbon atoms, alkynyl of 2–6 carbon atoms, azido, hydroxyalkyl of 1–6 carbon atoms, halomethyl, alkoxymethyl of 2–7 carbon atoms, alkanoyloxymethyl of 2–7 carbon atoms, alkoxy of 1–6 carbon atoms, alkylthio of 1–6 carbon atoms, hydroxy, trifluoromethyl, cyano, nitro, carboxy, carboalkoxy of 2–7 carbon atoms, carboalkyl of 2–7 carbon atoms, phenoxy, phenyl, thiophenoxy, benzoyl, benzyl, amino, alkylamino of 1–6 carbon atoms, dialkylamino of 2 to 12 carbon atoms, phenylamino, benzylamino, alkanoylamino of 1–6 carbon atoms, alkenoylamino of 3–8 carbon atoms, alkynoylamino of 3–8 carbon atoms, carboxyalkyl of 2–7 carbon atoms, carboalkoxyalky of 3–8 carbon atoms, aminoalkyl of 1–5 carbon atoms, N-alkylaminoalkyl of 2–9 carbon atoms, N,N-dialkylaminoalkyl of 3–10 carbon atoms, N-alkylaminoalkoxy of 2–9 carbon atoms, N,N-dialkylaminoalkoxy of 3–10 carbon atoms, mercapto, and benzoylamino; or X is a radical having the formula:

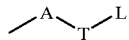

wherein

A is a pyridinyl, pyrimidinyl, or phenyl ring; wherein the pyridinyl, pyrimidinyl, or phenyl ring may be optionally mono- or di-substituted with a substituent selected from the group consisting of halogen, alkyl of 1–6 carbon atoms, alkenyl of 2–6 carbon atoms, alkynyl of 2–6 carbon atoms, azido, hydroxyalkyl of 1–6 carbon atoms, halomethyl, alkoxymethyl of 2–7 carbon atoms, alkanoyloxymethyl of 2–7 carbon atoms, alkoxy of 1–6 carbon atoms, alkylthio of 1–6 carbon atoms, hydroxy, trifluoromethyl, cyano, nitro, carboxy, carboalkoxy of 2–7 carbon atoms, carboalkyl of 2–7 carbon atoms, phenoxy, phenyl, thiophenoxy, benzoyl, benzyl, amino, alkylamino of 1–6 carbon atoms, dialkylamino of 2 to 12 carbon atoms, phenylamino, benzylamino, alkanoylamino of 1–6 carbon atoms, alkenoylamino of 3–8 carbon atoms, alkynoylamino of 3–8 carbon atoms, carboxyalkyl of 2–7 carbon atoms, carboalkoxyalky of 3–8 carbon atoms, aminoalkyl of 1–5 carbon atoms, N-alkylaminoalkyl of 2–9 carbon atoms, N,N-dialkylaminoalkyl of 3–10 carbon atoms, N-alkylaminoalkoxy of 2–9 carbon atoms, N,N-dialkylaminoalkoxy of 3–10 carbon atoms, mercapto, and benzoylamino;

T is bonded to a carbon of A and is:
—NH(CH$_2$)$_m$—, —O(CH$_2$)$_m$—, —S(CH$_2$)$_m$—, —NR(CH$_2$)$_m$—, —(CH$_2$)$_m$— —(CH$_2$)$_m$NH—, —(CH$_2$)$_m$O—, —(CH$_2$)$_m$S—, or —(CH$_2$)$_m$NR—;

L is an unsubsititued phenyl ring or a phenyl ring mono-, di-, or tri-substituted with a substituent selected from the group consisting of halogen, alkyl of 1–6 carbon atoms, alkenyl of 2–6 carbon atoms, alkynyl of 2–6 carbon atoms, azido, hydroxyalkyl of 1–6 carbon atoms, halomethyl, alkoxymethyl of 2–7 carbon atoms, alkanoyloxymethyl of 2–7 carbon atoms, alkoxy of 1–6 carbon atoms, alkylthio of 1–6 carbon atoms, hydroxy, trifluoromethyl, cyano, nitro, carboxy, carboalkoxy of 2–7 carbon atoms, carboalkyl of 2–7 carbon atoms, phenoxy, phenyl, thiophenoxy, benzoyl, benzyl, amino, alkylamino of 1–6 carbon atoms, dialkylamino of 2 to 12 carbon atoms, phenylamino, benzylamino, alkanoylamino of 1–6 carbon atoms, alkenoylamino of 3–8 carbon atoms, alkynoylamino of 3–8 carbon atoms, carboxyalkyl of 2–7 carbon atoms, carboalkoxyalky of 3–8 carbon atoms, aminoalkyl of 1–5 carbon atoms, N-alkylaminoalkyl of 2–9 carbon atoms, N,N-dialkylaminoalkyl of 3–10 carbon atoms, N-alkylaminoalkoxy of 2–9 carbon atoms, N,N-dialkylaminoalkoxy of 3–10 carbon atoms, mercapto, and benzoylamino; provided that L can be an unsubstituted phenyl ring only when m>0 and T is not —CH$_2$NH— or —CH$_2$O—; or L is a 5- or 6-membered heteroaryl ring where the heteroaryl ring contains 1 to 3 heteroatoms selected from N, O, and S, with the proviso that the heteroaryl ring does not contain O—O, S—S, or S—O bonds, and where the heteroaryl ring is optionally mono- or di-substituted with a substituent selected from the group consisting of halogen, oxo, thio, alkyl of 1–6 carbon atoms, alkenyl of 2–6 carbon atoms, alkynyl of 2–6 carbon atoms, azido, hydroxyalkyl of 1–6 carbon atoms, halomethyl, alkoxymethyl of 2–7 carbon atoms, alkanoyloxymethyl of 2–7 carbon atoms, alkoxy of 1–6 carbon atoms, alkylthio of 1–6 carbon atoms, hydroxy, trifluoromethyl, cyano, nitro, carboxy, carboalkoxy of 2–7 carbon atoms, carboalkyl of 2–7 carbon atoms, phenoxy, phenyl, thiophenoxy, benzoyl, benzyl, amino, alkylamino of 1–6 carbon atoms, dialkylamino of 2 to 12 carbon atoms, phenylamino, benzylamino, alkanoylamino of 1–6 carbon atoms, alkenoylamino of 3–8 carbon atoms, alkynoylamino of 3–8 carbon atoms, carboxyalkyl of 2–7 carbon atoms, carboalkoxyalky of 3–8 carbon atoms, aminoalkyl of 1–5 carbon atoms, N-alkylaminoalkyl of 2–9 carbon atoms, N,N-dialkylaminoalkyl of 3–10 carbon atoms, N-alkylaminoalkoxy of 2–9 carbon atoms, N,N-dialkylaminoalkoxy of 3–10 carbon atoms, mercapto, and benzoylamino;

Z is —NH—, —O—, —S—, or —NR—;

R is alkyl of 1–6 carbon atoms, or carboalkyl of 2–7 carbon atoms;

G$_1$, G$_2$, R$_1$, and R$_4$ are each, independently, hydrogen, halogen, alkyl of 1–6 carbon atoms, alkenyl of 2–6 carbon atoms, alkynyl of 2–6 carbon atoms, alkenyloxy of 2–6 carbon atoms, alkynyloxy of 2–6 carbon atoms, hydroxymethyl, halomethyl, alkanoyloxy of 1–6 carbon atoms, alkenoyloxy of 3–8 carbon atoms, alkynoyloxy of 3–8 carbon atoms, alkanoyloxymethyl of 2–7 carbon atoms, alkenoyloxymethyl of 4–9 carbon atoms, alkynoyloxymethyl of 4–9 carbon atoms, alkoxymethyl of 2–7 carbon atoms, alkoxy of 1–6 carbon atoms, alkylthio of 1–6 carbon atoms, alkylsulphinyl of 1–6 carbon atoms, alkylsulphonyl of 1–6 carbon atoms, alkylsulfonamido of 1–6 carbon atoms, alkenylsulfonamido of 2–6 carbon atoms, alkynylsulfonamido of 2–6 carbon atoms, hydroxy, trifluoromethyl, trifluoromethoxy, cyano, nitro, carboxy, carboalkoxy of 2–7 carbon atoms, carboalkyl of 2–7 carbon atoms, phenoxy, phenyl, thiophenoxy, benzyl, amino, hydroxyamino, alkoxyamino of 1–4 carbon atoms, alkylamino of 1–6 carbon atoms, dialkylamino of 2 to 12 carbon atoms, N-alkylcarbamoyl, N,N-dialkylcarbamoyl, N-alkyl-N-alkenylamino of 4 to 12 carbon atoms, N,N-dialkenylamino of 6–12 carbon atoms, phenylamino, benzylamino,

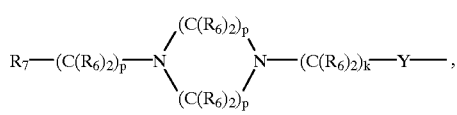

$R_8R_9$—CH—M—$(C(R_6)_2)_k$—Y—, $R_7$—$(C(R_6)_2)_g$—Y—,
$R_7$—$(C(R_6)_2)_p$—M—$(C(R_6)_2)_k$—Y—,
or Het-$(C(R_6)_2)_q$—W—$(C(R_6)_2)_k$—Y—;

or R1 and R4 are as defined above and $G_1$ or $G_2$ or both are $R_2$—NH—;

or if any of the substituents $R_1$, $G_2$, $G_3$, or $R_4$ are located on contiguous carbon atoms then they may be taken together as the divalent radical —O—$C(R_6)_2$—O—;

Y is a divalent radical selected from the group consisting of

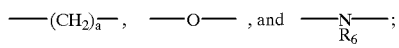

$R_7$ is —$NR_6R_6$, —$OR_6$, —J, —$N(R_6)_3^+$, or —$NR_6(OR_6)$;

M is >$NR_6$, —O—, >N—$(C(R_6)_2)_p NR_6R_6$, or >N—$(C(R_6)_2)_p$—$OR_6$;

W is >$NR_6$, —O— or is a bond;

Het is is selected from the group consisting of morpholine, thiomorpholine, thiomorpholine S-oxide, thiomorpholine S,S-dioxide, piperidine, pyrrolidine, aziridine, pyridine, imidazole, 1,2,3-triazole, 1,2,4-triazole, thiazole, thiazolidine , tetrazole, piperazine, furan, thiophene, tetrahydrothiophene, tetrahydrofuran, dioxane, 1,3-dioxolane, tetrahydropyran, and

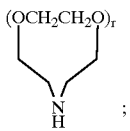

wherein Het is optionally mono- or di-substituted on carbon or nitrogen with $R_6$, optionally mono- or di-substituted on carbon with hydroxy, —$N(R_6)_2$, or —$OR_6$, optionally mono or di-substituted on carbon with the mono-valent radicals —$(C(R_6)_2)_s OR_6$ or —$(C(R_6)_2)_s N(R_6)_2$, and optionally mono or di-substituted on a saturated carbon with divalent radicals —O— or —$O(C(R_6)_2)_s O$—;

$R_6$ is hydrogen, alkyl of 1–6 carbon atoms, alkenyl of 2–6 carbon atoms, alkynyl of 2–6 carbon atoms, cycloalkyl of 1–6 carbon atoms, carboalkyl of 2–7 carbon atoms, carboxyalkyl (2–7 carbon atoms), phenyl, or phenyl optionally substituted with one or more halogen, alkoxy of 1–6 carbon atoms, trifluoromethyl, amino, alkylamino of 1–3 carbon atoms, dialkylamino of 2–6 carbon atoms, nitro, cyano, azido, halomethyl, alkoxymethyl of 2–7 carbon atoms, alkanoyloxymethyl of 2–7 carbon atoms, alkylthio of 1–6 carbon atoms, hydroxy, carboxyl, carboalkoxy of 2–7 carbon atoms, phenoxy, phenyl, thiophenoxy, benzoyl, benzyl, phenylamino, benzylamino, alkanoylamino of 1–6 carbon atoms, or alkyl of 1–6 carbon atoms; with the proviso that the alkenyl or alkynyl moiety is bound to a nitrogen or oxygen atom through a saturated carbon atom;

$R_2$, is selected from the group consisting of

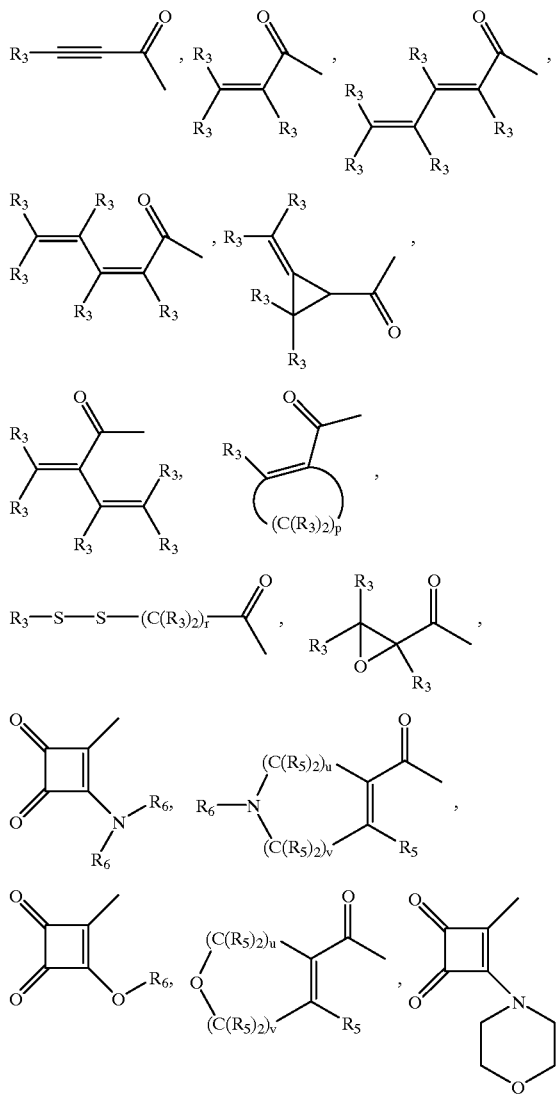

-continued

[chemical structures]

R₃ is independently hydrogen, alkyl of 1–6 carbon atoms, carboxy, carboalkoxy of 1–6 carbon atoms, phenyl, carboalkyl of 2–7 carbon atoms, $R_7$—$(C(R_6)_2)_p$—N$\begin{pmatrix}(C(R_6)_2)_p\\(C(R_6)_2)_p\end{pmatrix}$N—$(C(R_6)_2)_r$—, $R_7$—$(C(R_6)_2)_s$—,
$R_7(C(R_6)_2)_p$—M—$(C(R_6)_2)_r$—, $R_8R_9$—CH—M—$(C(R_6)_2)_r$—, or
Het-$(C(R_6)_2)_q$—W—$(C(R_6)_2)_r$—;

$R_5$ is independently hydrogen, alkyl of 1–6 carbon atoms, carboxy, carboalkoxy of 1–6 carbon atoms, phenyl, carboalkyl of 2–7 carbon atoms, $R_7$—$(C(R_6)_2)_p$—N$\begin{pmatrix}(C(R_6)_2)_p\\(C(R_6)_2)_p\end{pmatrix}$N—$(C(R_6)_2)_r$—, $R_7$—$(C(R_6)_2)_s$—,
$R_7$—$(C(R_6)_2)_p$—M—$(C(R_6)_2)_r$—, $R_8R_9$—CH—M—$(C(R_6)_2)_r$—, or
Het-$(C(R_6)_2)_q$—W—$(C(R_6)_2)_r$—;

$R_8$, and $R_9$ are each, independently, —$(C(R_6)_2)_r NR_6R_6$, or —$(C(R_6)_2)_r OR_6$;

J is independently hydrogen, chlorine, fluorine, or bromine;

Q is alkyl of 1–6 carbon atoms or hydrogen;

a=0 or 1;
g=1–6;
k=0–4;
n is 0–1;
m is 0–3;
p=2–4;
q=0–4;
r=1–4;
s=1–6;
u=0–4 and v=0–4, wherein the sum of u+v is 2–4;

or a pharmaceutically acceptable salt thereof, provided that when $R_6$ is alkenyl of 2–7 carbon atoms or alkynyl of 2–7 carbon atoms, such alkenyl or alkynyl moiety is bound to a nitrogen or oxygen atom through a saturated carbon atom;

and further provided that when Y is —$NR_6$— and $R_7$ is —$NR_6R_6$, —$N(R_6)_3^+$, or —$NR_6(OR_6)$, then g=2–6;

when M is —O— and $R_7$ is —$OR_6$ then p=1–4;

when Y is —$NR_6$— then k=2–4;

when Y is —O— and M or W is —O— then k=1–4 when W is not a bond with Het bonded through a nitrogen atom then q=2–4 and when W is a bond with Het bonded through a nitrogen atom and Y is —O— or —$NR_6$— then k=2–4.

15. A pharmaceutical composition which comprises a compound of formula 1 having the structure

[chemical structure of formula 1]

1 wherein:

X is a bicyclic aryl or bicyclic heteroaryl ring system of 8 to 12 atoms where the bicyclic heteroaryl ring contains 1 to 4 heteroatoms selected from N, O, and S with the proviso that the bicyclic heteroaryl ring does not contain O—O, S—S, or S—O bonds and where the bicyclic aryl or bicyclic heteroaryl ring may be optionally mono- di-, tri, or tetra-substituted with a substituent selected from the group consisting of halogen, oxo, thio, alkyl of 1–6 carbon atoms, alkenyl of 2–6 carbon atoms, alkynyl of 2–6 carbon atoms, azido, hydroxyalkyl of 1–6 carbon atoms, halomethyl, alkoxymethyl of 2–7 carbon atoms, alkanoyloxymethyl of 2–7 carbon atoms, alkoxy of 1–6 carbon atoms, alkylthio of 1–6 carbon atoms, hydroxy, trifluoromethyl, cyano, nitro, carboxy, carboalkoxy of 2–7 carbon atoms, carboalkyl of 2–7 carbon atoms, phenoxy, phenyl, thiophenoxy, benzoyl, benzyl, amino, alkylamino of 1–6 carbon atoms, dialkylamino of 2 to 12 carbon atoms, phenylamino, benzylamino, alkanoylamino of 1–6 carbon atoms, alkenoylamino of 3–8 carbon atoms, alkynoylamino of 3–8 carbon atoms, carboxyalkyl of 2–7 carbon atoms, carboalkoxyalky of 3–8 carbon atoms, aminoalkyl of 1–5 carbon atoms, N-alkylaminoalkyl of 2–9 carbon atoms, N,N-dialkylaminoalkyl of 3–10 carbon atoms, N-alkylaminoalkoxy of 2–9 carbon atoms, N,N-dialkylaminoalkoxy of 3–10 carbon atoms, mercapto, and benzoylamino; or X is a radical having the formula:

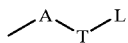

wherein
A is a pyridinyl, pyrimidinyl, or phenyl ring; wherein the pyridinyl, pyrimidinyl, or phenyl ring may be optionally mono- or di-substituted with a substituent selected from the group consisting of halogen, alkyl of 1–6 carbon atoms, alkenyl of 2–6 carbon atoms, alkynyl of 2–6 carbon atoms, azido, hydroxyalkyl of 1–6 carbon atoms, halomethyl, alkoxymethyl of 2–7 carbon atoms, alkanoyloxymethyl of 2–7 carbon atoms, alkoxy of 1–6 carbon atoms, alkylthio of 1–6 carbon atoms, hydroxy, trifluoromethyl, cyano, nitro, carboxy, carboalkoxy of 2–7 carbon atoms, carboalkyl of 2–7 carbon atoms, phenoxy, phenyl, thiophenoxy, benzoyl, benzyl, amino, alkylamino of 1–6 carbon atoms, dialkylamino of 2 to 12 carbon atoms, phenylamino, benzylamino, alkanoylamino of 1–6 carbon atoms, alkenoylamino of 3–8 carbon atoms, alkynoylamino of 3–8 carbon atoms, carboxyalkyl of 2–7 carbon atoms, carboalkoxyalky of 3–8 carbon atoms, aminoalkyl of 1–5 carbon atoms, N-alkylaminoalkyl of 2–9 carbon atoms, N,N-dialkylaminoalkyl of 3–10 carbon atoms, N-alkylaminoalkoxy of 2–9 carbon atoms, N,N-dialkylaminoalkoxy of 3–10 carbon atoms, mercapto, and benzoylamino;

T is bonded to a carbon of A and is:
—NH(CH$_2$)$_m$—, —O(CH$_2$)$_m$—, —S(CH$_2$)$_m$—, —NR(CH$_2$)$_m$—, —(CH$_2$)$_m$— —(CH$_2$)$_m$NH—, —(CH$_2$)$_m$O—, —(CH$_2$)$_m$S—, or —(CH$_2$)$_m$NR—;

L is an unsubstituted phenyl ring or a phenyl ring mono-, di-, or tri-substituted with a substituent selected from the group consisting of halogen, alkyl of 1–6 carbon atoms, alkenyl of 2–6 carbon atoms, alkynyl of 2–6 carbon atoms, azido, hydroxyalkyl of 1–6 carbon atoms, halomethyl, alkoxymethyl of 2–7 carbon atoms, alkanoyloxymethyl of 2–7 carbon atoms, alkoxy of 1–6 carbon atoms, allkylthio of 1–6 carbon atoms, hydroxy, trifluoromethyl, cyano, nitro, carboxy, carboalkoxy of 2–7 carbon atoms, carboalkyl of 2–7 carbon atoms, phenoxy, phenyl, thiophenoxy, benzoyl, benzyl, amino, alkylamino of 1–6 carbon atoms, dialkylamino of 2 to 12 carbon atoms, phenylamino, benzylamino, alkanoylamino of 1–6 carbon atoms, alkenoylamino of 3–8 carbon atoms, alkynoylamino of 3–8 carbon atoms, carboxyalkyl of 2–7 carbon atoms, carboalkoxyalky of 3–8 carbon atoms, aminoalkyl of 1–5 carbon atoms, N-alkylaminoalkyl of 2–9 carbon atoms, N,N-dialkylaminoalkyl of 3–10 carbon atoms, N-alkylaminoalkoxy of 2–9 carbon atoms, N,N-dialkylaminoalkoxy of 3–10 carbon atoms, mercapto, and benzoylamino; provided that L can be an unsubstituted phenyl ring only when m>0 and T is not —CH$_2$NH— or —CH$_2$O—; or L is a 5- or 6-membered heteroaryl ring where the heteroaryl ring contains 1 to 3 heteroatoms selected from N, O, and S, with the proviso that the heteroaryl ring does not contain O—O, S—S, or S—O bonds, and where the heteroaryl ring is optionally mono- or di-substituted with a substituent selected from the group consisting of halogen, oxo, thio, alkyl of 1–6 carbon atoms, alkenyl of 2–6 carbon atoms, alkynyl of 2–6 carbon atoms, azido, hydroxyalkyl of 1–6 carbon atoms, halomethyl, alkoxymethyl of 2–7 carbon atoms, alkanoyloxymethyl of 2–7 carbon atoms, alkoxy of 1–6 carbon atoms, alkylthio of 1–6 carbon atoms, hydroxy, trifluoromethyl, cyano, nitro, carboxy, carboalkoxy of 2–7 carbon atoms, carboalkyl of 2–7 carbon atoms, phenoxy, phenyl, thiophenoxy, benzoyl, benzyl, amino, alkylamino of 1–6 carbon atoms, dialkylamino of 2 to 12 carbon atoms, phenylamino, benzylamino, alkanoylamino of 1–6 carbon atoms, alkenoylamino of 3–8 carbon atoms, alkynoylamino of 3–8 carbon atoms, carboxyalkyl of 2–7 carbon atoms, carboalkoxyalky of 3–8 carbon atoms, aminoalkyl of 1–5 carbon atoms, N-alkylaminoalkyl of 2–9 carbon atoms, N,N-dialkylaminoalkyl of 3–10 carbon atoms, N-alkylaminoalkoxy of 2–9 carbon atoms, N,N-dialkylaminoalkoxy of 3–10 carbon atoms, mercapto, and benzoylamino;

Z is —NH—, —O—, —S—, or —NR—;

R is alkyl of 1–6 carbon atoms, or carboalkyl of 2–7 carbon atoms;

$G_1$, $G_2$, $R_1$, and $R_4$ are each, independently, hydrogen, halogen, alkyl of 1–6 carbon atoms, alkenyl of 2–6 carbon atoms, alkynyl of 2–6 carbon atoms, alkenyloxy of 2–6 carbon atoms, alkynyloxy of 2–6 carbon atoms, hydroxymethyl, halomethyl, alkanoyloxy of 1–6 carbon atoms, alkenoyloxy of 3–8 carbon atoms, alkynoyloxy of 3–8 carbon atoms, alkanoyloxymethyl of 2–7 carbon atoms, alkenoyloxymethyl of 4–9 carbon atoms, alkynoyloxymethyl of 4–9 carbon atoms, alkoxymethyl of 2–7 carbon atoms, alkoxy of 1–6 carbon atoms, alkylthio of 1–6 carbon atoms, alkylsulphinyl of 1–6 carbon atoms, alkylsulphonyl of 1–6 carbon atoms, alkylsulfonamido of 1–6 carbon atoms, alkenylsulfonamido of 2–6 carbon atoms, alkynylsulfonamido of 2–6 carbon atoms, hydroxy, trifluoromethyl, trifluoromethoxy, cyano, nitro, carboxy, carboalkoxy of 2–7 carbon atoms, carboalkyl of 2–7 carbon atoms, phenoxy, phenyl, thiophenoxy, benzyl, amino, hydroxyamino, alkoxyamino of 1–4 carbon atoms, alkylamino of 1–6 carbon atoms, dialkylamino of 2 to 12 carbon atoms, N-alkylcarbamoyl, N,N-dialkylcarbamoyl, N-alkyl-N-alkenylamino of 4 to 12 carbon atoms, N,N-dialkenylamino of 6–12 carbon atoms, phenylamino, benzylamino,

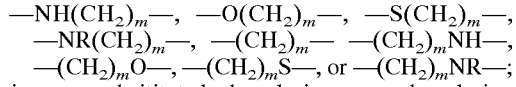

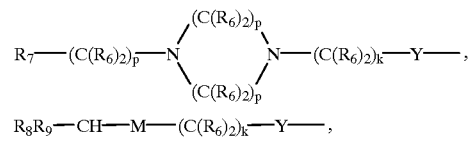

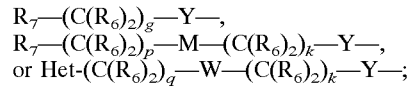

or R1 and R4 are as defined above and $G_1$ or $G_2$ or both are $R_2$—NH—;

or if any of the substituents $R_1$, $G_2$, $G_3$, or $R_4$ are located on contiguous carbon atoms then they may be taken together as the divalent radical —O—C(R$_6$)$_2$—O—;

Y is a divalent radical selected from the group consisting of

—(CH₂)ₐ—, —O—, and —N(R₆)—;

R₇ is —NR₆R₆, —OR₆, —J, —N(R₆)₃⁺, or —NR₆(OR₆);

M is >NR₆, —O—, >N—(C(R₆)₂)ₚNR₆R₆, or >N—(C(R₆)₂)ₚ—OR₆;

W is >NR₆, —O— or is a bond;

Het is selected from the group consisting of morpholine, thiomorpholine, thiomorpholine S-oxide, thiomorpholine S,S-dioxide, piperidine, pyrrolidine, aziridine, pyridine, imidazole, 1,2,3-triazole, 1,2,4-triazole, thiazole, thiazolidine, tetrazole, piperazine, furan, thiophene, tetrahydrothiophene, tetrahydrofuran, dioxane, 1,3-dioxolane, tetrahydropyran, and

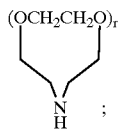

wherein Het is optionally mono- or di-substituted on carbon or nitrogen with R₆, optionally mono- or di-substituted on carbon with hydroxy, —N(R₆)₂, or —OR₆, optionally mono or di-substituted on carbon with the mono-valent radicals —(C(R₆)₂)ₛOR₆ or —(C(R₆)₂)ₛN(R₆)₂, and optionally mono or di-substituted on a saturated carbon with divalent radicals —O— or —O(C(R₆)₂)ₛO—;

R₆ is hydrogen, alkyl of 1–6 carbon atoms, alkenyl of 2–6 carbon atoms, alkynyl of 2–6 carbon atoms, cycloalkyl of 1–6 carbon atoms, carboalkyl of 2–7 carbon atoms, carboxyalkyl (2–7 carbon atoms), phenyl, or phenyl optionally substituted with one or more halogen, alkoxy of 1–6 carbon atoms, trifluoromethyl, amino, alkylamino of 1–3 carbon atoms, dialkylamino of 2–6 carbon atoms, nitro, cyano, azido, halomethyl, alkoxymethyl of 2–7 carbon atoms, alkanoyloxymethyl of 2–7 carbon atoms, alkylthio of 1–6 carbon atoms, hydroxy, carboxyl, carboalkoxy of 2–7 carbon atoms, phenoxy, phenyl, thiophenoxy, benzoyl, benzyl, phenylamino, benzylamino, alkanoylamino of 1–6 carbon atoms, or alkyl of 1–6 carbon atoms; with the proviso that the alkenyl or alkynyl moiety is bound to a nitrogen or oxygen atom through a saturated carbon atom;

R₂, is selected from the group consisting of

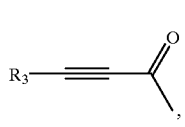, 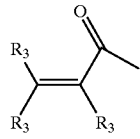,

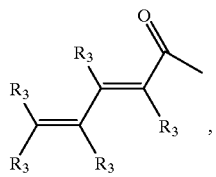, 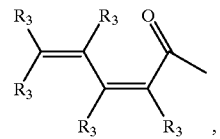,

-continued

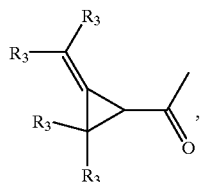, 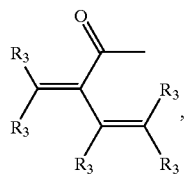,

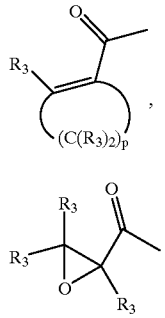 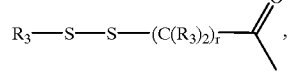,

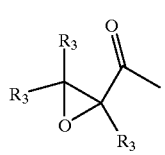, 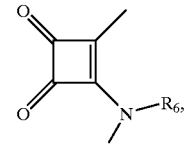,

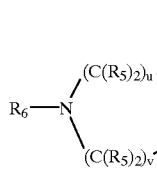, 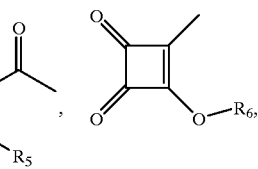,

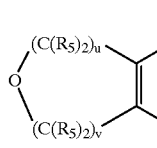, 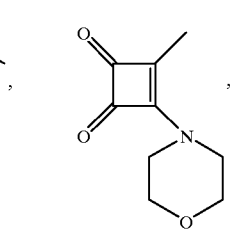,

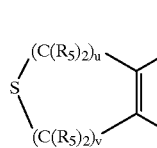, 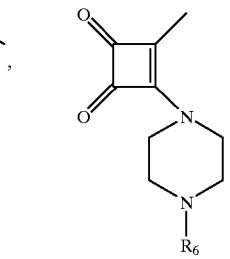,

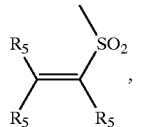, 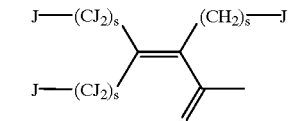,

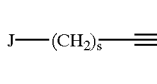, 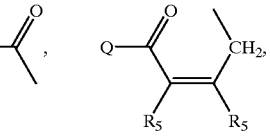,

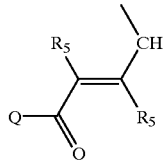, 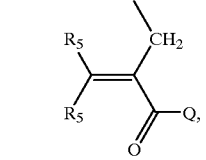,

-continued

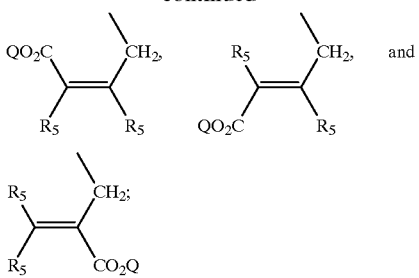

$R_3$ is independently hydrogen, alkyl of 1–6 carbon atoms, carboxy, carboalkoxy of 1–6 carbon atoms, phenyl, carboalkyl of 2–7 carbon atoms,

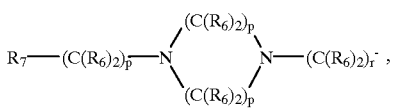

$R_7$—$(C(R_6)_2)_s$—, $R_7$—$(C(R_6)_2)_p$—M—$(C(R_6)_2)_r$—, $R_8R_9$—CH—M—$(C(R_6)_2)_r$—, or Het—$(C(R_6)_2)_q$—W—$(C(R_6)_2)_r$—;

$R_7$—$(C(R_6)_2)_s$—, $R_7$—$(C(R_6)_2)_p$—M—$(C(R_6)_2)_r$—, $R_8R_9$—CH—M—$(C(R_6)_2)_r$—, or Het-$(C(R_6)_2)_q$—W—$(C(R_6)_2)_r$—;

$R_5$ is independently hydrogen, alkyl of 1–6 carbon atoms, carboxy, carboalkoxy of 1–6 carbon atoms, phenyl, carboalkyl of 2–7 carbon atoms,

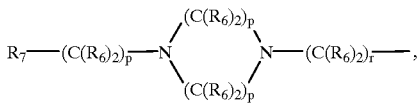

$R_7$—$(C(R_6)_2)_s$—, $R_7$—$(C(R_6)_2)_p$—M—$(C(R_6)_2)_r$—, $R_8R_9$—CH—M—$(C(R_6)_2)_r$—, or Het-$(C(R_6)_2)_q$—W—$(C(R_6)_2)_r$—;

$R_8$, and $R_9$ are each, independently, —$(C(R_6)_2)_r NR_6R_6$, or —$(C(R_6)_2)_r OR_6$;

J is independently hydrogen, chlorine, fluorine, or bromine;

Q is alkyl of 1–6 carbon atoms or hydrogen;

a=0 or 1;

g=1–6;

k=0–4;

n is 0–1;

m is 0–3;

p=2–4;

q=0–4;

r=1–4;

s=1–6;

u=0–4 and v=0–4, wherein the sum of u+v is 2–4;

or a pharmaceutically acceptable salt thereof, provided that when $R_6$ is alkenyl of 2–7 carbon atoms or alkynyl of 2–7 carbon atoms, such alkenyl or alkynyl moiety is bound to a nitrogen or oxygen atom through a saturated carbon atom;

and further provided that when Y is —$NR_6$— and $R_7$ is —$NR_6R_6$, —$N(R_6)_3^+$, or —$NR_6(OR_6)$, then g=2–6;

when M is —O— and $R_7$ is —$OR_6$ then p=1–4;

when Y is —$NR_6$— then k=2–4;

when Y is —O— and M or W is —O— then k=1–4 when W is not a bond with Het bonded through a nitrogen atom then q=2–4 and when W is a bond with Het bonded through a nitrogen atom and Y is —O— or —$NR_6$— then k=2–4 and a pharmaceutical carrier.

* * * * *

UNITED STATES PATENT AND TRADEMARK OFFICE
CERTIFICATE OF CORRECTION

PATENT NO. : 6,288,082 B1
DATED : September 11, 2001
INVENTOR(S) : Allan Wissner et al.

It is certified that error appears in the above-identified patent and that said Letters Patent is hereby corrected as shown below:

Column 106,
Line 25, replace "or Het-$(C(R_6)_2)_q$-W-$(C(R_6)_2$-Y-;" with
-- or Het-$(C(R_6)_2)_q$-W-$(C(R_6)_2)_k$-Y-; --.

Signed and Sealed this

Eighteenth Day of October, 2005

JON W. DUDAS
*Director of the United States Patent and Trademark Office*